(12) United States Patent
Cragg et al.

(10) Patent No.: US 10,178,995 B2
(45) Date of Patent: *Jan. 15, 2019

(54) METHODS AND DEVICES FOR ENDOVASCULAR EMBOLIZATION

(71) Applicant: NeuVT Limited, Dublin (IE)

(72) Inventors: Andrew H. Cragg, Edina, MN (US); John Logan, Plymouth, MN (US); Brett E. Naglreiter, Hollywood, FL (US); Scott R. Arp, Village of Palmetto Bay, FL (US); Alejandro Espinosa, Miami, FL (US); Nicholas A. Green, Jupiter, FL (US); Victor M. Gamez, Ft. Lauderdale, FL (US)

(73) Assignee: NeuVT Limited, Dublin (IE)

( * ) Notice: Subject to any disclaimer, the term of this patent is extended or adjusted under 35 U.S.C. 154(b) by 899 days.

This patent is subject to a terminal disclaimer.

(21) Appl. No.: 14/517,752

(22) Filed: Oct. 17, 2014

(65) Prior Publication Data

US 2015/0039020 A1 Feb. 5, 2015

Related U.S. Application Data

(62) Division of application No. 14/449,037, filed on Jul. 31, 2014, now Pat. No. 9,681,876.

(Continued)

(51) Int. Cl.
*A61B 17/12* (2006.01)
*A61F 2/01* (2006.01)
(Continued)

(52) U.S. Cl.
CPC .. *A61B 17/12172* (2013.01); *A61B 17/12031* (2013.01); *A61B 17/12036* (2013.01);
(Continued)

(58) Field of Classification Search
CPC .......... A61B 17/12168; A61B 17/1214; A61B 17/12131; A61B 17/12118
See application file for complete search history.

(56) References Cited

U.S. PATENT DOCUMENTS 3,613,661 A 10/1971 Shah
4,282,875 A 8/1981 Serbinenko et al.
(Continued)

FOREIGN PATENT DOCUMENTS

CN 103750920 A 4/2014
EP 1400219 A1 3/2004
(Continued)

OTHER PUBLICATIONS deSouza, N.M., et al., "Embolization with detachable balloons—Applications outside the head," Clinical Radiology, Sep. 1992; 46(3): 170-175.
(Continued)

*Primary Examiner* — Kathleen Holwerda
*Assistant Examiner* — Christina Lauer
(74) *Attorney, Agent, or Firm* — Knobbe Martens Olson & Bear LLP

(57) ABSTRACT

The present disclosure describes an occlusion device and methods of delivering the occlusion device. The occlusion device can include an expandable structure configured to move between an unexpanded configuration and an expanded configuration. The expandable structure can be configured to have an expansion ratio of at least about 5:1. Further, the occlusion device can be configured to prevent substantially all fluid from flowing past the occlusion device when the occlusion device is in the expanded configuration in the vessel.

21 Claims, 73 Drawing Sheets

Related U.S. Application Data

(60) Provisional application No. 61/860,856, filed on Jul. 31, 2013, provisional application No. 61/936,801, filed on Feb. 6, 2014, provisional application No. 61/975,631, filed on Apr. 4, 2014.

(51) Int. Cl.
*A61B 17/00* (2006.01)
*A61B 17/22* (2006.01)

(52) U.S. Cl.
CPC .. *A61B 17/12109* (2013.01); *A61B 17/12168* (2013.01); *A61B 17/12177* (2013.01); *A61B 2017/00526* (2013.01); *A61B 2017/00778* (2013.01); *A61B 2017/00995* (2013.01); *A61B 2017/1205* (2013.01); *A61B 2017/12054* (2013.01); *A61B 2017/22082* (2013.01); *A61F 2/01* (2013.01); *A61F 2002/018* (2013.01)

(56) References Cited

U.S. PATENT DOCUMENTS

| | | | |
|---|---|---|---|
| 4,665,906 | A | 5/1987 | Jervis |
| 4,705,517 | A | 11/1987 | DiPisa, Jr. |
| 4,710,192 | A | 12/1987 | Liotta et al. |
| 5,067,957 | A | 11/1991 | Jervis |
| 5,108,420 | A | 4/1992 | Marks |
| 5,190,546 | A | 3/1993 | Jervis |
| 5,382,261 | A | 1/1995 | Palmaz |
| 5,597,378 | A | 6/1997 | Jervis |
| 5,656,036 | A | 8/1997 | Palmaz |
| 5,683,411 | A | 11/1997 | Kavteladze et al. |
| 5,690,667 | A | 11/1997 | Gia |
| 5,725,552 | A | 3/1998 | Kotula et al. |
| 5,733,294 | A | 3/1998 | Forber et al. |
| 5,733,329 | A | 3/1998 | Wallace et al. |
| 5,749,891 | A | 5/1998 | Ken et al. |
| 5,769,884 | A | 6/1998 | Solovay |
| 5,797,953 | A | 8/1998 | Tekulve |
| 5,846,261 | A | 12/1998 | Kotula et al. |
| 5,919,224 | A | 7/1999 | Thompson et al. |
| 5,941,888 | A | 8/1999 | Wallace et al. |
| 5,944,738 | A | 8/1999 | Amplatz et al. |
| 5,957,948 | A | 9/1999 | Mariant |
| 5,976,162 | A | 11/1999 | Doan et al. |
| 6,010,517 | A | 1/2000 | Baccaro |
| 6,019,778 | A | 1/2000 | Wilson et al. |
| 6,033,423 | A | 3/2000 | Ken et al. |
| 6,063,113 | A | 5/2000 | Kavteladze et al. |
| 6,066,158 | A | 5/2000 | Engelson et al. |
| 6,090,125 | A | 7/2000 | Horton |
| 6,117,157 | A | 9/2000 | Tekulve |
| 6,120,534 | A * | 9/2000 | Ruiz ............... A61B 17/12109 606/194 |
| 6,123,715 | A | 9/2000 | Amplatz |
| 6,136,015 | A | 10/2000 | Kurz et al. |
| 6,168,622 | B1 | 1/2001 | Mazzocchi |
| 6,231,590 | B1 | 5/2001 | Slaikeu et al. |
| 6,267,783 | B1 | 7/2001 | Letendre et al. |
| 6,280,457 | B1 | 8/2001 | Wallace et al. |
| 6,306,141 | B1 | 10/2001 | Jervis |
| 6,334,864 | B1 | 1/2002 | Amplatz et al. |
| 6,358,228 | B1 | 3/2002 | Tubman et al. |
| 6,368,339 | B1 | 4/2002 | Amplatz |
| 6,371,972 | B1 | 4/2002 | Wallace et al. |
| 6,375,668 | B1 | 4/2002 | Gifford et al. |
| 6,383,204 | B1 | 5/2002 | Ferrera et al. |
| 6,402,772 | B1 | 6/2002 | Amplatz et al. |
| 6,419,686 | B1 | 7/2002 | McLeod et al. |
| 6,447,531 | B1 | 9/2002 | Amplatz |
| 6,511,492 | B1 | 1/2003 | Rosenbluth et al. |
| 6,533,801 | B2 | 3/2003 | Wallace et al. |
| 6,544,275 | B1 | 4/2003 | Teoh |
| 6,551,340 | B1 | 4/2003 | Konya et al. |
| 6,554,849 | B1 | 4/2003 | Jones et al. |
| 6,585,754 | B2 | 7/2003 | Wallace et al. |
| 6,589,256 | B2 | 7/2003 | Forber |
| 6,599,308 | B2 | 7/2003 | Amplatz |
| 6,623,518 | B2 | 9/2003 | Thompson et al. |
| 6,632,236 | B2 | 10/2003 | Hogendijk |
| 6,638,257 | B2 | 10/2003 | Amplatz |
| 6,638,293 | B1 | 10/2003 | Makower et al. |
| 6,656,201 | B2 | 12/2003 | Ferrera et al. |
| 6,660,020 | B2 | 12/2003 | Wallace et al. |
| 6,712,836 | B1 | 3/2004 | Berg et al. |
| 6,814,746 | B2 | 11/2004 | Thompson et al. |
| 6,872,218 | B2 | 3/2005 | Ferrera et al. |
| 6,953,468 | B2 | 10/2005 | Jones et al. |
| 6,984,240 | B1 | 1/2006 | Ken et al. |
| 7,014,645 | B2 | 3/2006 | Greene, Jr. et al. |
| 7,018,401 | B1 | 3/2006 | Hyodoh et al. |
| 7,048,014 | B2 | 5/2006 | Hyodoh et al. |
| 7,060,083 | B2 | 6/2006 | Gerberding |
| 7,070,608 | B2 | 7/2006 | Kurz et al. |
| 7,166,122 | B2 | 1/2007 | Aganon et al. |
| 7,175,660 | B2 | 2/2007 | Cartledge et al. |
| 7,297,150 | B2 | 11/2007 | Cartledge et al. |
| 7,300,661 | B2 | 11/2007 | Henson et al. |
| 7,303,571 | B2 | 12/2007 | Makower et al. |
| 7,316,695 | B2 | 1/2008 | Mialhe |
| 7,326,225 | B2 | 2/2008 | Ferrera et al. |
| 7,338,514 | B2 | 3/2008 | Wahr et al. |
| 7,344,515 | B2 | 3/2008 | Coyle |
| 7,442,382 | B2 | 10/2008 | Henson et al. |
| 7,445,623 | B2 | 11/2008 | Mialhe |
| 7,455,690 | B2 | 11/2008 | Cartledge et al. |
| 7,485,122 | B2 | 2/2009 | Teoh |
| 7,485,123 | B2 | 2/2009 | Porter |
| 7,488,332 | B2 | 2/2009 | Teoh et al. |
| 7,527,637 | B2 | 5/2009 | Sater et al. |
| 7,645,292 | B2 | 1/2010 | Porter |
| 7,665,466 | B2 | 2/2010 | Figulla et al. |
| 7,691,128 | B2 | 4/2010 | Blaeser et al. |
| 7,717,937 | B2 | 5/2010 | Wahr et al. |
| 7,753,925 | B2 | 7/2010 | Mialhe |
| 7,811,300 | B2 | 10/2010 | Feller, III et al. |
| 7,842,054 | B2 | 11/2010 | Greene, Jr. et al. |
| 7,856,264 | B2 | 12/2010 | Firlik et al. |
| 7,879,066 | B2 | 2/2011 | Desai et al. |
| 7,892,254 | B2 | 2/2011 | Klint et al. |
| 7,896,899 | B2 | 3/2011 | Patterson et al. |
| 7,955,343 | B2 | 6/2011 | Makower et al. |
| 7,972,354 | B2 | 7/2011 | Prestezog et al. |
| 7,976,564 | B2 | 7/2011 | Blaeser et al. |
| 8,025,495 | B2 | 9/2011 | Hardert et al. |
| 8,034,061 | B2 | 10/2011 | Amplatz et al. |
| 8,057,503 | B2 | 11/2011 | Fitzgerald et al. |
| 8,060,201 | B2 | 11/2011 | Holmström et al. |
| 8,114,123 | B2 | 2/2012 | Brenzel et al. |
| 8,133,187 | B2 | 3/2012 | Holmström et al. |
| 8,135,472 | B2 | 3/2012 | Fowler et al. |
| 8,167,839 | B2 | 5/2012 | Wilson et al. |
| 8,172,862 | B2 | 5/2012 | Wallace et al. |
| 8,226,660 | B2 | 7/2012 | Teoh et al. |
| 8,226,680 | B2 | 7/2012 | Wallace |
| 8,267,955 | B2 | 9/2012 | Patterson et al. |
| 8,308,751 | B2 | 11/2012 | Gerberding |
| 8,308,752 | B2 | 11/2012 | Tekulve |
| 8,313,505 | B2 | 11/2012 | Amplatz et al. |
| 8,323,306 | B2 | 12/2012 | Schaefer et al. |
| 8,323,309 | B2 | 12/2012 | Khairkhahan et al. |
| 8,328,840 | B2 | 12/2012 | Gailloud et al. |
| 8,333,786 | B2 | 12/2012 | Mirizzi et al. |
| 8,343,167 | B2 | 1/2013 | Henson |
| 8,361,104 | B2 | 1/2013 | Jones et al. |
| 8,361,138 | B2 | 1/2013 | Adams |
| 8,372,112 | B2 | 2/2013 | Christianson et al. |
| 8,382,796 | B2 | 2/2013 | Blaeser et al. |
| 8,382,825 | B2 | 2/2013 | Garcia et al. |
| 8,398,670 | B2 | 3/2013 | Amplatz et al. |
| 8,398,701 | B2 | 3/2013 | Berez et al. |
| 8,425,541 | B2 | 4/2013 | Masters et al. |
| 8,425,542 | B2 | 4/2013 | Moftakhar et al. |

(56) References Cited

U.S. PATENT DOCUMENTS

| | | |
|---|---|---|
| 8,425,549 B2 | 4/2013 | Lenker et al. |
| 8,444,661 B2 | 5/2013 | Nair et al. |
| 8,454,633 B2 | 6/2013 | Amplatz et al. |
| 8,491,649 B2 | 7/2013 | Mach |
| 8,511,214 B2 | 7/2013 | Mach |
| 8,574,258 B2 | 11/2013 | Braun et al. |
| 8,574,264 B2 | 11/2013 | Blaeser et al. |
| 8,585,723 B2 | 11/2013 | Nardone et al. |
| 8,597,322 B2 | 12/2013 | Cully et al. |
| 8,613,763 B2 | 12/2013 | Pavcnik et al. |
| 8,641,777 B2 | 2/2014 | Strauss et al. |
| 8,652,099 B2 | 2/2014 | Fierens et al. |
| 8,663,273 B2 | 3/2014 | Khairkhahan et al. |
| 8,690,938 B2 | 4/2014 | Tenne |
| 8,696,729 B2 | 4/2014 | Thompson et al. |
| 8,721,674 B2 | 5/2014 | Kusleika |
| 8,728,112 B2 | 5/2014 | Evert et al. |
| 8,747,430 B2 | 6/2014 | Porter |
| 8,758,384 B2 | 6/2014 | Brandeis |
| 8,764,772 B2 | 7/2014 | Tekulve |
| 8,858,612 B2 | 10/2014 | Ben-Muvhar et al. |
| 9,681,876 B2 | 6/2017 | Cragg et al. |
| 9,848,883 B2 | 12/2017 | Cragg et al. |
| 10,010,328 B2 | 7/2018 | Cragg et al. |
| 2001/0007954 A1 | 7/2001 | Shaolian et al. |
| 2002/0072730 A1* | 6/2002 | McGill .................. A61F 2/013 |
| | | 604/525 |
| 2002/0123759 A1 | 9/2002 | Amplatz |
| 2002/0123760 A1 | 9/2002 | Amplatz |
| 2002/0138134 A1 | 9/2002 | Kim et al. |
| 2002/0151958 A1 | 10/2002 | Chuter |
| 2002/0156499 A1 | 10/2002 | Konya et al. |
| 2003/0004568 A1 | 1/2003 | Ken et al. |
| 2003/0040772 A1 | 2/2003 | Hyodoh et al. |
| 2003/0093111 A1 | 5/2003 | Ken et al. |
| 2003/0120302 A1 | 6/2003 | Minck, Jr. et al. |
| 2003/0130689 A1 | 7/2003 | Wallace et al. |
| 2003/0139802 A1 | 7/2003 | Wulfman et al. |
| 2003/0153935 A1 | 8/2003 | Mialhe |
| 2003/0216772 A1 | 11/2003 | Konya et al. |
| 2003/0220667 A1 | 11/2003 | van der Burg et al. |
| 2003/0229366 A1 | 12/2003 | Reggie et al. |
| 2004/0002732 A1 | 1/2004 | Teoh et al. |
| 2004/0006362 A1 | 1/2004 | Schaefer et al. |
| 2004/0006363 A1 | 1/2004 | Schaefer |
| 2004/0143288 A1 | 7/2004 | Searle |
| 2004/0249409 A1 | 12/2004 | Krolik et al. |
| 2004/0260332 A1 | 12/2004 | Dubrul et al. |
| 2005/0033350 A1 | 2/2005 | Ken et al. |
| 2005/0038460 A1 | 2/2005 | Jayaraman |
| 2005/0055082 A1 | 3/2005 | Ben Muvhar et al. |
| 2005/0059993 A1 | 3/2005 | Ramzipoor et al. |
| 2005/0085826 A1 | 4/2005 | Nair et al. |
| 2005/0090856 A1 | 4/2005 | Porter |
| 2005/0113862 A1 | 5/2005 | Besselink et al. |
| 2005/0171572 A1 | 8/2005 | Martinez |
| 2005/0267570 A1 | 12/2005 | Shadduck |
| 2006/0004440 A1 | 1/2006 | Stinson |
| 2006/0085028 A1 | 4/2006 | Boock |
| 2006/0100661 A1 | 5/2006 | Jaeger et al. |
| 2006/0106449 A1 | 5/2006 | Ben Muvhar |
| 2006/0116709 A1 | 6/2006 | Sepetka et al. |
| 2006/0155324 A1 | 7/2006 | Porter et al. |
| 2006/0167489 A1 | 7/2006 | Satake et al. |
| 2006/0178697 A1 | 8/2006 | Carr-Brendel |
| 2006/0184196 A1 | 8/2006 | Schaefer et al. |
| 2006/0212055 A1 | 9/2006 | Karabey et al. |
| 2006/0224180 A1 | 10/2006 | Anderson et al. |
| 2006/0253099 A1 | 11/2006 | Noone |
| 2006/0253148 A1 | 11/2006 | Leone et al. |
| 2006/0282115 A1 | 12/2006 | Abrams et al. |
| 2007/0078479 A1 | 4/2007 | Belenkaya et al. |
| 2007/0100437 A1 | 5/2007 | Welborn et al. |
| 2007/0168019 A1 | 7/2007 | Amplatz et al. |
| 2007/0213765 A1 | 9/2007 | Adams et al. |
| 2007/0239193 A1 | 10/2007 | Simon et al. |
| 2007/0239194 A1 | 10/2007 | Tran et al. |
| 2007/0276469 A1 | 11/2007 | Tenne |
| 2007/0288054 A1 | 12/2007 | Tanaka et al. |
| 2008/0033341 A1 | 2/2008 | Grad |
| 2008/0086156 A1 | 4/2008 | Rosen et al. |
| 2008/0125807 A1 | 5/2008 | Wallace et al. |
| 2008/0188892 A1 | 8/2008 | Bates et al. |
| 2008/0269798 A1 | 10/2008 | Ramzipoor et al. |
| 2008/0312679 A1 | 12/2008 | Hardert et al. |
| 2009/0018636 A1 | 1/2009 | Gailloud et al. |
| 2009/0062841 A1 | 3/2009 | Amplatz et al. |
| 2009/0131972 A1 | 5/2009 | Wallace et al. |
| 2009/0171386 A1* | 7/2009 | Amplatz ............ A61B 17/0057 |
| | | 606/213 |
| 2009/0209855 A1 | 8/2009 | Drilling et al. |
| 2009/0216263 A1 | 8/2009 | Tekulve |
| 2009/0270908 A1 | 10/2009 | Tekulve et al. |
| 2009/0270978 A1 | 10/2009 | Virkler et al. |
| 2009/0292307 A1 | 11/2009 | Razack |
| 2009/0297582 A1 | 12/2009 | Meyer et al. |
| 2010/0004672 A1 | 1/2010 | Shirley et al. |
| 2010/0087850 A1 | 4/2010 | Razack |
| 2010/0114299 A1 | 5/2010 | Ben Muvhar et al. |
| 2010/0152839 A1 | 6/2010 | Shandas et al. |
| 2010/0185228 A1 | 7/2010 | Tekulve et al. |
| 2011/0017207 A1 | 1/2011 | Hendriksen et al. |
| 2011/0054512 A1* | 3/2011 | Hendriksen ...... A61B 17/12022 |
| | | 606/191 |
| 2011/0106240 A1 | 5/2011 | Chuter |
| 2011/0144689 A1 | 6/2011 | Isch et al. |
| 2011/0160753 A1 | 6/2011 | Bastin |
| 2011/0166593 A1 | 7/2011 | Paul, Jr. |
| 2011/0213405 A1 | 9/2011 | Porter et al. |
| 2011/0218560 A1 | 9/2011 | Ramzipoor et al. |
| 2011/0245863 A1 | 10/2011 | Martinez |
| 2011/0257674 A1 | 10/2011 | Evert et al. |
| 2011/0264132 A1 | 10/2011 | Strauss et al. |
| 2012/0046687 A1 | 2/2012 | Trommeter et al. |
| 2012/0089174 A1 | 4/2012 | Chen et al. |
| 2012/0101510 A1 | 4/2012 | Lenker et al. |
| 2012/0116350 A1 | 5/2012 | Strauss et al. |
| 2012/0116504 A1 | 5/2012 | Lyons et al. |
| 2012/0172914 A1 | 7/2012 | Welch |
| 2012/0226304 A1 | 9/2012 | Ryan et al. |
| 2012/0253381 A1 | 10/2012 | Forsythe et al. |
| 2012/0330348 A1 | 12/2012 | Strauss et al. |
| 2013/0035715 A1 | 2/2013 | Johnson et al. |
| 2013/0053883 A1 | 2/2013 | Kassab |
| 2013/0066359 A1 | 3/2013 | Murphy et al. |
| 2013/0073026 A1 | 3/2013 | Russo et al. |
| 2013/0085518 A1 | 4/2013 | Trommeter et al. |
| 2013/0096580 A1 | 4/2013 | Cohn et al. |
| 2013/0102996 A1 | 4/2013 | Strauss |
| 2013/0116774 A1 | 5/2013 | Strauss et al. |
| 2013/0138138 A1 | 5/2013 | Clark et al. |
| 2013/0184658 A1 | 7/2013 | Duncan |
| 2013/0184810 A1 | 7/2013 | Hall et al. |
| 2013/0225778 A1 | 8/2013 | Goodrich et al. |
| 2013/0245666 A1 | 9/2013 | Larsen et al. |
| 2013/0267992 A1 | 10/2013 | Tran et al. |
| 2013/0289714 A1 | 10/2013 | Strauss et al. |
| 2014/0031851 A1 | 1/2014 | Brandeis |
| 2014/0031925 A1 | 1/2014 | Garrison et al. |
| 2014/0039537 A1 | 2/2014 | Carrison |
| 2014/0046253 A1 | 2/2014 | Consigny et al. |
| 2014/0148843 A1 | 5/2014 | Strauss et al. |
| 2014/0207172 A1 | 7/2014 | Bodewadt et al. |
| 2014/0257361 A1 | 9/2014 | Prom |
| 2015/0039017 A1 | 2/2015 | Cragg et al. |
| 2015/0039018 A1 | 2/2015 | Cragg et al. |
| 2015/0039019 A1 | 2/2015 | Cragg et al. |
| 2015/0190141 A1 | 7/2015 | Cragg et al. |
| 2016/0030052 A1 | 2/2016 | Cragg et al. |
| 2016/0166257 A1 | 6/2016 | Allen et al. |
| 2016/0262769 A1 | 9/2016 | Cragg et al. |
| 2017/0086854 A1 | 3/2017 | Cragg et al. |

(56) References Cited

U.S. PATENT DOCUMENTS

FOREIGN PATENT DOCUMENTS

| | | |
|---|---|---|
| EP | 1479409 A1 | 11/2004 |
| EP | 1374801 B1 | 4/2006 |
| EP | 0941716 B1 | 3/2008 |
| EP | 1365707 B1 | 4/2010 |
| EP | 2198805 A1 | 6/2010 |
| WO | WO 95/27448 | 10/1995 |
| WO | WO 03/073961 | 9/2003 |
| WO | WO 2004/064671 | 8/2004 |
| WO | WO 2009/0124247 | 10/2009 |
| WO | WO 2013/188226 | 12/2013 |
| WO | WO 2015/015314 | 2/2015 |
| WO | WO 2017/051248 | 3/2017 |
| WO | WO 2017/062740 | 4/2017 |

OTHER PUBLICATIONS

Hirai, T., et al., "Emergency Balloon Embolization for Carotid Artery Rupture Secondary to Postoperative Infection," CardioVascular and Interventional Radiology, Jan./Feb. 1996; 19(1): 50-52.

International Search Report and Written Opinion for PCT/IB2014/002429 dated Jul. 6, 2015 in 21 pages.

Kallmes, D.F., et al., "The Use of Hydrocoil for Parent Artery Occlusion," American Society of Neuroradiology, Sep. 2004; 25: 1409-1410.

Kaufman, L., et al., "Detachable Balloon-modified Reducing Stent to Treat Hepatic Insufficiency after Transjugular Intrahepatic Portosystemic Shunt Creation," Journal of Vascular and Interventional Radiology, May 2003; 14(5): 635-638.

Makita, K., et al., "Guide-Wire-directed Detachable Balloon: Clinical Application in Treatment of Varicoceles," Radiology, May 1992; 183(2): 575-577.

Perala, J.M., et al., "Comparison of Early Deflation Rate of Detachable Latex and Silicone Balloons and Observations on Persistent Varicocele," Journal of Vascular and Interventional Radiology, Sep.-Oct. 1998; 9(5): 761-765.

Pollak, J.S., et al., "Clinical Results of Transvenous Systemic Embolotherapy with a Neuroradiologic Detachable Balloon," Radiology, May 1994; 191(2): 477-482.

Reidy, J.F., et al., "Transcatheter occlusion of coronary to bronchial anastomosis by detachable balloon combined with coronary angioplasty at same procedure," British Heart Journal; Mar. 1983; 49(3): 284-287.

Reidy, J.F., et al., "Transcatheter occlusion of a Blalock-Taussig shunt with a detachable balloon in a child," British Heart Journal; Jul. 1983; 50(1): 101-103.

Ross, I.B., et al., "The Vascular Plug: A New Device for Parent Artery Occlusion," American Journal of Neuroradiology, Feb. 2007; 28(2): 385-286.

Tasar, M., et al., "Intrahepatic arterioportal fistula and its treatment with detachable balloon and transcatheter embolization with coils and microspheres," Journal of Clinical Imaging, Sep.-Oct. 2005; 29(5): 325-330.

Wang, W., et al. "The Amplatzer Vascular Plug: A Review of the Device and its Clinical Applications," Cardiovascular and Interventional Radiology, Aug. 2012, 35(4): 725-740.

White, R.I., et al., "Occlusion of Variococeles with Detachable Balloons," Radiology, May 1981; 139(2): 327-334.

Aydogan, U. "Transcatheter Embolization Treatment of Coronary Arteriovenous Fistulas," Asian Cardiovascular and Thoracic Annals, Mar. 2003, 11(1): 63-67.

Castaneda-Zuniga, W.R., et al., "'Spiderlon': New Device for Simple, Fast Arterial and Venous Occlusion," American Roentgen Ray Society, Mar. 1981, pp. 627-628.

Cheng, et al., "Minimally Invasive Keyhole Approach for Removal of a Migratory Balloon Complicated by Endovascular Embolization of a Carotid-Cavernous Fistula," Minimally Invasive Neurosurgery, 2006; 49(5): 305-308.

Hawkins, T.D., et al., "The Permeability of Detachable Latex Rubber Balloons: An In Vitro Study," Investigative Radiology, Dec. 1987; 22(12): 969-972.

Serbinenko, F.A., "Balloon catheterization and occlusion of major cerebral vessels," Journal of Neurosurgery, Aug. 1974; 41(2): 125-145.

Wehman, et al., "Giant Cerebral Aneurysms: Endovascular Challenges," Neurosurgery, Nov. 2006, 59(5): S125-S138.

Berguer, R. et al. "Arteriovenous Vertebral Fistulae: Cure by Combination of Operation and Detachable Intravascular Balloon," Annals of Surgery, Jul. 1982, 196(1): 65-68.

* cited by examiner

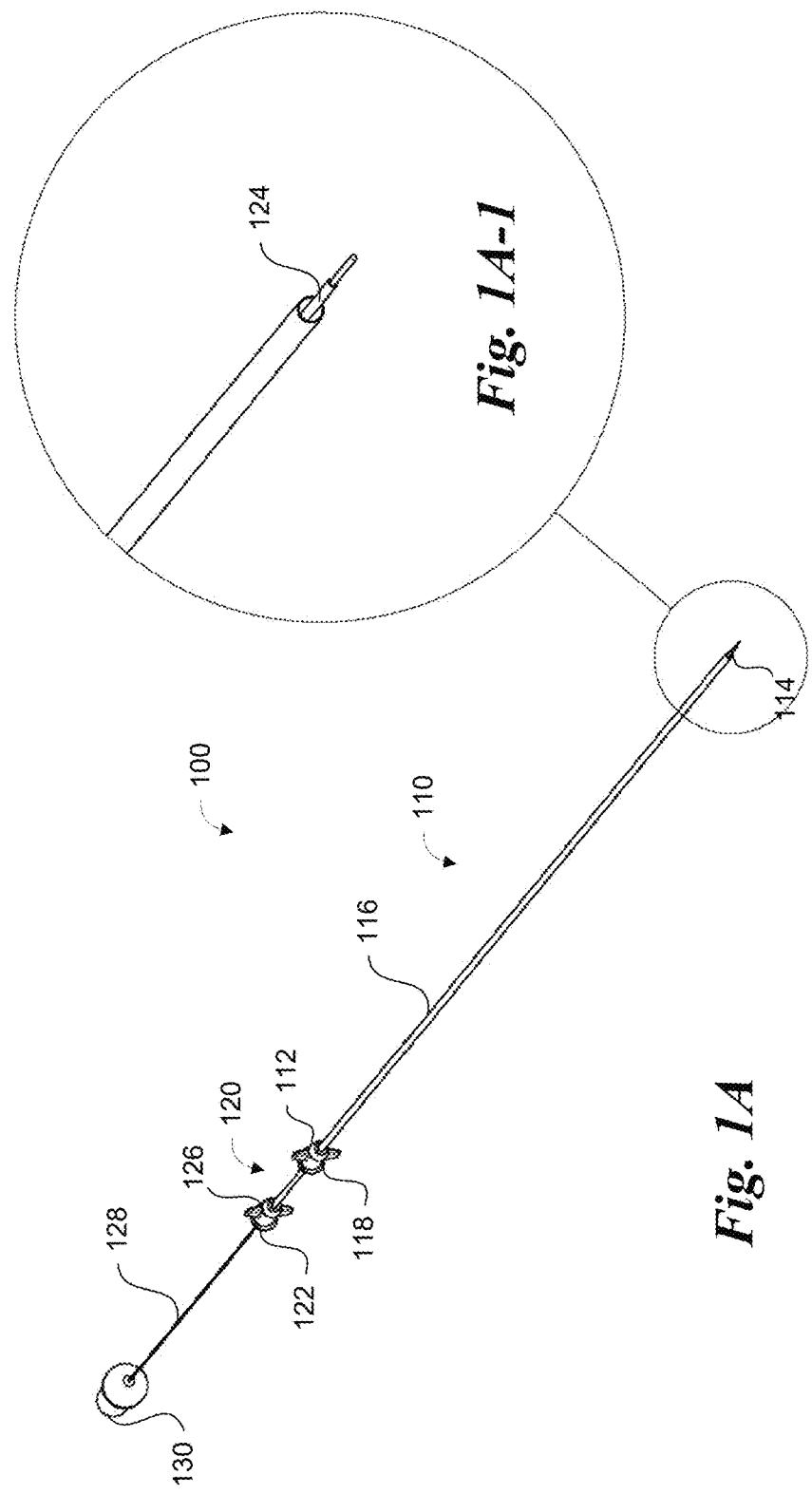

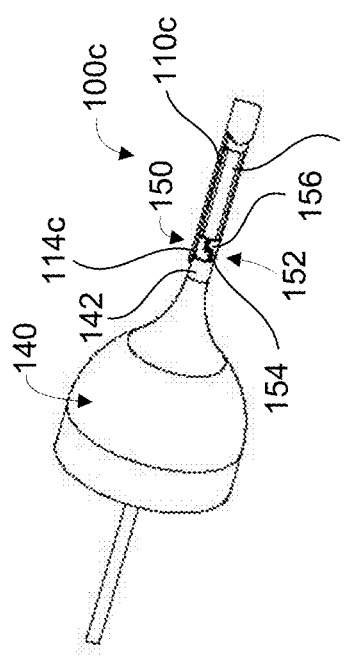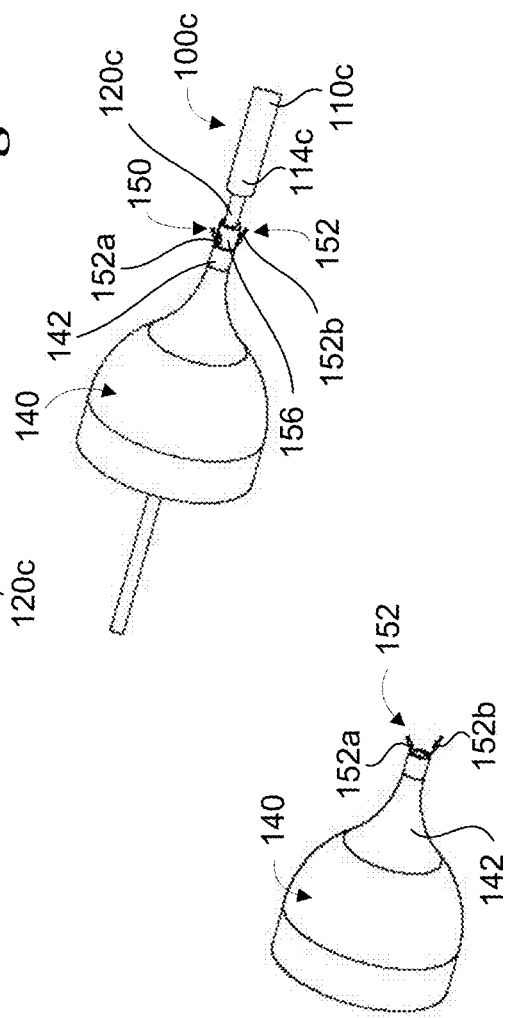

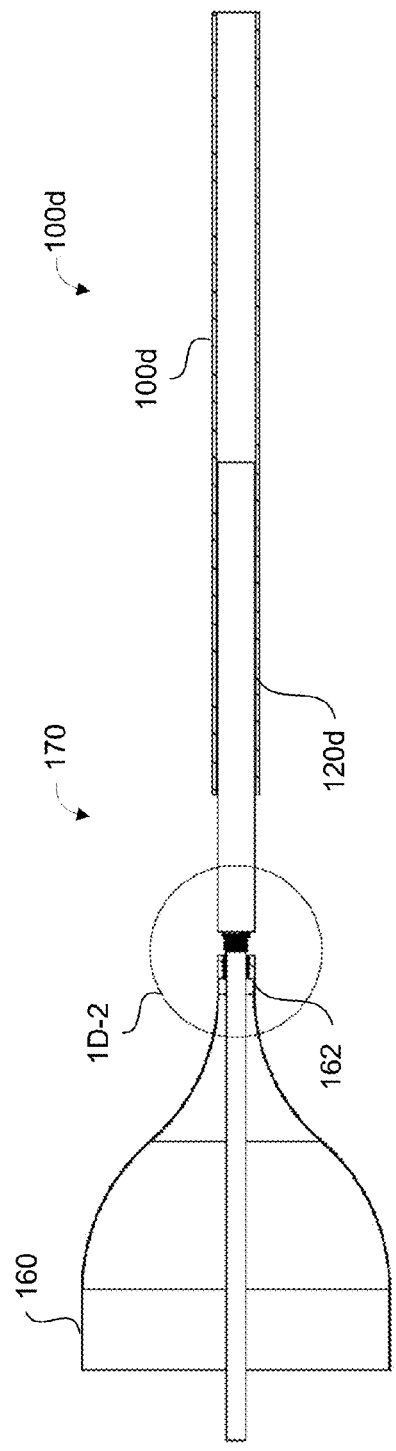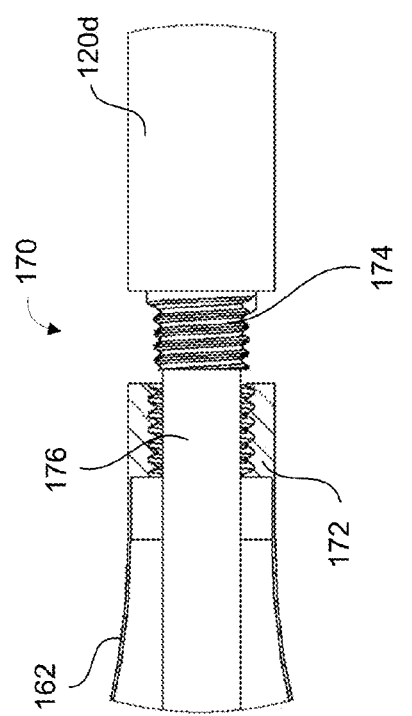
Fig. 1D-1
Fig. 1D-2

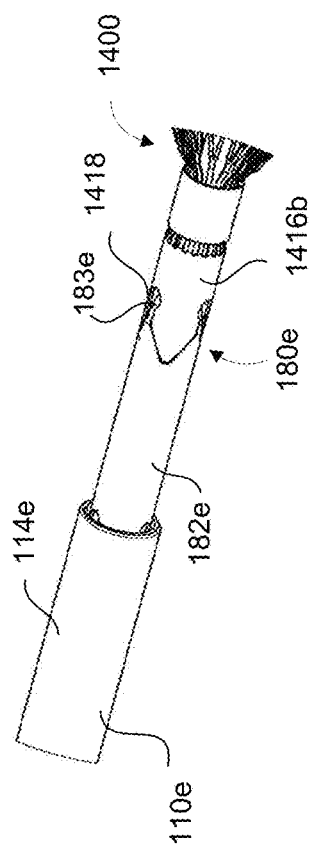
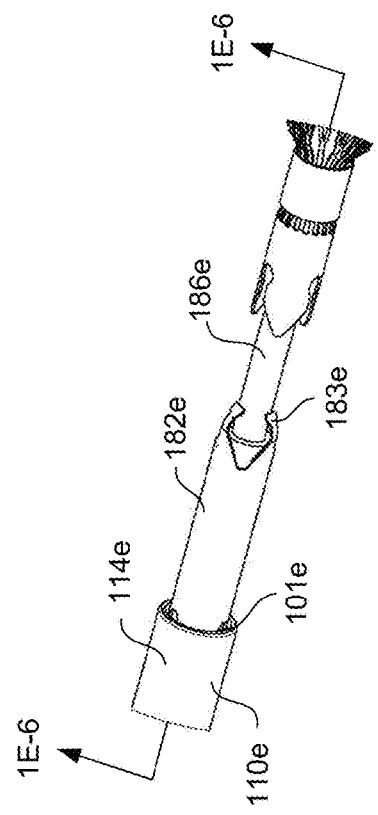
Fig. 1E-3
Fig. 1E-4

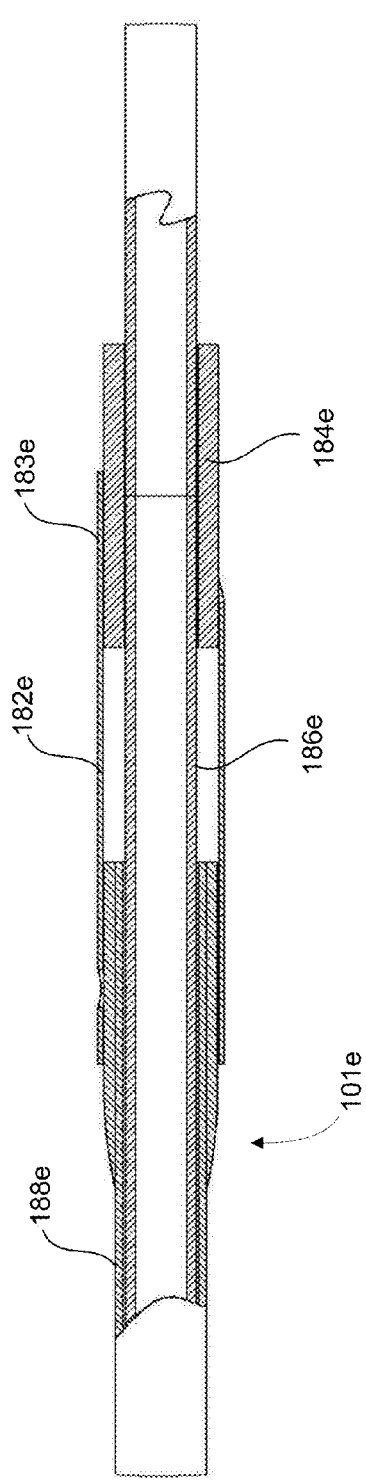
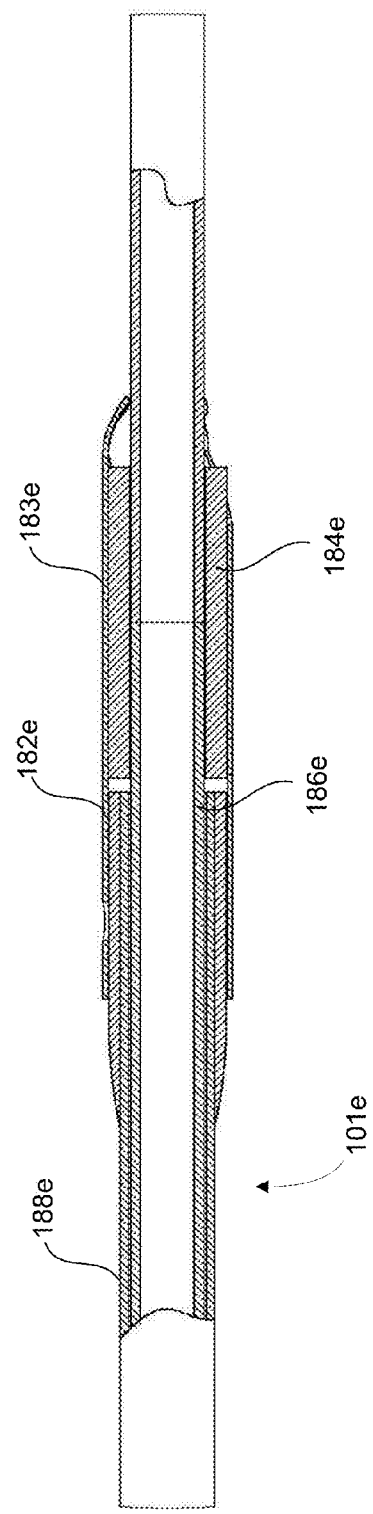

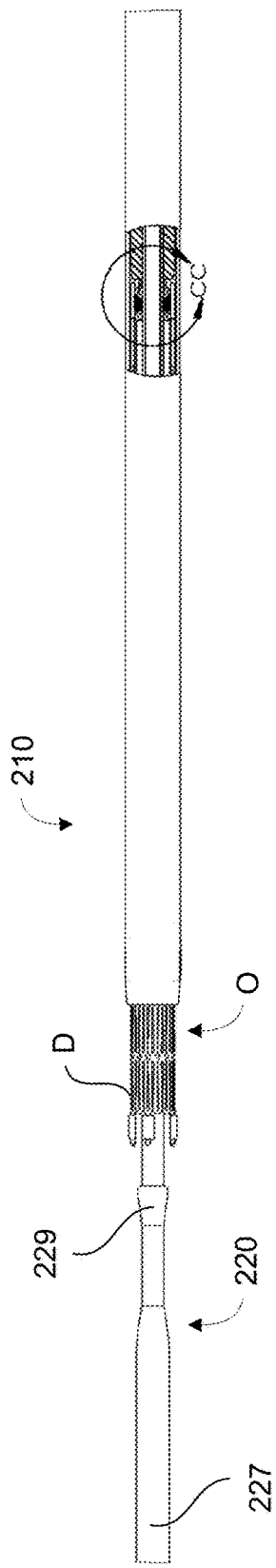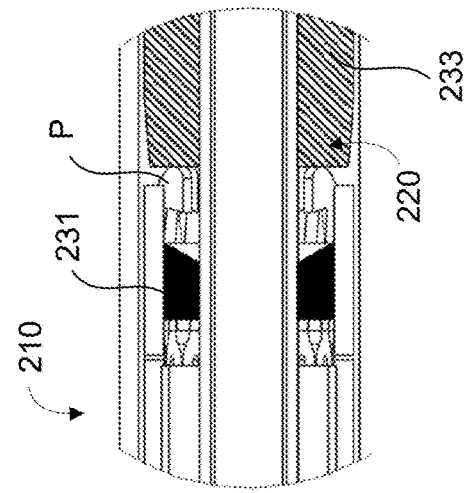
Fig. 2C
Fig. 2CC

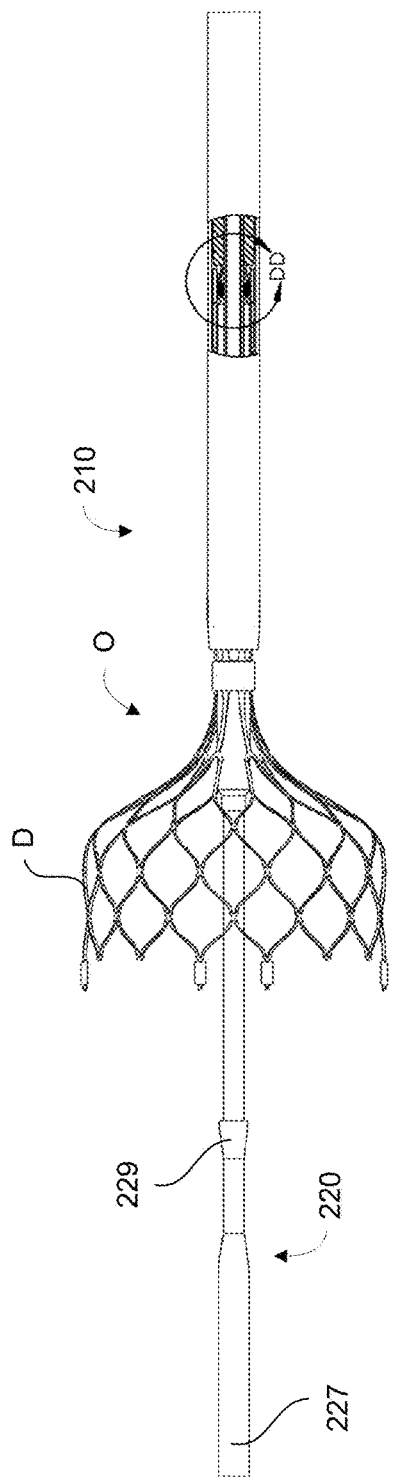
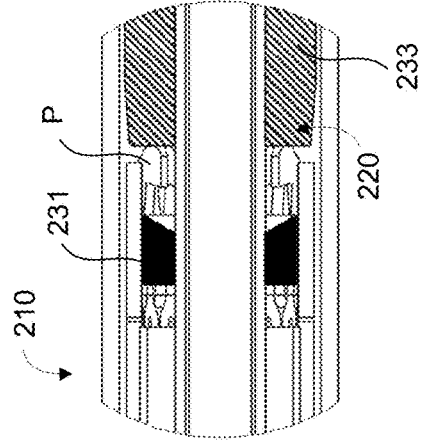
Fig. 2D
Fig. 2DD

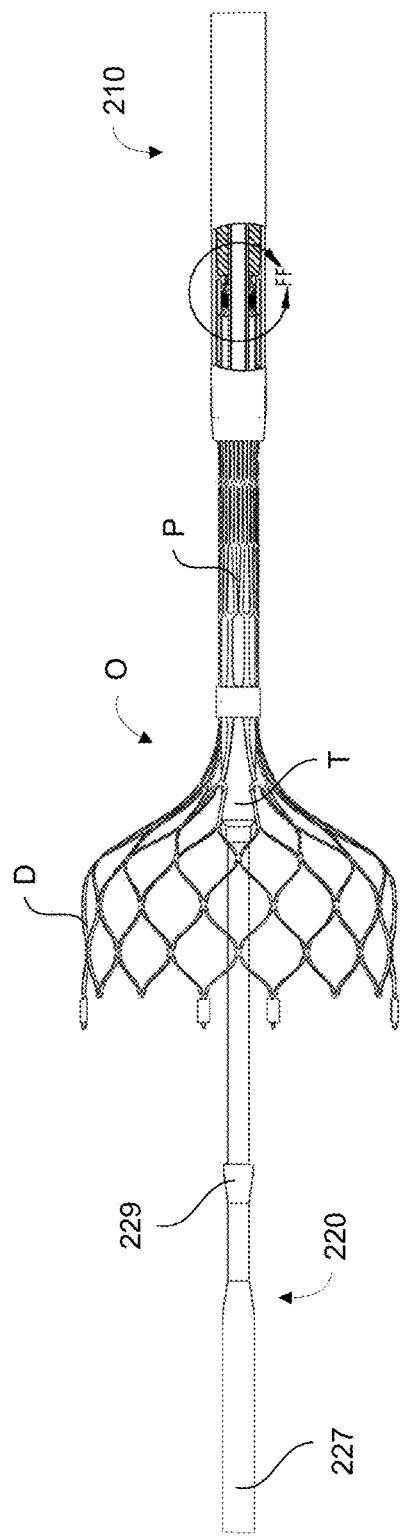
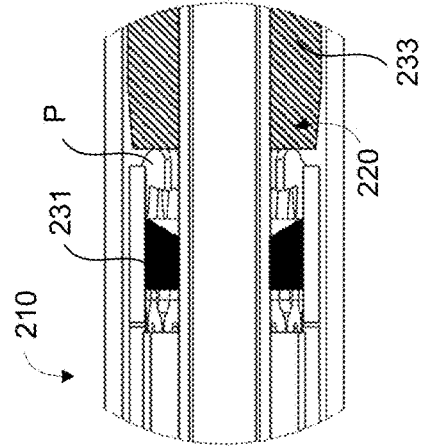
Fig. 2F
Fig. 2FF

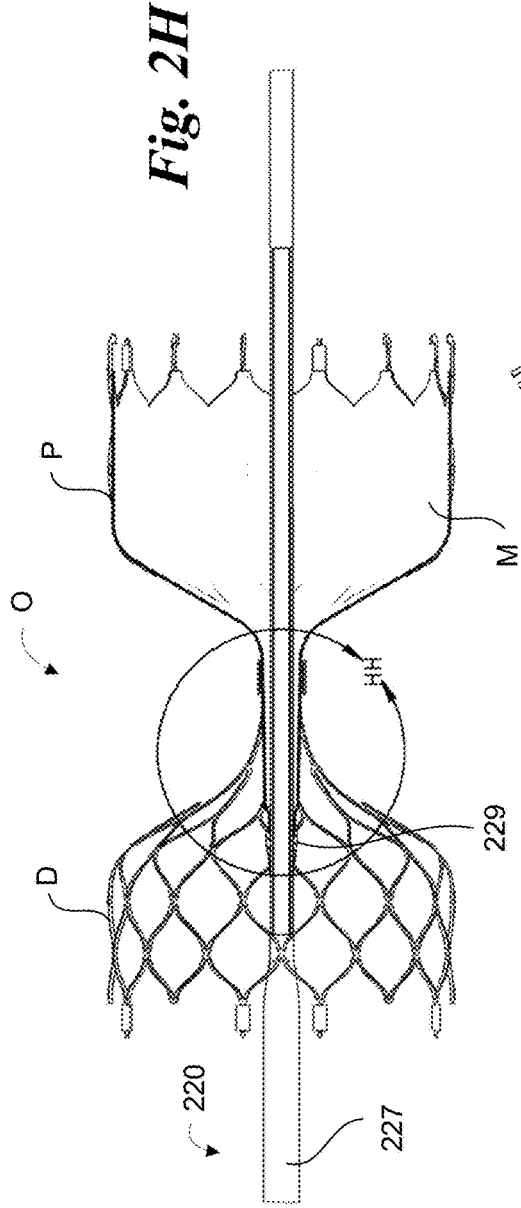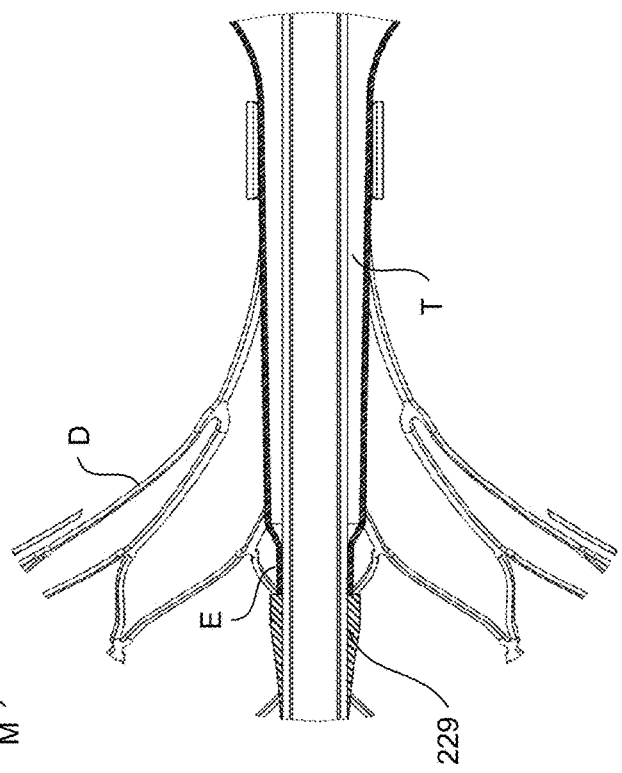

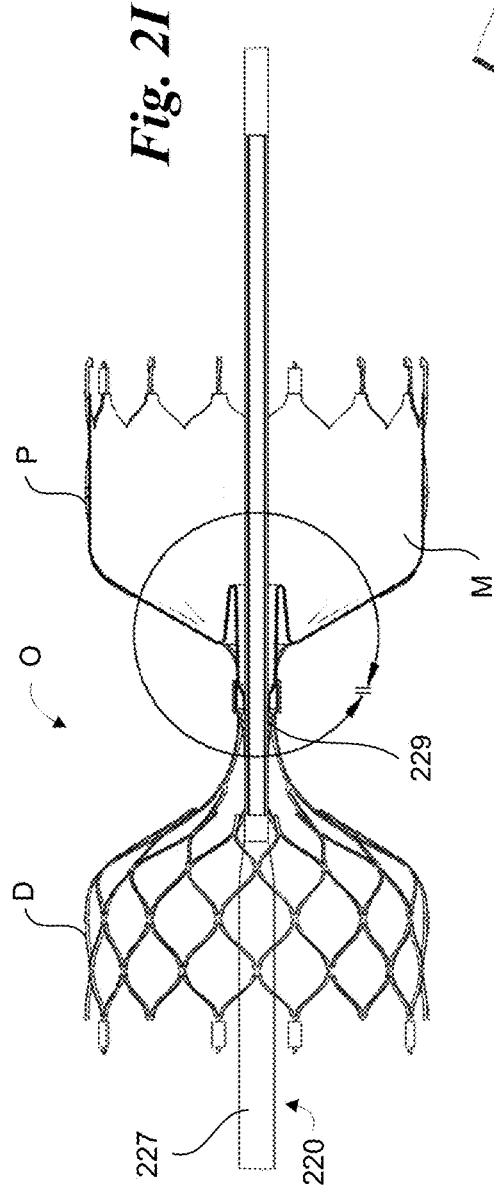
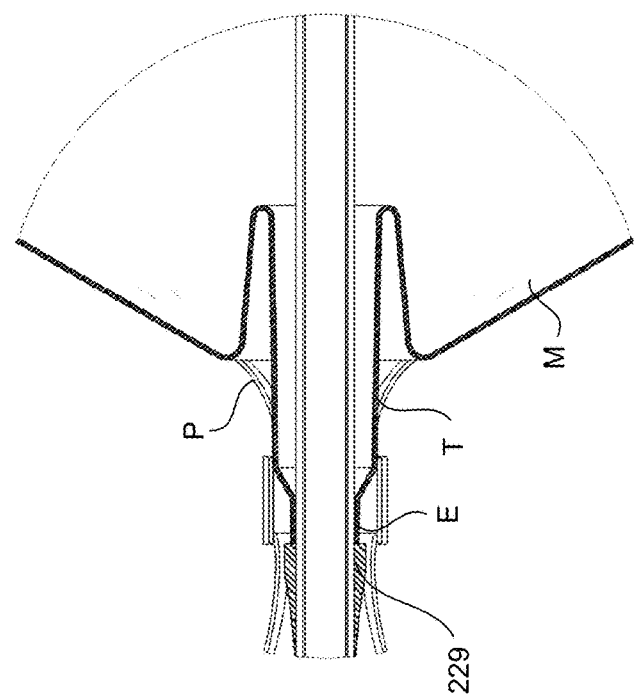
Fig. 2I
Fig. 2II

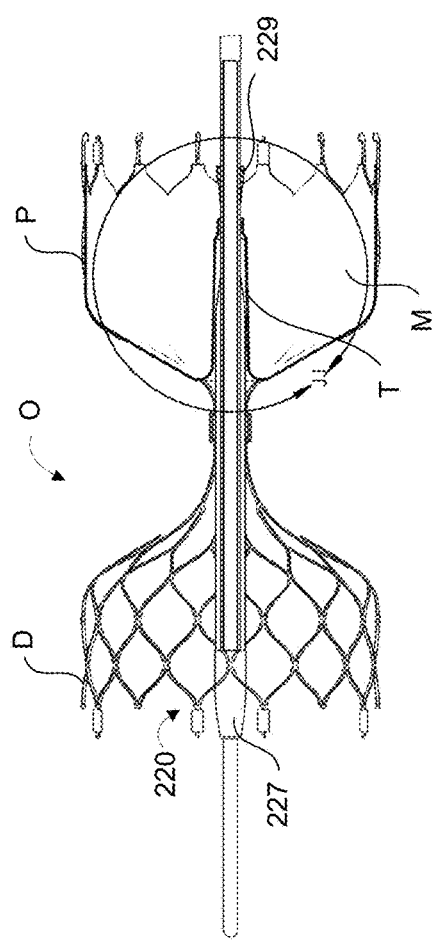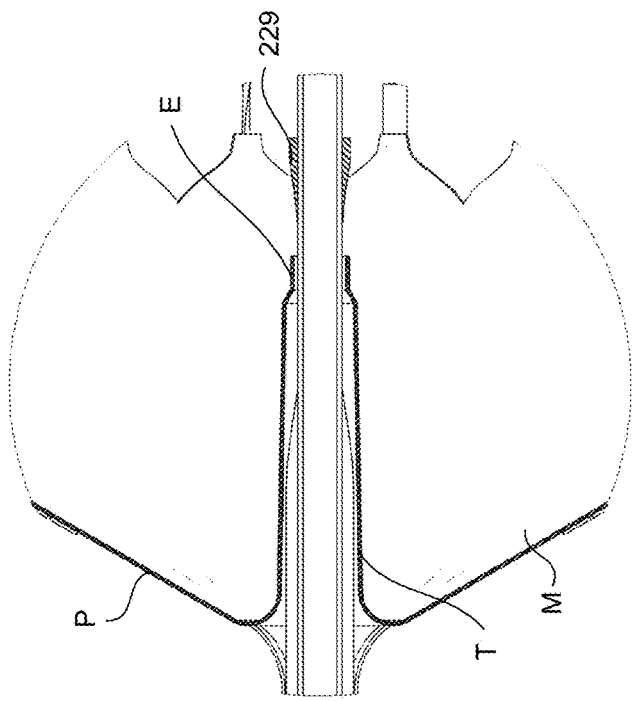
Fig. 2J
Fig. 2JJ

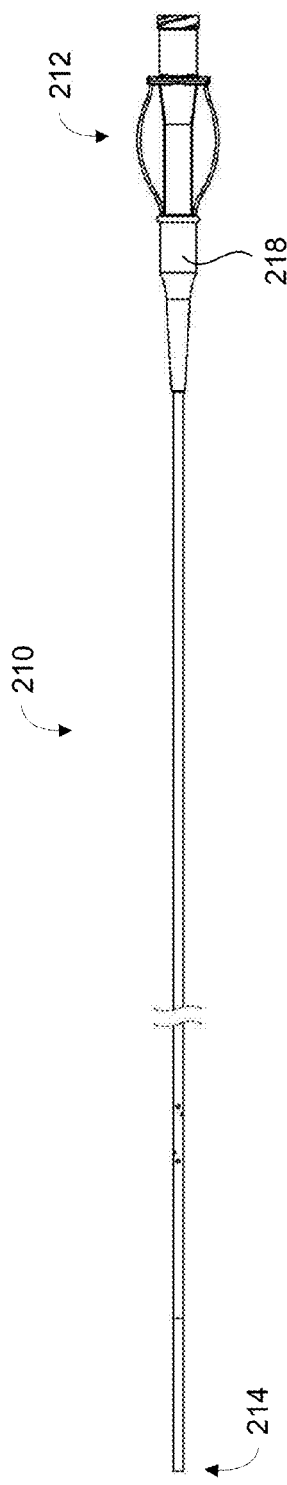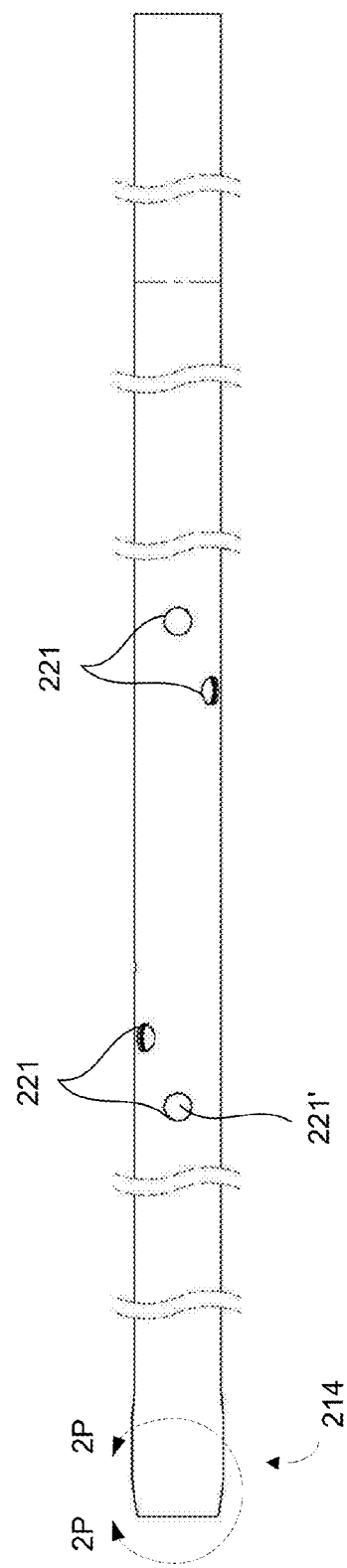
Fig. 2L
Fig. 2M

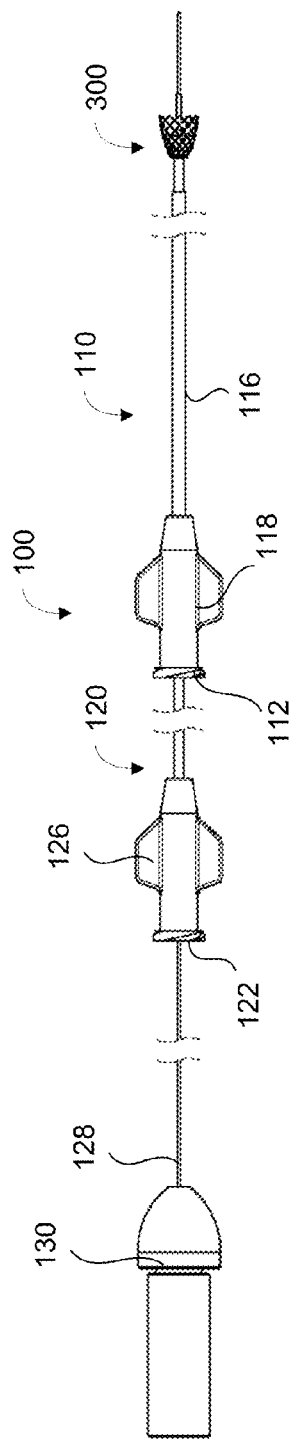
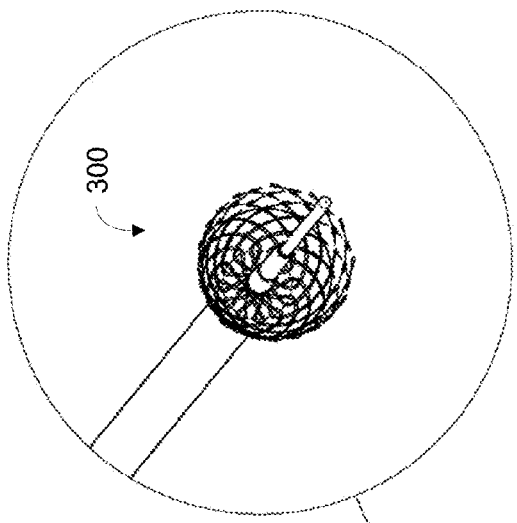
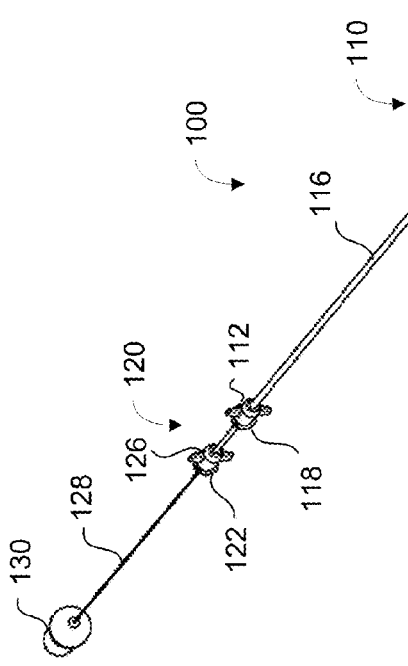
Fig. 3A
Fig. 3B
Fig. 3C

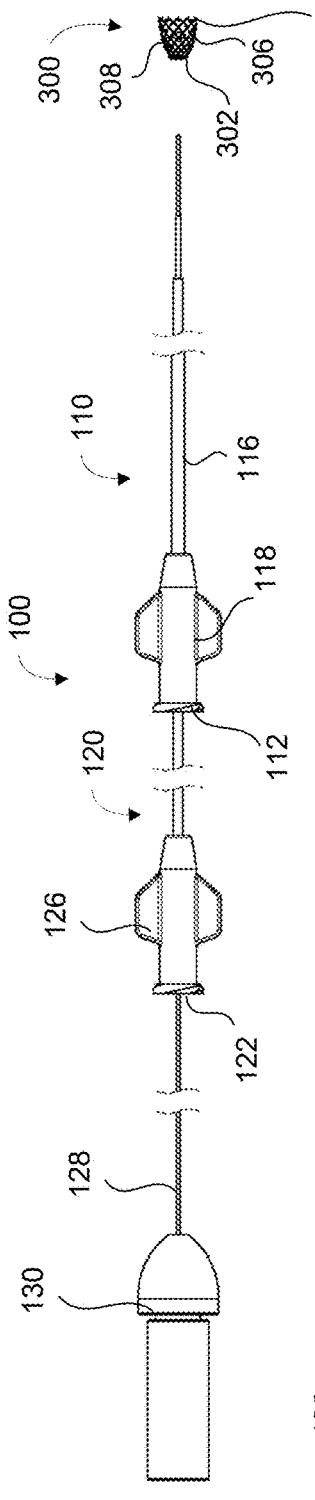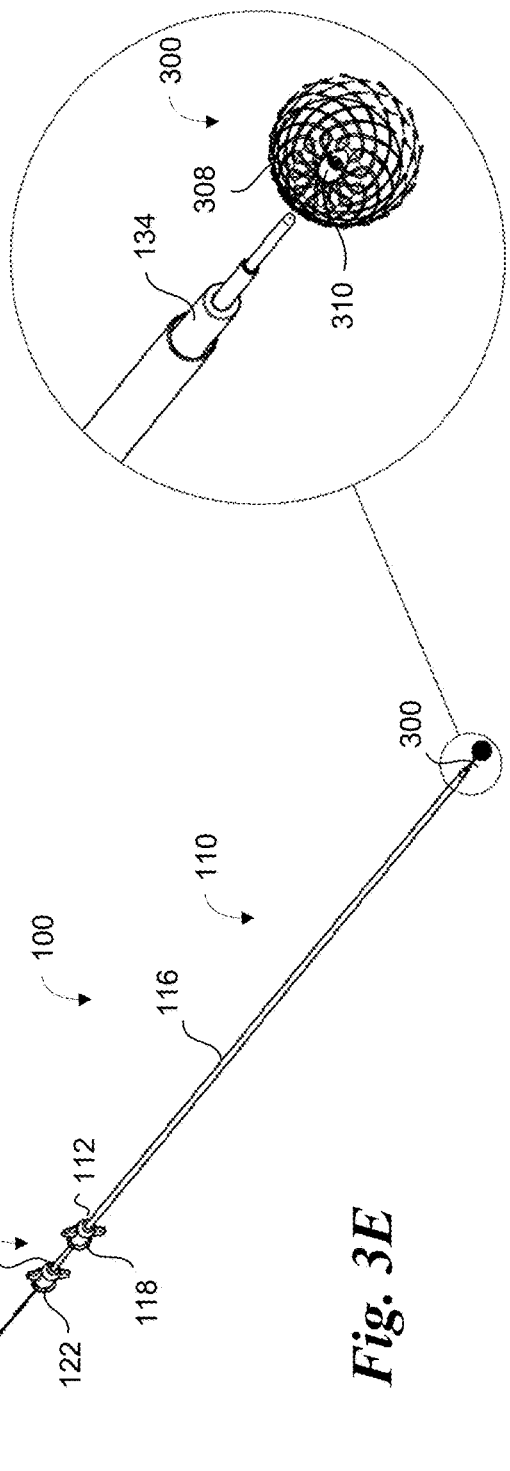

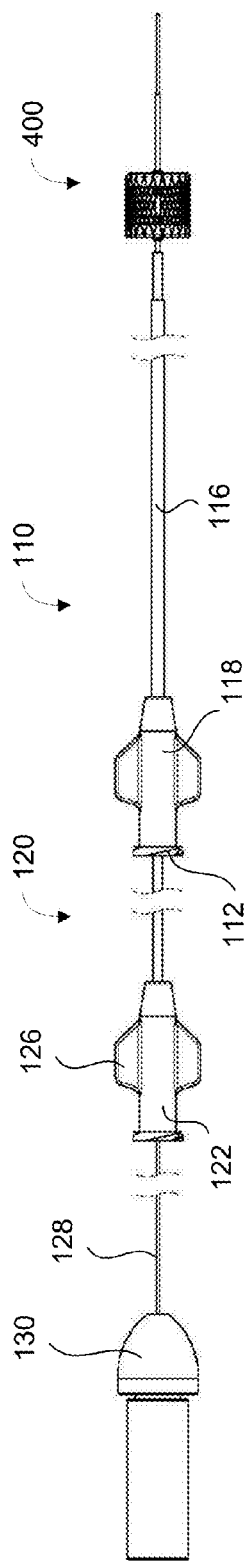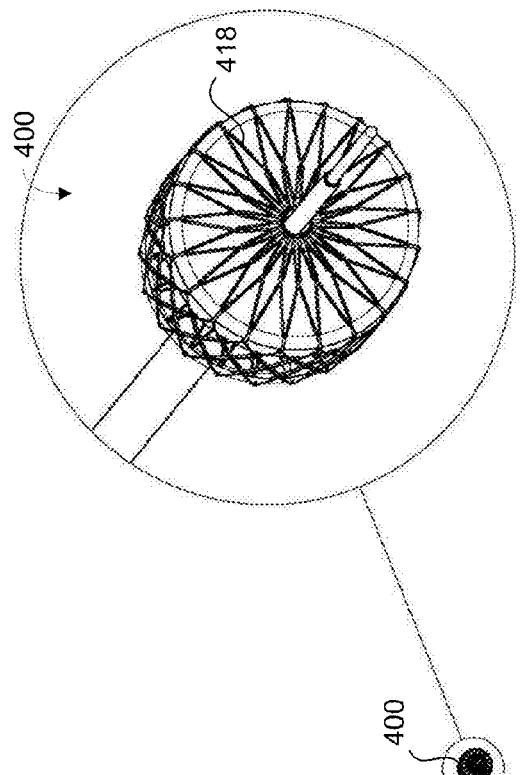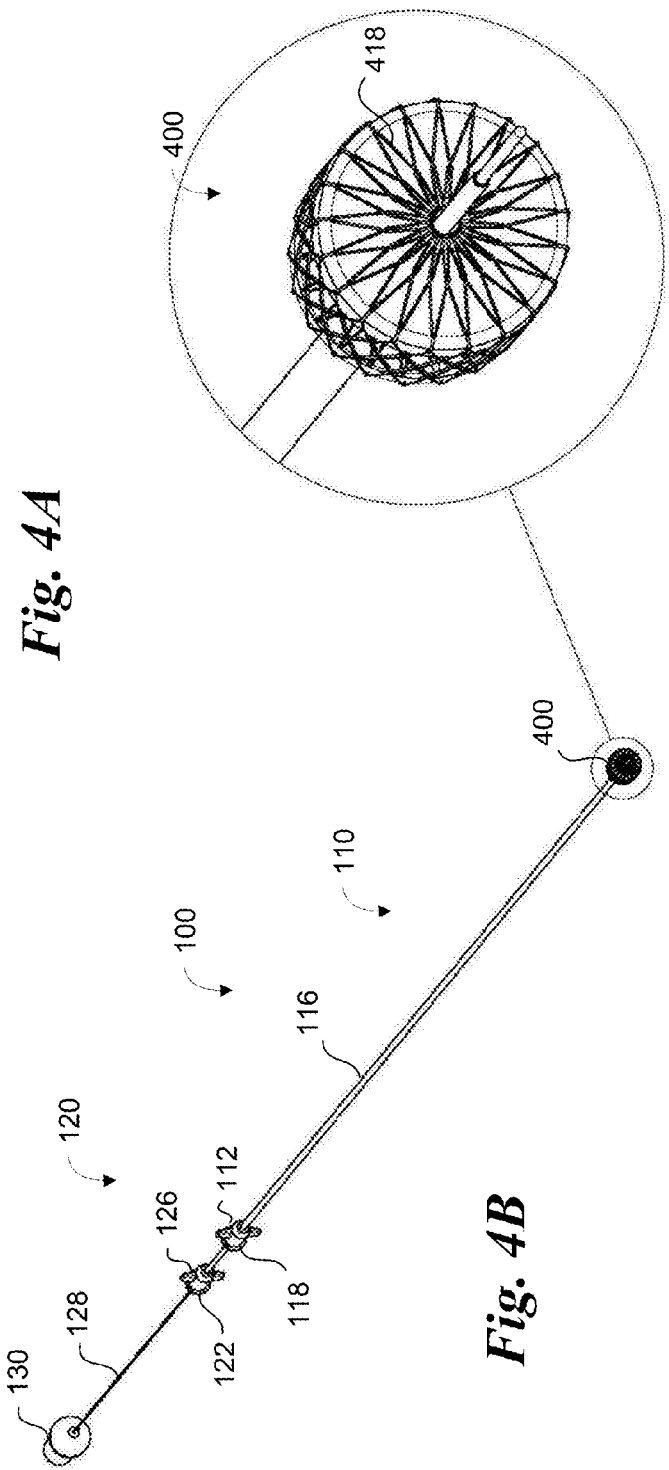
Fig. 4A
Fig. 4B
Fig. 4C

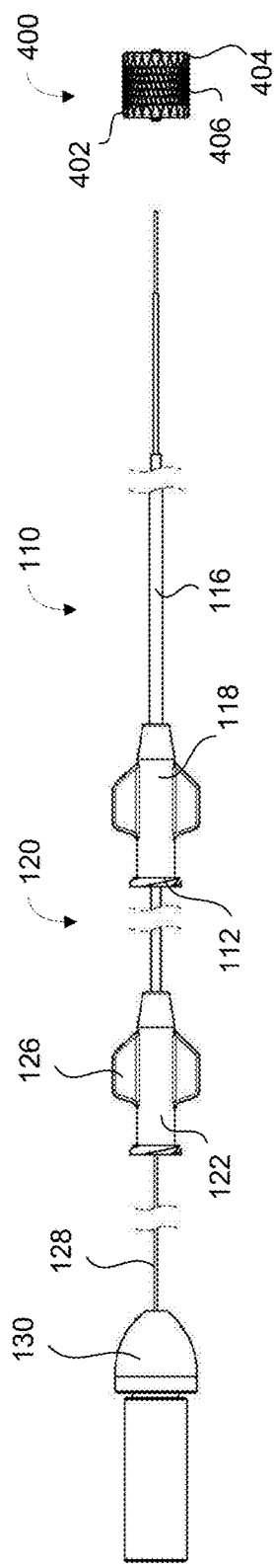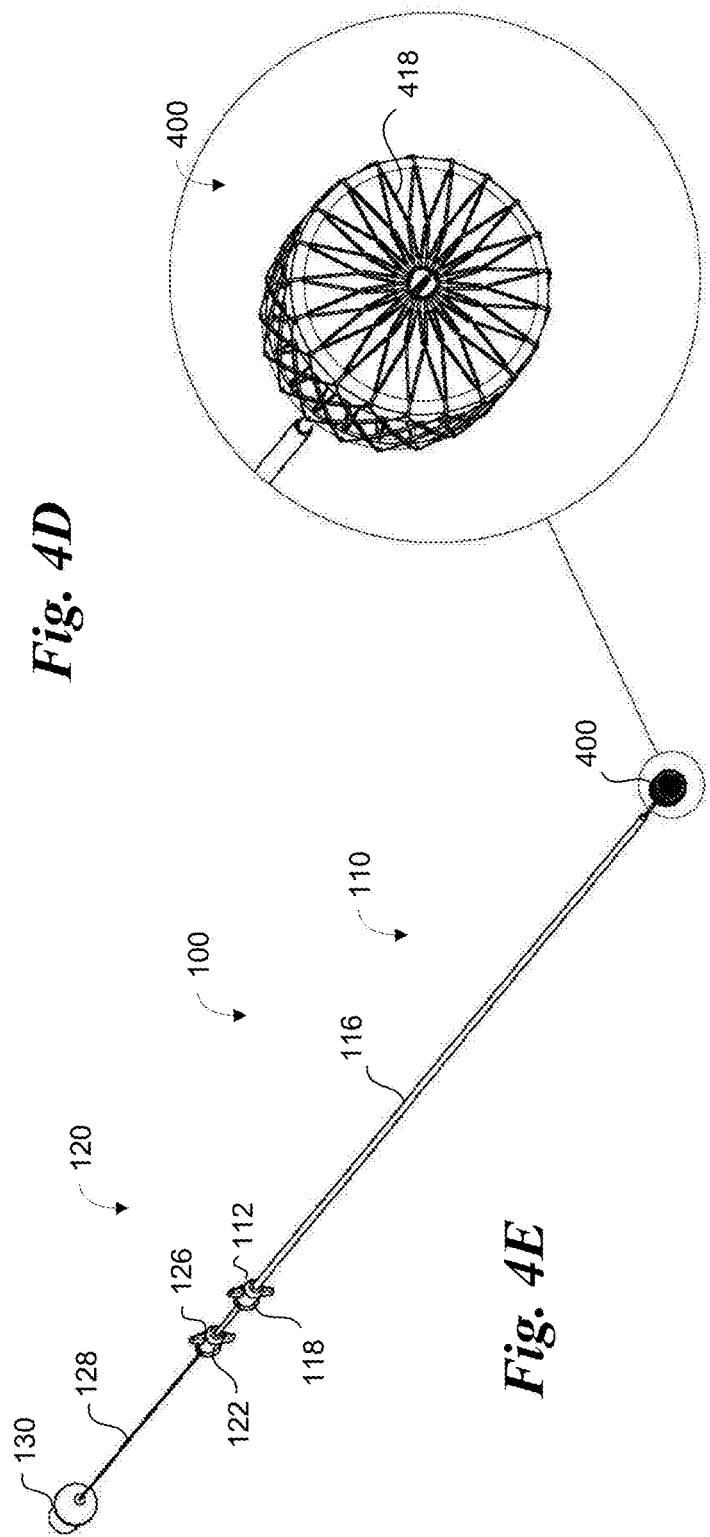

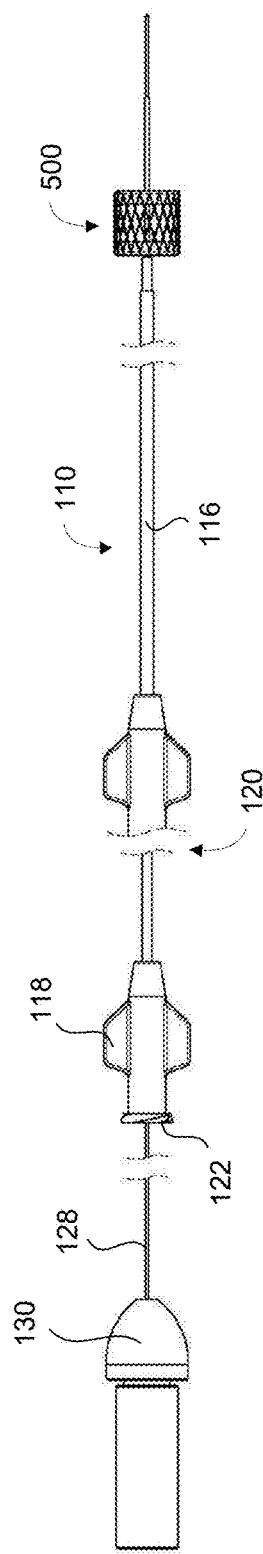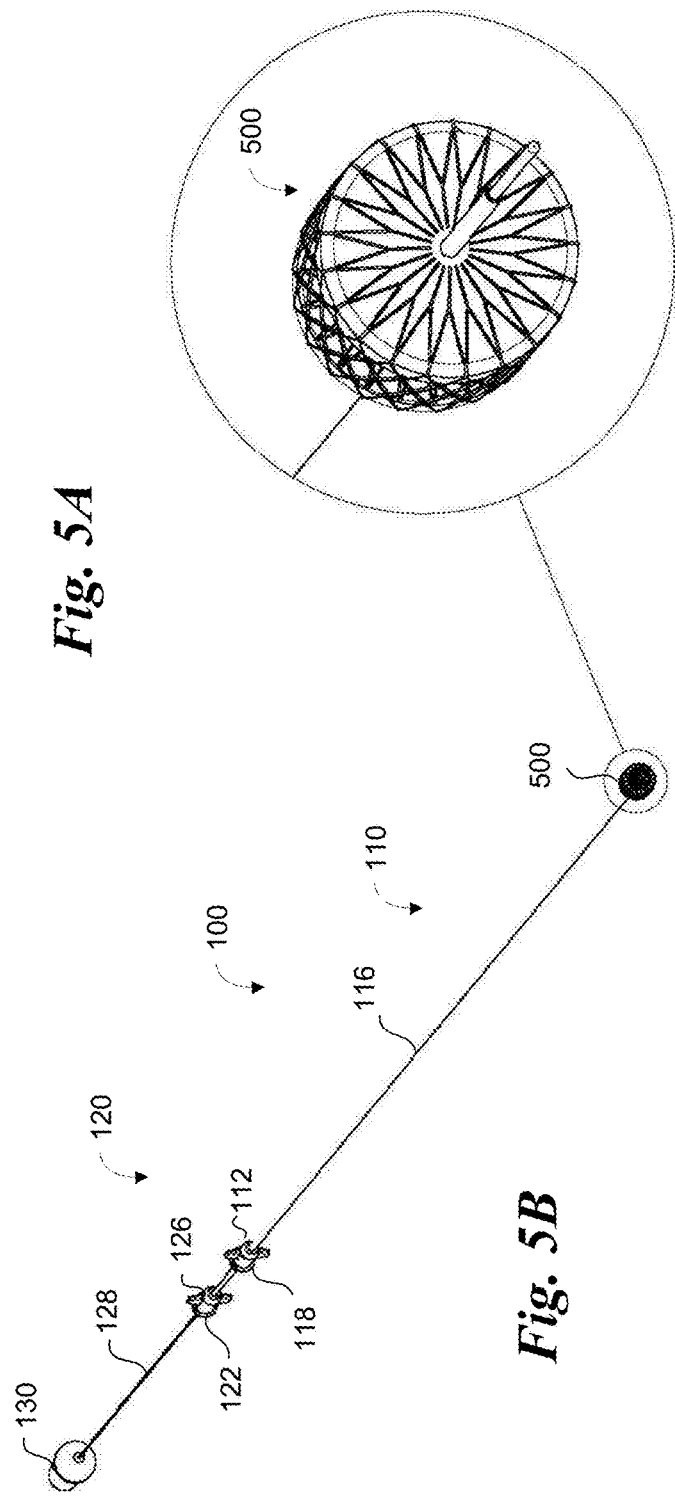
Fig. 5A
Fig. 5B
Fig. 5C

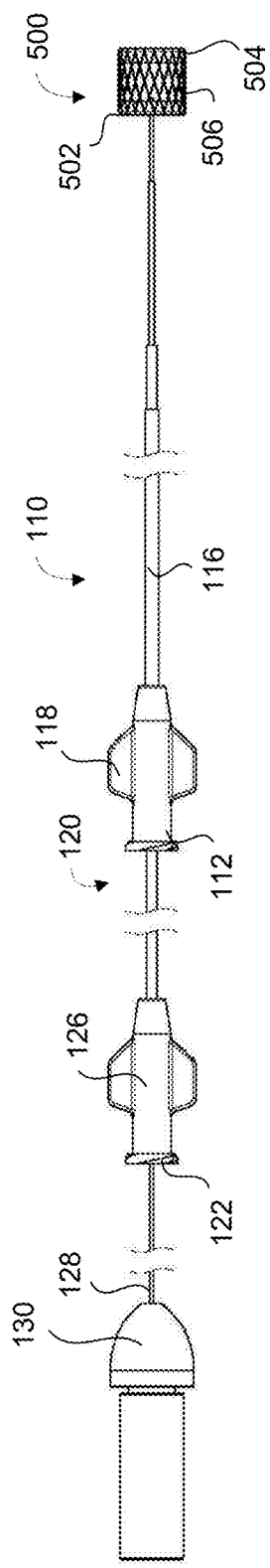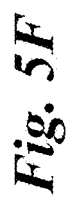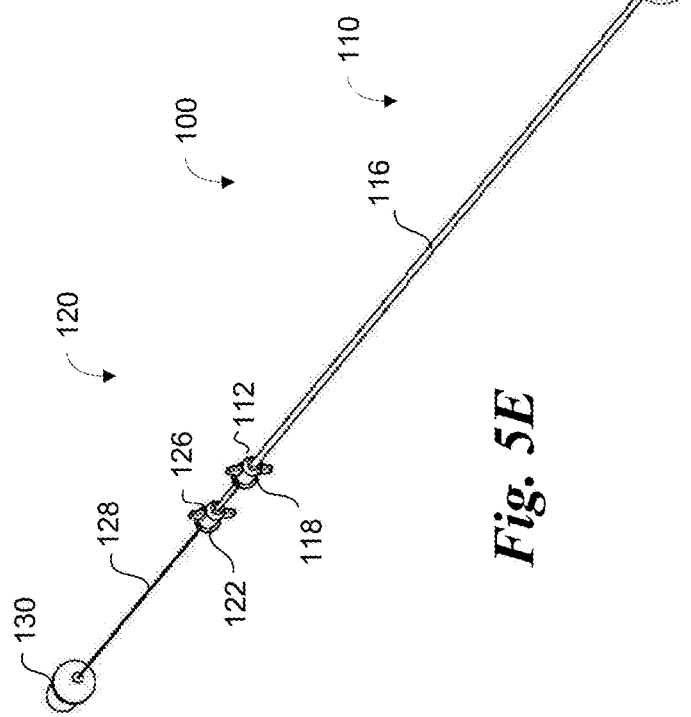
Fig. 5D
Fig. 5E
Fig. 5F

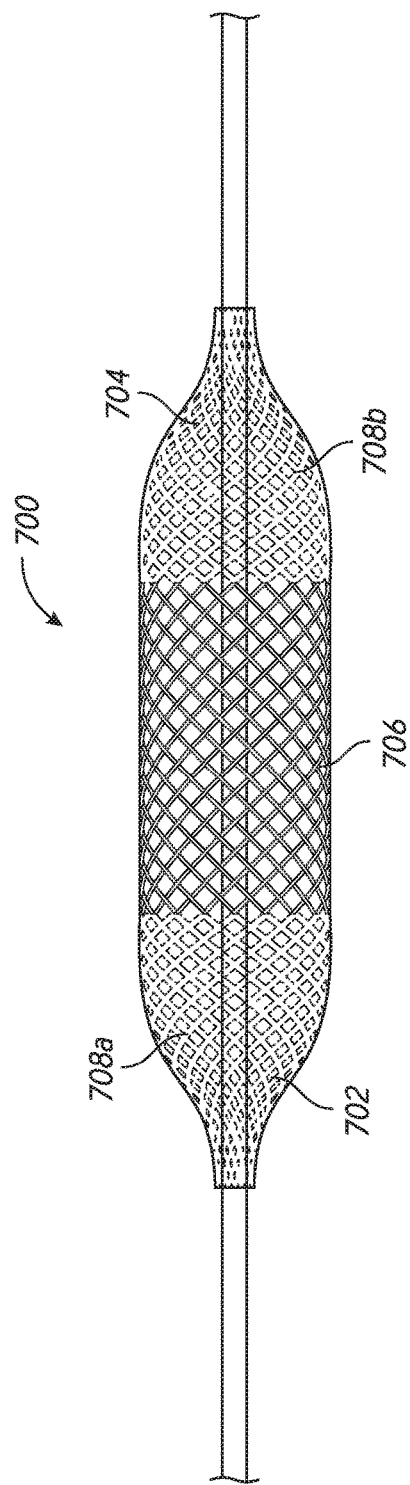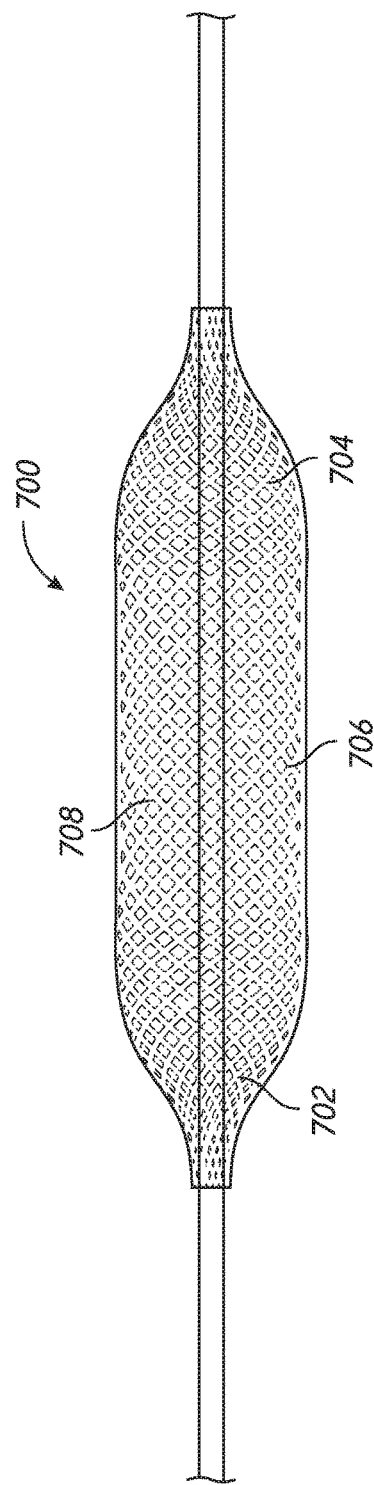
FIG. 7A
FIG. 7B

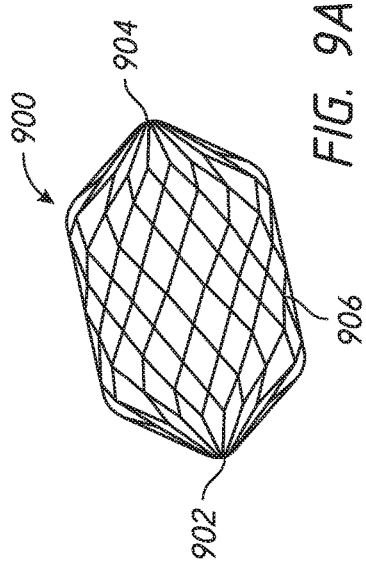
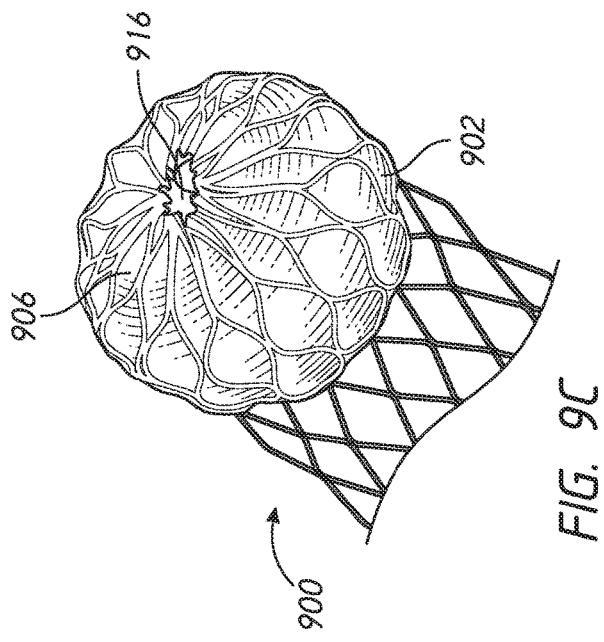
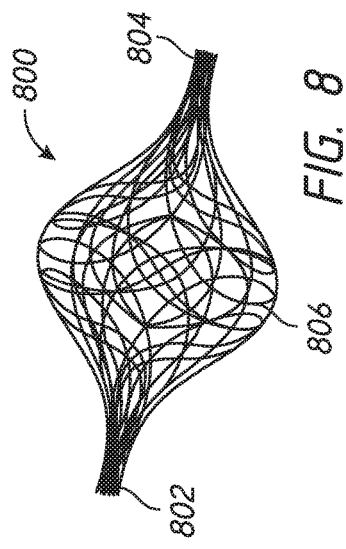
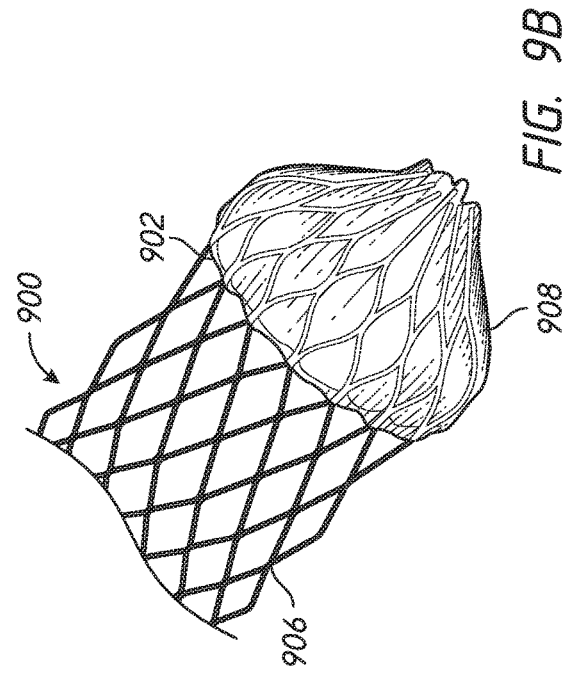
FIG. 9A
FIG. 9C
FIG. 8
FIG. 9B

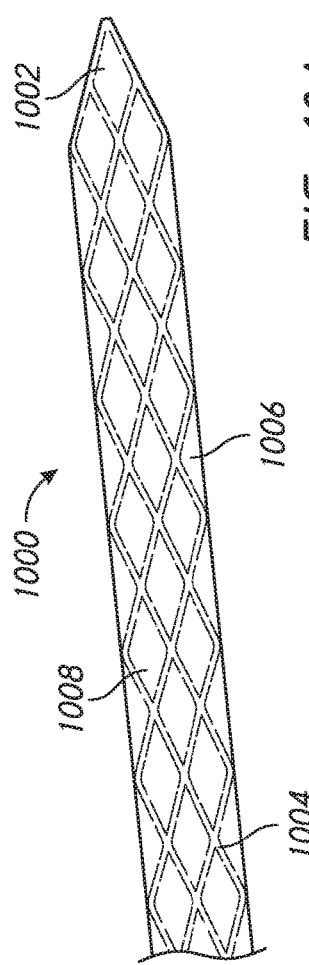
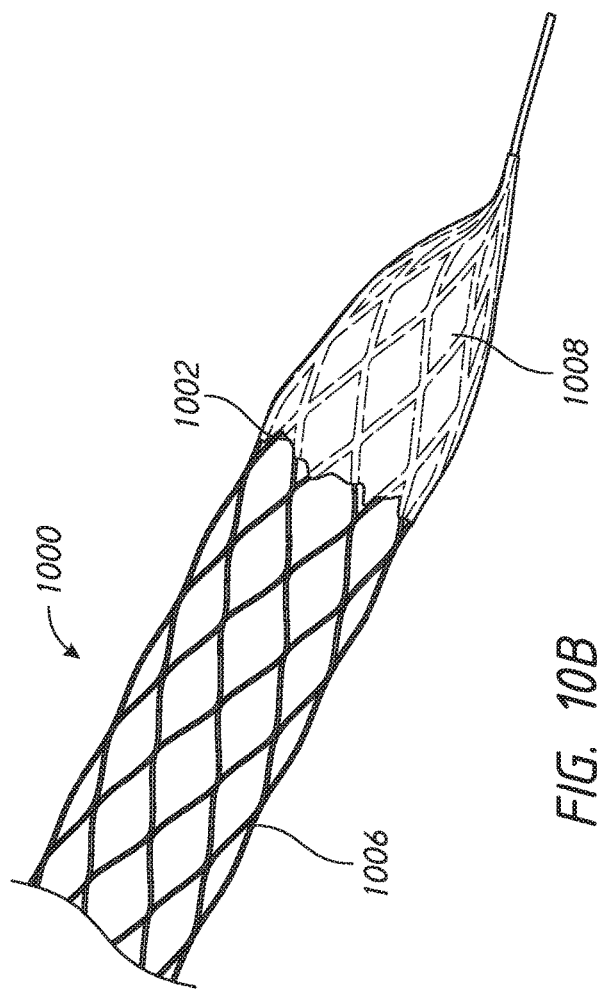

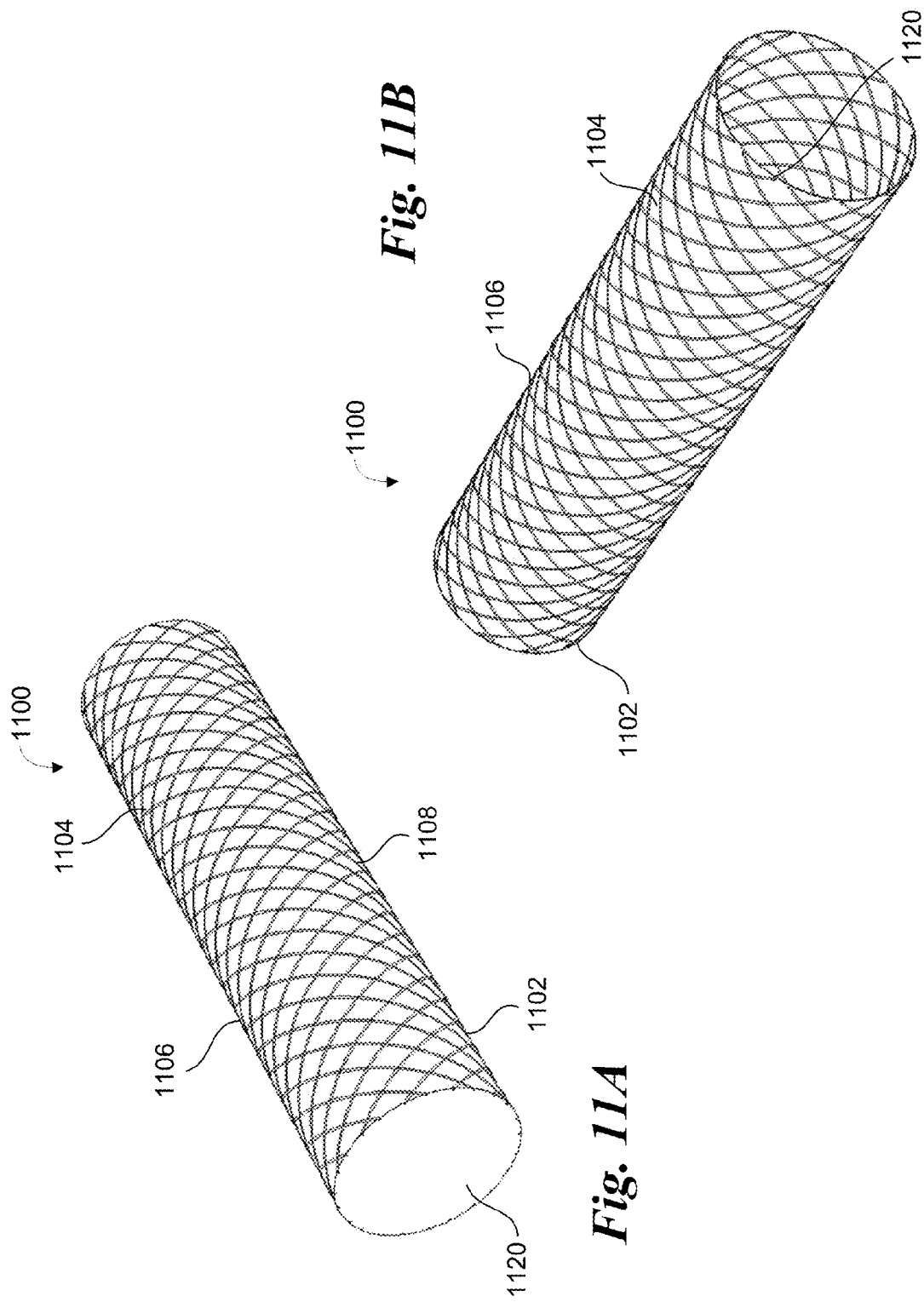

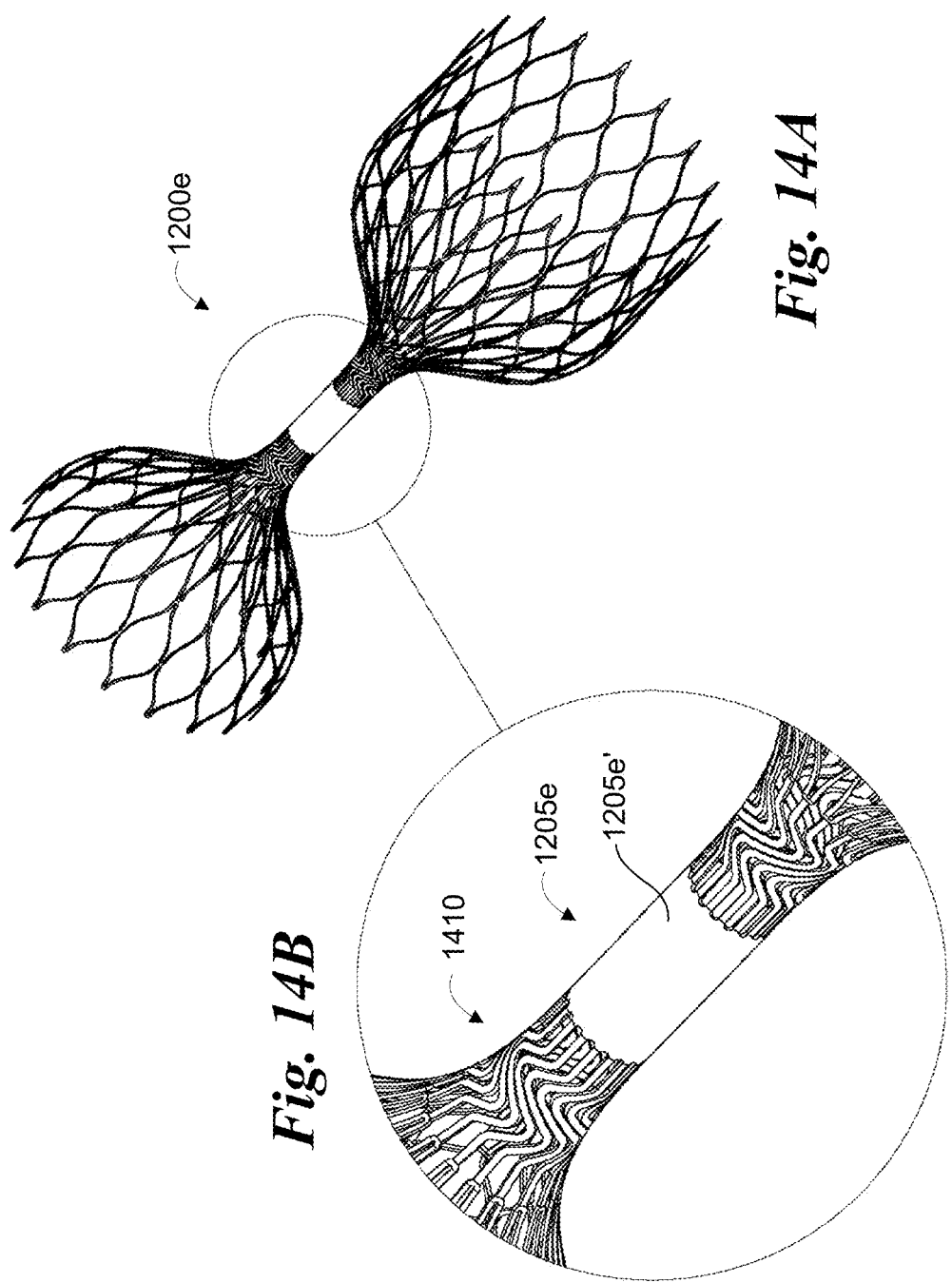

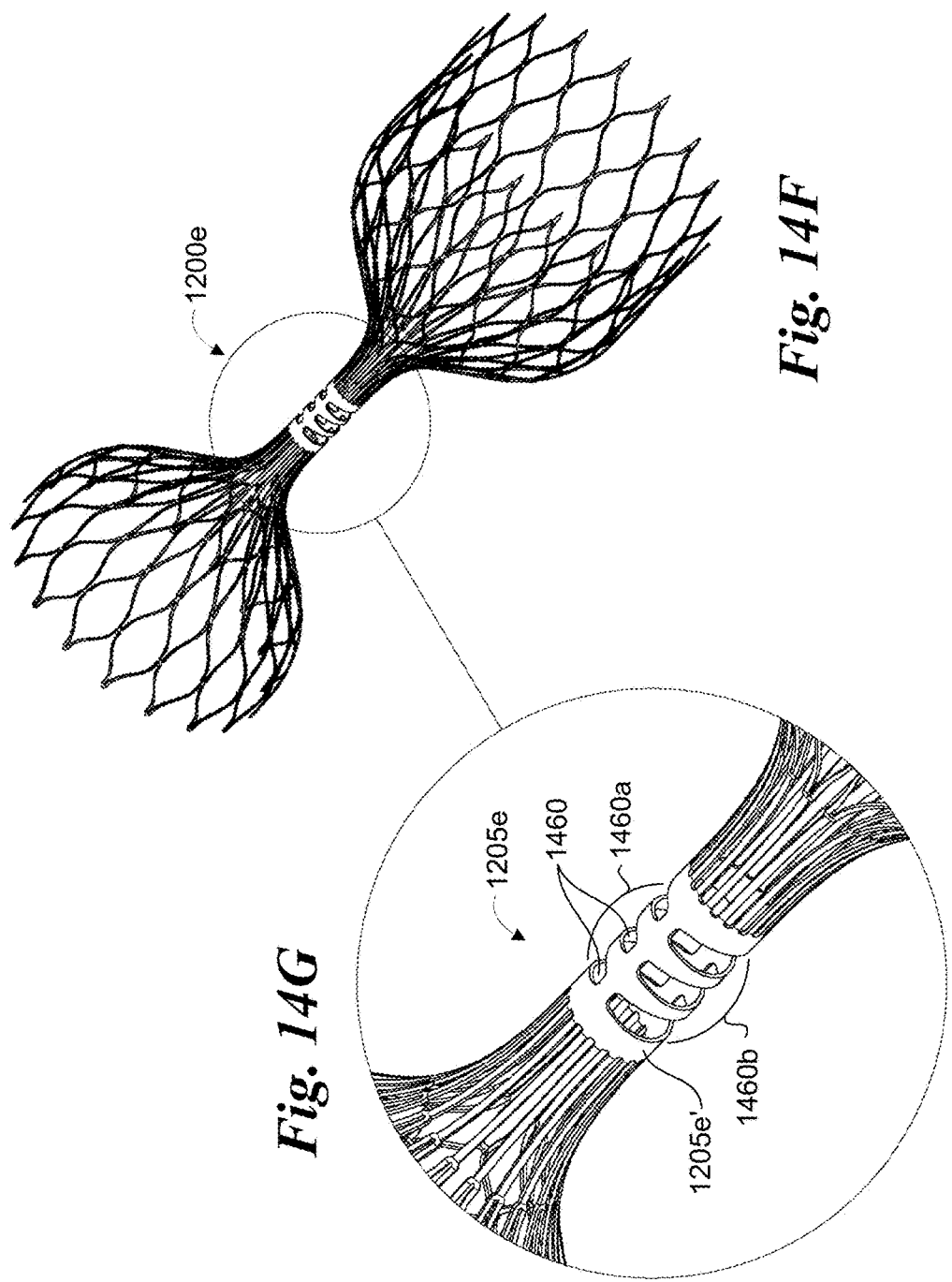

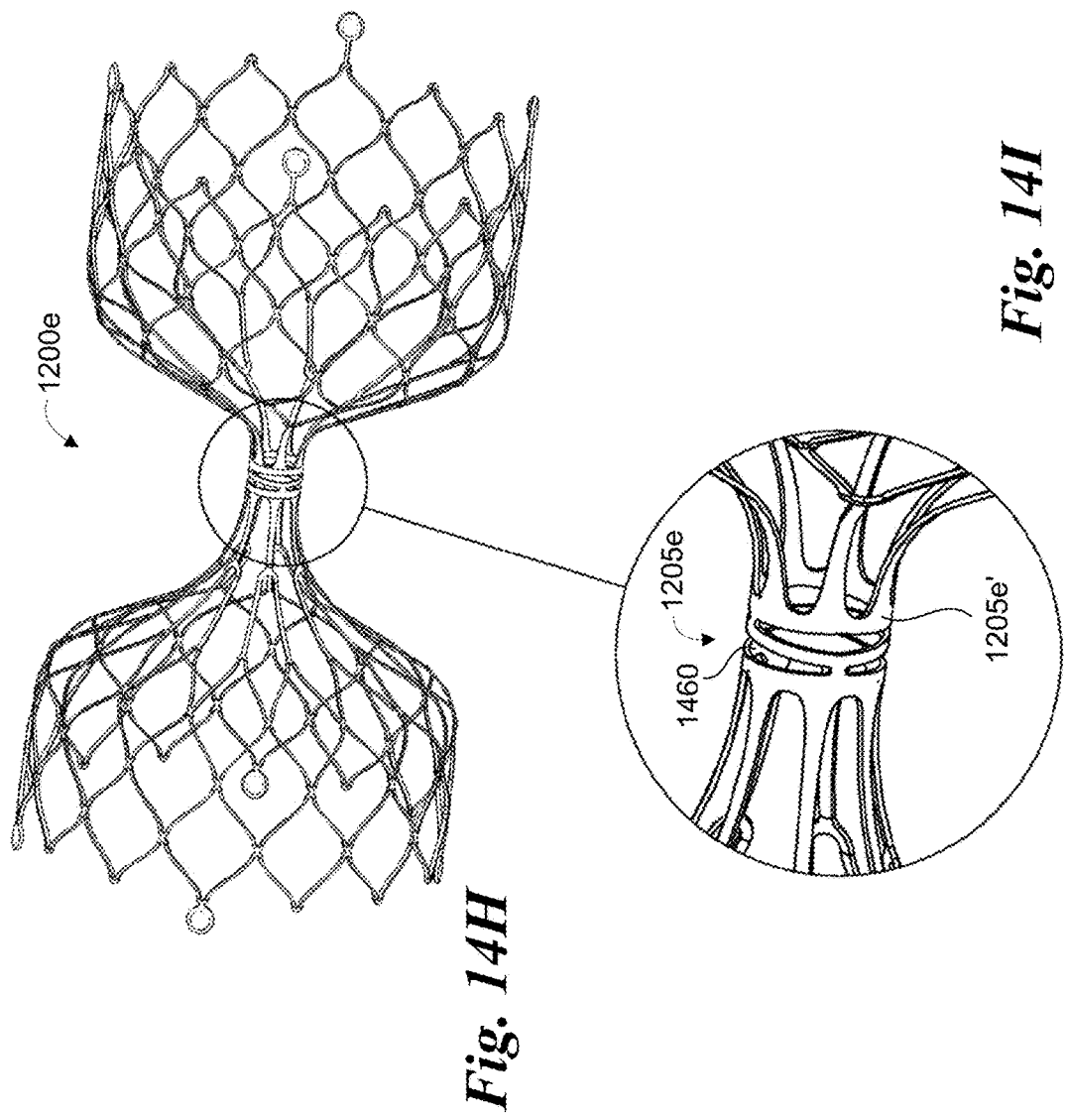

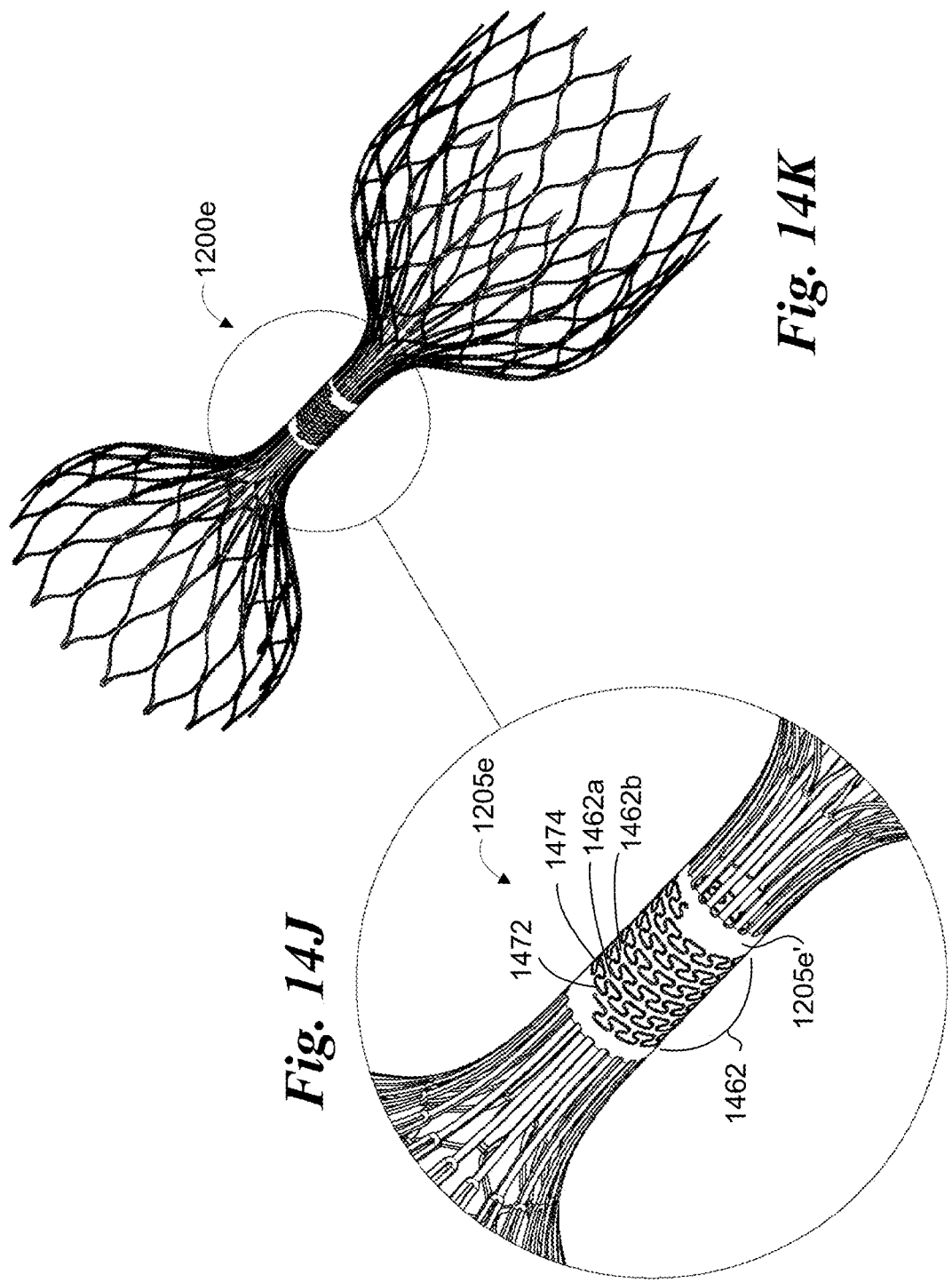

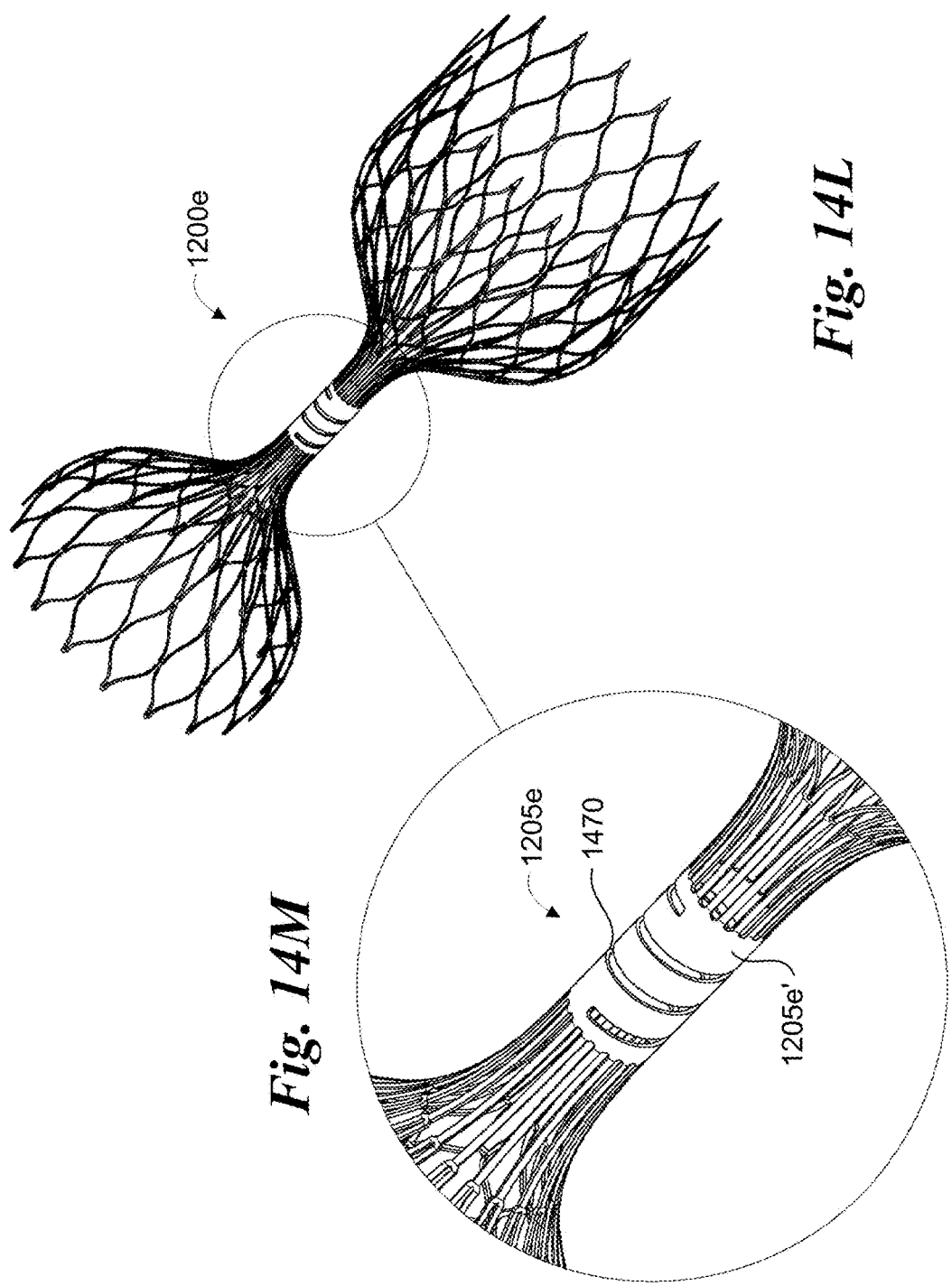

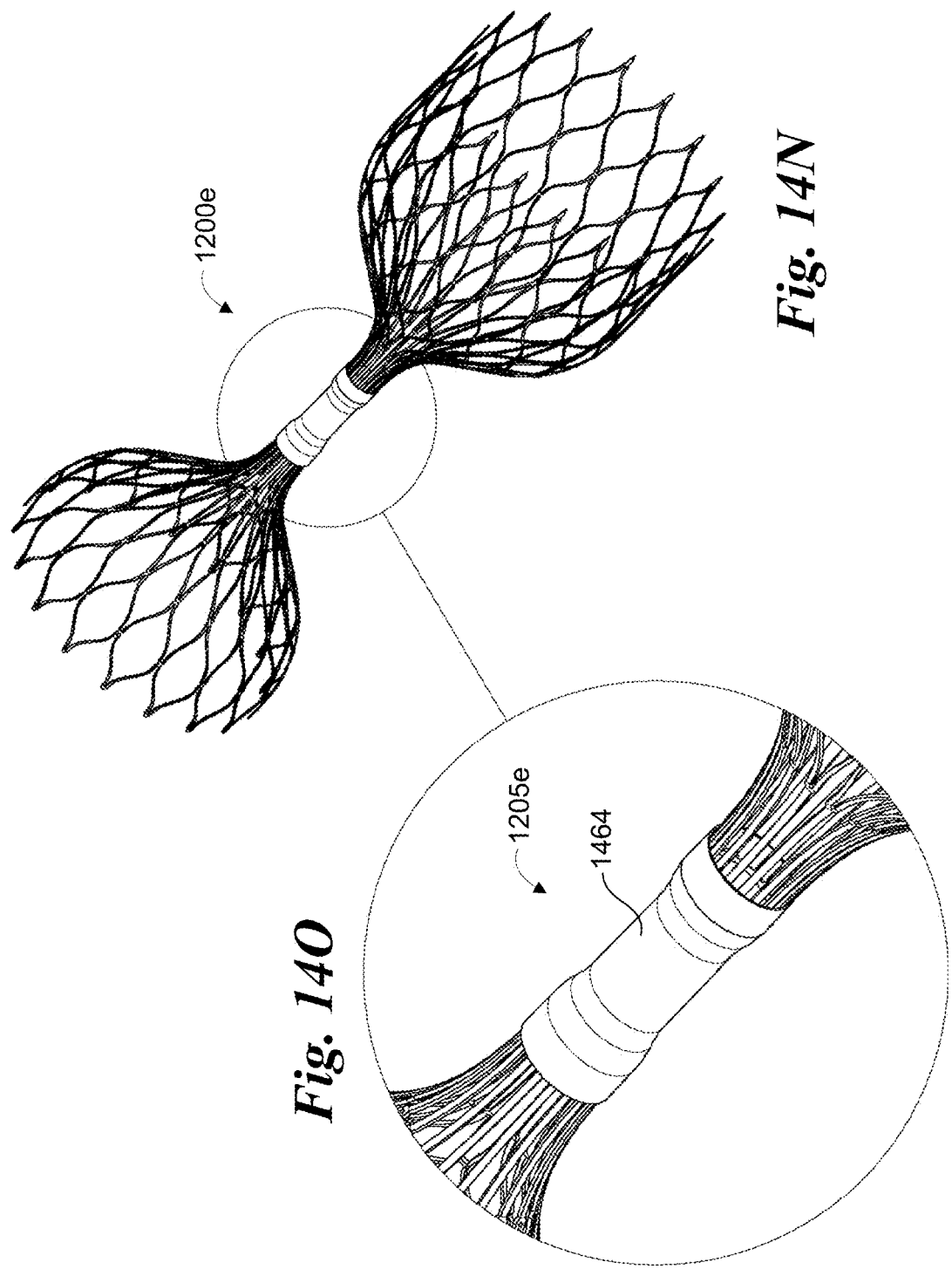

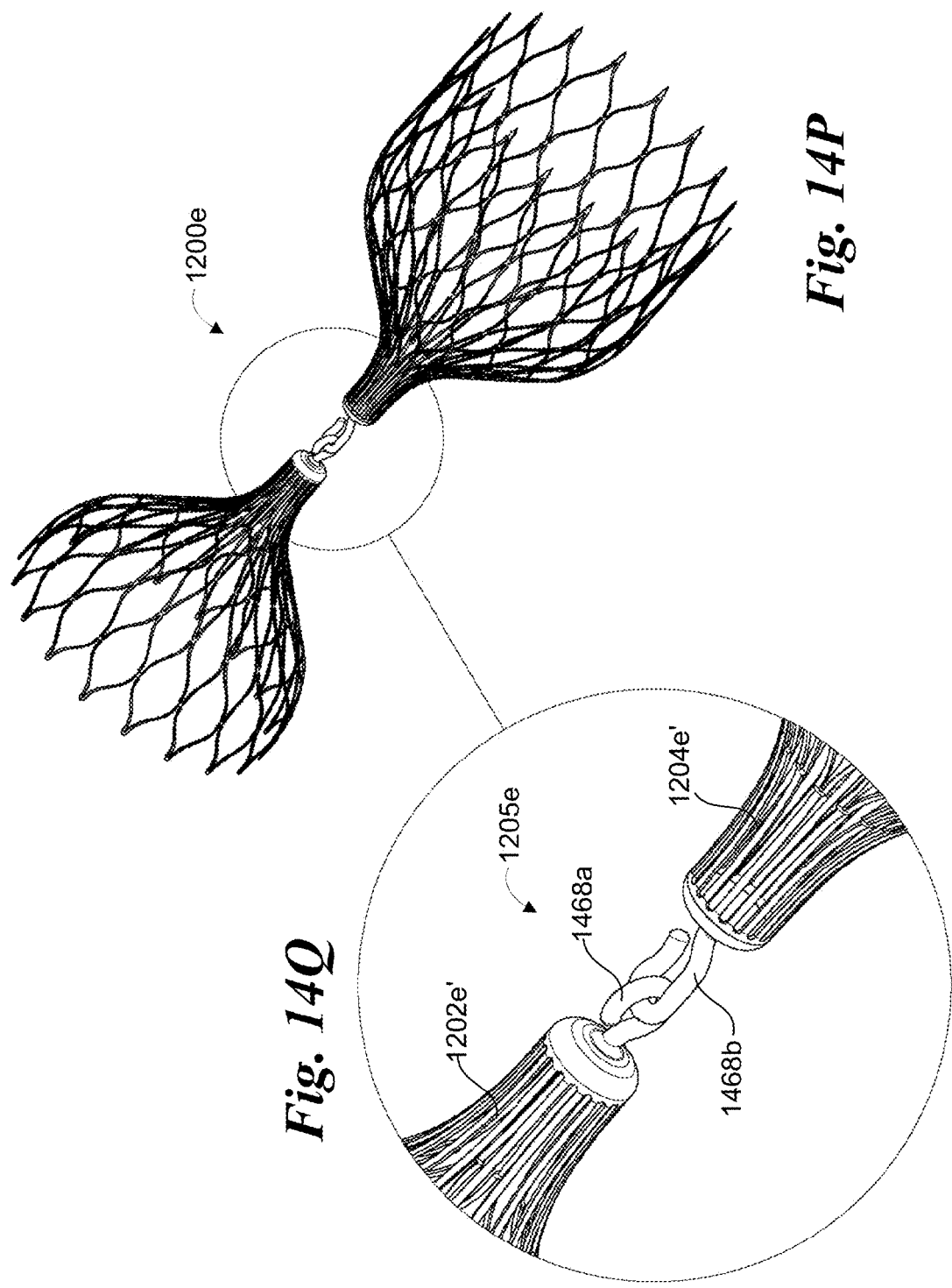

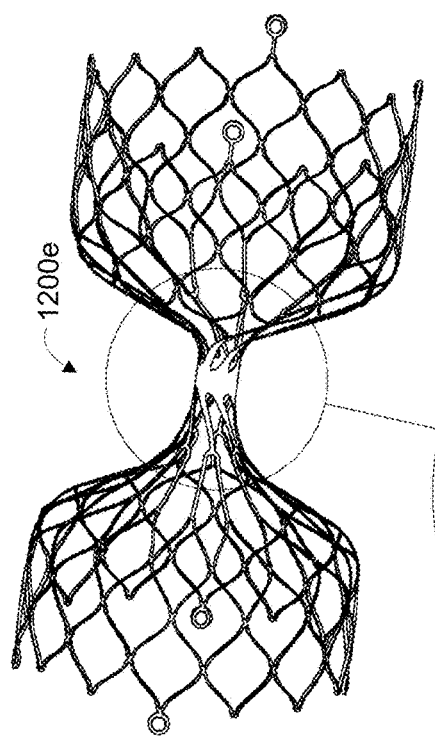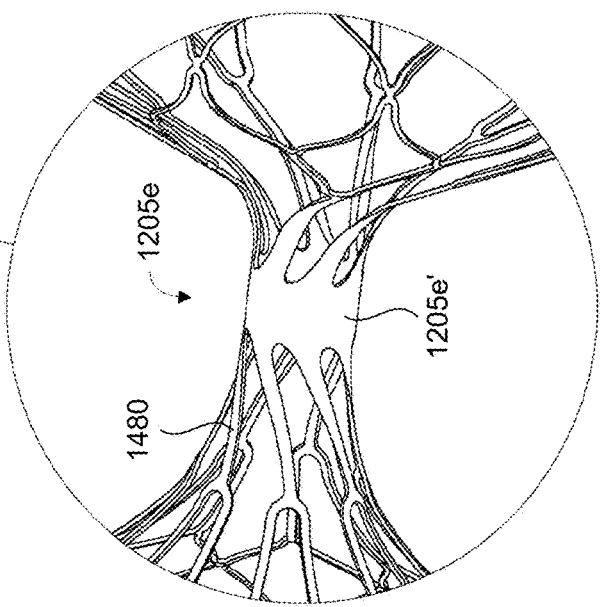
Fig. 14R
Fig. 14S

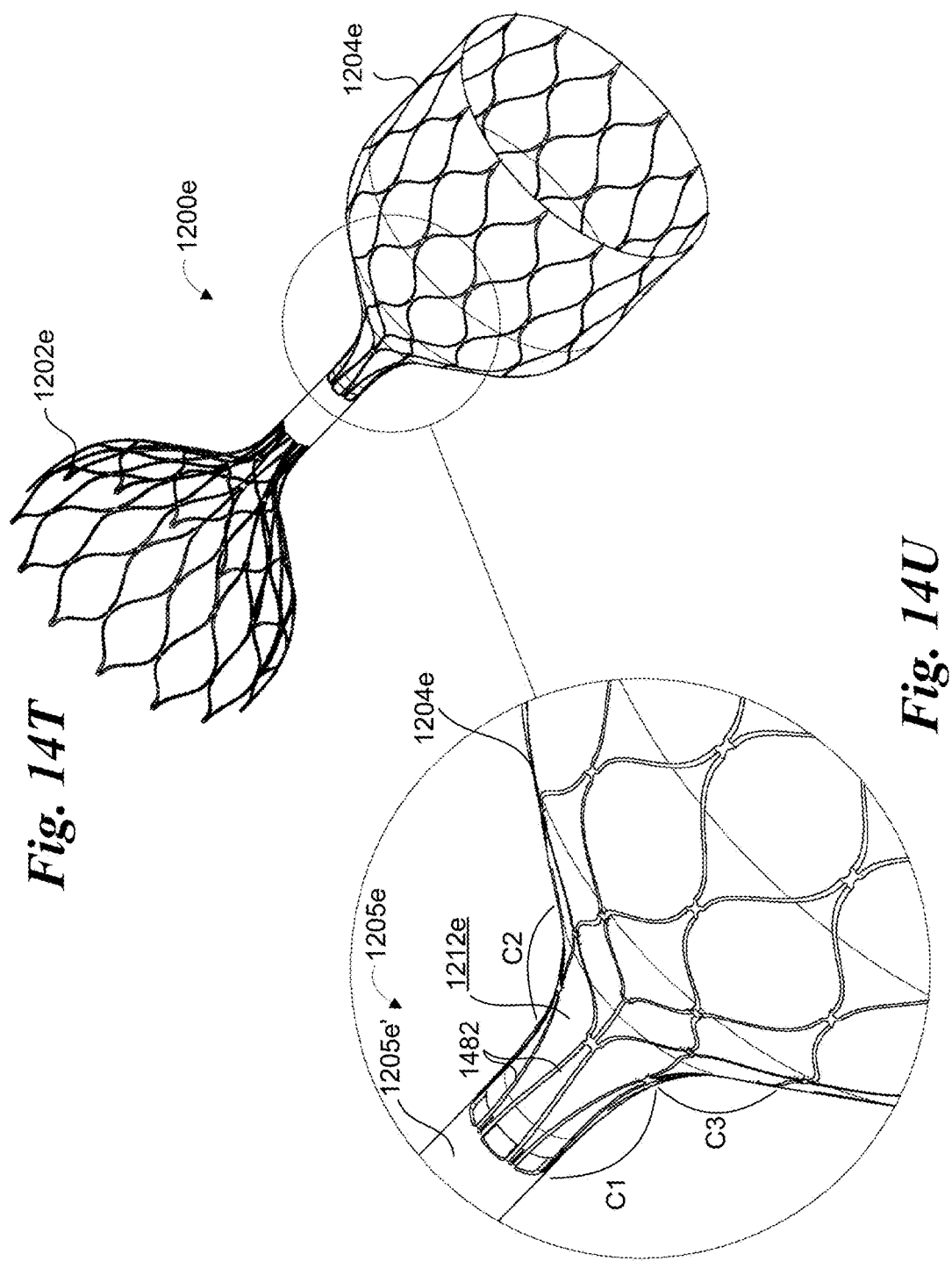

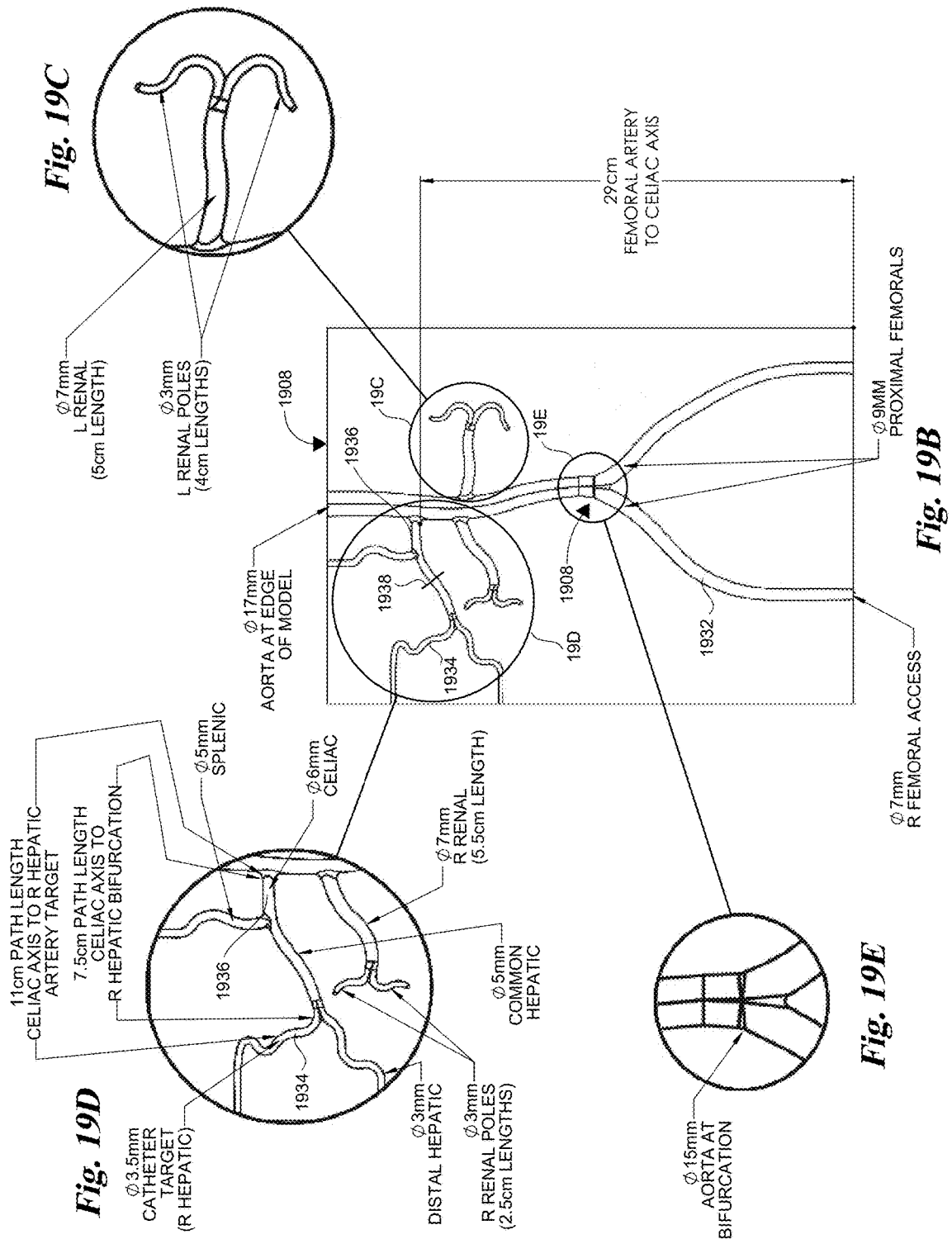

METHODS AND DEVICES FOR ENDOVASCULAR EMBOLIZATION

INCORPORATION BY REFERENCE TO ANY PRIORITY APPLICATIONS

This application is a divisional of U.S. application Ser. No. 14/449,037, filed Jul. 31, 2014, titled "METHODS AND DEVICES FOR ENDOVASCULAR EMBOLIZATION," which claims priority benefit under 35 U.S.C. § 119(e) of U.S. Provisional Application No. 61/860,856, filed Jul. 31, 2013, titled "METHODS AND DEVICES FOR ENDOVASCULAR EMBOLIZATION," U.S. Provisional Application No. 61/936,801, filed Feb. 6, 2014, titled "METHODS AND DEVICES FOR ENDOVASCULAR EMBOLIZATION," and U.S. Provisional Application No. 61/975,631, filed Apr. 4, 2014, titled "RETRACTABLE INTERLOCK DESIGN," each of which is hereby incorporated by reference in its entirety.

BACKGROUND

Field

The present disclosure generally relates to apparatuses and methods for occluding blood flow.

Description of the Related Art

A variety of endovascular devices have been proposed to occlude blood flow for various applications in the vascular system. Early devices used inflatable balloons, either non-detachable or later detachable, in order to block vessels, for example, in the treatment of carotid-cavernous fistulas and saccular aneurysms (Serbinenko, Neurosurg. 41: 125-145, 1974; Vopr. Neirokhir. July-August (4): 8-15. 1974; Vopr. Neirokhir. 35(6): 3-9, 1971).

Typically made from latex or silicone, balloons are delivered to a desired location in a vessel, and then inflated to occlude the vessel. While other devices have since been developed, balloon occlusion remains in use and is indicated for use in treating a variety of life-threatening conditions, including for example, giant cerebral and skull base aneurysms (Wehman et al., Neurosurg., 59: S125-S138, 2006), traumatic and non-traumatic vessel injury or rupture (Luo et al., J. Chin. Med. Assoc. 66: 140-147, 2003; Hirai et al., Cardiovasc. Intervent. Radiol. 19: 50-52, 1996), vertebro-vertebral arteriovenous fistulas (Berguer et al., Ann. Surg. 196: 65-68, 1982), and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency (Kaufman et al., J. Vas. Interv. Radiol. 14: 635-638, 2003), intrahepatic arterioportal fistulas (Tasar et al., Clin. Imag. 29: 325-330, 2005), treatment of varicoceles (White et al., Radiol. 139: 327-334, 1981; Pollak et al., Radiol. 191: 477-482, 1994; Makita et al., Radiol. 183: 575-577, 1992), shunt occlusion in patients with a Blalock-Taussig shunt (Reidy et al., Brit. Heart. J. 50: 101-103, 1983; DeSouza & Reidy, Clin. Radiol. 46: 170-175, 1992), obliteration of pulmonary arteriovenous fistulas, arteriovenous malformations or aortopulmonary anastomoses (Pollak et al., Radiol. 191: 477-482, 1994; DeSouza & Reidy, Clin. Radiol. 46: 170-175, 1992; Reidy et al., Brit. Heart J 49: 284-287, 1983), coronary arteriovenous fistulas (Aydogan, Asian Cardiovasc. Thorac. Ann. 11: 63-67, 2003), or renal arteriovenous fistulas (Kadir et al., J. Urol. 129: 11-13, 1983; Marshall et al., J. Urol. 122: 237-239). Detachable balloons are also used in preoperative devascularization before surgical resection of organs such as the kidney (Kadir et al., J. Urol. 129: 11-13, 1983).

Despite their usefulness, balloon occlusion devices suffer from limitations that affect their ease of use and safety. By its very nature, a balloon can expand and rupture, or alternatively it can spontaneously deflate over time (Hawkins & Szaz, Invest. Radiol. 22: 969-972, 1987). Deflation is more common with latex balloons, with some studies reporting 100% deflation rates (Perala et al., J. Vasc. Interv. Radiol. 9: 761-765, 1998). Spontaneous deflation can result in treatment failure and reoccurrence of the lesion (Pollak et al., Radiol. 191: 477-482, 1994; Perala et al., J. Vasc. Interv. Radiol. 9: 761-765, 1998).

Detachable balloon devices present other problems as well, and their use in the intracranial vasculature presents specific challenges. For example, balloons generally exhibit low trackability, meaning that they are difficult to navigate, especially through tortuous vessels, such as those commonly found in the intracranial circulation. In addition, premature (i.e., non-intentional) detachment from the delivery device can lead to adverse consequences such as cerebral artery blockage and stroke.

Even once in place, balloons can move forward during the process of inflation, making placement of the unexpanded balloon in order to achieve precise positioning after inflation relatively difficult. Balloons that dislodge and migrate can require open skull surgery especially where the balloon has become lodged in a major vessel, for example, in a cerebral artery (Cheng et al., Minim. Invasive Neurosurg., 49: 305-308, 2006).

An alternative approach has been to use hydrogel-coated coils in order to produce rapid vascular occlusion (Kallmes & Cloft, Am. J. Neuroradiol. 25: 1409-1410, 2004). However, there remains a significant period between placement of the coil and formation of the occlusive clot, even when using coated coils. This leads to concern that during formation of the clot, distal clot migration can occur, with potentially devastating consequences such as stroke. Further, the geometric configuration and unpredictability of coil-based embolization prevents precise occlusion of a short vascular segment. The risk of distal migration of a clot is also of concern when treating high-flow peripheral lesions such as pulmonary arteriovenous fistulas (Ferro et al., Cardiovasc. Intervent. Radiol. 30: 328-331, 2007).

A further alternative is an expandable mechanical occlusion device such as the Amplatzer Vascular Plug. Such devices are made of a self-expanding Nitinol mesh, and can be deployed intravascularly to block flow through a vessel by inducing formation of a clot. However, this device does not produce immediate occlusion. Further, the device may not produce a chronic occlusion leading to residual patency of the target vessel. The device is also limited by it navigability, and placement precision, which limits its utility to use in performing occlusions below the base of the skull (Ross & Buciuc, Amer. J. Neurorad. 28(2): 385-286, 2007).

Thus, notwithstanding the various efforts in the past, there remains a need for devices and methods for rapid, well-controlled, safe, and effective vessel occlusion.

SUMMARY

Certain aspects of this disclosure are directed toward an endovascular occlusion device. The device can include an expandable tubular frame having at least one closed end and an occlusive membrane extending across at least the closed end. Further, the occlusion device has an expansion ratio of at least about 5:1, at least about 6:1, or at least about 7:1. The occlusion device can also include a guidewire lumen, for removably receiving a guidewire therethrough.

The guidewire lumen may be provided with a valve to block blood flow therethrough following removal of the guidewire. The valve may comprise a polymeric membrane, such as in the form of a collapsible tube extending in the upstream direction. The tube is collapsible under blood pressure.

In the above-mentioned aspect, the device can have an unconstrained expanded diameter of at least about 1.5 mm, which can be deployed from a 0.7 mm (0.027") or smaller inside diameter lumen. In certain aspects, the device can have an unconstrained expanded diameter of at least about 6.0 mm, which can be deployed from a 0.7 mm (0.027") or smaller inside diameter lumen.

Certain aspects of this disclosure are directed toward an endovascular occlusion device having an expandable occlusive element for expansion within and occlusion of a vessel. The occlusive element can have an expansion ratio of at least about 5:1.

Certain aspects of this disclosure are directed toward an occlusion device for occluding a vessel. The occlusion device can include an expandable structure such as an hourglass configuration including a first lobe or end portion, a second lobe or end portion, and a middle or neck portion therebetween. The expandable structure can move between an unexpanded configuration and an expanded configuration. The expansion ratio of the expandable structure can be at least about 3:1, preferably at least about 5:1, and, in some instances, at least about 7:1, for example, about 8:1. Further, the occlusion device can be configured to prevent substantially all fluid from flowing past the occlusion device when the expandable structure is in the expanded configuration in the vessel.

In the above-mentioned aspect, a largest diameter of the expandable structure in the unexpanded configuration is less than or equal to about 2 mm, such as between about 1.25 mm and about 1.75 mm, preferably less than or equal to about 1.5 mm.

In any of the above-mentioned aspects, the expandable structure can include a uniform or a non-uniform diameter across a length of the expandable structure. For example, a diameter of the second end portion can be substantially larger than a diameter of the first end portion. As another example, a diameter of the middle portion can be substantially larger or smaller than a diameter of the first end portion and a diameter of the second end portion. In yet another example, the first and second end portions of the expandable structure can be tapered.

In any of the above-mentioned aspects, the occlusion device can include a cover membrane carried by at least one of the first and second end portions. For example, the cover can only be carried by the first end portion. As another example, the cover can surround the first and second end portions, and the middle portion can remain uncovered. In yet another example, the cover can surround substantially the entire expandable structure.

In any of the above-mentioned aspects, the occlusion device can include a cover having a thickness of less than or equal to about 30 microns. The cover can include a cover material including, but not limited to, TecoThane, nylon, PET, Carbothane (Bionate), fluoropolymer, SIBS, and PLGA.

In certain aspects, the occlusion device can include a drum head disposed within the first end portion of the expandable structure, such that the drumhead prevents fluid flow through the first end portion. In some instances, the occlusion device can include a cover surrounding the drumhead.

In any of the above-mentioned aspects, the expandable structure can include one or more strands. The one or more strands can be woven to form a wall pattern. In some instances, the wall pattern can be substantially uniform across a length of the expandable structure. Alternatively, the expandable structure can include a laser cut tubular element. In some instances, a wall pattern of the second end portion includes a greater amount of open area than a wall pattern of the first end portion.

In any of the above-mentioned aspects, the occlusion device can include features to prevent migration of the occlusion device after deployment. For example, the occlusion device can include one or more anchors disposed along an uncovered portion, such as an end lobe or middle portion the expandable structure. As another example, if the occlusion device is braided, each of the one or more strands includes strand ends. At least some of the strand ends can remain exposed to anchor the occlusion device to the vessel wall.

Certain aspects of the disclosure are directed toward a delivery system for delivering an occlusion device. The delivery system can include an outer catheter and an inner catheter axially movable within the outer catheter. The inner catheter can deliver the occlusion device out of the outer catheter. The outer catheter preferably includes an outer diameter of less than or equal to about 2.0 mm, preferably less than or equal to about 1.67 mm (5 F). In some instances, the delivery system can include a support tube axially disposed between the outer catheter and the inner catheter, for example, when the inner catheter is configured to carry the expandable structure on a distal portion of the inner catheter. The occlusion device can include any of the above-mentioned occlusion device aspects.

Certain aspects of this disclosure are directed toward a method of occluding a vessel. The method can include positioning a delivery system in the vessel and deploying a single occlusion device from the delivery system. In some instances, the positioning step can include advancing the delivery system over a guide wire. The delivery system can include any of the above-mentioned delivery system aspects. Further, the single occlusion device can include any of the above-mentioned occlusion device aspects.

Certain aspects of the disclosure are directed toward an endovascular occlusion device for occluding blood flow through a vessel. The endovascular occlusion device can include an expandable frame and a membrane carried by the frame. The frame and the membrane can be dimensioned for deployment from a tube having an inside diameter of less than or equal to about 2 mm, preferably less than or equal to about 1.5 mm, such as less than or equal to about 1.3 mm. The tube can have an outside diameter of less than or equal to about 2 mm, preferably less than or equal to about 1.67 mm. Further, the frame and the membrane can be expandable to a diameter of at least about 8 mm following deployment from the tube. The membrane can have a porosity that achieves a reduction in blood flow of at least about 80% within about five minutes of deployment from the tube in a blood vessel, preferably within about two minutes of deployment from the tube in a blood vessel or within about one minute of deployment from the tube in a blood vessel. In certain aspects, the occlusion device can be configured to achieve total occlusion within about two minutes of deployment from the tube in a blood vessel, preferably within about one minute of deployment from the tube in a blood vessel.

In certain aspects, the occlusion device can achieve 80% occlusion in less than or equal to about 30 seconds, 90% occlusion in less than or equal to about 3 minutes, and/or 100% occlusion in less than or equal to about 5 minutes according to the Occlusion Protocol described below. Due to the physical or mechanical occlusion mechanism of action, the foregoing occlusion characteristics are unaffected by the patients' anticoagulant status.

In the above-mentioned endovascular occlusion device, the occlusion device can have an expansion ratio of at least about 6:1, preferably at least about 7:1.

In any of the above-mentioned endovascular occlusion devices, the occlusion device can be delivered over a 0.018-inch or smaller guidewire.

In any of the above-mentioned endovascular occlusion devices, the membrane can include an average pore size of no more than about 100 microns, preferably no more than about 50 microns.

In any of the above-mentioned endovascular occlusion devices, the device can have an average COP across a diameter between about 2.5 mm and about 8.0 mm (e.g., a diameter between about 3.0 mm and about 8.0 mm) of between about 20 mmHg and about 250 mmHg, such as between about 30 mmHg and about 140 mmHg, between about 30 mm Hg and 80 mmHg, between about between about 70 mmHg and 100 mmHg, between about 90 mmHg and 120 mmHg, or between about 100 mmHg and 140 mmHg.

Another aspect of the disclosure is directed toward an endovascular occlusion device for achieving mechanical occlusion of blood flow in a vessel without requiring biological processes to achieve occlusion. The occlusion device can include an expandable support structure carrying a porous membrane. The membrane can be configured to obstruct blood flow through the vessel when the support structure is in an expanded configuration. The membrane can have an average pore size of no more than about 100 microns, preferably no more than about 50 microns.

In the above-mentioned occlusion device, the membrane can include an average thickness of no more than about 30 microns.

In any of the above-mentioned endovascular occlusion devices, the occlusion device can be deliverable from a lumen having an inside diameter less than or equal to about 2 mm, preferably less than or equal to about 1.67 mm.

In any of the above-mentioned endovascular occlusion devices, the device can have an average COP across a diameter of 2.5 mm to 8.0 mm (e.g., between about 3.0 mm and about 8.0 mm) of between about 20 mmHg and about 250 mmHg, such as between about 30 mmHg and about 140 mmHg, between about 30 mm Hg and 80 mmHg, between about between about 70 mmHg and 100 mmHg, between about 90 mmHg and 120 mmHg, or between about 100 mmHg and 140 mmHg.

Yet another aspect of the disclosure is directed toward an endovascular occlusion device for occluding blood flow through a vessel. The occlusion device can include a frame that is expandable through a range from a first, compressed diameter to a second, maximum expanded diameter. The range of expansion can be sufficient to occlude blood vessels having inside diameters anywhere within the range from about 2.5 mm to about 8 mm, such as within the range from about 3 mm to about 7 mm.

Certain aspects of the disclosure are directed to a low crossing profile, high dynamic range endovascular occlusion device having an opening for receiving a guidewire therethrough. The occlusion device can be expandable from a first diameter for transvascular navigation within a deployment catheter to a deployment site, to a second diameter for occluding a vessel following deployment from the catheter. The catheter can include a diameter of no greater than about 5 French and the expansion ratio can be at least about 6×, preferably at least about 8×. In certain aspects, the occlusion device can include an expandable frame and an occlusion membrane.

In any of the above-mentioned low crossing profile occlusion devices, the occlusion device can be deliverable from a lumen having an inside diameter of less than or equal to about 2 mm, preferably less than or equal to about 1.67 mm.

In any of the above-mentioned low crossing profile occlusion devices, the occlusion device can be delivered over a 0.018 inch or smaller guidewire.

In any of the above-mentioned low crossing profile occlusion devices, the membrane can include an average pore size of no more than about 100 microns, preferably no more than about 50 microns, such as an average pore size between about 5 microns and 10 microns or between about 10 microns and 15 microns.

Certain aspects of the disclosure are directed toward an endovascular occlusion deployment system for navigating tortuous vasculature to deploy an occlusion device at a target site in a vessel. The deployment system can include an elongate, flexible tubular body, having a proximal end, a distal end, and a diameter of no more than about 5 French. The deployment system can also include an occlusion device releasably carried in the distal end of the tubular body. Further, the occlusion device has an expansion ratio of at least about 5 to 1. The distal end of the tubular body can be advanced to the target vessel with sufficient trackability as determined by the Trackability Protocol described below (e.g., access a minimum of 4 cm into the right hepatic artery). Further, the occlusion device can include any of the aforementioned occlusion device aspects.

Another aspect of the disclosure is directed toward a low crossing profile, high dynamic range endovascular occlusion device with low elongation. The occlusion device can be expandable from a first diameter for transvascular navigation within a deployment catheter to a deployment site to a second diameter for occluding a vessel following deployment from the catheter. The catheter can have a diameter of less than or equal to about 5 French. The occlusion device can have an expansion ratio of at least about 5×, and the elongation of the device between the first diameter and the second diameter can be no more than about 20%. Further, the occlusion device can include any of the aforementioned occlusion device aspects.

Yet another aspect of the disclosure is directed toward a migration resistant endovascular occlusion device for occluding blood flow through a vessel. The occlusion device can include an expandable frame and a membrane carried by the frame. The frame and membrane can be dimensioned for deployment from a tube having an inside diameter of no more than about 2 mm and can be expandable to a diameter of at least about 8 mm following deployment from the tube. The occlusion device can exhibit a migration of less than about 5.0 mm at about 120 mmHg, preferably at 200 mmHg or 300 mmHg, as determined by the Migration Protocol described herein. Further, the occlusion device can include any of the aforementioned occlusion device aspects.

Another aspect of the disclosure is directed toward an endovascular occlusion deployment system with contrast injection capability for navigating tortuous vasculature to deploy an occlusion device at a target site in a vessel. The deployment system can include an elongate, flexible tubular body, having a proximal end, a distal end, and a diameter of no more than about 5 French. An occlusion device can be releasably carried in the distal end of the tubular body, the occlusion device having an expansion ratio of at least about 5 to 1. The deployment system can also include a contrast injection port on the body, proximal to the occlusion device. The contrast injection port permits injection of contrast while the occlusion device is in an expanded configuration and prior to release of the occlusion device from the tubular body. In certain aspects, the distal end of the tubular body can be advanced to the target vessel with sufficient trackability as determined by the Trackability Protocol described herein. Further, the occlusion device can include any of the aforementioned occlusion device aspects.

For purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1A illustrates a delivery system for delivering an occlusion device.

FIG. 1A-1 illustrates an enlarged view of a distal portion of the delivery system shown in FIG. 1A.

FIG. 1B-1 illustrates an embodiment of an outer catheter that can be used with the delivery system shown in FIG. 1A.

FIG. 1B-2 illustrates an enlarged view of the working length of the outer catheter shown in FIG. 1B-1.

FIG. 1B-3 illustrates an embodiment of an inner catheter that can be used with the delivery system shown in FIG. 1A.

FIG. 1B-4 illustrates an enlarged view of a distal portion of the inner catheter shown in FIG. 1B-3 through line 1B-3-1B-3.

FIG. 1C-1 illustrates an embodiment of a delivery system having a pusher interlock assembly in a locked configuration.

FIG. 1C-2 illustrates the pusher interlock assembly shown in FIG. 1C-1 in an unlocked configuration.

FIG. 1C-3 illustrates an embodiment of an occlusion device having a portion of the pusher interlock assembly shown in FIG. 1C-1 and detached from the delivery system.

FIG. 1D-1 illustrates another embodiment of a delivery system having a threaded interlock assembly.

FIG. 1D-2 illustrates an enlarged view of the threaded interlock assembly through line 1D-2 shown in FIG. 1D-1.

FIG. 1E-1 illustrates another embodiment of a delivery system having an interlock catheter.

FIG. 1E-2 illustrates an enlarged view of a portion of the delivery system shown in FIG. 1E-1 taken through line 1E-2 to 1E-4 with the interlock assembly in a locked configuration.

FIG. 1E-3 illustrates an enlarged view of a portion of the delivery system shown in FIG. 1E-1 taken through line 1E-2 to 1E-4 with the interlock assembly in an unlocked configuration.

FIG. 1E-4 illustrates an enlarged view of a portion of the delivery system shown in FIG. 1E-1 taken through line 1E-2 to 1E-4 with the occlusion device detached.

FIG. 1E-5 illustrates a cross-section of FIG. 1E-2 taken through line 1E-5 to 1E-5 without the occlusion device.

FIG. 1E-6 illustrates a cross-section of FIG. 1E-4 taken through line 1E-6 to 1E-6.

FIG. 2C illustrates the distal portion of the delivery system shown in FIG. 2A with the distal lobe of the occlusion device partially deployed.

FIG. 2CC illustrates an enlarged cross-section of the distal portion shown in FIG. 2C taken through line CC.

FIG. 2D illustrates the distal portion of the delivery system shown in FIG. 2A with the distal lobe of the occlusion device fully deployed.

FIG. 2DD illustrates an enlarged cross-section of the distal portion shown in FIG. 2D taken through line DD.

FIG. 2EE illustrates a cross-section of the distal portion shown in FIG. 2E taken through line EE.

FIG. 2F illustrates the distal portion of the delivery system shown in FIG. 2A with a majority of the occlusion device deployed.

FIG. 2FF illustrates a cross-section of the distal portion shown in FIG. 2F taken through line FF.

FIG. 2H illustrates a cross-section of the occlusion device shown in FIG. 2G with the inner catheter partially retracted.

FIG. 2HH illustrates an enlarged view a tubular membrane portion of the occlusion device shown in FIG. 2H taken through line HH.

FIG. 2I illustrates a cross-section of the occlusion device shown in FIG. 2H with the inner catheter further retracted.

FIG. 2II illustrates an enlarged view of the tubular membrane portion of the occlusion device shown in FIG. 2I taken through line II.

FIG. 2J illustrates a cross-section of the occlusion device shown in FIG. 2I with the inner catheter further retracted.

FIG. 2JJ illustrates an enlarged view of the tubular membrane portion of the occlusion device shown in FIG. 2J taken through line JJ.

FIG. 2L illustrates the inner catheter of the delivery system shown in FIG. 2A.

FIG. 2M illustrates an enlarged view of a distal portion of the inner catheter shown in FIG. 2L.

FIGS. 3A-3F illustrate another delivery system and an occlusion device having a tapered proximal end.

FIGS. 4A-4F illustrate yet another delivery system and a generally cylindrical occlusion device.

FIGS. 5A-5F illustrate a delivery system and another generally cylindrical occlusion device.

FIG. 6 illustrates a partially covered, hourglass-shaped occlusion device.

FIG. 7A illustrates a partially covered occlusion device having tapered ends.

FIG. 7B illustrates a fully covered occlusion device having tapered ends.

FIG. 8 illustrates an expandable structure having a non-uniform diameter.

FIG. 9A illustrates another expandable structure having tapered ends.

FIGS. 9B-9C illustrate the expandable structure in FIG. 9A partially covered with a cover.

FIG. 10A illustrates a fully covered occlusion device having a first, closed end portion and a second, opened end portion.

FIG. 10B illustrates a partially covered occlusion device having a first, closed end portion and a second, opened end portion.

FIGS. 11A-11C illustrate different views of an occlusion device having a drumhead and a cover.

FIG. 19B illustrates a model for the Trackability Protocol fixture.

FIG. 19C illustrates an enlarged view of a portion of the model shown in FIG. 19A through circle 19C.

FIG. 19D illustrates an enlarged view of a portion of the model shown in FIG. 19A through circle 19D.

FIG. 19E illustrates an enlarged view of a portion of the model shown in FIG. 19A through circle 19E.

DETAILED DESCRIPTION

The following discussion is presented to enable a person skilled in the art to make and use one or more embodiments of the invention. The general principles described herein may be applied to embodiments and applications other than those detailed below without departing from the spirit and scope of the invention. Therefore the present invention is not intended to be limited to the embodiments shown, but is to be accorded the widest scope consistent with the principles and features disclosed or suggested herein.

Delivery System

Figures 1, 1B, 2:
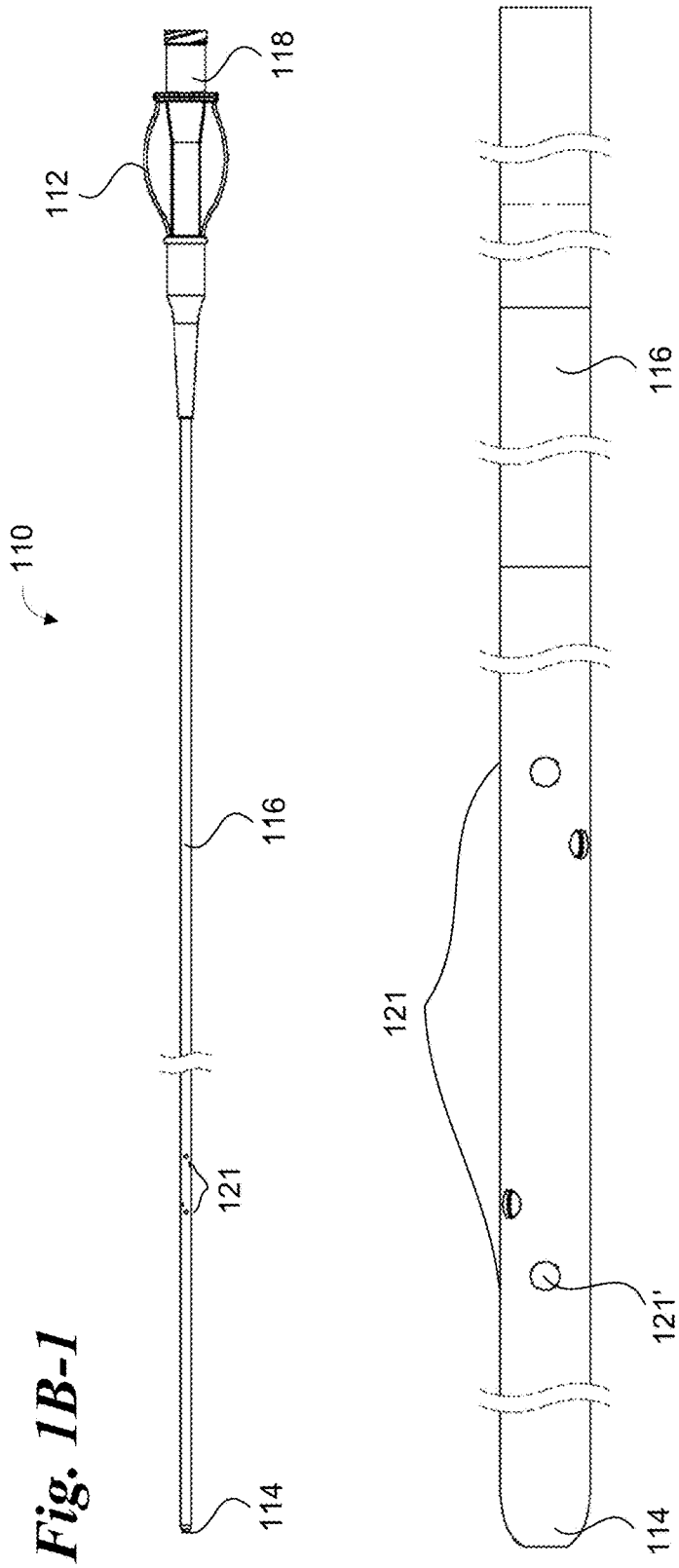

FIGS. 1A and 1A-1 illustrate an exemplary delivery system 100 for delivering any of the occlusion devices illustrated herein. The delivery system 100 can include an outer catheter 110 and an inner catheter 120 extending through the outer catheter 110. Although primarily described in the context of an intravascular embolic deployment catheter with a single central lumen, catheters of the present invention can readily be modified to incorporate additional structures, such as permanent or removable column strength enhancing mandrels, two or more lumen such as to permit drug or irrigant infusion or aspiration or radiation delivery or to supply inflation media to an inflatable balloon, or combinations of these features, as will be readily apparent to one of skill in the art in view of the disclosure herein.

The catheters and occlusion devices disclosed herein may readily be adapted for use throughout the body wherever it may be desirable to introduce an occluder. For example, occlusion devices may be deployed throughout the coronary and peripheral vasculature, neurovasculature, the gastrointestinal tract, the urethra, ureters, Fallopian tubes, and other lumens and potential lumens, as well.

Generally, the occlusion devices described herein can be delivered via a low profile outer catheter 110 (e.g., having an outer diameter from about 2.8 F (0.93 mm) to about 6 F (2.0 mm), typically from about 3 F (1.0 mm) to about 5 F (1.67 mm), preferably less than about 5 F (1.67 mm), such as about 4.7 F (1.57 mm)). Further, the occlusion devices described herein can be delivered over a guide wire having a diameter of at least about 0.010 inches and/or less than or equal to about 0.02 inches to facilitate trackability of the delivery catheter, while still utilizing a low profile delivery catheter. For example, the guide wire can have a diameter of about 0.01 inches, 0.014 inches, or about 0.018 inches.

The outer catheter 110 can generally include an elongate tubular body 116 extending between a proximal end 112 and a distal end 114. The length of the tubular body 116 depends upon the desired application. For example, lengths in the area of from about 120 cm to about 140 cm or more are typical for use in femoral access percutaneous transluminal coronary applications. Further, the outer catheter 110 should have sufficient working length to reach the target vessel. The minimum working length for these applications can be at least about 75 cm about 90 cm, or at least about 100 cm, but no more than about 175 cm. Intracranial or other applications may call for a different catheter shaft length depending upon the vascular access site, as will be understood in the art. Deployment catheters adapted for intracranial applications generally have a total length in the range from 60 cm to 250 cm, usually from about 135 cm to about 175 cm.

In general, neurovascular devices may be deployable from catheters having a length of at least about 120 cm or 125 cm or greater, to allow access to the carotid artery bifurcation and above. Devices configured for coronary or peripheral applications may have shorter delivery catheters and other dimensional modifications as are understood in the art.

The catheters of the present invention may be composed of any of a variety of biologically compatible polymeric resins having suitable characteristics when formed into the tubular catheter body segments. Exemplary materials include polyvinyl chloride, polyethers, polyamides, polyethylenes, polyurethanes, a polycarbonate blend, copolymers thereof, and the like. Optionally, the tubular body may be reinforced with a metal or polymeric braid or other conventional reinforcing layer.

The catheter material should be selected such that the delivery system demonstrates acceptable trackability and deployment forces to enable access to the target vessel and delivery of the implant to the target vascular. Further, the material of the outer catheter 110 should be sufficient to maintain its integrity during flushing and hemostasis. For example, the outer catheter 110 should be able to resist a pressure of at least about 45 psi/min.

Further, the outer catheter 110 must have sufficient structural integrity (e.g., column strength or "pushability") to permit the outer catheter 110 to be advanced to distal locations without buckling or undesirable bending of the tubular body 116. The ability of the outer catheter 110 to transmit torque may also be desirable, such as to avoid kinking upon rotation, to assist in steering. The outer catheter 110, and particularly the distal portion, may be provided with any of a variety of torque and/or column strength enhancing structures. For example, axially extending stiffening wires, spiral wrapped support layers, and/or braided or woven reinforcement filaments may be built into or layered on the tubular body 116.

The delivery system 100 and its variants described herein are capable of penetrating the target vessel by at least 4 cm, such as between about 4 cm and 6 cm, for example, at least 5 cm, or preferably at least about 5.5 cm as determined by the Trackability Protocol described below.

The proximal portion of the outer catheter 110 may have a shore hardness in the range from 50 D to 100 D, often being about 70 D to 80 D. Usually, the proximal portion of the outer catheter 110 will have a flexural modulus from 20,000 psi to 1,000,000 psi, preferably from 100,000 psi to 600,000 psi. The distal portion of the outer catheter 110 will be sufficiently flexible and supple so that it may navigate the patient's distal vasculature. In highly flexible embodiments, the shore hardness of the distal portion may be in the range from about 20 A to about 100 A, and the flexural modulus for the distal portion may be from about 50 psi to about 15,000 psi.

The outer catheter 110 may be produced in accordance with any of a variety of known techniques for manufacturing interventional catheter bodies, such as by extrusion of appropriate biocompatible polymeric materials. At least a proximal portion or all of the length of outer catheter 110 may comprise a polymeric or metal spring coil, solid walled hypodermic needle tubing, or braided reinforced wall, as is known in the microcatheter arts.

The proximal end 112 of outer catheter 110 can include a manifold 118 having one or more access ports as is known in the art. Generally, the manifold 118 can include a guidewire port. Additional access ports may be provided as needed, depending upon the functional capabilities of the catheter. The manifold 118 can be compatible with luer connections from related accessories. Further, the manifold 118 may be injection molded from any of a variety of medical grade plastics, or formed in accordance with other techniques known in the art.

Manifold 118 can also include a control (not shown), for controlling deployment of the occlusion device. The control may take any of a variety of forms depending upon the mechanical structure of the support. For example, the control can include a slider switch, which can connect to the inner catheter 120. Distal axial advancement of the slider switch can produce an axial advance of the connected feature. When the occlusion device advances from the distal end of the outer catheter 110, the occlusion device can move from the reduced diameter to the enlarged diameter.

Any of a variety of controls may be utilized, including switches, levers, rotatable knobs, pull/push wires, and others that will be apparent to those of skill in the art in view of the disclosure herein.

The outer catheter 110 can define a lumen through which the inner catheter 120 can move axially. The inner catheter 120 can include a proximal end 122 and a distal end 124. Similar to the outer catheter 110, the inner catheter 120 can include a manifold 126 disposed at the proximal end 122 of the inner catheter 120. The manifold 126 can be configured to control movement of the inner catheter 120, deployment of the occlusion device, and/or fluid flow through the inner catheter 120. The inner catheter 120 should be sufficiently long to deliver the occlusion device out of the distal end 114 of the outer catheter 110. Further, the inner catheter 120 can include a material exhibiting any of the material properties described in connection with the outer catheter 110.

The inner catheter 120 can define a lumen through which a conventional guide wire can move axially. In an alternate configuration, the outer catheter 110 can include a second lumen having a guide wire axially movable therein. In either scenario, the guide wire lumen should be sufficiently large to accommodate a guide wire 128 having a diameter between about 0.25 mm and about 0.5 mm. As shown in FIG. 1A, the guide wire 128 can include a hub 130 disposed at a proximal end of the guide wire 128.

Avoiding a tight fit between the guide wire 128 and inside diameter of guidewire lumen enhances the slideability of the delivery system 100 over the guidewire. In ultra-small diameter catheter designs, it may be desirable to coat the outside surface of the guidewire 128 and/or the inside surface of the inner catheter 120 with a lubricous coating to minimize friction as the inner catheter 120 is axially moved with respect to the guidewire 128. A variety of coatings may be utilized, such as Parylene, Teflon, silicone rubber, polyimide-polytetrafluoroethylene composite materials, or others known in the art and suitable depending upon the material of the guidewire or inner tubular wall.

The delivery system 100 can include different features depending on whether the occlusion device is self-expanding or balloon expandable. For example, if the occlusion device is balloon expandable, the inner catheter 120 can carry the occlusion device on a balloon (not shown).

Figures 1, 1B, 2, 3:
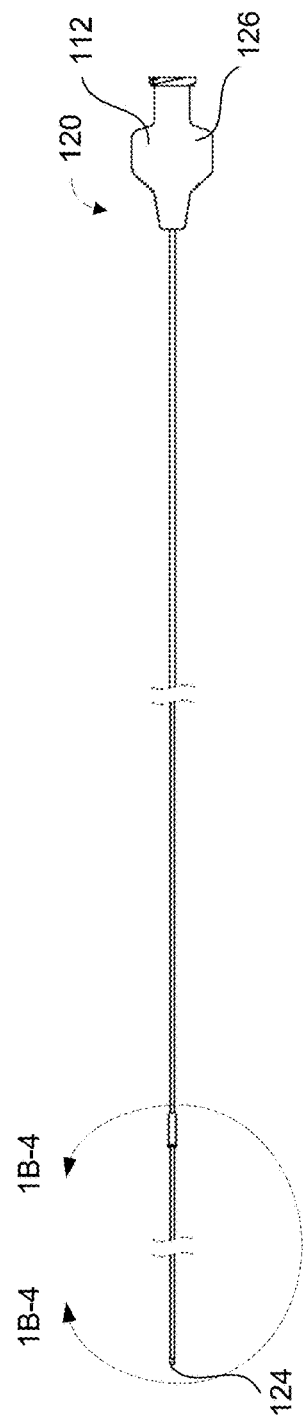
Figures 1, 1B, 2, 3, 4:
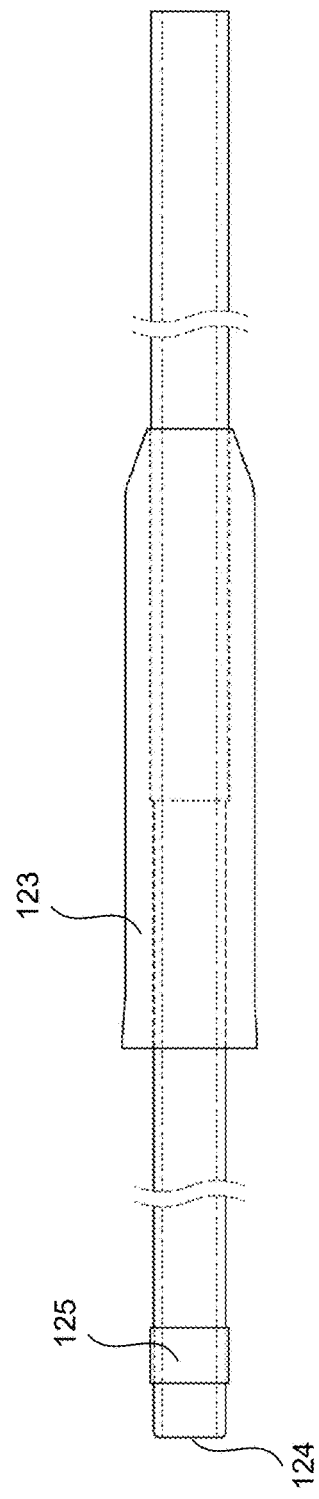

For example, if the occlusion device is self-expanding, the occlusion device can be constrained by a distal portion of the outer catheter 110, and the inner catheter 120 can push the occlusion device out from the distal end 114 of the catheter 110. As another example, as shown in FIG. 3F, the delivery system 100 can include a support tube 134 axially disposed between the outer catheter 110 and the inner catheter 120. The support tube 134 can move axially to push the occlusion device off the inner catheter 120. The force necessary to push the occlusion device off the inner catheter 120 can be less than or equal to about 5 N, for example, within about 0.25 N of about 4.5 N or within about 0.25 N of about 4.0 N.

Other conventional mechanisms can be used to release the occlusion device, including, but not limited to, a ratcheting mechanism, an electrolytically erodible attachment, involuted deployment, a threaded attachment, or other torque releasing attachment.

In some situations, it may be necessary to resheath the occlusion device to deliver the occlusion device to the target vessel. The delivery system 100 can be configured to resheath and reposition the occlusion device after deployment, but before release. Prior to release, the inner catheter 120 can be retracted to pull the occlusion device back into the outer catheter 110. The retraction force necessary to retract the occlusion device should be less than or equal to about 5 N, for example, between about 3 N and about 4 N, or between about 3.5 N and about 4.5 N. The interlock interference feature can have a dimension between about 0.15 mm and about 0.25 mm, for example, within about 0.02 mm of about 0.2 mm.

The delivery system 100 may further comprise other components, such as radiopaque fillers, colorants, reinforcing materials, reinforcement layers, such as braids and helical reinforcement elements, or the like. In particular, at least the proximal portion may be reinforced in order to enhance its column strength and torqueability while preferably limiting its wall thickness and outside diameter. Further, radiopaque markers may be positioned on the inner and/or outer catheters 120, 110 to monitor the delivery system 100 during the procedure.

Fluoroscopic guidance can be used to monitor the delivery of the occlusion device. For example, the delivery system can include radiopaque features that allow for their fluoroscopic visualization during delivery, deployment, and/or retraction. Usually, the delivery system can include marker bands or coiled wires disposed along one or more of the outer catheter 110, inner catheter 120, and the guide wire 128. The bands or coils can include a minimum thickness of at least about 0.02 mm and a minimum length of about 0.5 mm. Suitable marker bands can be produced from any number of a variety of materials, including platinum, gold, tantalum, and tungsten/rhenium alloy. Preferably, the radiopaque metal band will be recessed in an annular channel formed in the tubular body.

FIGS. 1B-1 and 1B-2 illustrate a possible embodiment the outer catheter 110 of the delivery system. The outer catheter permits contrast dye to be injected through the delivery system and can be used to determine the position of the occlusion device before detaching the occlusion device from the delivery system.

The outer catheter 110 can have a working length of about 120 cm or any other suitable working length described above. An internal diameter of the outer catheter 110 can be less than or equal to about 0.10 inches, such as about 0.05 inches. The distal end 114 of the outer catheter 110 can have a reduced diameter between about 0.02 inches and about 0.04 inches. The outer catheter 110 can include a plurality of openings 121 (e.g., at least two, five, six, eight, or more openings) disposed near a distal end 114 of the outer catheter 110, such that contrast dye can be released near the proximal side of the occlusion device. The placement of the openings 121 can remove the pressure of the contrast on the occlusion device to mitigate the likelihood of damaging the occlusion device prior to deployment (see FIG. 1B-2). For instance, the distal most opening 121' can be positioned less than or equal to about 2.0 inches from the distal end 114 or at a location that is between about 1.5% and 2.5% of the working length of the catheter from the distal end 114. The plurality of openings 121 can be positioned in a helical configuration spanning less than or equal to about 0.5 inches measured in an axial direction (e.g., about 0.3 inches, about 0.35 inches, or about 0.4 inches). Further, the plurality of holes 121 can be equally, axially spaced apart (e.g., less than about 0.10 inches, such as about 0.05 inches). In some embodiments, the contrast flow rate can be at least about 2 cc/second or at least about 5 cc/second under an infusion pressure of no more than about 500 psi, preferably no more than about 250 psi as measured under the Injection Protocol described herein. For example, the contrast flow rate can between about 2 cc/second and 5 cc/second under infusion pressures between about 100 psi and 200 psi or between about 100 psi and 150 psi, such as about 2.0 or 2.3 cc/min. Additionally, the openings 121 provide a sufficient flow rate to prevent the buildup of pressure distal to the openings 121 such that the occlusion device is not inadvertently deployed simply by injecting contrast. The flow rate through the openings 121 prevents a distal pressure higher than 50 psi when a 200 psi infusion pressure is applied or a distal pressure of no more than 10 psi.

FIGS. 1B-3 and 1B-4 illustrate a possible embodiment of the inner catheter 120. The inner catheter 120 can include manifold 126 that provides access to a lumen of the inner catheter 120. Further, the inner catheter 120 can include a pusher member 123. When the delivery system is assembled, the occlusion device can be positioned between the distal end 124 and the pusher member 123 of the inner catheter 120. The pusher member 123 can be used to push the occlusion device out of the outer catheter 110. As shown in FIG. 1B-4, the inner catheter 120 can also include a radiopaque marker 125 disposed near the distal end 124 of the inner catheter 120, so the user can monitor placement of the occlusion device.

Interlock Assembly with Resilient Members

It can be clinically desirable to assess the performance of the occlusion device prior to releasing the occlusion device from the delivery system 100. Thus, in some embodiments, as shown in FIGS. 1C-1 to 1C-3, the delivery system 100c (including one or more features of the delivery system 100) and the occlusion device 140 can include an interlock assembly 150 that allows the occlusion device 140 to be resheathed or repositioned. The interlock assembly 150 can removably secure the inner catheter 120c to the occlusion device 140. In some examples, the occlusion device 140 can resemble 1500 any of the occlusion devices described below.

The interlock assembly 150 can include one or more resilient members 152 and a corresponding number of recesses 154 (e.g., channels or grooves). As shown in FIG. 1C-3, the interlock assembly 150 can include a first resilient member 152a and a second resilient member 152b; however, more resilient members can be utilized (e.g., three or four). The resilient members 152 can extend from one of a reduced diameter portion (e.g., a proximal end 142) of the occlusion device 140 or a distal end of the inner catheter 120c, and the recesses 154 can be disposed on the other of the reduced diameter portion (e.g., the proximal end 142) of the occlusion device 140 or the distal portion 156 of the inner catheter 120c. When the recesses 154 are disposed on the distal portion 156 of the inner catheter 120c, a diameter of the distal end portion 156 can be greater than a remaining portion of the inner catheter 120c and less than or equal to a diameter of the proximal end 142 of the occlusion device 140 (see FIG. 1C-1). For example, as shown in FIG. 1C-1, the resilient members 152 can extend proximally from a proximal end 142 of the occlusion device 140, and the recesses 154 can be disposed at the distal end portion 156 of the inner catheter 120c.

As shown in FIG. 1C-3, the resilient members 152 can be biased toward an outward extending position. Further, the resilient members 152 can each have a Z-shape, such that a first end of a resilient member 152 is axially displaced from a second end of the resilient member 152. In certain variants, the resilient members 152 can have a T-shape, a lollipop shape, a Christmas tree shape, or any other suitable shape, which provides at least a first interference surface for engaging with a second complementary interference surface to releasably retain the occlusion device on the catheter.

Additionally, the shape of the recesses 154 can generally correspond to the shape of the resilient members 152, such that when the resilient members 152 are constrained within the outer catheter 110c, the resilient members 152 can engage the corresponding recesses 154.

The interlock assembly 150 maintains the inner catheter 120c and the occlusion device 140 in a locked configuration (see FIG. 1C-1) until the resilient members 152 are pushed beyond the distal end 114c of the catheter body 110c (see FIG. 1C-2). When the resilient members 152 are pushed beyond the distal end 114c of the catheter 110c, the resilient members 152 move back to the outward extending position, thereby releasing the occlusion device 140 from the inner catheter 120c (see FIG. 1C-3). Advantageously, the interlock assembly 150 allows the occlusion device 140 to be resheathed and repositioned so long as the resilient members 152 do not extend beyond the distal end 114c of the catheter 110c. Further, the interlock assembly 150 requires no additional movable members for actuation, which has a number of benefits, including, but not limited to, a reduced profile delivery system, a more flexible delivery system, fewer components for manufacturing, and fewer steps during the procedure.

Threaded Interlock Assembly

FIGS. 1D-1 and 1D-2 illustrate another embodiment of an interlock assembly 170 that can be used with delivery system 100d (including one or more features of the delivery system 100). The interlock assembly 170 can include a first threaded region 172 at a reduced diameter portion (e.g., a proximal portion 162) of an occlusion device 160 and a second, corresponding threaded region 174 at a distal portion 156 of the inner catheter 120d. For example, as shown in FIG. 1D-2, the first threaded region 172 can be disposed around an interior surface of the proximal portion 162 of the occlusion device 160, and the second region 174 can be disposed around an exterior surface of the distal end portion 176. An outer diameter of the distal portion 176 can be less than an interior diameter of the proximal portion 162 of the occlusion device 160, such that the second threaded region 174 can threadably engage the first threaded region 172.

The interlock assembly 170 can maintain the inner catheter 120d and the occlusion device 160 in a locked configuration (see FIG. 1D-2) until the inner catheter 120d is rotated counterclockwise and unscrewed from the occlusion device 160. Advantageously, the interlock assembly 170 allows the occlusion device 160 to be resheathed and repositioned so long as the inner catheter 120d remains threadably engaged with the occlusion device 160. Further, the interlock assembly 170 requires no additional movable members for actuation, which has a number of benefits, including, but not limited to, a reduced profile delivery system, a more flexible delivery system, fewer components for manufacturing, and fewer steps during the procedure.

Delivery System with Interlock Catheter

With reference to FIGS. 1E-1 to 1E-6, another illustrative embodiment of a delivery system is shown. Portions of the delivery system 100e resemble the delivery system 100 discussed above. Accordingly, numerals used to identify features of the delivery system 100 include an "e" to identify like features of the delivery system 100e (e.g., the outer catheter 110e can resemble the outer catheter 110).

Figures 1, 1E:
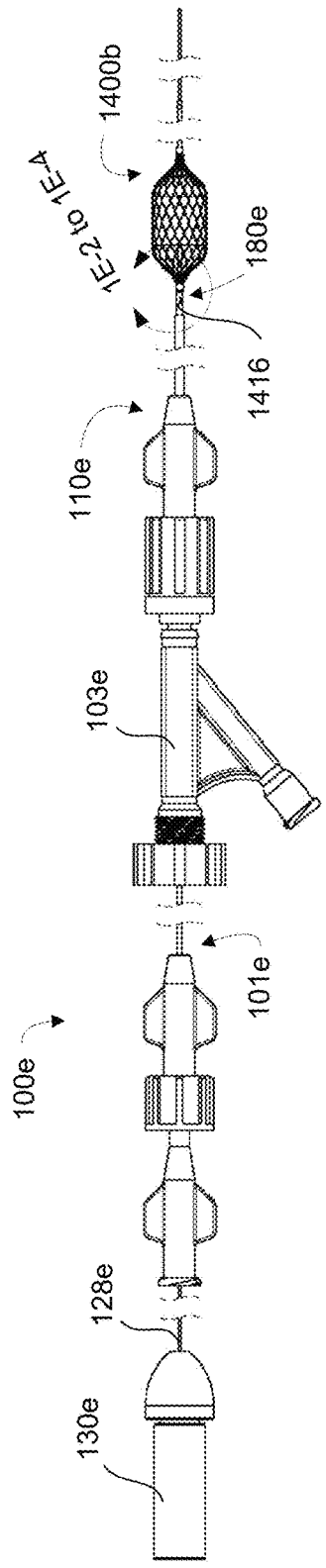
Figures 1, 1E, 2:
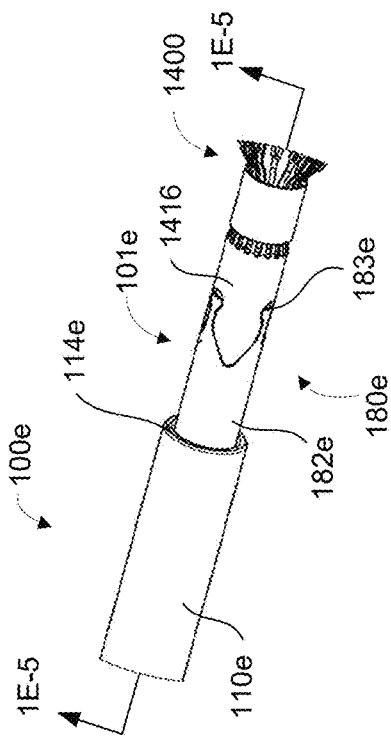

As shown in FIG. 1E-1, the delivery system 100e can include an interlock catheter 101e extending through the outer catheter 110e. The interlock catheter 101 can include an outer pusher 188e and an inner pusher 186e (see FIGS. 1E-5 and 1E-6). Further, a hemostasis valve 103e can form a seal between the outer catheter 110e and the interlock catheter 101e. For purposes of illustration, the delivery system 100e is described in connection with the occlusion device 1500 (described in further detail below); however, the delivery system 100e can be used with other occlusion devices, such as the occlusion device 1500.

Additionally, the interlock catheter 100e and the occlusion device 1500 can include an interlock assembly 180e. The interlock assembly 180e can include a key ring 182e that can be secured to a distal portion of the outer pusher 188e. As shown in FIG. 1E-2, an inner diameter of the key ring 182e can be greater than an outer diameter of the distal portion of the outer pusher 188e, such that the key ring 182e can be secured over the distal portion of the outer pusher 188e. Further, one or more locking tabs 183e (e.g., two, three, or four) can extend from a distal end of the key ring 182e. The locking tabs 183e can be biased inward toward the inner pusher 186e. Additionally, as shown in FIG. 1E-1, the locking tabs 183e can have a generally lollipop shape. Although, in other embodiments, the locking tab 183e can have a T-shape, Z-shape, Christmas Tree shape, or any other suitable shape.

The interlock assembly 180e can also include a locking drum 184e that is coaxial with the outer pusher 188e (see FIGS. 1E-5 and 1E-6). The locking drum 184e can be secured to the inner pusher 186e, and thus advanceable relative to the outer pusher 188e. To secure the interlock catheter 101e to the occlusion device 1500, the inner pusher 186e is advanced until the locking drum 184e pushes the locking tabs 183e outward into a corresponding interlock feature 1518 on a reduced diameter portion (e.g., a proximal collar 1516) of the occlusion device 1500 (see FIGS. 1E-2 and 1E-5). In this locked configuration, the occlusion device 1500 can be advanced through the outer catheter 110e using the interlock catheter 101e.

To release the occlusion device 1500 from the outer pusher 188e, the inner pusher 186e is advanced further until a proximal end of the locking drum 184e is distal to the locking tabs 183e (see FIG. 1E-3). In this configuration, the locking tabs 183e can return to the inward extending position such that the occlusion device 1500 can be detached from the outer pusher 188e (see FIGS. 1E-4 and 1E-6). Advantageously, the interlock assembly 180e allows the occlusion device 1500 to be resheathed and repositioned so long as the outer pusher 188 is secured to the occlusion device 1500.

Delivery System with Interlocking Attachment Member and Contrast Injection

FIGS. 2A to 2K illustrate a method of using another embodiment of a delivery system 200 having an interlocking attachment member 231 that interfaces with an occlusion device O. Portions of the delivery system 200 resemble the delivery system 100 discussed above. Accordingly, numerals used to identify features of the delivery system 100 are incremented by a factor of "100" to identify like features of the delivery system 200 (e.g., the outer catheter 210 can resemble the outer catheter 110).

Generally, the delivery system 200 can include an inner catheter 220 adapted to advance an occlusion device O (e.g., an hourglass-shaped occlusion device as described below) through the outer catheter 210 and into the target vessel (see FIG. 2A). The inner catheter 220 can include an interlocking attachment member 231 that enables the clinician to advance and retract the occlusion device O, so long as the proximal end of the occlusion device O remains constrained within the outer catheter 210 and interfaces within the interlocking attachment member 231 (see FIGS. 2L and 2M). When the proximal end of the occlusion device O is advanced distally of the distal end 214 of the outer catheter 210, the proximal end of the occlusion device O expands and releases from the interlocking attachment member 231 (see FIG. 2G). Advantageously, the interlocking attachment member 231 enables the clinician to assess the performance of the occlusion device O prior to releasing the occlusion device O from the delivery system 200.

Figure 2A:
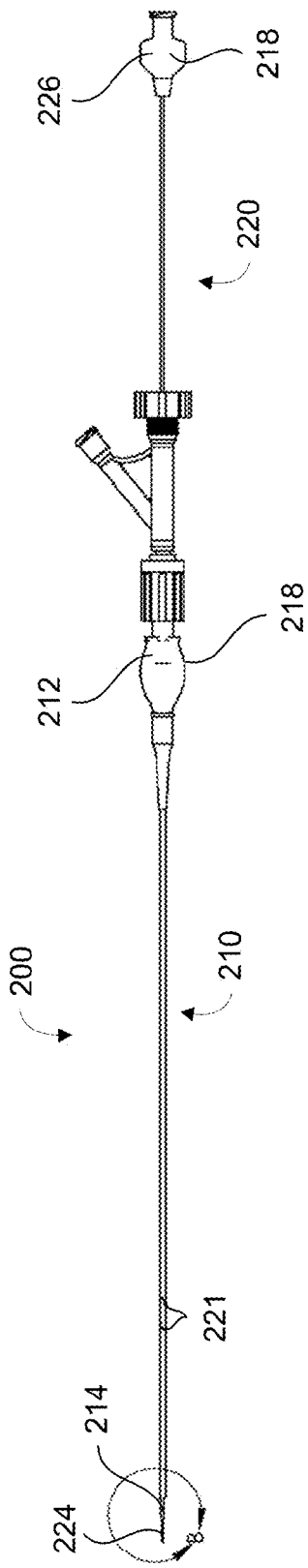
FIG. 2A illustrates another embodiment of a delivery system.
Figure 2B:
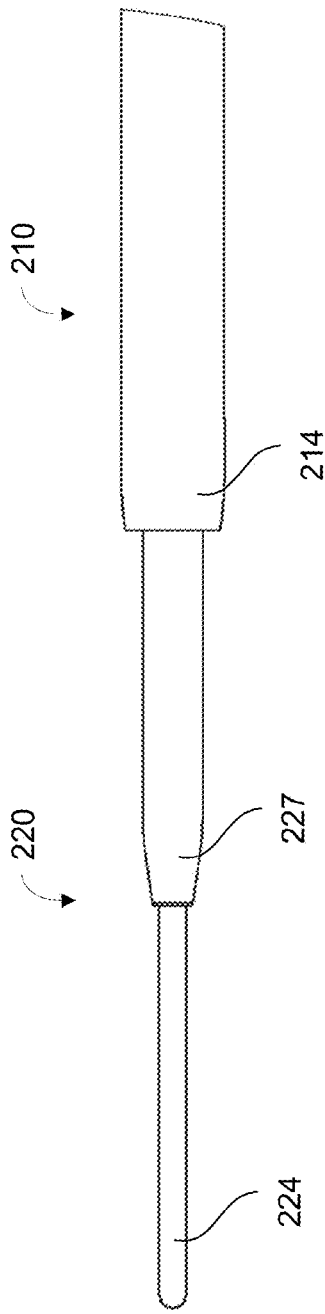
FIG. 2B illustrates an enlarged view of a distal portion of the delivery system shown in FIG. 2A through line B prior to deployment.

FIGS. 2A and 2B illustrates a fully assembled delivery system 200 with the inner catheter 220 extending through the outer catheter 210. To begin deployment, the distal lobe of the occlusion device D can be deployed. The occlusion device O can be deployed by advancing the inner catheter 220 relative to the outer catheter 210 (see FIGS. 2C and 2D). With only the distal lobe of the occlusion device D deployed, contrast injection can be delivered to confirm the position of the occlusion device O. Since the distal lobe of the occlusion device D is uncovered (e.g., bare metal struts), the occlusion device O does not occlude flow of the dye. As shown in FIGS. 2CC and 2DD, as the inner catheter 220 is advanced, a distal face of the interlock attachment member 231 interfaces with the occlusion device O at a location distal to the proximal end of the occlusion device O, such that the interlock attachment member 231 urges the occlusion device O in a distal direction.

Figure 2E:
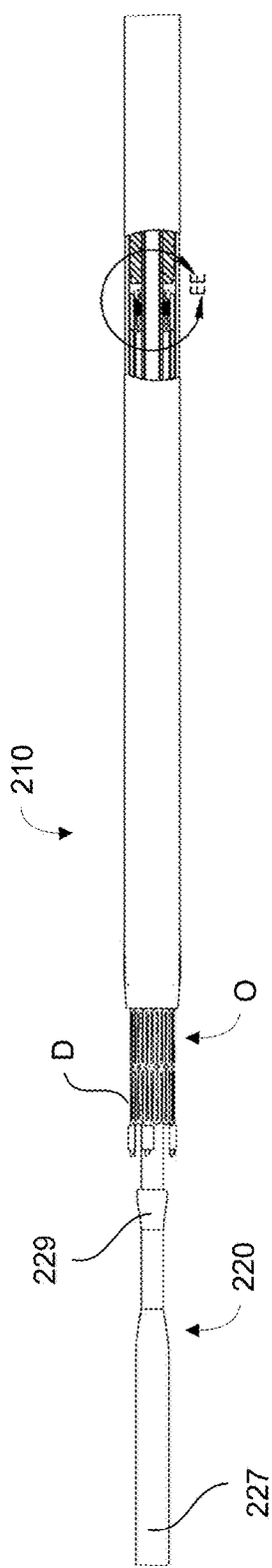
FIG. 2E illustrates the distal portion of the delivery system shown in FIG. 2A with the distal lobe of the occlusion device partially retracted.
Figure 2E:
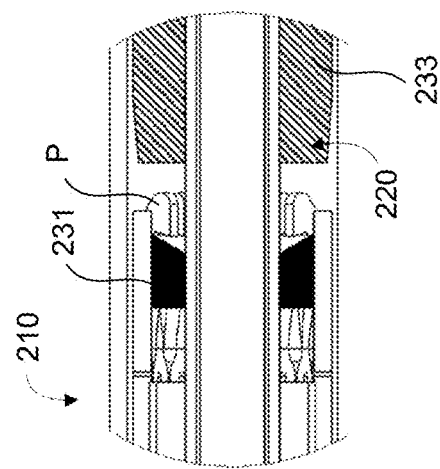

If the distal lobe D is improperly positioned, the inner catheter 220 can be retracted to retract the occlusion device O (see FIG. 2E). As shown in FIG. 2EE, as the inner catheter is retracted, a proximal face of the interlock attachment member 231 interfaces with the occlusion device O (e.g., proximal hooks of the occlusion device O), such that the interlock attachment 231 urges the occlusion device O in a proximal direction.

Figure 2G:
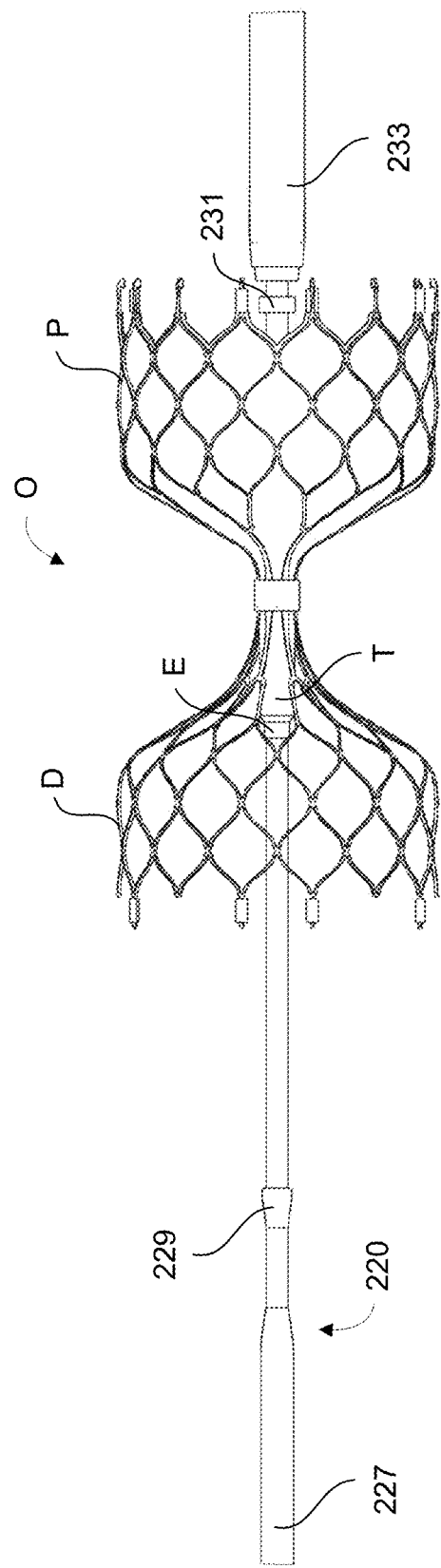
FIG. 2G illustrates the distal portion of the delivery system shown in FIG. 2A with the occlusion device fully deployed.
Figure 2K:
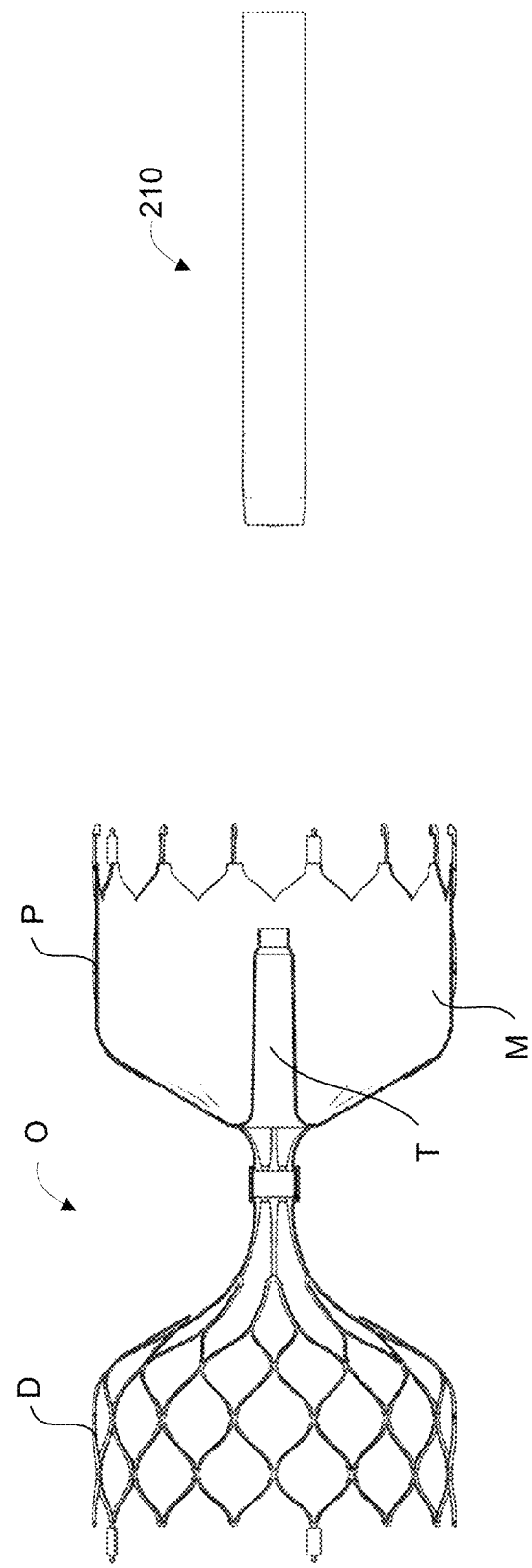
FIG. 2K illustrates a cross-section of the occlusion device shown in Figure JJ with the delivery system fully withdrawn from the occlusion device.

Once the distal lobe 1202e of the occlusion device 1200e is properly position, the remaining portion of the occlusion device can be deployed (see FIGS. 2F and 2G). Next, the inner catheter 220 can be retracted relative to the outer catheter 210 (see Figure H). As shown in FIG. 2HH, a proximal face of the ramp 229 is larger than an end portion E of the tubular membrane portion of the occlusion device T (e.g., a larger diameter or larger surface area). Consequently, as the inner catheter 220 is further withdrawn, the ramp 229 forces the tubular portion T to invert (see FIGS. 2I and 2II), such that a proximal portion of the tubular membrane portion T that is within the proximal lobe P begins to fold over a remaining portion of the tubular membrane portion T. Viewed another way, an inner surface of the tubular portion T becomes an external surface of the tubular portion T. During the inversion process, the tubular portion T moves from being positioned within the distal lobe D (see FIGS. 2H and 2HH) to being positioned within the proximal lobe P (see FIGS. 2J and 2JJ). Viewed another way, the tubular portion T moves from being external to a membrane cover M (see FIGS. 2H and 2HH) to being positioned within the membrane cover M (see FIGS. 2J and 2JJ). When the inner catheter 220 is fully removed from the occlusion device O (see FIG. 2K), the tubular portion T closes like a valve to prevent blood from flowing through the tubular portion T. The tubular portion T has sufficiently low collapse resistance such that when the delivery system 200' (and guidewire, if present) is removed, the tubular portion T collapses (e.g., kinks, folds, buckles, flops over, or likewise) into a closed position (see FIG. 12G).

Figure 2N:
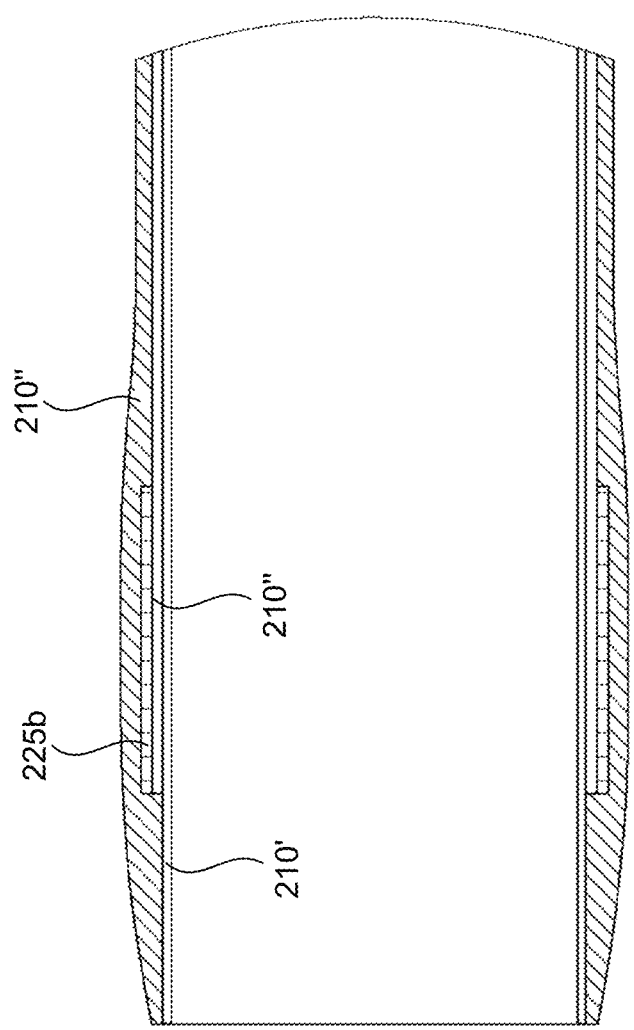
FIG. 2N illustrates a cross-section of a distal portion through line 2N of the outer catheter shown in FIG. 2M.

FIGS. 2L to 2N illustrate the outer catheter 210 of the delivery system 200. The outer catheter 200 permits contrast dye to be injected through the delivery system 200 and can be used to determine the position of the occlusion device before detaching the occlusion device from the delivery system 200.

The outer catheter 210 can have a working length of about 120 cm or any other suitable working length described above. An internal diameter of the outer catheter 210 can be less than or equal to about 0.10 inches, such as about 0.05 inches. A distal portion of the outer catheter 210 can be bulbous shaped if a marker band 225 is embedded within the outer catheter 210 (see FIG. 2N). As shown in FIG. 2N, the outer catheter 210 can include at least three concentric layers, e.g., an inner layer 210', an intermediate layer 210", and an outer layer 210′′′. The outer layer 210′′′ can be constructed from Pebax or other medical grade polymer materials. The intermediate layer 210′′ can be a stainless steel braid to reinforce the outer catheter 210. The inner layer 210′ can be constructed from PTFE or other suitable medical grade polymer materials. If present, the radiopaque marker 225 can be embedded radially between the outer layer 210′ and the intermediate layer 210′′.

The outer catheter 210 can include a plurality of openings 221 (e.g., at least two, five, six, eight, or more openings) disposed near a distal end 114*h* of the outer catheter 210, such that contrast dye can be released near the proximal side of the occlusion device (see FIG. 2M). The placement of the openings 221 can remove the pressure of the contrast on the occlusion device to mitigate the likelihood of damaging the occlusion device prior to deployment. For instance, the distal most opening 221′ can be positioned less than or equal to about 2.0 inches from the distal end 114*h* or at a location that is between about 1.5% and 2.5% of the working length from the distal end 114*h*. The plurality of openings 221 can be positioned in a helical configuration spanning less than or equal to about 0.5 inches measured in an axial direction (e.g., about 0.3 inches, about 0.35 inches, or about 0.4 inches). Further, the plurality of holes 221 can be equally, axially spaced apart (e.g., less than about 0.10 inches, such as about 0.05 inches). The contrast flow rate can be at least about 2 cc/second or at least about 5 cc/second under an infusion pressure of no more than about 500 psi, preferably no more than about 250 psi as measured under the Injection Protocol described herein. For example, the contrast flow rate can between about 2 cc/second and 5 cc/second under infusion pressures between about 100 psi and 200 psi or between about 100 psi and 150 psi, such as about 2.0 or 2.3 cc/min. Additionally, the openings 221 provide a sufficient flow rate to prevent the buildup of pressure distal to the openings 221 such that the occlusion device is not inadvertently deployed simply by injecting contrast. The flow rate through the openings 221 prevents a distal pressure higher than 50 psi when a 200 psi infusion pressure is applied or a distal pressure of no more than 10 psi.

Figure 2O:
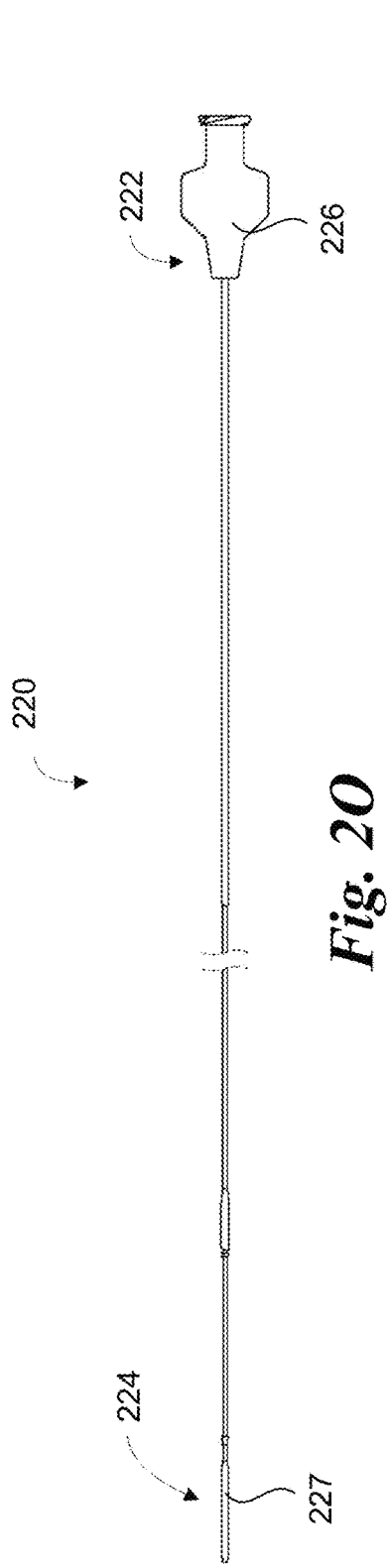
FIG. 2O illustrates the outer catheter of the delivery system shown in FIG. 2A for contrast dye injection.
Figure 2P:
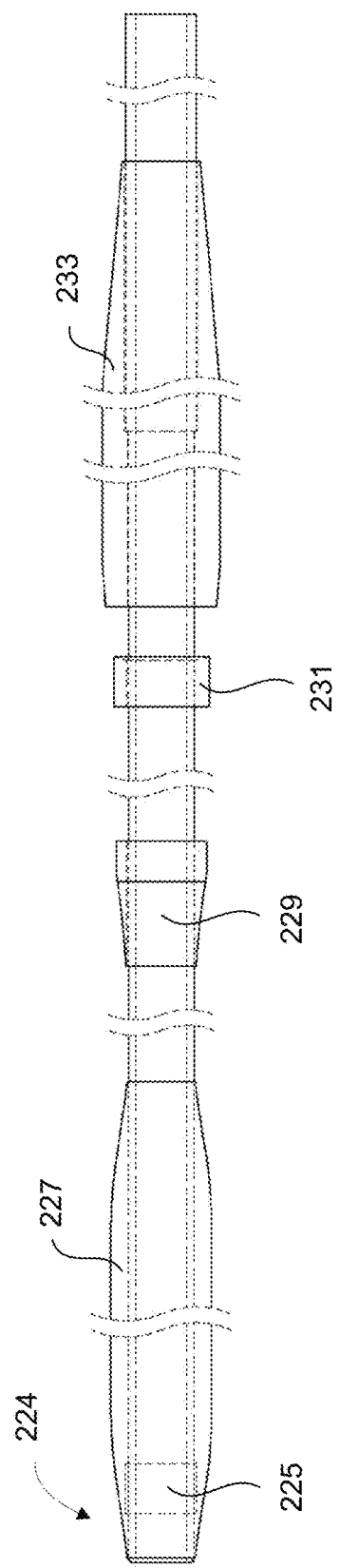
FIG. 2P illustrates an enlarged view of a working length of the outer catheter shown in FIG. 2O.

FIGS. 2O and 2P illustrate the inner catheter 220 of the delivery system 200. The inner tubular body 220 has a proximal end 222 and a distal end 224. A proximal hub 226 can be positioned at the proximal end 222 of the inner catheter 220 to provide access to a lumen of the inner catheter 220. A pusher tip 227 can be positioned at the distal end 224 of the inner catheter 220. The pusher tip 227 can be tapered at a distal and/or a proximal portion of the pusher tip 227, with a uniform diameter section therebetween. If the pusher tip 227 and the inner catheter 220 are separate components, a radiopaque marker 225 can be positioned radially between the pusher tip 227 and the inner catheter 220.

As shown in FIG. 2P, a distal ramp 229 can be positioned proximal to the pusher tip 227. The distal ramp 229 can be tapered in a distal direction. As explained in further detail below, when the delivery system 200 is used with an hourglass-shaped occlusion device having a tubular membrane portion (as described below), the ramp 229 can invert a tubular section of an occlusion membrane as the inner catheter 220 is retracted through the occlusion device.

As mentioned above, the delivery system 200 can include an interlocking attachment member 231 positioned proximal to the distal ramp 229. As shown in FIG. 2P, the interlocking attachment member 231 can be ring-shaped. The interlocking attachment member 231 can interface with an occlusion device having proximal hooks, barbs, or the like (see e.g., occlusion device 1200*e*). The proximal hooks of the occlusion device can interface with the interlocking attachment member 231 so long as the proximal end of the occlusion device remains constrained within the outer catheter 210. The outer catheter 210 constrains the proximal end of the occlusion device, thereby allowing the occlusion device to interface with the interlocking attachment member 231.

The length of the proximal hooks of the occlusion device and the length of the interlocking attachment member 231 can be optimized to provide a controlled amount of axial clearance in between proximal hooks of the occlusion device and the interlocking attachment member 231 (see FIGS. 2DD and 2EE). When the inner catheter 220 advances the occlusion device distally, the interlocking attachment member 231 pushes on a portion of the occlusion device distal to the proximal end of the occlusion device but does not engage the proximal hooks of the occlusion device (see FIG. 2DD). The axial clearance enables the proximal end of the occlusion device to expand when advanced out of the outer catheter 210. Prior to the proximal end of the occlusion device being advanced distally of the distal end of the outer catheter 210, retracting the inner catheter 220 causes the interlocking attachment member 231 to engage the proximal hooks and retract the occlusion device (see FIG. 2EE).

As shown in FIG. 2P, a proximal coupler 233 can be positioned proximal to the interlocking attachment member 231. The proximal coupler 233 can be tapered in a proximal direction. The proximal coupler 233 can prevent the occlusion device from moving proximally prior to deployment.

Figures 2Q, 2R:
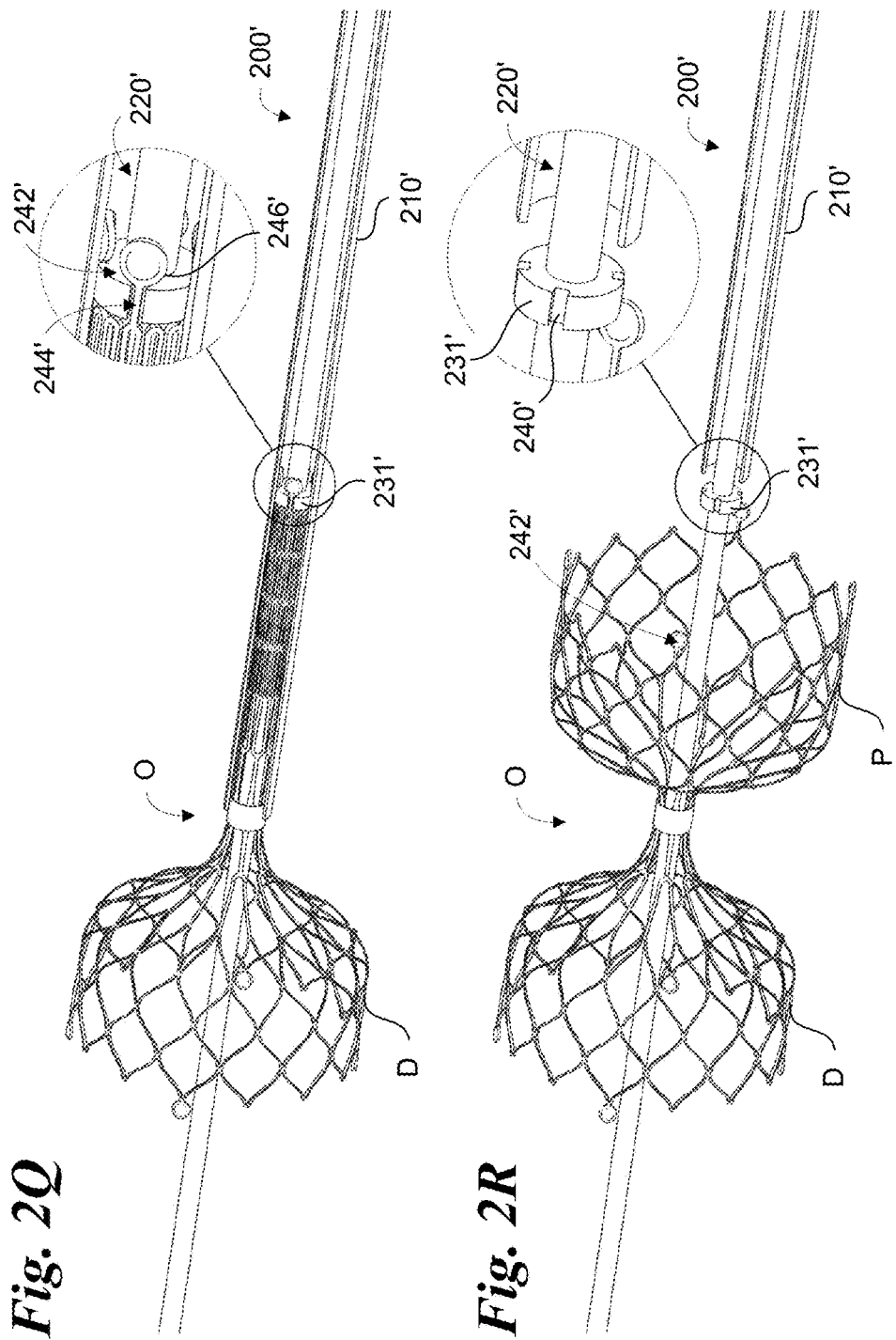
FIG. 2Q illustrates another deployment system having an interlock attachment member interfacing with an occlusion device.
FIG. 2R illustrates another deployment system having an interlock attachment member released from the occlusion device.

FIGS. 2Q and 2R illustrate another delivery system 200′. Portions of the delivery system 200′ resemble the delivery system 200 discussed above. Accordingly, numerals used to identify features of the delivery system 200 are include an apostrophe (′) to identify like features of the delivery system 200′ (e.g., the outer catheter 210′ can resemble the outer catheter 210).

The interlock attachment member 231′ can have a number of longitudinally extending grooves 240′ (indentations, openings, or the like) circumferentially positioned around the interlock attachment member 231′. These grooves 240′ are shaped to receive a neck portion 244′ of a marker 242′ (see FIG. 2Q).

As shown in FIG. 2R, at least a proximal lobe P of the occlusion device O can include a number of markers 242′. Each of these markers 242′ can include an aperture 246′ (eyelet, opening, or the like) and a neck portion 244′. These markers 242′ can be press-fit onto the strut endings of the proximal lobe P. The markers 242′ can be radiopaque to facilitate visualization of the occlusion device O.

The method of delivering the occlusion device O is similar to the method described in FIGS. 2A to 2K. Prior to full release (see FIG. 2Q), the occlusion device O can be retracted and repositioned. The occlusion device O is configured to interface with the interlock attachment member 231′ until a proximal end of the occlusion device O has been released from the delivery system 200′ (see FIG. 2R).

Occlusion Device

The occlusion devices described herein can include an expandable structure configured to move between an unexpanded or constrained configuration and an expanded or unconstrained or enlarged configuration. The expandable structure can include any of a number of medical grade materials, including, but not limited to, polymers (e.g., PET) or non-ferrous metals (e.g., nitinol, stainless steel, or cobalt chrome).

The expansion ratio of the expandable structure should be sufficiently large such that the occlusion device is capable of compressing to a minimum size suitable for delivery through a catheter having an outer diameter of 6 F (i.e., 2.0 mm) or less, thereby minimizing trauma to the vessel during delivery. Further, the expansion ratio should be sufficiently large such that a single, expanded occlusion device is capable of preventing substantially all fluid from flowing past the occlusion device in vessel range of different sized target vessels. Although, additional occlusion devices (e.g., two or three) can be delivered depending on clinical judgment.

The expandable structure can be configured to include an expansion ratio that is at least about 3:1, at least about 5:1, preferably at least about 7:1, and more preferably at least about 8:1. In some examples, the expansion ratio can be about 7:1 or about 8:1. In other words, a diameter of the expandable structure in the expanded configuration can be at least about three times, at least about five times, preferably at least about seven times, and more preferably at least about eight times, a diameter of the expandable structure in the unexpanded configuration. For example, the diameter of the expandable structure in the expanded configuration can be between about three times and about nine times greater, preferably at least about seven times greater, than the diameter of the expandable structure in the unexpanded configuration. In some examples, the diameter of the expandable structure can be at least about seven times or about eight times greater than a diameter of the expandable structure in the unexpanded configuration.

As described above, the delivery system preferably has a sufficiently small diameter to avoid causing damage to the vessel wall during delivery. Therefore, the occlusion device should be configured for delivery through a catheter having an outer diameter that is less than 7 F (2.3 mm), preferably less than 6 F (2.0 mm), for example 5F (1.67 mm), 4 F (1.33 mm), or 3 F (1.0 mm). In the unexpanded configuration, the occlusion device can include an outer diameter that is less than or equal to about 2 mm or less than or equal to about 1.75 mm, preferably less than or equal to about 1.5 mm. For example, the outer diameter of the occlusion device in the unexpanded configuration can be within about 0.5 mm, or within about 0.25 mm, of about 1.25 mm. Further, a length of the occlusion device in the unexpanded configuration can be less than or equal to about 3 cm or less than or equal to about 2.5 cm, for example, within about 0.5 cm of about 2 cm.

As explained in further detail below, the expandable structure can include one or more strands braided to form the expandable structure. Each strand can include a diameter between about 0.025 mm and about 0.05 mm. In the unexpanded configuration, the braided expandable structure can include a pore size of no more than about 1.5 sq. mm, preferably no more than about 1.25 sq. mm, for example, within about 0.25 sq. mm of about 1.0 sq. mm. Further, in the unexpanded configuration, the braided strands can form intersecting angles between about 70 degrees and about 130 degrees, for example, between about 70 degrees and 90 degrees, between about 80 degrees and about 100 degrees, between about 90 degrees and about 110 degrees, between about 100 degrees and about 120 degrees, or between about 110 degrees and about 130 degrees.

An expanded diameter of the expandable structure can vary depending on the application of the occlusion devices. For example, the diameter can vary depending on whether the occlusion device is delivered within a renal vessel, a cardiovascular vessel, a pulmonary vessel, a neurovascular vessel, or otherwise. In any of these vessels, the expanded configuration must have an acceptable diameter, length, and radial outward forces to maintain proper vessel wall apposition and resist migration. In some implementations, the aspect ratio between the expanded diameter and the expanded length can be less than or equal to about 1:1, such as 1:2, or the length can be proportionally longer depending on the desired application.

In the unconstrained expanded configuration, a maximum diameter of the occlusion device can be between about 1.0 to about 1.5 times or more a diameter of the target site in a vessel. In some applications, the occlusion device can expand to a diameter between about 5.0 mm and about 11 mm, for example, within about 0.5 mm of each of about 6.0 mm, 7.0 mm, 8.0 mm, 9.0 mm, or 10.0 mm. In some applications, the expanded diameter can be between about 4.0 mm and about 6.0 mm, for example, within about 0.5 mm of about 4.5 mm. In other applications, the expanded diameter can be between about 2.0 mm and about 3.0 mm, for example, within about 0.25 mm of about 2.5 mm.

For example, in neurovascular applications, the expanded diameter can be between about 1.5 mm and about 4.0 mm, for example, within about 0.5 mm of each of about 2.0 mm, 2.5 mm, 3.0 mm, or 3.0 mm. Each of these occlusion devices can be delivered through a catheter having an internal diameter of less than or equal to about 0.7 mm (0.027"). The expansion ratio can be at least about 5:1, for example, between about 5:1 and 5.5:1 or between about 5.5:1 and about 6:1, such as about 5.8:1.

In some peripheral applications, the expanded diameter can be between about 4.0 mm and about 6.0 mm, for example, within about 0.25 mm of each of about 4.25 mm, 4.5 mm, 4.75 mm, 5.0 mm, 5.25 mm, 5.5 mm, or 5.75 mm. Each of these occlusion devices can be delivered through a catheter having an internal diameter of no more than about 1.0 mm (0.038"). The expansion ratio can be at least about 5:1, preferably at least about 6:1, for example, between about 6:1 and about 7:1, such as about 6.2:1.

In other peripheral applications, the expanded diameter can be between about 7.0 mm and about 12.0 mm, for example, within 0.5 mm of each of about 7.5 mm, 8.0 mm, 8.5 mm, 9.0 mm, 9.5 mm, 10.0 mm, 10.5 mm, 11.0 mm, or 11.5 mm. Each of these occlusion devices can be delivered through a catheter having an outer diameter of less than or equal to about 2.0 mm, for example, between about 1.5 mm and about 2.0 mm (e.g., 1.67 mm (5 F)).

The expanded length should be between about 0.5 times and about 1.5 times the diameter of the target vessel, or greater depending on the desired performance. In some applications, the expanded length can be between about 2.5 mm to about 7.5 mm, for example, between about 4.0 mm to about 6.0 mm, or within about 0.5 mm of about 5.0 mm. In some applications, the expanded length can be between about 2.0 mm to about 6.0 mm, for example, between about 3.0 mm and about 5.0 mm, or within about 0.5 mm of about 4.5 mm. In some applications, the expanded length can be between about 1.0 mm and about 3.0 mm, for example, within about 0.5 mm of about 2.5 mm.

In some applications, the expanded lengths can vary from 1 cm to 5 cm (e.g., from 1 cm to 4 cm, from 2 cm to 5 cm, from 2 cm to 4 cm, overlapping ranges thereof, 1 cm, 1.5 cm, 2 cm. 2.5 cm, 3 cm, 3.5 cm, 4 cm, 4.5 cm, 5 cm), and the expansion diameter can vary from 1 mm to 6 mm (e.g., from 1 mm to 4 mm, from 2 mm to 6 mm, from 3 mm to 5 mm, overlapping ranges thereof, 1 mm, 2 mm, 3 mm, 4 mm, 5 mm, 6 mm) depending on the vessel to be addressed. In some applications, the expandable structure can be configured to expand to diameters larger than 5 mm (e.g., 6 mm, 7 mm, 8 mm, 9 mm, 10 mm) or less than 2 mm (e.g., 1.8 mm, 1.6 mm, 1.4 mm, 1.2 mm, 1.0 mm).

As shown in at least FIGS. 7A to 10B, in some instances, one or both ends of the occlusion device can be tapered. A proximal end which tapers down in diameter in the proximal direction can be useful to facilitate retraction. For example, an angle of a proximal tapered end can be less than or equal to about 45 degrees, for example, between about 15 degrees and about 30 degrees or between about 30 degrees and about 45 degrees.

Clinically, it can be desirable for the occlusion device to exert sufficient radial outward pressure to maintain proper vessel wall apposition and resist migration of the occlusion device after deployment. The occlusion device can have an average COP across a diameter between about 2.5 mm and about 8.0 mm (e.g., a diameter between about 3.0 mm and about 8.0 mm) of between about 20 mmHg and about 250 mmHg, such as between about 30 mmHg and about 140 mmHg, between about 30 mm Hg and 80 mmHg, between about between about 70 mmHg and 100 mmHg, between about 90 mmHg and 120 mmHg, or between about 100 mmHg and 140 mmHg. The occlusion devices described herein can exert a radial outward pressure between about 30 mmHg and about 50 mmHg, for example, between about 30 mmHg and about 40 mmHg, between about 35 mmHg and about 45 mmHg, or between about 40 mmHg and about 50 mmHg at the diameter of an intended target site in a vessel. In some instances, a proximal end of the occlusion device can include features to cause radial outward force to increase at the center of the occlusion device without traumatizing the vessel. The radial outward force at the center of the occlusion device can increase by up to 20 mmHg, for example, between about 10 mmHg to about 15 mmHg, or between about 15 mmHg and about 20 mmHg.

The expandable structure should include a wall pattern configured to facilitate proper vessel wall apposition and resist migration after delivery. At the same time, the wall pattern preferably permits the occlusion device to be collapsed inside the delivery system without negatively impacting trackability and accurate deployment. In general, the wall pattern can include struts that run diagonal or perpendicular to blood flow to maintain proper vessel wall apposition and resist migration. For example, the occlusion device can include a wall pattern configured such that a backpressure generated from the blood flow can help stabilize the occlusion device without causing trauma to the vessel wall. In some instances, the wall pattern can be substantially uniform along an entire length of the expandable structure. In some instances, the wall pattern can vary between the first and second end portions and the middle portion. In some instances, the density of the wall pattern can vary across the length of the occlusion device, for example, the pore size of the occlusion device can gradually increase across the length of the occlusion device or towards both ends from the center.

In any of these wall patterns, the pore size should be sufficiently large to maintain proper vessel wall apposition and resist migration. For example, the expanded average pore size can be greater than or equal to about 0.75 sq. mm, for example, within about 0.25 sq. mm of about 1.0 sq. mm, within about 0.5 sq. mm of about 1.25 sq. mm, or within about 0.5 sq. mm. of about 4.5 sq. mm.

Other methods for reducing migration can include incorporating one or more anchors, such as barbs, hooks, or likewise, along any portion of the occlusion device, preferably an uncovered bare strut portion, such as the middle portion or one of two end lobes of the occlusion device.

As another example, if the occlusion device is braided, the occlusion device can include one or more exposed strands or strand ends. The braided occlusion device can include one or more strands each having strand ends. At least some of those strand ends can remain exposed and can be configured to anchor the occlusion device to the vessel wall. In other words, at least some of the strand ends can be secured to another of the strand ends, looped backed and secured to the same strand, or otherwise transformed to an atraumatic end, while at least some other of the strand ends can remain unsecured and can be configured to anchor the occlusion device to the vessel wall. These unsecured strand ends can be disposed anywhere along the occlusion device, for example, at least at one of the first and second end portions.

It can also be desirable to encourage endothelial growth or the formation of blood clots to ensure the permanency of the occlusion device. For example, the occlusion device can be coated with a substance to promote endothelial growth or the formation of clots. In some instances, the occlusion device can be coated with a chemical sclerosing agent. In some instances, the occlusion device can be coated with a liquid embolic (e.g., cohesives (i.e., Onyx) or adhesives (i.e. n-BCA).

The occlusion device can be configured to occlude substantially all fluid flow through a vessel using a single occluder, although multiple occlusion devices can be delivered. Further, the single occluder can be configured to immediately occlude fluid flow through the vessel using a single occluder (e.g., upon expansion). Substantial occlusion can include occluding at least about 80%, at least about 85%, at least about 90%, at least about 95%, or at least about 98% of fluid flow through the vessel.

As described below, the occlusion device can include a cover at least partially covering the expandable structure. The cover can include a cover material including, but not limited to, PTFE, PET, silicone, latex, TecoThane, nylon, PET, Carbothane (Bionate), fluoropolymers, SIBS, TecoFlex, Pellethane, Kynar, or PLGA.

The cover should be substantially impermeable to blood with a biostability for at least about two weeks. Preferably, the permeability is less than about 0.1 mL/sq. cm/min. In some instances, the cover can include a pore size of less than or equal to about 0.075 sq. mm. In some instances, the cover has less than or equal to about 20 percent open area, less than or equal to about 15 percent open area, or within about 2 percent of each of about 10 percent, 12 percent, 14 percent, 16 percent, or 18 percent. Further, the cover should include sufficient elasticity and lubricity to permit the occlusion device to be deployed in catheters having An outer diameter of less than or equal to about 6 F (2.0 mm) or less than or equal to about 5 F (1.67 mm) and expand to a diameter at least about 2.5 mm and/or less than or equal to about 8.0 mm. In some instances, the cover can be electronically charged or chemically modified to promote thrombogenicity. However, the covering material may be coated with a material to inhibit thrombus formation temporarily (i.e. hydrophilic coating) so that the device can be retracted and repositioned prior to final placement. In addition, the cover should have sufficient tensile strength to resist yielding, stretching, or breaking under at least normal blood pressures. For example, the cover should be able to withstand pressures of at least about 140 mmHg, preferably at least about 160 mmHg.

The length of the fibers creating the covering material allows the elongation of the covering material to far greater with less force (0.25-0.75×) than that of the native cover materials described above of the same thickness. The length of the fibers can be between about 5 microns and about 25 microns, such as within about 5 microns of each of about 10 microns, 15 microns, or 20 microns, although greater lengths may be used depending on desired parameters. These lengths permit the elongate of the cover material to at least two times greater. In some cases, the elongation is between about two times greater and about five times greater, for example, about three times greater or about four times greater. This elongation occurs with less than or equal to about 75 percent, less than or equal to about 50 percent, or even about 25 percent of the force necessary for native cover materials described above having the same thickness (e.g., between about 10 and about 30 microns).

It can be desirable for the cover to include a thickness that is sufficiently large to resist perforation during and after delivery, but sufficiently thin to minimize the diameter of the occlusion device in the unexpanded configuration and the diameter of the delivery device. Preferably, the thickness of the cover is less than or equal to about 30 microns, for example, within about 5 microns of each of about 15 microns, 20 microns, or 25 microns.

The cover can surround at least a portion of the expandable structure. The surrounded portion of the expandable structure should be sufficiently large to prevent fluid from flowing past the occlusion device when the occlusion device is expanded in the vessel. For example, the cover can surround the entire circumference of a covered portion of the expandable structure. Further, the cover can surround the expandable structure such that at least one end of the occlusion device is substantially closed. As shown in FIGS. 9B and 9C, the cover may only surround one of the first or second end portions of the expandable structure. In some instances, a length of the covered portion can be between about approximately 15 percent and about 35 percent of a diameter of the target vessel or the expanded occlusion device, for example, approximately 25 percent of a diameter of the target vessel or the expanded occlusion device. In other examples, as shown in at least FIG. 7A, the cover can surround the first end portion and the second end portion of the expandable structure, but leave a middle portion uncovered. In yet other examples, as shown in at least FIG. 7B, the cover can surround substantially the entire expandable structure.

In some clinical scenarios, it can be more desirable to cover only a portion of the expandable structure, such that at least the middle portion remains uncovered. The exposed wall pattern of the expandable structure can help maintain proper vessel wall apposition and resist migration of the occlusion device.

The expandable structure can be coated with the cover using an electrospinning process. Electrospinning refers generally to processes involving the expulsion of flowable material from one or more orifices, and the material forming fibers are subsequently deposited on a collector. Examples of flowable materials include dispersions, solutions, suspensions, liquids, molten or semi-molten material, and other fluid or semi-fluid materials. In some instances, the rotational spinning processes are completed in the absence of an electric field. For example, electrospinning can include loading a polymer solution or dispersion, including any of the cover materials described herein, into a cup or spinneret configured with orifices on the outside circumference of the spinneret. The spinneret is then rotated, causing (through a combination of centrifugal and hydrostatic forces, for example) the flowable material to be expelled from the orifices. The material may then form a "jet" or "stream" extending from the orifice, with drag forces tending to cause the stream of material to elongate into a small diameter fiber. The fibers may then be deposited on a collection apparatus.

Further information regarding electrospinning can be found in U.S. Publication No. 2013/0190856, filed Mar. 13, 2013, and U.S. Publication No. 2013/0184810, filed Jan. 15, 2013, which are hereby incorporated by reference in their entirety.

To facilitate occlusion of the target vessel site, the occlusion device in an over the wire embodiment should include a sufficiently small residual guide wire hole after deployment or a valve for occluding the guidewire opening. After full deployment, the occlusion device should include a residual guidewire hole having a diameter of less than or equal to about 0.25 mm. However, prior to deployment, the guide wire hole must be sufficiently large in both the unexpanded and expanded configuration to accommodate a standard guide wire having a diameter of at least about 0.25 mm, preferably at least about 0.4 mm.

Any of the occlusion devices described herein can include a number of radiopaque features that permit the fluoroscopic visualization of the occlusion device during one or more of delivery, deployment, post-deployment, and retraction. The marker bands can be positioned along the expandable structure. The marker bands can have a thickness of at least about 0.01 mm and a length of at least about 0.1 mm. Suitable marker bands can be produced from any number of a variety of materials, including platinum, gold, tantalum, and tungsten/rhenium alloy.

Turning to the figures, FIGS. 3A-3F illustrate the delivery system including any of the features of the delivery system 100 shown in FIGS. 1A and 1B. The delivery system can be used to deliver the occlusion device 300. As shown in the figures, the occlusion device can include a braided expandable structure having a tulip shape (e.g., laser cut with a woven pattern or braided from a plurality of strands). In other words, a diameter of a first end portion 302 can be smaller than a diameter of a second end portion 304. Further, a diameter of the middle portion 306 can be greater than the diameter of the first end portion 302, but smaller than the diameter of the second end portion 304. The diameter can gradually decrease from the second end portion 304 to the first end portion 302.

As shown in FIG. 3D, the occlusion device 300 can include a cover 308 surrounding at least the first end portion 302. The cover 308 can surround the entire circumference of the first end portion 302 and close the first end such that fluid cannot flow through the first end portion 302. In some instances, the cover 308 can surround at least 20 percent of a length of the expandable structure, for example, between about 20 percent and about 40 percent or between about 30 percent and about 50 percent of the length of the expandable structure. Although, in other embodiments, the cover 308 can surround substantially the entire expandable structure, leaving a second end opened or substantially closed.

As shown in FIG. 3F, the occlusion device 300 can include a central hub 310 for engaging the inner catheter 120 prior to delivery. If the occlusion device 300 is formed from a plurality of braided wire strands, the central hub can also be configured to secure the strand ends of the braided wire strands. Although the occlusion device 300 is described with the central hub 310, a central hub 310 is not necessary, and the inner catheter 120 may carry the occlusion device 300 without the central hub 310. Further, if the occlusion device 300 is formed from a plurality of braided wire strands, the braided wire strands can be heat-treated to maintain the position of the heated strands, or the strand ends can be secured to each other.

FIGS. 4A-4G illustrate the delivery system including any of the features of the delivery system 100 shown in FIGS. 1A and 1B. The delivery system can be used to deliver the occlusion device 400. As shown in the figures, the occlusion device can include a braided expandable structure having a substantially cylindrical or barrel shape (e.g., laser cut with a woven pattern or braided from a plurality of strands). In other words, a diameter of a first end portion 402 can substantially the same as a diameter of a second end portion 404. In some instances, a diameter of the middle portion 406 can substantially the same as the diameters of the first end portion 402 and the second end portion 404. In other instances, a diameter of the middle portion 406 can be no more than about 25 percent larger, or no more than about 10 percent larger, than the diameters of the first and second end portions 402, 404.

The occlusion device 400 can include a diamond wall pattern across the length of the occlusion device. As shown in FIG. 4D, the first and second end portions 402, 404 can include a different wall pattern than the middle portion 406. For example, the percentage of open area of the first and second end portions 402, 404 can be greater than the percentage of open area of the middle portion 406. Although, in other examples, the wall pattern can be substantially the same across a length of the occlusion device 400.

The first and second ends can each include a diamond pattern. Further, each end can include an inner band 412 of strand portions and an outer band 414 of strand portions. Each band 412, 414 can form the same number of apexes and form a diamond pattern therebetween. The inner band 412 can define a guide wire opening 416 at the center of the inner band 412, through which a guide wire can pass.

Figure 4G:
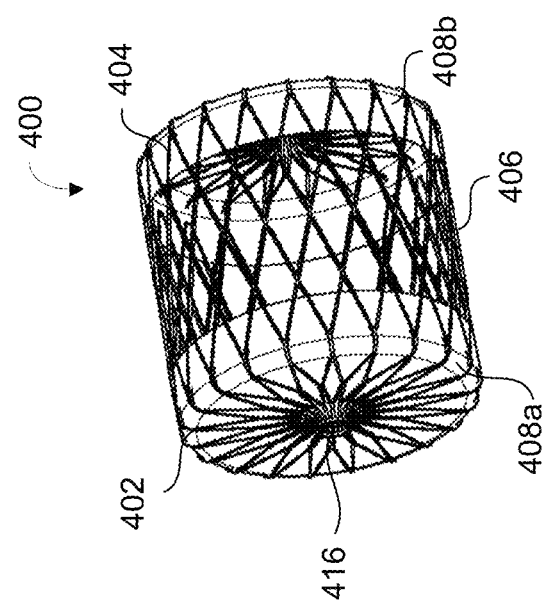
FIG. 4G illustrates an enlarged view of the occlusion device shown in FIGS. 4A-4F.

The occlusion device 400 can include a cover surrounding at least one of the first and second end portions 402, 404. The cover can surround the entire circumference of the first end portion 402 and/or second end portion 404 and substantially close the first and/or second ends such that fluid cannot flow through the covered end(s). In some instances, the cover can surround substantially the entire occlusion device 400. As shown in FIG. 4G, the cover portion 408a can surround the first end portion 402 and the cover portion 408b can cover the second end portion 404, thereby substantially closing both the first and second ends. In some instances, each cover portion 408a, 408b can surround at least 20 percent of a length of the occlusion device 400, for example, between about 20 percent and about 40 percent or between about 30 percent and about 50 percent.

FIGS. 5A-5G illustrate the delivery system including any of the features of the delivery system 100 shown in FIGS. 1A and 1B. The delivery system can be used to deliver the occlusion device 500. As shown in the figures, the occlusion device can include a braided expandable structure having a substantially cylindrical or barrel shape (e.g., laser cut with a woven pattern or braided from a plurality of strands). In other words, a diameter of a first end portion 502 can be substantially the same as a diameter of a second end portion 504. In some instances, a diameter of the middle portion 506 can substantially the same as the diameter of the first end portion 502 the second end portion 504. In other instances, a diameter of the middle portion 506 can be no more than about 25 percent larger, or no more than about 10 percent larger, than the diameters of the first and second end portions 502, 504.

Similar to the occlusion device 400, the occlusion device 500 can include a diamond wall pattern across the length of the occlusion device. As shown in FIG. 5D, the wall pattern can be substantially the same across a length of the occlusion device 500. However, in other examples, the first and second end portions 502, 504 can include a different wall pattern than the middle portion 506. For example, the percentage of open area of the first and second end portions 502, 504 can be greater than the percentage of open area of the middle portion 506.

Figure 5G:
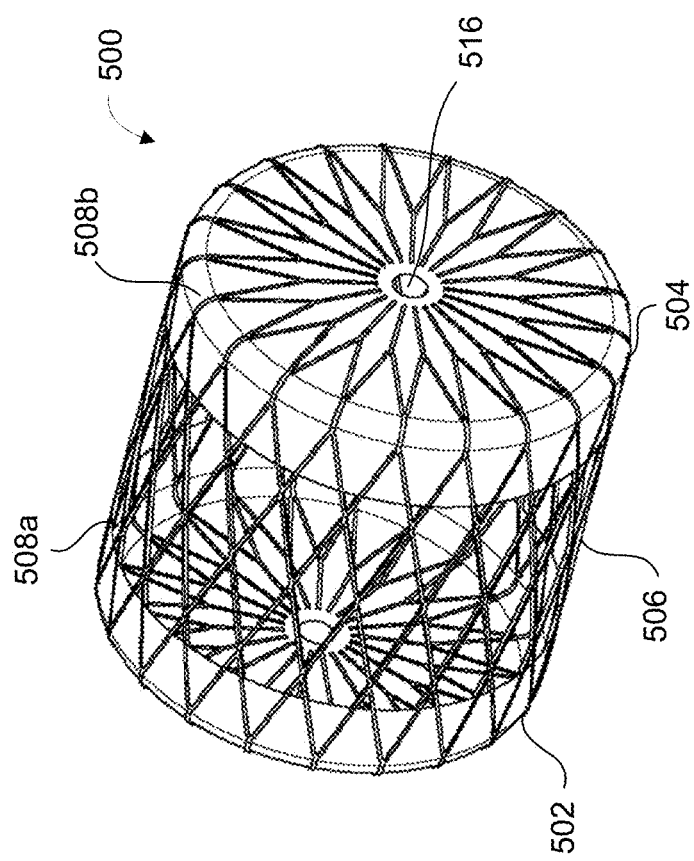
FIG. 5G illustrates an enlarged view of the occlusion device shown in FIGS. 5A-5F.

The first and second ends can each include a diamond pattern. As shown in FIGS. 5F and 5G, each end can include a band 518 of circumferentially disposed diamonds. The band 518 can define a guide wire hole 516 at the center of the inner band, through which a guide wire can pass.

The occlusion device 500 can include a cover surrounding at least one of the first and second end portions 502, 504. The cover can surround the entire circumference of the first end portion 502 and/or second end portion 504 and substantially close the first and/or second ends such that fluid cannot flow through the covered end(s). In some instances, the cover can surround substantially the entire occlusion device 400. As shown in FIG. 5G, the cover portion 508a can surround the first end portion 502, and the cover portion 508b can cover the second end portion 504, thereby substantially closing both the first and second ends. In some instances, each cover portion 508a, 508b can surround at least 20 percent of a length of the expandable structure, for example, between about 20 percent and about 40 percent or between about 30 percent and about 50 percent.

Figure 6:
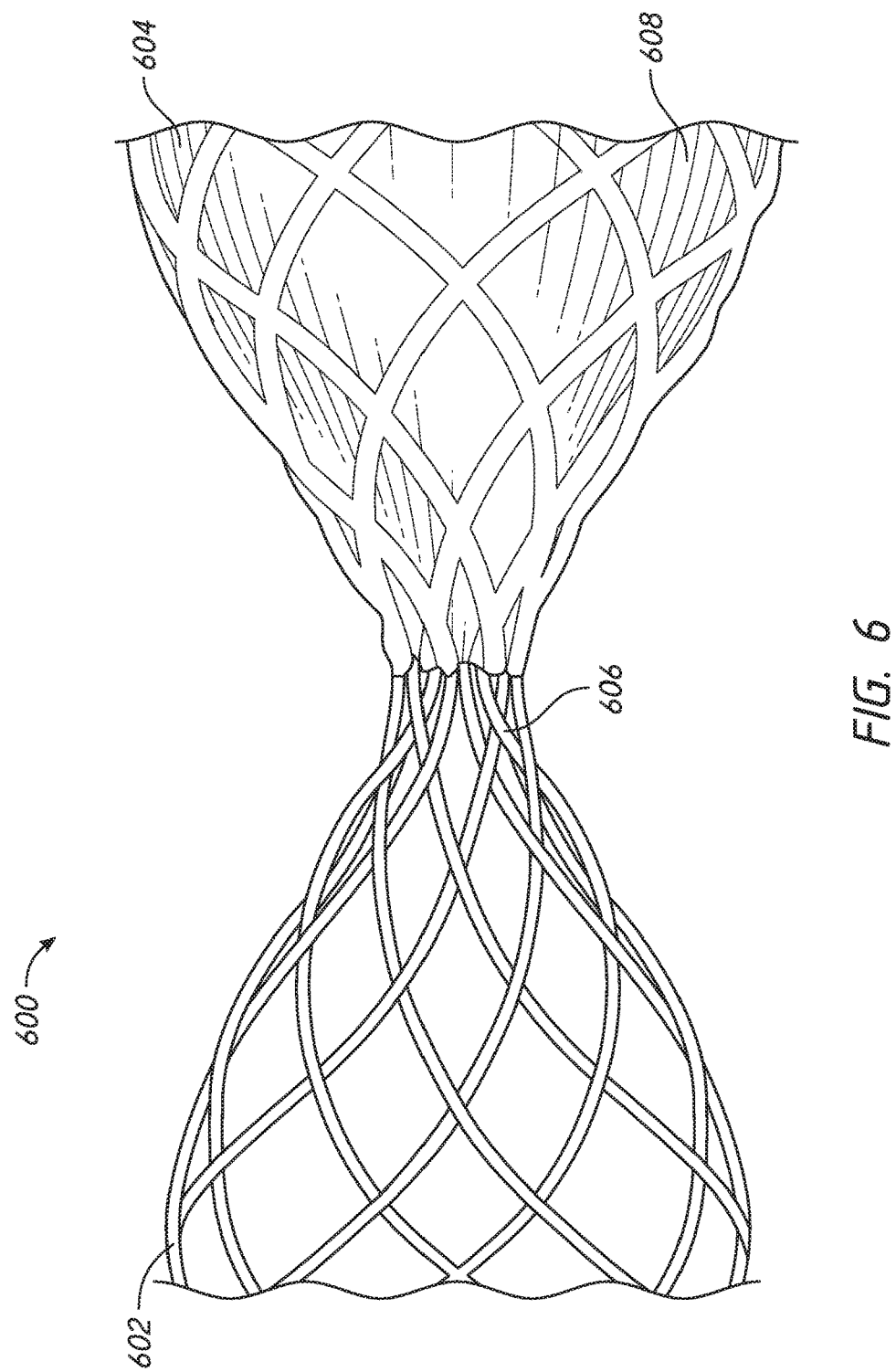

FIG. 6 illustrates an occlusion device 600 having a braided expandable structure (e.g., laser cut with a woven pattern or braided from a plurality of strands). The expandable structure can include a substantially hourglass shape. In other words, a diameter of a first end portion 602 can be substantially the same as a diameter of a second end portion 604. Further, a diameter of the middle portion 606 can be substantially smaller than the diameters of the first and second end portions 602, 604. In some instances, the diameter of the middle portion 606 can be at least about 50 percent, at least about 60 percent, at least about 70 percent, at least about 80 percent, or at least about 90 percent smaller than the diameters of the first and second end portions 602, 604. The middle portion 606 can define a guide wire passage large enough for a conventional guide wire to pass.

The occlusion device 600 can include a cover surrounding the outside surface or the inside surface on at least one of the first and second lobes or end portions 602, 604. The cover can surround the entire circumference of the first end portion 602 and/or second end portion 604. In some instances, the cover can surround substantially the entire occlusion device 600. As shown in FIG. 6, the cover 608 can surround the second end portion 604. In some instances, each cover 608 can surround at least 25 percent of a length of the expandable structure, for example, between about 40 percent and about 60 percent of the length of the expandable structure, such as about 50 percent of the length of the expandable structure.

FIGS. 7A-7B illustrate the occlusion device 700. As shown in the figures, the occlusion device 700 can include a braided, elongate expandable structure (e.g., laser cut with a woven pattern or braided from a plurality of strands). As shown in the figures, the expandable structure can define a diamond wall pattern along a length of the expandable structure. Further, the expandable structure can include tapered first and second end portions 702, 704. The first and second end portions 702, 704 can each define a guide wire hole large enough to permit a conventional guide wire to pass through the occlusion device.

A diameter of a middle portion 706 can be greater than a diameter of a first end portion 702 and a diameter of a second end portion 704. The diameter of the middle portion 706 can be no more than about 60 percent, 50 percent, or 40 percent larger than the diameters of the first and second end portions 702, 704. In some instances, the middle portion 706 can be at least as long as the first and second end portions 702, 704 combined.

The occlusion device 700 can include a cover surrounding at least one of the first and second end portions 702, 704. The cover can surround the entire circumference of the first end portion 702 and/or second end portion 704 and substantially close the first and/or second ends such that fluid cannot flow through the covered end(s). As shown in FIG. 7A, the cover portion 708a can surround the first end portion 702, and the cover portion 708b can cover the second end portion 704, thereby substantially closing both the first and second ends. In some instances, each cover portion 708a, 708b can surround at least 10 percent of a length of the expandable structure, for example, between about 10 percent and about 20 percent or between about 20 percent and about 30 percent. In some instances, as shown in FIG. 7B, the cover 708c can surround substantially the entire occlusion device 700.

FIG. 8 illustrates an occlusion device 800 formed from one or more strands woven to form an expandable structure. The expandable structure can include a first portion 802, a second portion 804, and a middle portion 806 therebetween. The first and second end portions 802, 804 can include tapered ends. Further, the first and second end portions 802, 804 can each include a smallest diameter that is at least large enough to permit a conventional guide wire to pass through.

The middle portion 806 can include a diameter that is substantially larger than a diameter of the first and second end portions 802, 804. For example, the diameter of the middle portion 806 can be at least about 50 percent or at least about 75 percent larger than a diameter of the first and second end portions 802, 804. In some instances, the diameter of the middle portion 806 can be between about 60 percent and 80 percent larger or between about 70 percent and about 90 percent larger. Further, as shown in FIG. 8, the middle portion 806 can include a non-uniform diameter; for example, the middle portion 806 can be generally rounded to form a bulbous shape.

Although not shown, the occlusion device 800 can include a cover surrounding at least one of the first and second end portions 802, 804. The cover can surround the entire circumference of the first end portion 802 and/or second end portion 804 and substantially close the first and/or second ends such that fluid cannot flow through the covered end(s). In some instances, each cover portion can surround at least 10 percent of a length of the expandable structure, for example, between about 10 percent and about 20 percent or between about 20 percent and about 30 percent. In some instances, the cover can surround substantially the entire occlusion device 800.

FIG. 9A illustrates an occlusion device 900 formed from one or more strands woven to form an expandable structure. The expandable structure can include a first portion 902, a second portion 904, and a middle portion 906 therebetween. The first and second end portions 902, 904 can include tapered ends. Further, the first and second end portions 902, 904 each include a smallest diameter that is at least large enough to permit a conventional guide wire to pass through.

The middle portion 906 can include a diameter that is substantially larger than a diameter of the first and second end portions 902, 904. For example, the diameter of the middle portion 906 can be at least about 50 percent, or at least about 75 percent larger than a diameter of the first and second end portions 902, 904. In some instances, the diameter of the middle portion 906 can be between about 60 percent and 80 percent larger or between about 70 percent and about 90 percent larger. Further, as shown in FIG. 9, the middle portion 906 can include a substantially uniform diameter.

The occlusion device 900 can include a cover 908 surrounding at least one of the first and second end portions 902, 904. The cover 908 can surround the entire circumference of the first end portion 902 and/or second end portion 904 and substantially close the first and/or second ends such that fluid cannot flow through the covered end(s). In some instances, each cover portion can surround at least 10 percent of a length of the expandable structure, for example, between about 10 percent and about 20 percent or between about 20 percent and about 30 percent. As shown in the figures, the cover 908 surrounds the first end portion 902. However, in some instances, the cover can surround the second end portion 904 or substantially the entire occlusion device 900.

FIGS. 10A-10B illustrate the occlusion device 1000. As shown in the figures, the expandable structures can define a diamond wall pattern along a length of the expandable structure. Further, the expandable structure can include tapered first end portion 1002 and an opened second end portion 1004. Although the first end portion 1002 is tapered, the first end portion 1002 still defines a guide wire hole large enough to permit a conventional guide wire to pass through the occlusion device. A diameter of a middle portion 1006 can be substantially the same as a diameter of the second end portion 1004.

As shown in FIG. 10B, the occlusion device 1000 can include a cover 1008 surrounding at least the first end portion 1002. The cover 1008 can surround the entire circumference of the first end portion 1002 such that fluid cannot flow through the covered end. In some instances, the cover 1008 can surround at least 10 percent of a length of the expandable structure, for example, between about 10 percent and about 20 percent or between about 20 percent and about 30 percent. As shown in FIG. 10A, the cover 1008 can surround substantially the entire expandable structure.

Figure 11C:
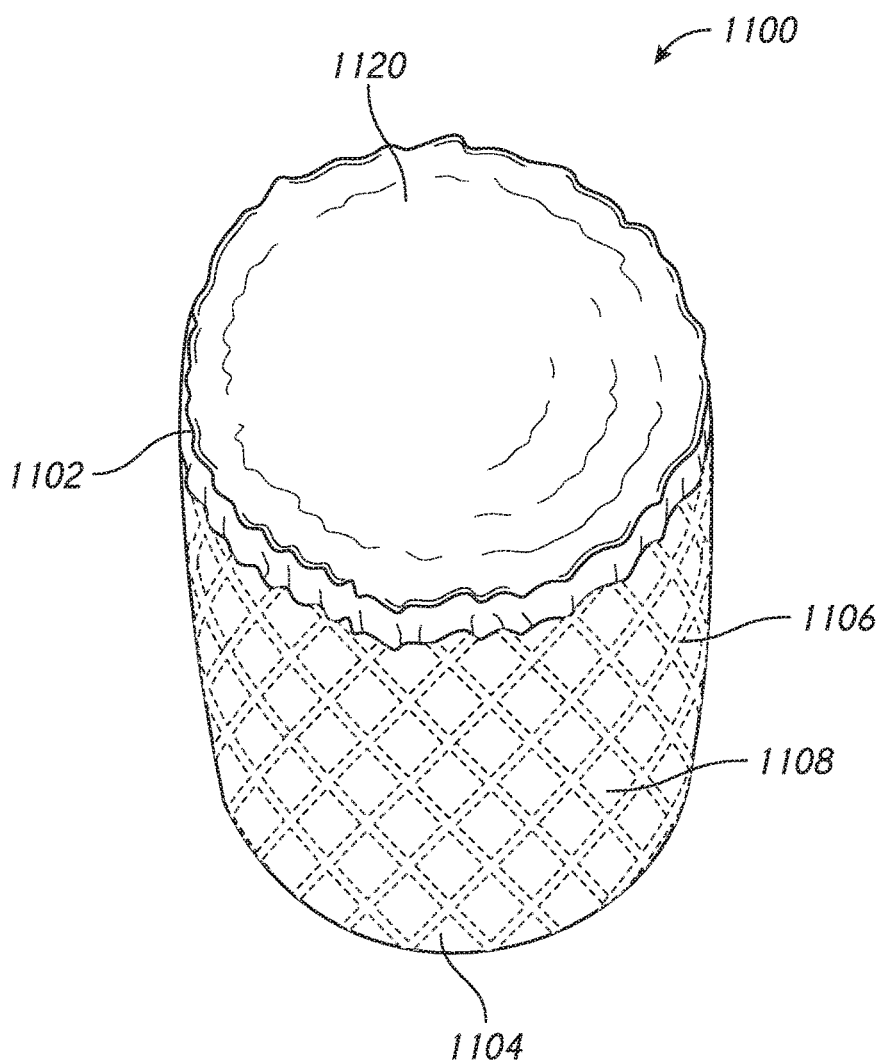

FIGS. 11A-11C illustrate another exemplary embodiment of an occlusion device 1100. As shown in the figures, the occlusion device 1000 can include a substantially uniform diameter. The occlusion device 1100 also defines a substantially uniform diamond wall pattern along a length of the occlusion device 1100.

As shown in FIG. 11C, the occlusion device 1100 can include a drumhead 1120 disposed within the first end portion 1102. The drumhead 1120 can be configured to close the first end 1102 such that fluid is prevented from flowing through the occlusion device 1100.

Further, the occlusion device 1100 can include a cover 1108 surrounding at least a portion of the occlusion device 1100. For instance, the cover 1108 can cover the drumhead 1120, or, as shown in FIGS. 11A-11C, the cover 1108 can surround at least the middle portion 1106 and the second end portion 1104. Although, depending on the desired performance of the cover 1108, the cover 1108 can extend along different lengths of the occlusion device. In some scenarios, it may be desirable to have greater overlap between the cover 1108 and the frame to adequately anchor the cover 1108 to the frame. For example, the cover 1108 can extend along at least about 50 percent, as at least about 60 percent, at least about 70 percent, at least about 80 percent, or at least about 90 percent of the length of the occlusion device 1100. In some examples, the cover 1108 extends along substantially the entire length of the occlusion device 1100. In other scenarios, it may be desirable to leave a higher percentage of the frame uncovered to facilitate endothelization, for example, across less than about 50 percent, less than about 40 percent, less than about 30 percent, or less than about 20 percent of the length of the occlusion device 1100. Preferably, to achieve both endothelization and sufficient overlap, the cover 1108 should extend across at least about 25 percent of the length of the frame and no more than about 50 percent of the length of the frame, for example, within about 5 percent of each of about 30 percent, 35 percent, 40 percent, or 45 percent.

Although certain embodiments have been described herein within respect to the illustrated expandable structures, the occlusion devices described herein can include differently shaped or differently formed expandable structures. For example, the expandable structure can be substantially conical, coiled, or any other conventional stent shape. As another example, the expandable structure can include a laser cut frame. In some instances, the frame can include a first closed end and a second opened end. The percentage of open area of the second opened end can be greater than the percentage of open area of the first closed end.

The specific examples described above in connection with FIGS. 3A-11C are for illustrative purposes only and should not be construed as limiting. Any combination of the configuration, shape, or wall pattern of the expandable structure can be combined with any type or amount of covering described herein.

Further, any of the features of the occlusion devices (e.g., expansion ratio, shapes, dimensions, materials, covers, etc.) disclosed herein can be accomplished in a stent, having two open ends and a central lumen to maintain vascular patency and permit perfusion.

Figure 12A:
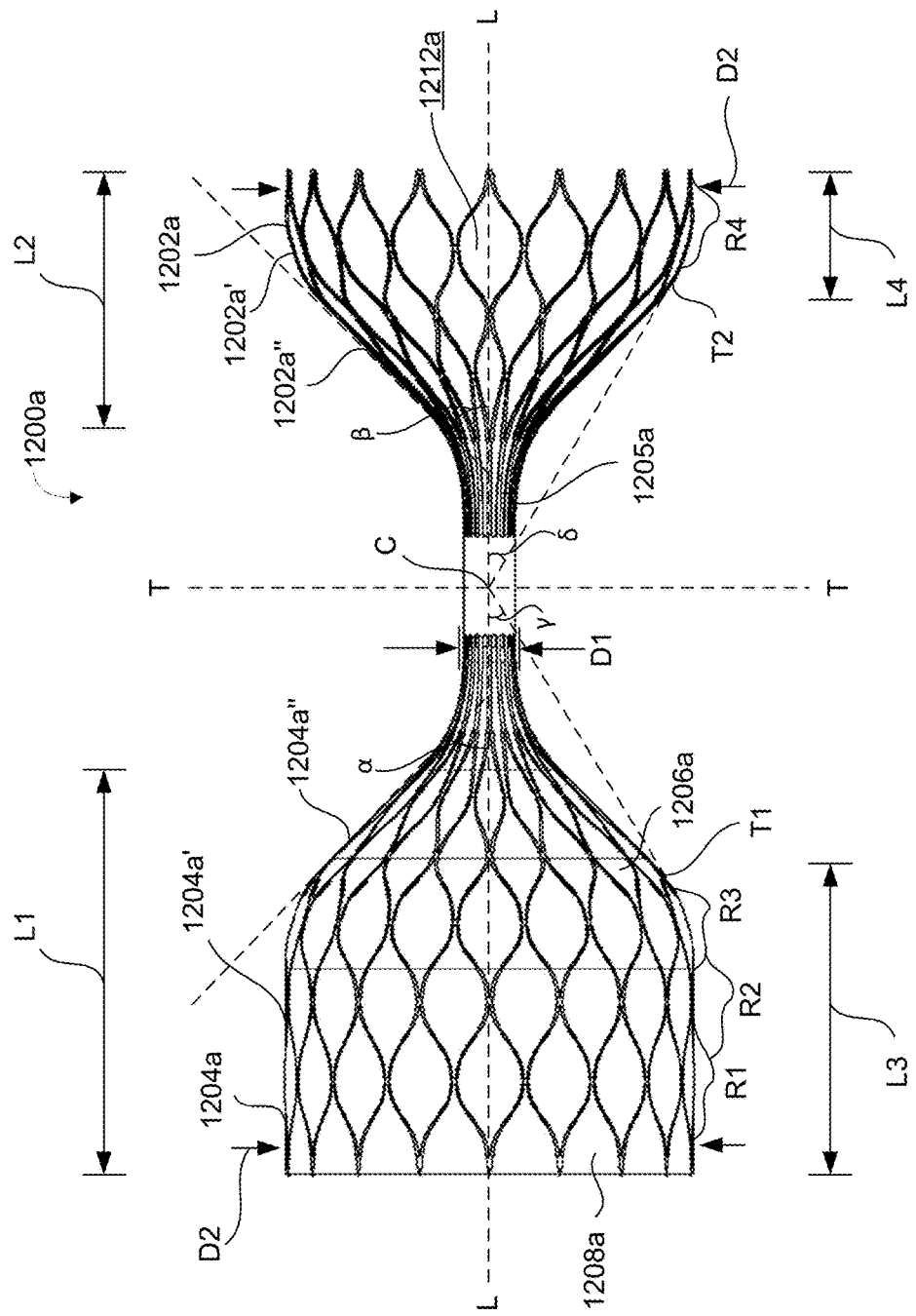
FIG. 12A illustrates an embodiment of an occlusion device having an asymmetrical hourglass shape.
Figure 12B:
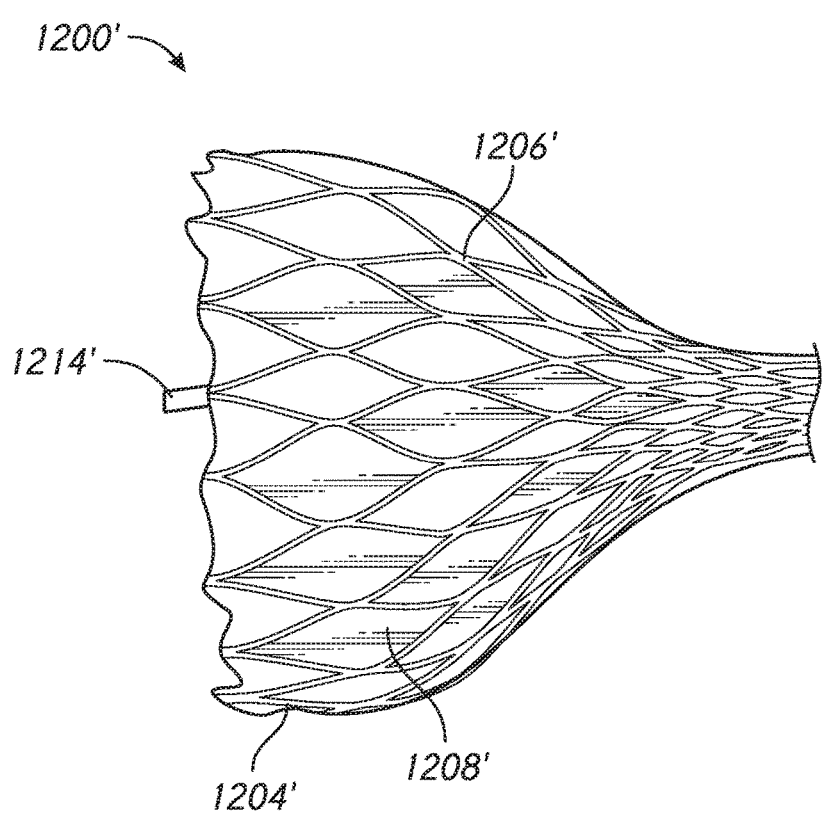
FIG. 12B illustrates the embodiment of the occlusion device shown in FIG. 12A having a radiopaque marker secured to a proximal end of the occlusion device.
Figure 12C:
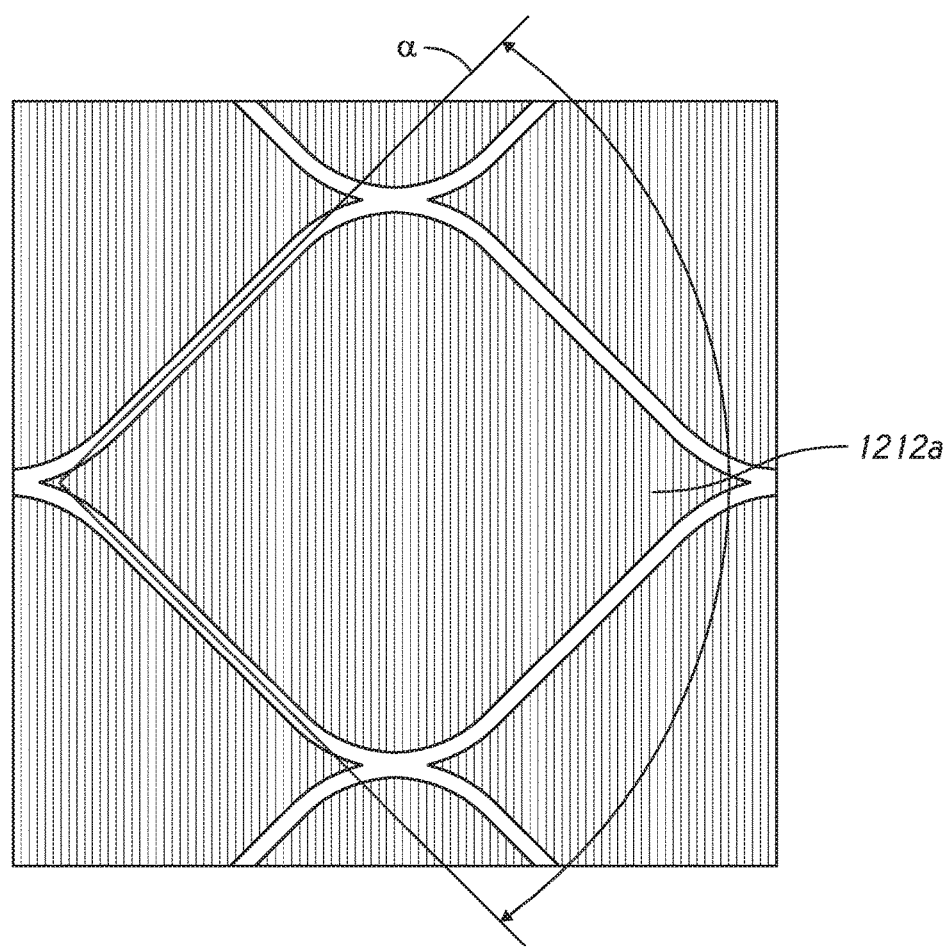
FIG. 12C illustrates an enlarged view of a cell structure of the occlusion device shown in FIG. 12A.
Figure 12D:
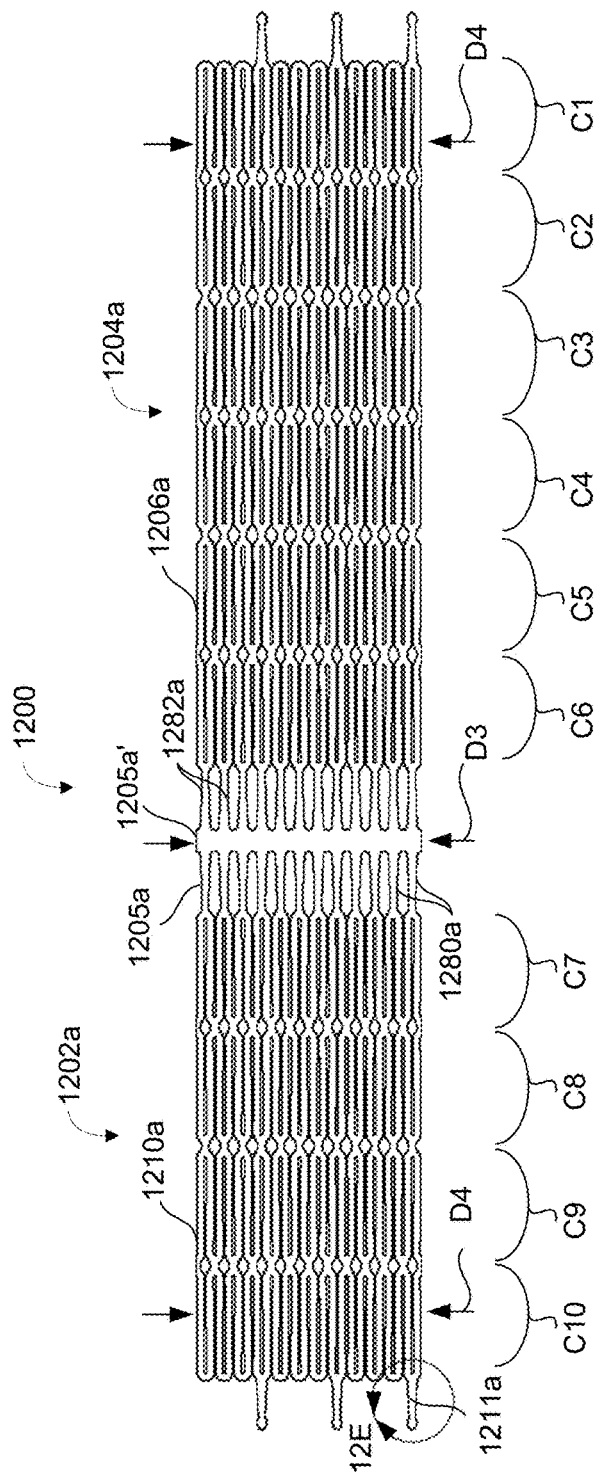
FIG. 12D illustrates a schematic view of the occlusion device shown in FIG. 12A in a collapsed configuration.
Figure 12E:
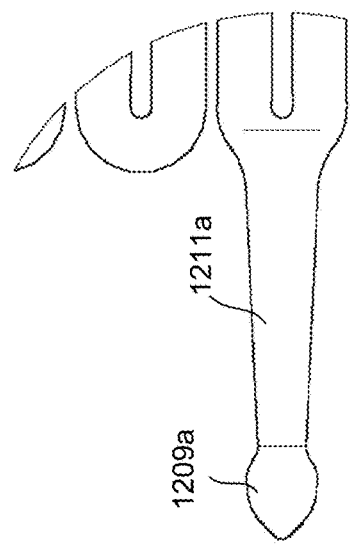
FIG. 12E illustrates an enlarged view of an end portion of the occlusion device shown in FIG. 12D through line A.
Figure 12F:
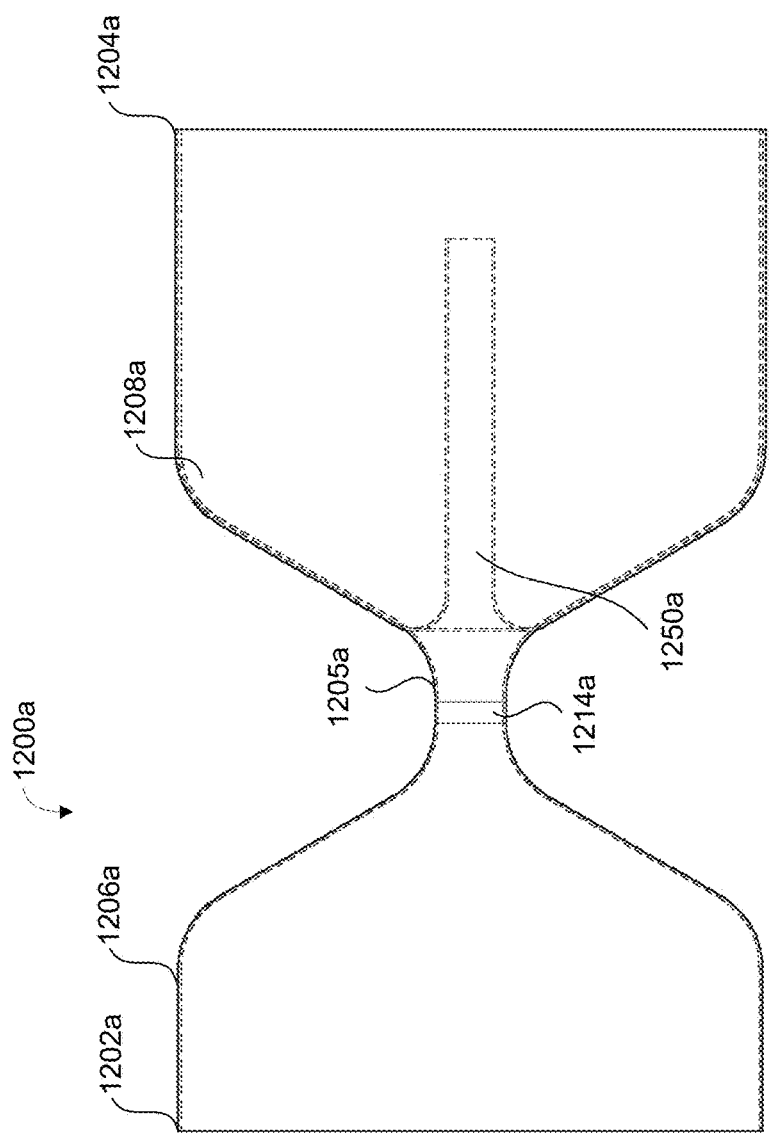
FIG. 12F illustrates a schematic cross-section of the occlusion device shown in FIG. 12A having a valve-like tubular section.

Hourglass-Shaped Occlusion Device—Axially Asymmetrical in Constrained Configuration FIGS. 12A and 12F illustrate an occlusion device 1200a having a first lobe or end portion 1202a, a second lobe or end portion 1204a, and a central or neck portion 1205a extending between the first and second end portions 1202a, 1204a. The first end portion 1202a can generally refer to the distal end portion or the anchor portion of the occlusion device 1200a and the second end portion 1204a can generally refer to the proximal end portion or the occlusive portion of the occlusion device 1200a when the occlusion device 1200a is introduced into the patient. As described in further detail below, the second end portion 1204a can be coated such that the second end portion 1204a provides occlusion, while the first end portion 1202a maintains an open cell structure to anchor the occlusion device 1200a and permit lateral flow. Further, the open cell structure of the first end portion 1202a enables the clinician to partially deploy the occlusion device 1200a against the wall of the vessel (e.g., just the first end portion 1202a) and confirm the position of the occlusion device 1200a by injecting contrast (e.g., by using delivery system 200) without materially impeding flow or raising hydrostatic pressure. In contrast, if a mechanically occlusive element were partially deployed, the mechanically occlusive element would impede flow and raise hydrostatic pressure.

As shown in FIG. 12A, the diameter of the central portion 1205a can be less than a diameter of the first or second end portions 1202a, 1204a, e.g., the occlusion device 1200a can have a generally hourglass shape (see FIG. 12A). For example, the diameter $D_1$ of the central portion 1205a can be between about 5% and about 25% of the diameter $D_2$ of the first or second end portions 1202a, 1204a, preferably less than or equal to about 15%, or less than or equal to about 10% of the diameter $D_2$ of the first or second end portions 1202a, 1504. The diameter of the hub (e.g., uncut hypotube portion 1205a') $D_3$ can be substantially equal to the diameter of the proximal and distal lobes $D_4$ when in the collapsed configuration (see FIG. 12D). The diameter $D_4$ across the proximal and distal lobes can be substantially the same in the collapsed configuration (see FIG. 12D).

The occlusion device 1200a can be asymmetrical about a transverse axis T-T of the occlusion device 1200a in the expanded and/or unexpanded configurations (see FIG. 12A). For example, in the expanded configuration, the occlusion device 1200a can be asymmetrical about a transverse axis T-T.

As shown in FIG. 12A, a uniform portion 1204a' of the second end portion 1204a can have a generally uniform diameter (e.g., cylindrical) and a tapered portion 1204a" of the second end portion 1204a can taper towards the central portion 1205a. The tapered portion 1204a" of the second end portion 1204a can form an angle $\alpha$ between about 45 degrees and about 75 degrees, between about 55 degrees and about 65 degrees, preferably about 60 degrees with respect to the longitudinal axis.

Similarly, a uniform portion 1202a' (e.g., cylindrical) of the first end portion 1202a can have a generally uniform diameter and a tapered portion 1202a" of the first end portion 1202a can taper toward the central portion 1205a. The tapered portion 1202a" of the first end portion 1202a can form an angle $\beta$. Angle $\beta$ can be substantially the same as angle $\alpha$.

Even if the angle of the tapered portions 1202a", 1204a" is substantially the same, an angle $\gamma$ can be different from an angle $\delta$ relative to the longitudinal axis. The angle $\gamma$ can be measured from a line extending through a transition point $T_1$ (between the tapered portion 1204a" and the cylindrical portions 1204a') and the axial center C of the occlusion device 1200a. The angle $\delta$ can be measured from a line extending through a transition point $T_2$ (between the tapered portion 1202a" and the cylindrical portions 1202a') and the axial center C of the occlusion device 1200a. Angle $\delta$ can be less than angle $\gamma$ to reduce the force necessary to retract the first end portion 1202a into the delivery system.

Figure 13B:
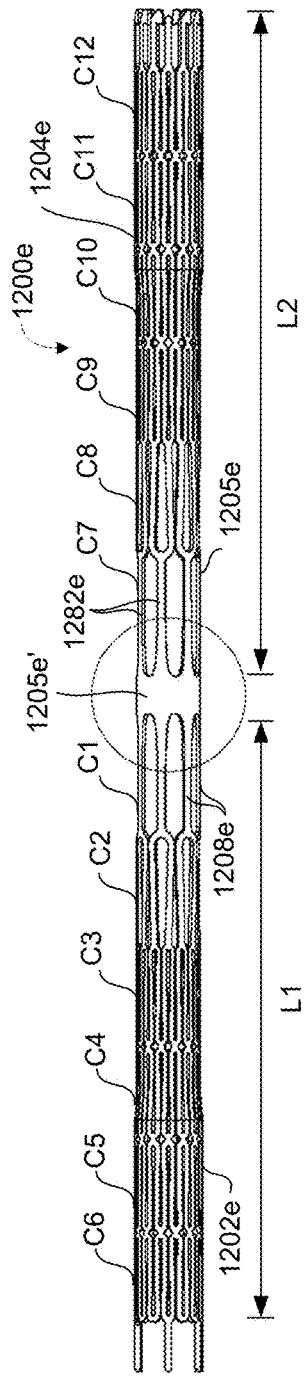
FIG. 13B illustrates the occlusion device shown in FIG. 13A in an unexpanded configuration.
Figure 13A:
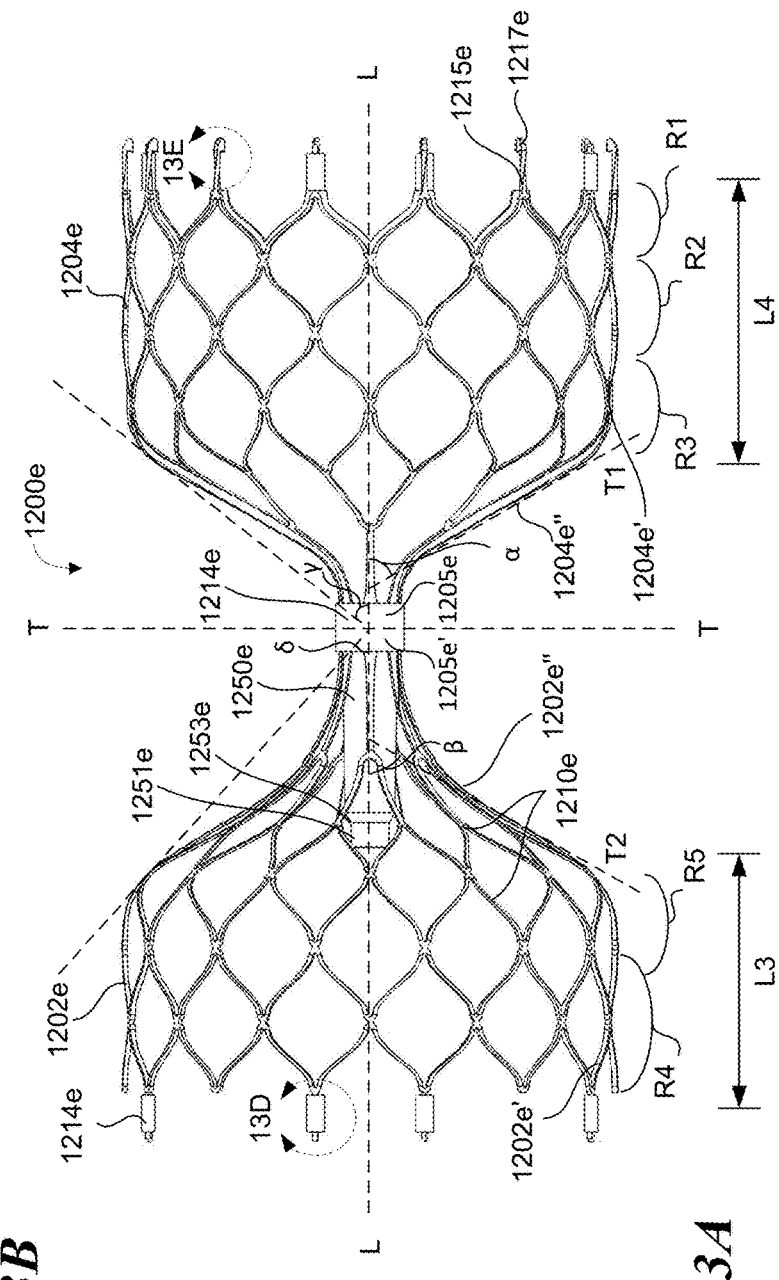
FIG. 13A illustrates another embodiment of an hourglass-shaped occlusion device in an expanded configuration with a portion of the membrane removed to show the tubular portion of the membrane.
Figure 13C:
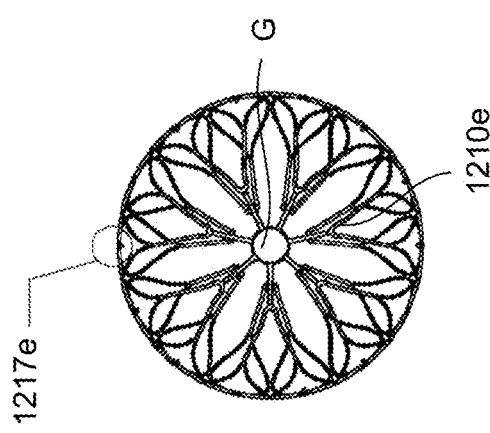
FIG. 13C illustrates an end view of the occlusion device shown in FIG. 13A.
Figure 13E:
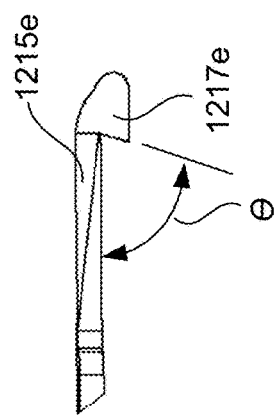
FIG. 13E illustrates an enlarged view of a strut ending at a proximal portion of the occlusion device shown in FIG. 13A through line 13E.
Figure 13D:
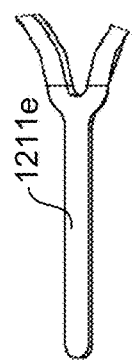
FIG. 13D illustrates an enlarged view of a strut ending at a distal portion of the occlusion device shown in FIG. 13A through line 13D.
Figure 13F:
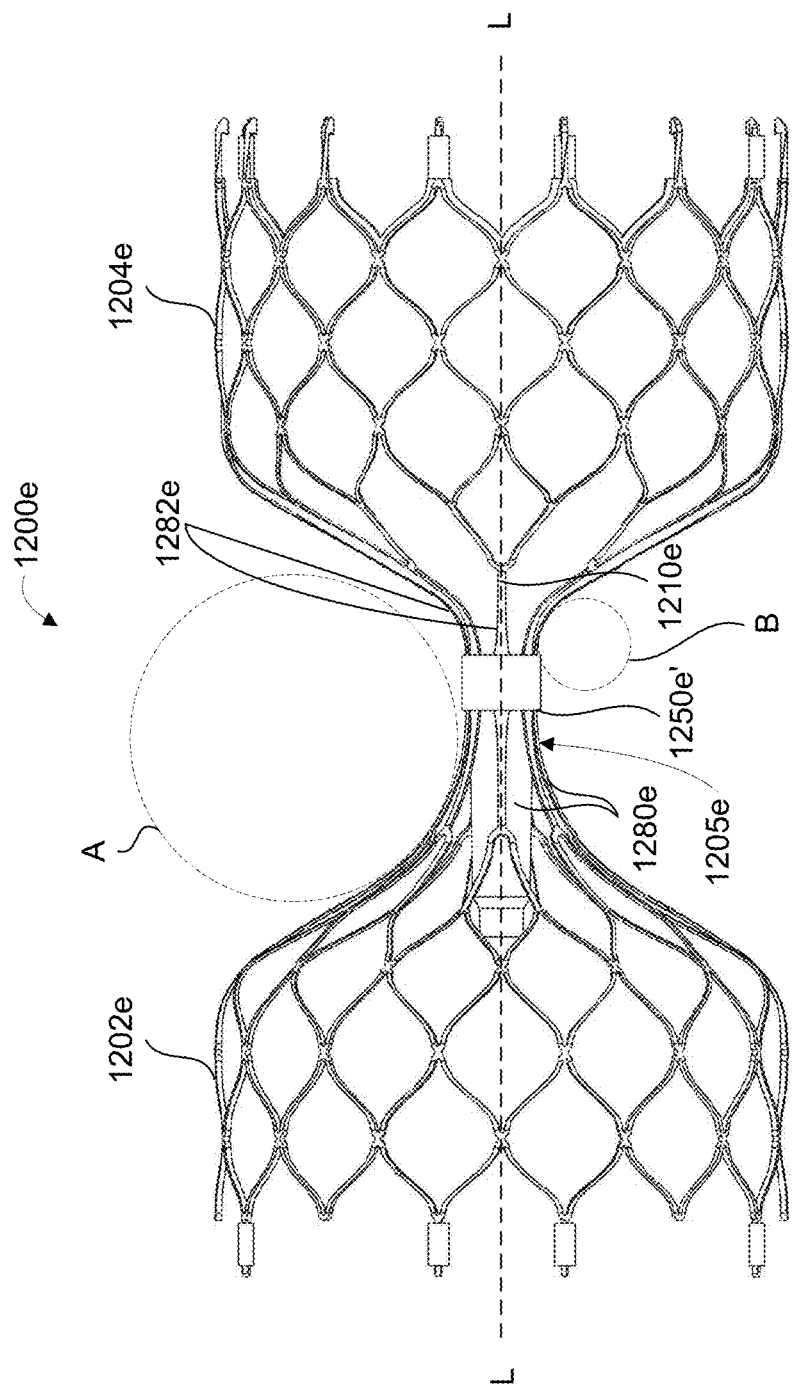
FIG. 13F illustrates the hourglass-shaped occlusion device shown in FIG. 13A, annotated to illustrate the curvature of the proximal and distal struts.

As illustrated in FIG. 13F, each of the proximal (covered) 1204e and distal (typically bare strut) 1202e lobes are connected to the central hub 1205e' by a plurality of struts 1210e which incline radially outwardly in their respective directions away from the hub 1205e'. In the illustrated embodiment, a shallower distal lobe strut 1280e launch angle between the curved axis of the strut and the longitudinal axis of the implant is clinically desirable because it provides a ramped surface that facilitates easy resheathing of the deployed distal lobe of the implant as it is pulled proximally back into the tubular deployment catheter. Preferably, the expanded implant is bilaterally asymmetrical, with the proximal struts 1282e exhibiting a steeper launch angle from the hub. This enables the implant to reach the fully expanded diameter of the proximal lobe 1204e over the shortest possible axial length. Thus, the shallow launch angle distal struts 1280e and steeper launch angle proximal struts 1282e optimize retrievability of the partially deployed implant while at the same time minimizes overall implant length. As seen in FIG. 13B, the wall pattern of the implant may in one embodiment exhibit bilateral symmetry in the collapsed configuration but expands to demonstrate the bilateral asymmetry described above due to a preset shape in the Nitinol or other shape memory material of the frame.

The distal struts 1280e are concave outwardly in a side elevational view, defining a generally trumpet shaped or flared configuration. The curvature of the struts 1280e as they leave the hub 1205e' and incline radially outwardly do not necessarily have a constant radius of curvature, but can be considered to conform to a best fit circle A having a constant radius (see FIG. 13F). The radius is generally at least about 25%, in some embodiments at least about 30% or 35% or more of the unconstrained diameter of the expanded distal lobe 1202e. For example, in an implant having an unconstrained distal lobe diameter of about 10 mm, the radius is generally within the range of from about 2.5 mm to about 5.5 mm, and in some embodiments between about 3 mm and 5 mm, or approximately 4 mm.

The proximal lobe struts 1282e can have a steeper launch angle to enable the proximal lobe 1202e to reach full diameter over a short axial distance from the hub. Thus, the radius of circle B which best fits the launch geometry of the proximal struts is generally less than about 25%, preferably less than about 20% or 15% or less of the expanded diameter of the proximal lobe 1202e, depending upon the physical properties and dimensions of the strut material (see FIG. 13F).

The best fit circles A, B described above will preferably be located against the strut such that it is approximately symmetrical about the midpoint of the arc of the struts that define the concave outwardly concave curvature section. Thus, the midpoint of the arc in the distal strut 1280e illustrated in FIG. 13F is a greater radial distance from the longitudinal axis of the implant than is the midpoint of the arc in the proximal strut 1282e due to the proximal strut transitioning from the arc to a substantially linear shoulder which extends out to the generally cylindrical body of the proximal lobe.

As shown in FIG. 12A, a length $L_1$ of the second end portion 1204a (including the tapered portion 1204a" and generally uniform portion 1204a') can be greater than a length $L_2$ of the first end portion 1202a (including the tapered portion 1202a" and generally uniform portion 1202a'). For example, $L_2$ can be between about 25% and about 75% of $L_1$, such as between about 50% and about 60%. Forces directed at a concave surface of the second end portion 1204a can provide a radially outward directed force to push the second end portion 1204a open and increase radial outward forces acting on the occlusion device 1200a and the vessel wall, when the occlusive concave side is facing an upstream direction with respect to blood flow in the vessel. The occlusive lobe (e.g., the second end portion 1204a) also places the hub under axial compression, which increases the radial force on the bare metal strut lobe (e.g., the first end portion 1202a). In certain aspects, the length of the second end portion $L_1$ can be about the same as a diameter of the second end portion 1204a. This ensures that the second end portion 1204a does not rotate perpendicular to an axis of the vessel and ensures that other anti-migration features remain properly aligned and positioned.

A length $L_3$ of the uniform portion 1204a' of the second end portion 1204a can be longer than a length $L_4$ of the uniform portion 1202a' of the first end portion 1202a' (see FIG. 12A). For example, in the unconstrained configuration, the uniform portion 1204a' can include a greater number of circumferential rings R1, R2, R3 of open cells 1212a than the uniform portion 1202a'. For example, the uniform portion 1204a' can include three circumferential rings R1, R2, R3 of open cells 1212a, while the uniform portion 1202a' can include one circumferential ring R4 of open cells 1212a. A size of an open cell 1212a in circumferential ring R1 can be substantially the same size as the size of an open cell 1212a in circumferential ring R4. In the constrained configuration, the second end portion 1204a can include a greater number of circumferential rings of struts than the first end portion. For example, the second end portion 1204a can include six circumferential rings C1, C2, C3, C4, C5, C6, of struts 1210a, while the first end portion 1202a can include four circumferential rings C7, C8, C9, C10 of struts 1210a.

The occlusion device 1200a can have an aspect ratio less than or equal to about 2:1 (unconstrained length to unconstrained lobe diameter), such as between about 1:1 and about 2:1 or between about 1.5:1 and about 2:1. An unconstrained length of the occlusion device 1200a can be between about 10 mm and about 25 mm, in some implementations from about 15 mm to about 22 mm. The first end portion 1202a having an unconstrained length of less than about 50% of a length of the occlusion device 1200a (e.g., when the unconstrained length is 20 mm, the length of the proximal portion is less than about 10 mm), less than about 40% of a length of the occlusion device 1200a (e.g., when the unconstrained length is 20 mm, the length of the proximal portion is less than about 8 mm), or less than about 30% of a length of the occlusion device 1200a (e.g., when the unconstrained length is 20 mm, the length of the proximal portion is less than about 6 mm). An unconstrained expanded diameter of the occlusion device 1200a can be between about 5 mm and about 15 mm, such as about 10 mm.

The occlusion device 1200a can include an expandable frame 1206a and a membrane 1208a carried by the expandable frame 1206a (see FIG. 12F). The expandable frame 1206a can define a lumen therethrough to facilitate delivery of the occlusion device 1200a over a guide wire (e.g., a 0.018-inch guidewire). Further, the expandable frame 1206a can have a wall thickness of less than or equal to about 0.003 inches, such as about 0.002 inches.

Figure 12H:
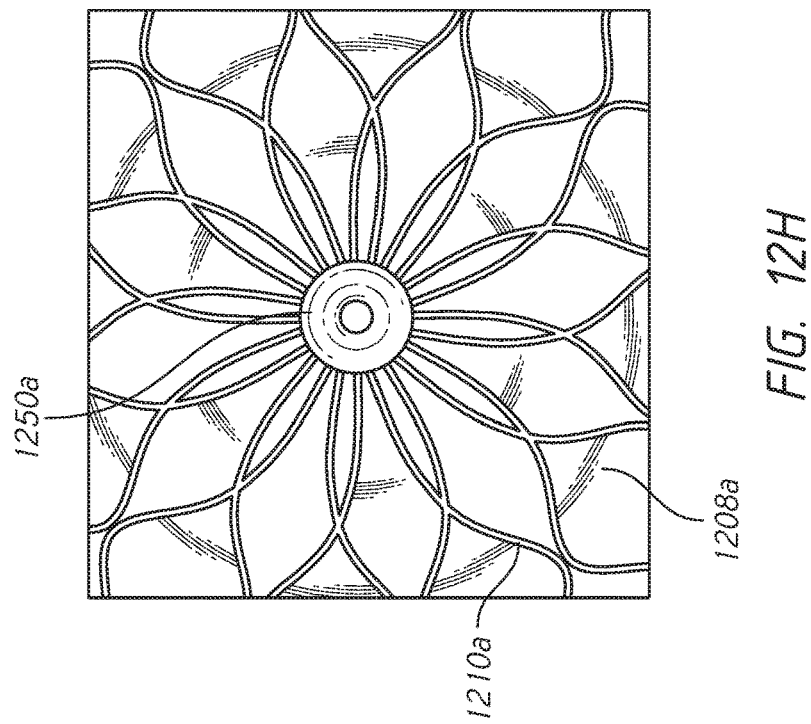
FIG. 12H illustrates the occlusion device shown in FIG. 12G with the tubular section in a closed configuration.

As shown in FIG. 12D, the first end portions and the second end portions 1202a, 1204a of the expandable frame 1206a can include a plurality of interconnected struts 1210a that can be laser cut from a Nitinol hypotube. At least a portion of the central portion 1205a can be a bare hypotube section 1205a' (e.g., uncut). The circumferential thickness of the struts 1210a can generally increase from the ends of the occlusion device toward the central portion 1205a. For example, as shown in FIG. 12D, the struts 1210a at the central portion 1205a can have a greater circumferential thickness than the struts 1210a at the first and second end portions 1202a, 1204a (e.g., struts 1280a, 1282a can be thicker than the struts in circumferential rings C1 and C2). The ends of the struts 1280a, 1282a that are adjoined to the central hub 1205a' are spaced apart, while the other ends of the struts 1280a, 1282a are each adjoined to two struts in the adjacent circumferential rings C6, C7 (see FIG. 12D). The struts in the central portion 1205a are positioned such that the central portion 1205a forms a star shape when viewed from an end of the occlusion device 1200a (see FIG. 12H). The laser cut design can help reduce foreshortening to less than or equal to about 20%.

As shown in FIG. 12C, the struts 1210a can be at least partially curved and form a plurality of generally rhombus-shaped open areas 1212a. The distal and proximal ends of the rhombus-shaped open areas 1212a can form an angle α between about 55 degrees and about 95 degrees, such as between about 55 degrees and 70 degrees or between about 70 degrees and about 85 degrees (see FIG. 12C). In some embodiments, an angle between about 85 degrees and about 95 degrees may be preferable to increase the expansion ratio. In other embodiments, an angle between about 55 degrees and about 65 degrees may be preferable to reduce chronic outward pressure (described in further detail below).

The open areas 1212a can be generally smaller closer to the central portion 1205a compared to the ends of the occlusion device 1200a. Additionally, portions of the expandable frame 1206a on which hydraulic pressure would force the expandable frame 1206a inward can be more porous to prevent the occlusion device 1200a from collapsing. By leveraging the hydraulic blood pressure to create a radial outward force, the occlusion device 1200a can be made smaller and lighter, thus allowing greater expansion ratios and smaller catheter French sizes.

FIG. 12D illustrates the occlusion device 1200a in a collapsed configuration. The occlusion device 1200a can include a number of interconnected circumferential rings C each having a plurality of struts 1210a. As shown in FIG. 12D, in an embodiment where the axial length of each of the circumferential rings is approximately equal, the first end portion 1202a can include a fewer number of circumferential rings C than the second end portion 1204a. For example, the first end portion 1202a can include two or three or four circumferential rings C7, C8, C9, C10, while the second end portion 1204a can include five or six or more circumferential rings C1, C2, C3, C4, C5, C6. Additionally, the occlusion device 1200a can include a number of strut endings 1211a extending from either end of the occlusion device 1200a. As shown in FIG. 12E, the strut ending 1211a can be generally tapered with a bulbous shaped end 1209a. The bulbous shaped end 1209a can help retain marker bands if present or be provided with an aperture to receive a press fit marker disc (e.g., lollipop shaped with an aperture) as is known in the art (see FIGS. 2Q and 2R).

The expandable frame 1206a can be at least partially covered by a thin membrane 1208a (e.g., between about 10 microns and about 30 microns thick) (see FIG. 12F). The membrane 1208a should be sufficiently thick to facilitate occlusion, while still minimizing the profile of the collapsed occlusion device 1200a. Possible materials for the membrane 1208a can include PTFE, PET, silicone, latex, TecoThane, nylon, PET, Carbothane (Bionate), fluoropolymers, SIBS, TecoFlex, Pellethane, Kynar, or PLGA.

The membrane 1208a can be applied to the expandable frame 1206a in a manner that encapsulates at least some of the struts 1210a, such that the membrane 1208a is present along either or both an interior surface and an exterior surface of the expandable frame 1206a. Possible methods of applying the membrane 1208a are described in further detail below.

As shown in FIG. 12F, the membrane 1208a can cover at least one end of the expandable frame 1206a and extend across at least a partial length of the expandable frame 1206a. In some embodiments, the membrane 1208a at least coats a portion of the occlusion device 1200a that is concave to the direction of the blood flow, which can be more occlusive and resist more migration than occlusion devices that only coat a surface convex to the direction of the blood flow or coat the entire occlusion device or coat the entire occlusion device. For example, the membrane 1208a can cover at least a portion of or the entire the second end portion 1204a and the first end portion 1202a can be a bare frame. When the bare first end portion 1202a is deployed before the covered second end portion 1204a, the bare first end portion 1202a can at least partially anchor the occlusion device 1200a in the vessel and allow visualization before deploying the covered second end portion 1204a, which facilitates precise placement of the occlusion device 1200a.

When the covered second end portion 1204a is upstream (i.e., anatomically proximal) from the bare first end portion 1202a, the increase in arterial pressure at the second end portion 1204a increases the radially outward forces directed toward the membrane 1208a, which helps the occlusion device 1200a resist migration. A higher blood pressure difference between the proximal and distal ends of the occlusion device 1200a will cause higher outward forces. Further, when the covered second end portion 1204a is upstream from the bare first end portion 1202a, forward pressure from blood flow acts on the central portion 1205a. After the occlusion device 1200a expands, forces acting on the central portion 1205a cause the tapered portion 1202a" of the first end portion 1202a (e.g., struts closer to or adjacent to the central portion 1205a) to collapse (e.g., bend inward), which causes the uniform portion 1202a' (e.g., struts closer to or at a distal end of the occlusion device) to move outward and further anchor the first end portion 1202a in the vessel.

Additionally, the membrane 1208a can be positioned on portions of the expandable frame 1206a on which hydraulic pressure will force the expandable frame 1206a outward. In some embodiments, portions of the expandable frame 1206a where the hydraulic pressure would force the expandable frame 1206a inward are not coated.

Figure 12G:
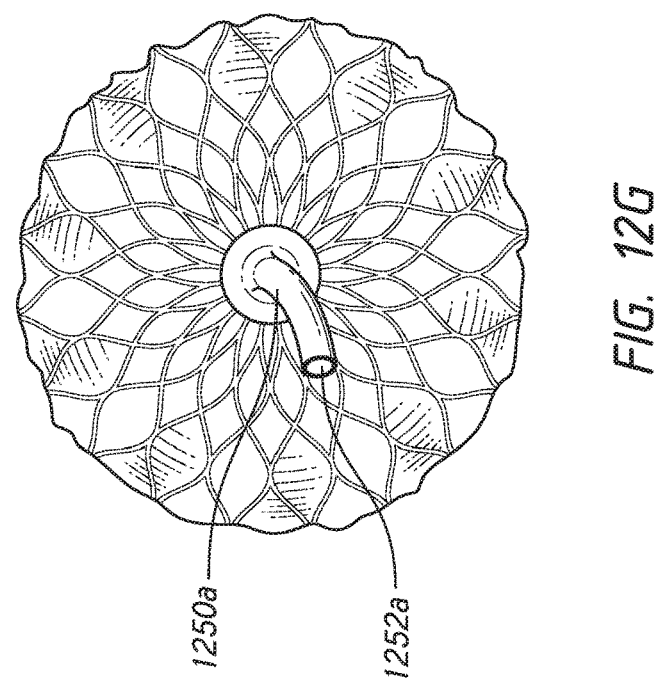
FIG. 12G illustrates an end view of the occlusion device shown in FIG. 12F with the tubular section in an open configuration.

The membrane 1208a can extend to form a thin extended tubular section of coating 1250a through which the guidewire (e.g., a 0.018" guidewire) can be introduced (see FIGS. 12F and 12G). The thin tube 1250a can extend through the first end portion 1202a or the second end portion 1204a. As described in further detail below, the thin tube 1250a can be configured to invert from a position extending through the first end portion 1202a such as during deployment to a position extending through the second end portion 1204a following deployment. The thin tube 1250a can extend across less than or equal to about 85% (e.g., between about 75% and about 85%), less than or equal to about 75%, less than or equal to about 60%, or less than or equal to about 50% of the length of the second end portion 1204a. In use, the thin tube 1250a can have sufficiently low collapse resistance such that blood pressure will cause the thin tube 1250a to collapse (e.g., kink, fold, buckle, flop over, or likewise) when the guidewire is removed (see FIG. 12H). The thin tube 1250a acts like a valve (e.g., a duckbill valve) to occlude the guidewire lumen 1252a and aid in the capture and formation of clots. FIG. 12F illustrates a schematic cross-sectional view of the occlusion device 1200a having the valve-like thin tube 1250a. The tube 1250a may be formed integrally with the formation of the membrane, during the spin coating process. Alternatively, the tube 1250a may be separately formed and attached to the hub and/or membrane using suitable adhesives, solvent bonding, heat bonding, or other techniques known in the art. Alternatively, one, two, or more flaps or leaflets may be provided, to occlude the guidewire opening following removal of the guidewire, preferably on the upstream blood flow side of the hub.

After the occlusion device 1200a has been deployed, the occlusion device 1200a can resist migration (e.g., migrate less than about 5.0 mm from the deployed position, preferably less than about 4.0 mm, or less than about 2.0 mm) for at least 10 minutes under pressures of at least about 100 mmHg and/or less than or equal to about 300 mmHg, for example, between about 100 mmHg and 150 mmHg, between about 150 mmHg and about 300 mmHg, between about 200 mmHg and about 300 mmHg, between about 250 mmHg and about 300 mmHg, such as about 270 mmHg, as determined by the Migration Protocol described below.

In at least a straight 8 mm vessel or curved 8 mm vessel with a 20 mm radius to centerline of vessel, the structure of the deployed occlusion device 1200a permits the device to resist migration under at least average blood pressure (e.g., 120 mmHg) according to the Migration Protocol described below. In at least a straight 8 mm vessel or curved 8 mm vessel with a 20 mm radius to centerline of vessel, under retrograde venous deployment conditions, the structure of the deployed occlusion device 1200a permits the device to resist migration under at least 7 mmHg of pressure according to the Migration Protocol described below. Migration is defined as continuous movement of the embolic device or movement of the proximal end of the embolic device by greater than 5 mm from the initial location.

When the occlusion device 1200a is deployed in the vessel, the occlusion device 1200a can occlude at least about 80% of blood flow within 30 seconds, at least about 90% of blood flow within about 3 minutes, and/or about 100% of blood flow within about five minutes, without reliance on biological processes. Because of the mechanical mechanism of occlusion, performance is the same whether or not the patient has been anticoagulated (e.g., heparin, aspirin, warfarin, Plavix, etc.). In some implementations, the occlusion device 1200a can achieve complete occlusion within about two minutes or within about one minute. Using the Occlusion Protocol described below, the occlusion device 1200a can limit the flow rate through a vessel to no more than about 200 cc/min at 20 mmHg, such as to between about 50 cc/min and about 150 cc/min, preferably less than about 130 cc/min, less than about 100 cc/min at 20 mmHg or less than about 65 cc/min at 20 mmHg within about five minutes. Further, the occlusion device 1200a can limit the flow rate through a vessel to no more than about 400 cc/min at 60 mmHg or no more than about 330 cc/min at 60 mmHg, such as to between about 150 cc/min and about 250 cc/min, preferably less than or equal to about 175 cc/min at 60 mmHg within about five minutes. The occlusion device 1200a can limit the flow rate through a vessel to about no more than 600 cc/min at about 100 mmHg or 430 cc/min at 100 mmHg, such as to between about 200 mmHg and about 250 mmHg, preferably less than about 225 cc/min at about 100 mmHg within about five minutes.

In at least a 3 mm curved vessel with a 7.5 mm radius to centerline of vessel or a 8 mm vessel with a 20 mm radius to centerline of vessel, using the Occlusion Protocol described below, the occlusion device 1200a will permit a maximum flow rate of 130 cc/min at 20 mmHg (e.g., a maximum flow rate of 70 cc/min at 20 mmHg or 40 cc/min at 20 mmHg), 330 cc/min at 60 mmHg (e.g., a maximum flow rate of 175 cc/min at 60 mmHg or 125 cc/min at 60 mmHg), or 430 cc at 100 mmHg (e.g., a maximum flow rate of 315 cc/min at 100 mmHg or 185 cc/min at 100 mmHg) after about one minute. In at least a 3 mm curved vessel with a 7.5 mm radius to centerline of vessel or an 8 mm vessel with a 20 mm radius to centerline of vessel, under retrograde venous deployment conditions, using the Occlusion Protocol described below, the occlusion device 1200a will permit a maximum flow rate of 130 cc/min at 20 mmHg after about one minute.

The occlusion device 1200a has an expansion ratio of at least about 5:1. The expansion ratio of the occlusion device 1200a allows the occlusion device 1200a to treat different sized vessels between about 2.5 mm and about 8.0 mm. For example, the same occlusion device 1200a that can occlude a 2.5 mm vessel can occlude a 6.0 mm vessel.

The expansion ratio of the occlusion device 1200a can be between about 5:1 to about 10:1, such as at least about 5:1, at least about 6:1, at least about 7:1, at least about 8:1, or at least about 9:1. In some implementations, the expansion ratio can be at least about 10:1. In other words, a diameter of the occlusion device 1200a in the expanded configuration can be between about five times and about ten times greater than the diameter of the occlusion device 1200a in the unexpanded configuration, such as at least about five times, at least about six times, at least about seven times, at least about eight times, or at least about nine times. In some implementations, the diameter of the expanded configuration can be at least about ten times greater than the diameter of the unexpanded configuration. The expansion ratio of the occlusion device 1200a is sufficiently large such that the occlusion device 1200a is capable of compressing to a minimum size suitable for delivery through a catheter having a diameter of less than about 5 F, thereby minimizing trauma to the vessel during delivery. Further, the expansion ratio of the occlusion device 1200a is sufficiently large that a single, expanded occlusion device is capable of preventing substantially all fluid from flowing past the occlusion device in the target vessel. Generally, the expansion ratio of each lobe is equal to the ratio of the hub to the lobe in an unconstrained expansion.

A single occlusion device 1200a can be used to treat a wide range of vessel diameters. For example, the occlusion device 1200a can have an expansion range when delivered from a lumen having an internal diameter of at least about 2.0 mm up to at least about 8.0 mm or 10.0 mm or more, such as at least about 3.0 mm, at least about 4.0 mm, or at least about 5.0 mm. For instance, a single occlusion device 1200a can treat vessels having a diameter between about 2.5 mm and about 8.0 mm, or between about 3.0 mm and 7.0 mm. Using a single occlusion device 1200a to treat a wide range of vessels can be desirable to reduce the total stock of occlusion devices that must be kept on hand, and the ability to occlude large vessels with a single occlusion device 1200a can reduce costs.

Further, the single occlusion device 1200a having an expansion range of at least about 2.0 mm, 4.0 mm, or more, and also exhibits less than 20 percent elongation when moving from the unexpanded configuration to the expanded configuration, preferably less than about 15 percent. Minimizing elongation can help ensure accurate positioning of the occlusion device 1200a.

In the expanded state, the occlusion device 1200a can have an unconstrained diameter that is between about 30% and about 50% larger than the vessel diameter. For vessels sized between about 2.0 mm and about 8.5 mm in diameter, the diameter of the expanded occlusion device 1200a can be at least about 2.6 mm and/or less than or equal to about 12.75 mm, e.g., between about 9 mm and about 11 mm, such as about 10 mm.

The occlusion device 1200a may provide a chronic outward pressure ("COP"). As used herein, COP is the radial pressure (expressed in terms of mmHg) necessary to maintain stability of the occlusion device in a vessel under normal physiological blood pressure (i.e., about 135 mmHg). Radial forces used to determine the following COP values were based on data collected using the Migration Protocol described below. Further, the calculation of the COP assumes that the occlusion device 1200a forms a complete seal, and thus the flow rate equals zero and shear forces equal zero. The calculation also assumes that the occlusion device 1200a is rigid, and thus the normal force due to transfer of hydraulic force to the vessel wall equals zero.

Using these assumptions, the occlusion device can provide a COP between about 20 mmHg and about 250 mmHg, such as between about 30 mmHg and about 140 mmHg, between about 30 mm Hg and 80 mmHg, between about between about 70 mmHg and 100 mmHg, between about 90 mmHg and 120 mmHg, or between about 100 mmHg and 140 mmHg., for vessels having a diameter between about 3 mm and about 8 mm under a physiological pressure of about 135 mmHg, preferably between about 20 N/mm² (2.67 kPa) and about 50 N/mm² (6.67 kPa). For example, the occlusion device 1200a can provide about 48 mmHg (6.4 kPa) of radial pressure in a 7 mm vessel with a physiological pressure of about 135 mmHg pressure when the length of the contact area between an exemplary embodiment of the occlusion device 1200a and the vessel wall is about 12.5 mm (e.g., $L_1$=4.5 mm, $L_2$=8.0 mm). The occlusion device 1200a can provide about 20 mmHg (2.67 kPa) of radial pressure in a 7 mm vessel with a physiological pressure of about 135 mmHg pressure when the length of the contact area is about 30.0 mm, the entire length of an exemplary embodiment of the occlusion device 1200a. The latter calculation assumes that a thrombus will form and that the occlusion device 1200a will transfer radial force through the thrombus and across the entire length of the occlusion device 1200a.

Hourglass-Shaped Occlusion Device—Axially Symmetrical in Constrained Configuration FIGS. 13A through 13E illustrate another hourglass-shaped occlusion device 1200e having the same general structure and properties as occlusion device 1200a. In generally, the occlusion device 1200e is adapted to move between a constrained configuration (FIG. 13B) and an unconstrained configuration (FIG. 13A). The occlusion device 1200e can have any number of the characteristics (e.g., dimensions, construction, performance, etc.) as the occlusion device 1200a except as described below.

Similar to the occlusion device 1200a, as shown in FIG. 13A, the occlusion device 1200e can have a first lobe or end portion 1202e, a second lobe or end portion 1204e, and a central or neck portion 1205e extending between the first and second end portions 1202e, 1204e. The first end portion 1202e can generally refer to the distal end portion or the anchor portion of the occlusion device 1200e and the second end portion 1204e can generally refer to the proximal end portion or the occlusive portion of the occlusion device 1200e when the occlusion device 1200e is introduced into the patient. The second end portion 1204e can be coated such that the second end portion 1204e provides occlusion, while the first end portion 1202e maintains an open cell structure to anchor the occlusion device 1200e and permit lateral flow. Further, the open cell structure of the first end portion 1202e enables the clinician to partially deploy the occlusion device 1200e against the wall of the vessel (e.g., just the first end portion 1202e) and confirm the position of the occlusion device 1200a by injecting contrast (e.g., by using delivery system 200) without materially impeding flow or raising hydrostatic pressure. In contrast, if a mechanically occlusive element were partially deployed, the mechanically occlusive element would impede flow and raise hydrostatic pressure.

As shown in FIG. 13A, the diameter of the central portion 1205e can be less than a diameter of the first or second end portions 1202e, 1204e, e.g., the occlusion device 1200e can have a generally hourglass shape (see FIG. 13A). For example, the diameter $D_1$ of the central portion 1205e can be between about 5% and about 25% of the diameter $D_2$ of the first or second end portions 1202a, 1504, preferably less than or equal to about 15%, or between about 10% and about 15% of the diameter $D_2$ of the first or second end portions 1202e, 1204e. The diameter of the hub can be substantially equal to the diameter of the proximal and distal lobes when in the collapsed configuration.

As shown in FIG. 13A, the occlusion device 1200e can be asymmetrical about a transverse axis T-T of the occlusion device 1200a in the expanded. As shown in FIG. 13B, in an constrained position, the length $L_1$ of the first end portion 1202e can be substantially the same as the length $L_2$ of the second end portion 1204e. For example, in the constrained configuration, the second end portion 1204e can include the same number of circumferential rings as the first end portion, such as six rings C1, C2, C3, C4, C5, C6, of struts 1210e (or four or five or more) in the first end portion 1202e and six rings C7, C8, C9, C10, C11, C12, of struts 1210e (or four or five or more) in the second end portion 1204e.

However, as shown in FIG. 13A, in the unconstrained position, the length $L_3$ of the generally uniform portion 1204e' of the second end portion 1204e can be less than the length $L_4$ of the generally uniform portion 1202e' of the first end portion 1202e. For example, $L_3$ can span about two circumferential rings $R_4$, $R_5$ or less than three full circumferential rings of open cells 1212e, while $L_4$ can span about three full circumferential rings R1, R2, R3 of open cells 1212e. Although the first end portion 1202e and the second end portion 1204e have the same length in the unconstrained configuration, the first end portion 1202e and the second end portion 1204e to expand into different configurations. A size of an open cell 1212e in circumferential ring R1 can be substantially the same size as the size of an open cell 1212e in circumferential ring R4.

As shown in FIG. 13A, the angle α of the tapered portion 1204a" or angle β of the tapered portion 1202a" can be between about 45 degrees and about 75 degrees, between about 55 degrees and about 65 degrees, preferably about 60 degrees with respect to the longitudinal axis. The angle α can be substantially the same as angle β.

However, even if the angle of the tapered portions 1202e", 1204e" is substantially the same, an angle γ can be different from an angle δ relative to the longitudinal axis. The angle γ can be measured from a line extending through a transition point (between the tapered portion 1204e" and the cylindrical portions 1204e') and the axial center of the occlusion device 1200e. The angle δ can be measured from a line extending through a transition point (between the tapered portion 1202e" and the cylindrical portions 1202a') and the axial center of the occlusion device 1200e. Angle δ can be less than angle γ to reduce the force necessary to retract the first end portion 1202e into the delivery system.

During the manufacturing process, after the hypotube is laser cut, two different sized mandrels are inserted into the occlusion device 1200e. A first mandrel having a desired shape of the first end portion 1202e can be inserted through a distal end of the occlusion device 1200e and a second mandrel having a desired shape of the second end portion 1204e can be inserted through a proximal end of the occlusion device 1200e. The first mandrel can be locked together with the second mandrel. With the occlusion device 1200e loaded on the first and second mandrels, the occlusion device 1200e can be heat treated to the shape described herein.

The occlusion device 1200e can have an aspect ratio less than or equal to about 2:1 (unconstrained length to unconstrained lobe diameter), such as between about 1:1 and about 2:1 or between about 1.5:1 and about 2:1. An unconstrained length of the occlusion device 1200e can be between about 10 mm and about 25 mm, in some implementations from about 15 mm to about 22 mm. The first end portion 1202e having an unconstrained length of less than about 50% of a length of the occlusion device 1200e (e.g., when the unconstrained length is 20 mm, the length of the proximal portion is less than about 10 mm), less than about 40% of a length of the occlusion device 1200e (e.g., when the unconstrained length is 20 mm, the length of the proximal portion is less than about 8 mm), or less than about 30% of a length of the occlusion device 1200e (e.g., when the unconstrained length is 20 mm, the length of the proximal portion is less than about 6 mm). An unconstrained expanded diameter of the occlusion device 1200e can be between about 5 mm and about 15 mm, such as about 10 mm.

The occlusion device 1200e can include an expandable frame 1206e and a membrane 1208e (not shown) carried by the expandable frame 1206e (see FIG. 13A). The expandable frame 1206e can define a lumen G therethrough to facilitate delivery of the occlusion device 1200e over a guide wire (e.g., a 0.018 inch guidewire) (see FIG. 13C). Further, the expandable frame 1206e can have a wall thickness of less than or equal to about 0.003 inches, such as about 0.002 inches.

As shown in 13B, the first end portions and the second end portions 1202e, 1204e of the expandable frame 1206e can include a plurality of interconnected struts 1210e that can be laser cut from a Nitinol hypotube. At least a portion of the central portion 1205e can be a bare hypotube section 1205e' (e.g., uncut).

A length of each strut 1210e can generally vary from an end of the occlusion device 1200e toward the central portion 1205e of the occlusion device 1200e (see FIG. 13B). For example, a length of each strut 1210e can generally increase from one or both ends of the occlusion device 1200e to a central portion 1205e of the occlusion device (e.g., from about 0.05 cm at the proximal and distal ends to about 0.25 cm at the central portion 1205e). For example, a length of a strut closest to the center can be about 150% of a length of a strut closest to an end of the occlusion device 1200e. For example, a length of a strut closest to the center of the occlusion device can be about 0.09 inches and a length of a strut closest to an end of the occlusion device can be about 0.06 inches.

As an example, a first ring of struts R1 can have an axial length that is about 115% of a length of a second, adjacent ring of struts R2. For example, a first ring of struts R1 can have an axial length of about 0.0910 inches and a second ring of struts R2 can have an axial length of about 0.0785 inches. A second ring of struts R2 can have an axial length that is about 112% of a length of a third, adjacent ring of struts R3. For example, a second ring of struts R2 can have an axial length of about 0.0785 inches and a third ring of struts R3 can have an axial length of about 0.0700 inches. A third ring of struts R3 can have an axial length that is about 113% of a length of a fourth, adjacent ring of struts R4. For example, a third ring of struts R3 can have an axial length of about 0.0700 inches and a second ring of struts R2 can have an axial length of about 0.0620 inches. A fourth ring of struts R4 can have an axial length that is about the same as a fifth adjacent ring of struts R5. For example, a fourth ring of struts R4 and a fifth ring of struts R5 can have an axial length of about 0.0.0620 inches. A fifth ring of struts R5 can have an axial length that is about 103% of a length of a sixth, adjacent ring of struts R6. For example, a fifth ring of struts R5 can have an axial length of about 0.0620 inches and a sixth ring of struts R6 can have an axial length of about 0.06 inches.

A thickness in a circumferential direction of each strut 1210e can generally vary from an end of the occlusion device 1200e toward the central portion 1205e of the occlusion device 1200e. For example, a thickness of each strut 1200e can generally decrease from one or both ends of the occlusion device toward the central portion 1205e of the occlusion device 1200e. Varying the lengths and thicknesses of the struts can evenly distribute force across the occlusion device 1200e, which can decrease the chronic outward pressure the occlusion device 1200e exerts on the vessel or decrease the total length of the occlusion device 1200e. As shown in FIG. 13B, in the constrained configuration, a diameter of the occlusion device 1200e can decrease from the ends of the occlusion device 1200e toward the central portion 1205e of the occlusion device 1200e. For example, there can be a gradual decrease in diameter at an intermediate portion of the first end portion 1202e and an intermediate portion of the second end portion 1204e. The intermediate portions can be positioned the same distance from a center of the occlusion device 1200e. The intermediate portions can extend across a same axial length of the occlusion device 1200e. For example, each of the intermediate portions can extend across about less than 5 percent of an axial length of the entire length of the occlusion device 1200e, such as about three percent. The intermediate portions can begin at a position about 20 percent to about 40 percent of the axial length from an end of the occlusion device, such as between about 20 percent and about 30 percent or between about 30 percent and about 40 percent. Although the profile of the occlusion device 1200e can be symmetrical in the constrained position, as described above, the first and second end portions 1202e, 1204e can expand into different configurations (see FIG. 13A).

As shown in FIG. 13B, the struts in the circumferential rings C1 and C7 (e.g., struts 1280e, 1282e) can be thicker than the struts in circumferential rings C6 and C12. Ends of the struts 1280e, 1282e that are adjoined to the central hub 1205e' can be spaced apart, while the other ends of the struts 1280e, 1282e can be each adjoined to two struts in the adjacent circumferential rings C2, C8 (see FIG. 13B). The struts 1280e, 1282e in circumferential rings C1 and C7 are positioned such that the central portion 1205e forms a star shape when viewed from an end of the occlusion device 1200e.

As shown in FIG. 13D, the strut endings 1211e at the first end portion 1202e can be generally straight. FIG. 13E illustrates strut endings 1215e at the second end portion 1204e of the occlusion device 1200e. A length of each strut ending 1215e can be between about 0.10 cm and 0.20 cm. One or more of the strut endings 1215e can have a hook 1217e for interfacing with an interlock system described above.

When the occlusion device 1200e is deployed using the delivery system 200 (described above), the angle θ of the proximal hooks 1217e of the occlusion device 1200e can be optimized to maintain engagement between the occlusion device 1200e and the interlocking attachment member 231 during retraction (described above) (see FIG. 13E). For example, the angle θ can be between about 60 degrees and about 90 degrees, such as about 75 degrees.

When expanded, the ratio of strut width/thickness causes the struts and the hooks to twist approximately 90 degrees. Twisting the hooks allows for a relatively "tall" hook while keeping the embolic strut thickness low to provide a greater profile for secure fixation.

Similar to the occlusion device 1200a, the expandable frame 1206e can be at least partially covered by a thin membrane (partially removed to show tubular section 1250e) (e.g., between about 10 microns and about 30 microns thick) (see FIG. 13A). The membrane should be sufficiently thick to facilitate occlusion, while still minimizing the profile of the collapsed occlusion device 1200e.

Possible materials for the membrane can include PTFE, PET, silicone, latex, TecoThane, nylon, PET, Carbothane (Bionate), fluoropolymers (e.g., PVDF), SIBS, TecoFlex, Pellethane, Kynar, or PLGA.

As described below, the membrane (not shown) can be applied to the expandable frame 1206e in a manner that encapsulates at least some of the struts 1210e, such that the membrane 1208e is present along either or both an interior surface and an exterior surface of the expandable frame 1206e. Possible methods of applying the membrane 1208e are described in further detail below.

The membrane can cover a portion of the occlusion device 1200e that is concave to the direction of the blood flow, which can be more occlusive and resist more migration than occlusion devices that only coat a surface convex to the direction of the blood flow or coat the entire occlusion device or coat the entire occlusion device. For example, the membrane 1208e can cover at least a portion of or the entire the second end portion 1204e and the first end portion 1202e can be a bare frame. When the bare first end portion 1202e is deployed before the covered second end portion 1204e, the bare first end portion 1202e can at least partially anchor the occlusion device 1200e in the vessel and allow visualization before deploying the covered second end portion 1204e, which facilitates precise placement of the occlusion device 1200e.

The membrane can extend to form a thin extended tubular section of coating 1250e through which the guidewire (e.g., a 0.018" guidewire) can be introduced (see FIG. 13A). The thin tube 1250e acts like a valve (e.g., a duckbill valve) to occlude the guidewire lumen 1252e and aid in the capture and formation of clots. An end portion 1251e of the thin tube 1250e can have a reduced diameter compared to a remaining portion of the thin tube 1250e to facilitate the closing of the valve. The thin tube 1250e can include a portion 1253e that tapers toward the reduced diameter end portion 1251e.

The central portion 1205e enables the occlusion device 1200e to bend around approximately a 90 degree bend at a vessel bifurcation according to the Trackability Protocol described below (e.g., in a simulated 3 mm vessel having a 7.5 mm radius to centerline of vessel or in a simulated 8 mm vessel having a 20 mm radius to centerline of vessel). The central portion 1205e can include flexibility features to increase the flexibility of the occlusion device 1200e. For example, the thickness of the struts 1210e near or at the central portion 1205e can be less than the thickness of the struts 1210e near or at the ends of the occlusion device 1200e.

Figure 14C:
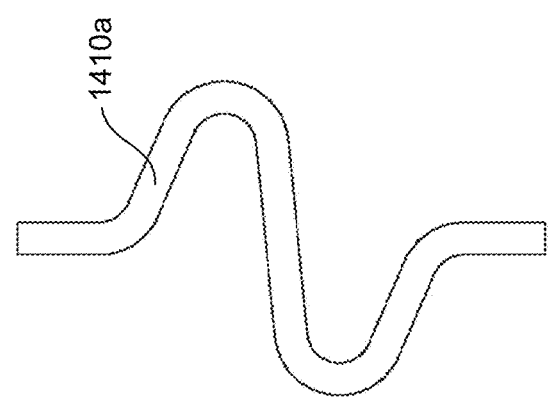
FIGS. 14A to 14U illustrate alternative embodiments of providing bending flexibility to the occlusion device.
Figure 14D:
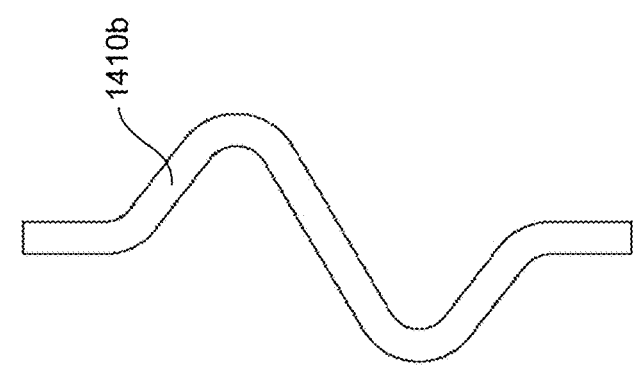
Figure 14E:
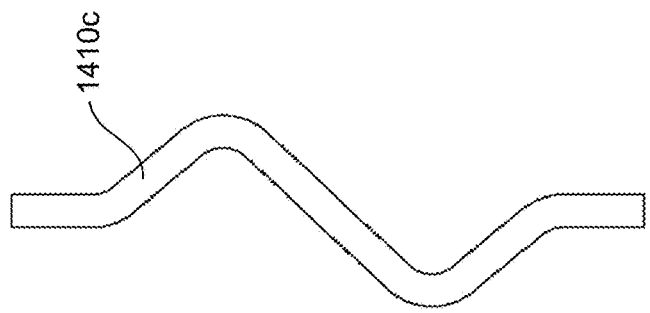

FIGS. 14A to 14U illustrate alternative central portions 1205e for imparting sufficient flexibility. For example, as shown in FIGS. 14A and 14B, one or more of the struts 1410 at the central portion 1205e can have a sinusoidal shape to permit the occlusion device 1200e to conform to an arcuate portion of the vessel. Each of the struts 1410 can be shaped such that they are nested when the occlusion device 1200e is in the constrained configuration. As shown in FIG. 14B, adjacent struts 1410 can have varying radii of curvature. For example, the struts 1410 can have an increasing radii of curvature around a circumference of the central portion 1205e (compare struts 1410a, 1410b, 1410c shown in FIGS. 14C to 14E).

FIGS. 14F to 14I illustrate a central portion 1205e with a series of cutouts (e.g., such as a spiral cut 1470 or a plurality of slots 1460) to allow the occlusion device 1200e to bend, while still maintaining the patency of the guidewire lumen. For example, the central portion 1205e can include two arrays of slots 1460a, 1460b extending longitudinally across the bare metal hub 1205e'. Each array 1460a, 1460b can have three slots 1460 (or two, four, five, or more) Each of the slots 1416 can extend at least partially around a circumference of the bare metal hub 1205e'. FIGS. 14H and 14I illustrate an alternative slot configuration 1460. As shown in FIG. 14I, adjacent slots 1460 can be staggered, rather than form separate arrays (as shown in FIG. 14G).

FIGS. 14J and 14K illustrate a central portion 1205e formed from a series of interlocking rings 1462. Each of the rings, e.g., 1462a, has a number of projections 1472 and indentations 1474 to interface with the adjacent ring 1462b.

FIGS. 14L and 14M illustrate another occlusion device 1200e having a spiral-shaped cut 1470 extending around the hub 1205e', such that the hub 1205e' forms a coil.

FIGS. 14N to 14Q illustrate a central portion 1205e formed from two interconnected hook structures 1468a, 1468b (see FIG. 14Q) that join the first end portion 1202e' with the second end portion 1204e'. A cover portion 1464 can surround the interconnected hook structures 1468a, 1468b.

FIGS. 14R and 14S illustrate a central portion 1205e with struts 1480 extending from the central hub 1205e' that are heat treated to form coils to provide flexibility to the central portion.

FIGS. 14T and 14U illustrate a central portion 1205e with struts 1482 extending from the central hub 1205e'. Unlike the strut pattern shown in FIGS. 12A to 13F, the struts 1482 at the central portion 1205e are positioned to form cell strutures 1212e similar to the remaining portions of the lobes 1202e, 1204e, as opposed to a star pattern (see FIG. 12H). There are an increasing number of cells 1212e from the central portion 1205e toward the ends of the occlusion device 1200e (e.g., circumferential ring C1 has fewer cells 1212e than circumferential ring C2 and circumferential ring C2 has fewer cells 1212e than circumferential ring C1) (see FIG. 14U). This cell pattern reduces any kinking at the central portion 1205e when the occlusion device 1200e is deployed in a curved vessel.

Laser Cut, Football-Shaped Occlusion Device

Figure 15A:
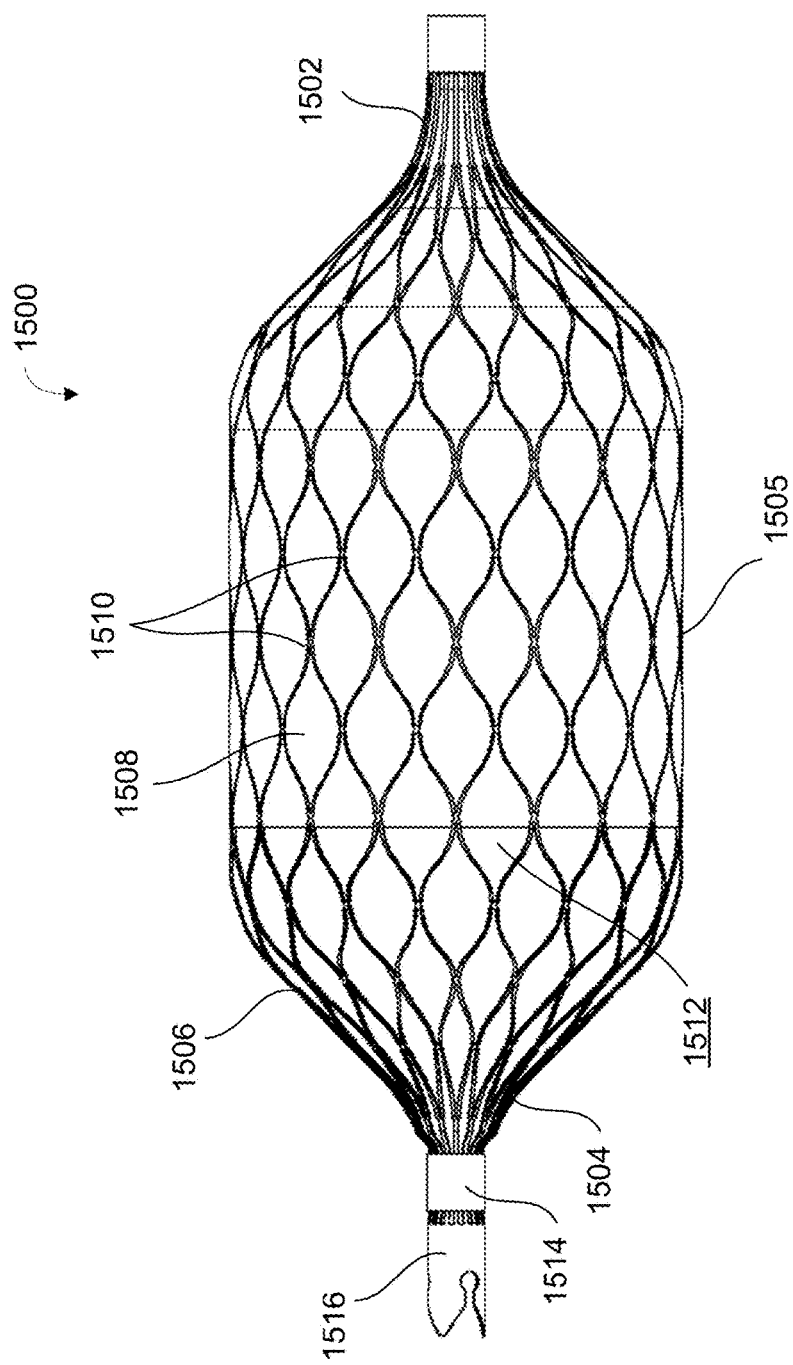
FIG. 15A illustrates another embodiment of the occlusion device having tapered ends.

FIG. 15A illustrates an occlusion device 1500 having a first end portion 1502, a second end portion 1504, and a central portion 1505 extending between the first and second end portions 1502, 1504. The occlusion device 1500 can have a generally cylindrical central portion 1505 and tapered first and second end portions 1502, 1504, such that a diameter of the central portion 1505 is greater than a diameter of the first and second end portions 1502, 1504. The central portion 1505 can extend across at least about 50% of the length of the occlusion device 1500, such as between about 50% and about 60%. The first end portion 1502 can generally refer to the distal end portion of the occlusion device 1500 and the second end portion 1504 can generally refer to the proximal end portion of the occlusion device 1500 when the occlusion device is introduced into the patient.

The occlusion device 1500 can include an expandable frame 1506 and a membrane 1508 carried by the expandable frame 1506. The expandable frame 1506 can define a lumen therethrough to facilitate delivery of the occlusion device 1500 over a guide wire. Further, the expandable frame 1506 can have a wall thickness of less than or equal to about 0.003 inches, such as about 0.002 inches.

The expandable frame 1506 can include a plurality of interconnected struts 1510 that can be laser cut from a Nitinol hypotube. Advantageously, the laser cut design can help reduce foreshortening.

As shown in FIG. 15A, the struts 1510 can be at least partially curved and form a plurality of generally rhombus-shaped open areas 1512. Portions of the expandable frame 1506 on which hydraulic pressure would force the expandable frame 1506 inward can be more porous to inhibit blood-induced occlusion. Further, the struts 1510 at the second end portion 1504 can narrow toward a collar 1516 having a diameter sized for delivery over a guidewire. The collar 1516 can include an interlock feature 1518 according to any of the interlock assemblies described herein.

The expandable frame 1506 can be at least partially covered by a thin membrane 1508 (e.g., between about 10 microns and about 30 microns thick). The membrane 1508 should be sufficiently thick to facilitate occlusion, while still minimizing the profile of the occlusion device 1500.

The membrane 1508 can be applied to the expandable frame 1506 in a manner that encapsulates at least some of the struts 1510, such that the membrane 1508 is present along both an interior surface and an exterior surface of the expandable frame 1506. Possible methods of applying the membrane 1508 are described in further detail below.

As shown in FIG. 15A, the membrane 1508 can cover at least one end of the expandable frame 1506 and extend across at least a partial length of the expandable frame 1506. In some embodiments, the membrane 1508 at least coats a portion of the occlusion device 1500 that is concave to the direction of the blood flow, which can be more occlusive and resist more migration than occlusion devices that only coat a surface convex to the direction of the blood flow. For example, the membrane 1508 can cover the first end portion 1502 and extend across at least a portion of the central portion 1505, or even at least a majority of the central portion 1505. For example, the membrane 1508 can extend across at least about 50% and/or less than or equal to about 75% of the expandable frame 1506, such as between about 60% and about 70%. Although not shown, in some examples, the membrane 1508 can cover both the first and second end portions 1502, 1504 of the expandable frame 1506 and extend along at least a portion of the central portion 1505.

The membrane 1508 can be positioned on portions of the expandable frame 1506 which incline radially outwardly in an upstream direction on which hydraulic pressure will force the expandable frame 1506 outward. In some embodiments, portions of the expandable frame 1506 that incline radially outward in an upstream direction where the hydraulic pressure would force the expandable frame 1506 inward are not coated.

After the occlusion device 1500 has been deployed, the occlusion device 1500 can resist migration (e.g., migrate less than about 5.0 mm from the deployed position, preferably less than about 4.0 mm, or less than about 2.0 mm) under pressures of at least about 100 mmHg and/or less than or equal to about 200 mmHg, for example, between about 150 mmHg and about 200 mmHg, such as about 180 mmHg, as determined by the Migration Protocol described below.

When the occlusion device 1500 is deployed in the vessel, the occlusion device 1500 can occlude at least about 80% of blood flow within 30 seconds, at least about 90% of blood flow within about 3 minutes, and/or at least about 100% of blood flow within about 5 minutes, without reliance on biological processes. In some implementations, the occlusion device 1500 can include complete occlusion within about two minutes or within about one minute. Using the Occlusion Protocol described below, the occlusion device 1500 can limit the flow rate through a vessel to 200 cc/min at 20 mmHg, such as to between about 50 cc/min and about 100 cc/min, preferably less than about 50 cc/min at 20 mmHg. Further, the occlusion device 1500 can limit the flow rate through a vessel to 400 cc/min at 60 mmHg, such as to between about 100 cc/min and about 150 cc/min at 60 mmHg, preferably less than about 125 cc/min at 60 mmHg. The occlusion device 1500 can limit the flow rate through a vessel to about 600 cc/min at about 100 mmHg, such as to between about 175 cc/min and about 225 cc/min, preferably less than about 200 cc/min at about 100 mmHg.

Additionally, a single occlusion device 1500 can be used to treat a wide range of vessels. For example, the occlusion device 1500 can have an expansion range of at least about 2.0 mm and/or less than or equal to about 10.0 mm, such as at least about 3.0 mm, at least about 4.0 mm, or at least about 5.0 mm. For instance, a single occlusion device 1500 can treat vessels having a diameter between about 2.5 mm and about 8.0 mm. Using a single occlusion device 1500 to treat a wide range of vessels can be desirable to reduce the total stock of occlusion devices that must be kept on hand, and the ability to occlude large vessels with a single occlusion device 1500 can reduce costs.

Further, the single occlusion device 1500 having an expansion range of at least about 2.0 mm and can have less than 20 percent elongation when moving from the unexpanded configuration to the expanded configuration, preferably less than about 15 percent. Minimizing elongation can help ensure accurate positioning of the occlusion device 1500.

The expansion ratio of the occlusion device 1500 can be between about 5:1 to about 10:1, such as at least about 5:1, at least about 6:1, at least about 7:1, at least about 8:1, or at least about 9:1. In some implementations, the expansion ratio can be at least about 10:1. In other words, a diameter of the occlusion device 1500 in the unconstrained expanded configuration can be between about five times and about ten times greater than the diameter of the occlusion device 1500 in the unexpanded configuration, such as at least about five times, at least about six times, at least about seven times, at least about eight times, or at least about nine times. In some implementations, the diameter of the expanded configuration can be at least about ten times greater than the diameter of the unexpanded configuration. The expansion ratio of the occlusion device 1500 is sufficiently large that the occlusion device 1500 is capable of compressing to a minimum size suitable for delivery through a catheter having a diameter of less than about 5 F, thereby minimizing trauma to the vessel during delivery. Further, the expansion ratio of the occlusion device 1500 is sufficiently large that a single, expanded occlusion device is capable of preventing substantially all fluid from flowing past the occlusion device in the target vessel.

In the unconstrained expanded state, the occlusion device 1500 can have a diameter that is between about 30% and about 50% larger than the vessel diameter. For vessels sized between about 2.0 mm and about 8.5 mm in diameter, the diameter of the expanded occlusion device 1500 can be at least about 2.6 mm and/or less than or equal to about 12.75 mm, preferably at least about 8.0 mm.

Laser Cut, Tulip-Shaped Occlusion Device

Figure 16:
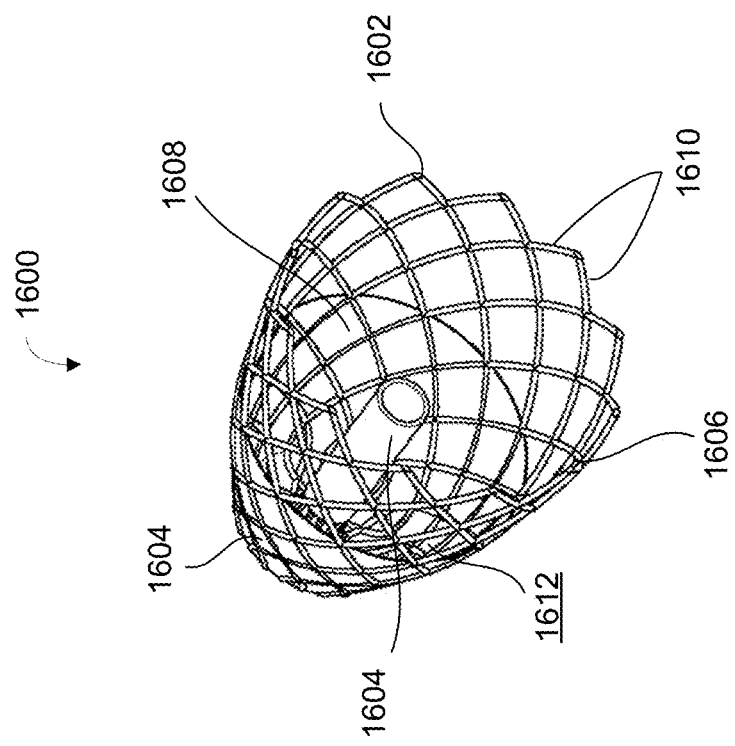
FIG. 16 illustrates yet another embodiment of the occlusion device having a closed proximal end and an open distal end.

FIG. 16 illustrates an occlusion device 1600 having a substantially cylindrical body 1605. The cylindrical body 1605 can have an open first end 1602 and a second end 1604 formed by struts 1610 extending toward a collar 1616, such that the occlusion device 1600 forms a closed end or tulip shape. The first end 1602 can generally refer to the distal end of the occlusion device 1600 and the second end 1604 can generally refer to the proximal end of the occlusion device 1600 when the occlusion device is introduced into the patient.

The occlusion device 1600 can include an expandable frame 1606 and a membrane (not shown) carried by the expandable frame 1606. The expandable frame 1606 can define a lumen therethrough to facilitate delivery of the occlusion device 1600 over a guide wire. Further, the expandable frame 1606 can have a wall thickness of less than or equal to about 0.003 inches. As mentioned above, the struts 1610 can narrow toward a collar 1616 having a diameter sized for delivery over a guidewire. The collar 1616 can include an interlock feature 1618 according to any of the interlock assemblies described herein.

The expandable frame 1606 can include a plurality of interconnected struts 1610 that can be laser cut from a Nitinol hypotube. As shown in FIG. 16, the struts 1610 can be at least partially curved and form a plurality of generally rhombus-shaped open areas 1612. Advantageously, the laser cut design can help reduce foreshortening.

The expandable frame 1606 can be at least partially covered by a thin membrane 1608 (e.g., between about 10 microns and about 30 microns thick). The membrane 1608 should be sufficiently thick to facilitate occlusion, while still minimizing the profile of the occlusion device 1600. The membrane 1608 can be applied to the expandable frame 1606 in a manner that encapsulates at least some of the struts 1610, such that the membrane 1608 is present along both an interior surface and an exterior surface of the expandable frame 1606. Possible methods of applying the membrane 1608 are described in further detail below.

The membrane 1608 can be positioned on portions of the expandable frame 1606 on which hydraulic pressure will force the expandable frame 1606 outward. In some embodiments, portions of the expandable frame 1606 where the hydraulic pressure would force the expandable frame 1606 inward are not coated.

Laser Cut, Umbrella-Shaped Occlusion Device

Figure 17:
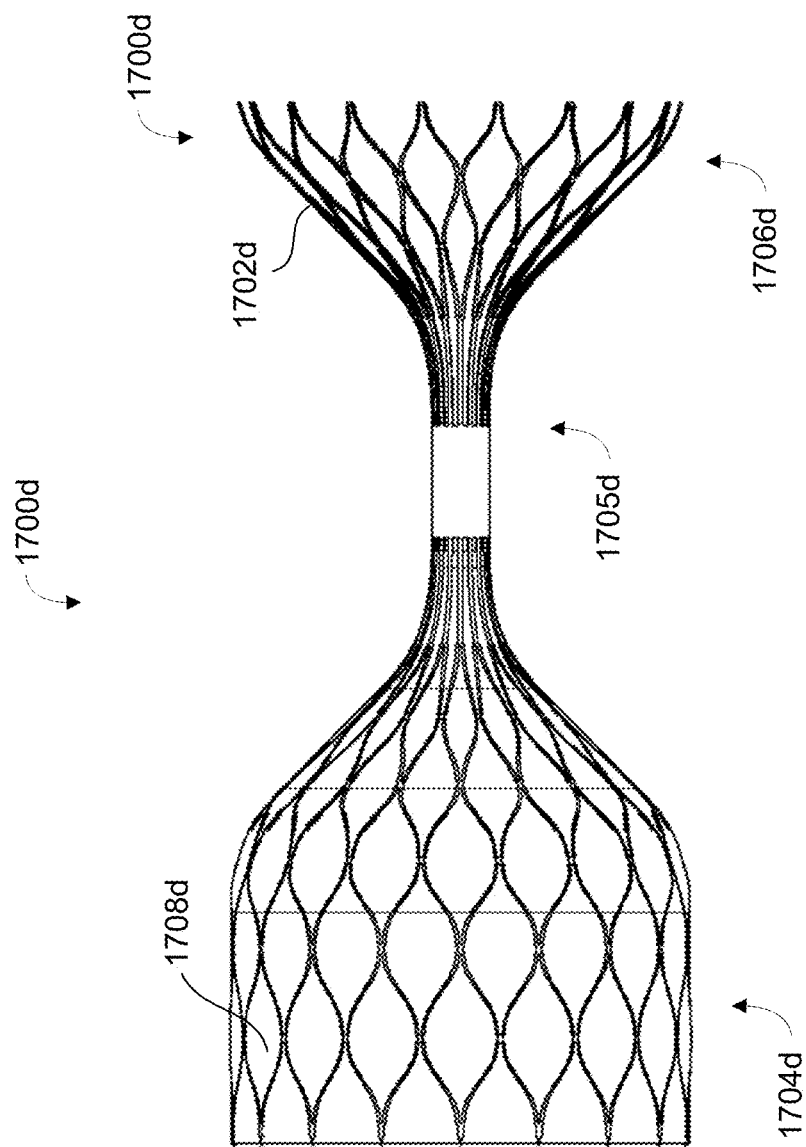
FIG. 17 illustrates another embodiment of the occlusion device having a wedge-shaped end portion.

FIG. 17 illustrates an occlusion device 1700 having a wedge-shaped first end portion 1702, a second end portion 1704, and a central portion 1705 therebetween. The first end portion 1702 can have a generally increasing diameter from the central portion 1705 to the end of the occlusion device 1700. The angle of the first end portion 1702 can be optimized to translate axial force directed at a surface of the first end portion 1702 into radial outward force to resist migration. Unlike the first end portion 1702, at least a portion of the second end portion 1704 can be substantially cylindrical (e.g., having a substantially uniform diameter).

The first end portion 1702 can generally refer to the distal end portion of the occlusion device 1700 and the second end portion 1704 can generally refer to the proximal end portion of the occlusion device 1700 when the occlusion device 1700 is introduced into the patient. In this configuration, the second end portion 1704 provides a concave surface to the direction of the blood flow.

The occlusion device 1700 can include an expandable frame 1706 and a membrane 1708 carried by the expandable frame 1706. The expandable frame 1706 can define a lumen therethrough to facilitate delivery of the occlusion device 1700 over a guide wire. Further, the expandable frame 1706 can have a wall thickness of less than or equal to about 0.003 inches.

The expandable frame 1706 can include a plurality of interconnected struts 1710 that can be laser cut from a Nitinol hypotube. As shown in FIG. 17, the struts 1710 can be at least partially curved and form a plurality of generally rhombus-shaped open areas 1712. Advantageously, the laser cut design can help reduce foreshortening.

Additionally, the expandable frame 1706 can be at least partially covered by a thin membrane 1708 (e.g., between about 10 microns and about 30 microns thick). The membrane 1708 should be sufficiently thick to facilitate occlusion, while still minimizing the profile of the occlusion device 1700. The membrane 1708 can be applied to the expandable frame 1706 in a manner that encapsulates at least some of the struts 1710, such that the membrane 1708 is present along both an interior surface and an exterior surface of the expandable frame 1706. Possible methods of applying the membrane 1708 are described in further detail below.

As shown in FIG. 17, the membrane 1708 can cover at least one end of the expandable frame 1706 and extend across at least a partial length of the expandable frame 1706. In some embodiments, the membrane 1708 coats at least a portion of the occlusion device 1700 that is concave to the direction of the blood flow, which can be more occlusive and resist more migration than occlusion devices that only coat a surface convex to the direction of the blood flow. For example, the membrane 1708 can cover the second end portion 1704 and the first end portion 1702 can be a bare frame. When the bare first end portion 1702 is deployed before the covered second end portion 1704, the bare first end portion 1702 can at least partially anchor the occlusion device 1700 in the vessel before deploying the covered second end portion 1704, which facilitates precise placement of the occlusion device 1700.

The membrane 1708 can be positioned on portions of the expandable frame 1706 on which hydraulic pressure will force the expandable frame 1706 outward. In some embodiments, portions of the expandable frame 1706 where the hydraulic pressure would force the expandable frame 1706 inward are not coated.

After the occlusion device 1700 has been deployed, the occlusion device 1700 can resist migration (e.g., migrate less than about 5.0 mm from the deployed position, preferably less than about 4.0 mm, or less than about 2.0 mm) under pressures of at least about 100 mmHg and/or less than or equal to about 300 mmHg, for example, between about 100 mmHg and about 300 mmHg, such as about 250 mmHg, as determined by Migration Protocol described below.

When the occlusion device 1700 is deployed in the vessel, the occlusion device 1700 can occlude at least about 80% of blood flow within 30 seconds, at least about 90% of blood flow within about 3 minutes, and/or at least about 100% of blood flow within about 5 minutes, without reliance on biological processes. In some implementations, the occlusion device 1700 can include complete occlusion within about two minutes or within about one minute. Using the Occlusion Protocol described below, the occlusion device 1700 can limit the flow rate through a vessel to 200 cc/min at 20 mmHg, such as to between about 100 cc/min and about 150 cc/min, preferably less than or equal to about 110 cc/min at 20 mmHg. Further, the occlusion device 1700 can limit the flow rate through a vessel to 400 cc/min at 60 mmHg, such as to between about 150 cc/min and about 200 cc/min at 60 mmHg, preferably less than about 175 cc/min at 60 mmHg. The occlusion device 1700 can limit the flow rate through a vessel to about 600 cc/min at about 100 mmHg, such as to between about 175 cc/min and about 225 cc/min, preferably less than about 200 cc/min at about 100 mmHg.

Additionally, a single occlusion device 1700 can be used to treat a wide range of vessels. For example, the occlusion device 1700 can have an expansion range of at least about 2.0 mm and/or less than or equal to about 10.0 mm, such as at least about 3.0 mm, at least about 4.0 mm, or at least about 5.0 mm. For instance, a single occlusion device 1700 can treat vessels having a diameter between about 2.5 mm and about 8.0 mm. Using a single occlusion device 1700 to treat a wide range of vessels can be desirable to reduce the total stock of occlusion devices that must be kept on hand, and the ability to occlude large vessels with a single occlusion device 1700 can reduce costs.

Further, the single occlusion device 1700 having an expansion range of at least about 2.0 mm and can have less than 20 percent elongation when moving from the unexpanded configuration to the expanded configuration, preferably less than about 15 percent. Minimizing elongation can help ensure accurate positioning of the occlusion device 1700.

The expansion ratio of the occlusion device 1700 can be between about 5:1 to about 10:1, such as at least about 5:1, at least about 6:1, at least about 7:1, at least about 8:1, or at least about 9:1. In some implementations, the expansion ratio can be at least about 10:1. In other words, a diameter of the occlusion device 1700 in the expanded configuration can be between about five times and about ten times greater than the diameter of the occlusion device 1700 in the unexpanded configuration, such as at least about five times, at least about six times, at least about seven times, at least about eight times, or at least about nine times. In some implementations, the diameter of the expanded configuration can be at least about ten times greater than the diameter of the unexpanded configuration. The expansion ratio of the occlusion device 1700 is sufficiently large that the occlusion device 1700 is capable of compressing to a minimum size suitable for delivery through a catheter having a diameter of less than about 5 F, thereby minimizing trauma to the vessel during delivery. Further, the expansion ratio of the occlusion device 1700 is sufficiently large that a single, expanded occlusion device is capable of preventing substantially all fluid from flowing past the occlusion device in the target vessel.

In the expanded state, the occlusion device 1700 can have a diameter that is between about 30% and about 50% larger than the vessel diameter. For vessels sized between about 2.0 mm and about 8.5 mm in diameter, the diameter of the expanded occlusion device 1700 can be at least about 2.6 mm and/or less than or equal to about 12.75 mm, preferably at least about 8.0 mm.

Radiopacity

It can be clinically desirable for any of the occlusion devices mentioned above to include one or more radiopaque markers. For example, the occlusion device can include one or more tubular markers positioned along a length of the expandable frame. The marker can have an outer diameter that is less than or equal to a diameter of the tube from which a laser cut expandable frame is formed. Use of the tubular marker can be especially advantageous for occlusion devices having a collar. The tubular marker 15141514 can be slid from a distal end of the occlusion device 1500 towards the collar 1516 on the second end portion 1504 or central portion 1505 of the occlusion device (see FIG. 15A). Since an outer diameter of the collar 1516 is larger than an inner diameter of the tubular marker 1514, the collar 1516 prevents the tubular marker 1514 from moving proximally. Further, the expanded central portion 1505 of the occlusion device prevents the band 1514 from moving distally. In some embodiments, the occlusion device can include a ringlet (not shown) for receiving the tubular marker 1514. Optionally, the marker 1514 can be held in place using an adhesive and/or a rivet.

As another example, as shown in FIG. 12A, a tubular marker 1214*a* can be positioned around a central portion 1205*a*, such that the expanded first and second end portions 1202*a*, 1204*a* prevent migration of the tubular marker 1214*a*.

In either example, the shape of the expandable frame fully constrains the tubular marker without crimping the marker to the frame, which reduces stress applied to the underlying frame. Further, since the diameter of the tubular markers is no greater than the outer diameter of the occlusion device, the tubular markers do not increase the delivery profile of the occlusion device. In certain aspects, a coating can be applied over the tubular markers.

In some embodiments, at least one radiopaque marker (e.g., two, three, or four) can be positioned (e.g., crimped, press-fit) on at least one end of the expandable frame. For example, one radiopaque marker 1214' can be positioned at the second end portion 1204' of the occlusion device 1200*a*' (see FIG. 12B), and another radiopaque marker can be positioned at the second end portion of the occlusion device (not shown). Positioning these markers on the ends of an occlusion device having expanding ends (e.g., occlusion device 1200*a*-1) facilitates visualization of the occlusion device moving between the compressed and expanded configurations. FIGS. 2Q and 2R illustrate another occlusion device O having markers 242' that are press-fit onto strut endings of the occlusion device O. The markers 242' can include an aperture 246' and a neck portion 244' (e.g., a lollipop shape) to facilitate certain retraction capabilities, as described above.

Figure 15B:
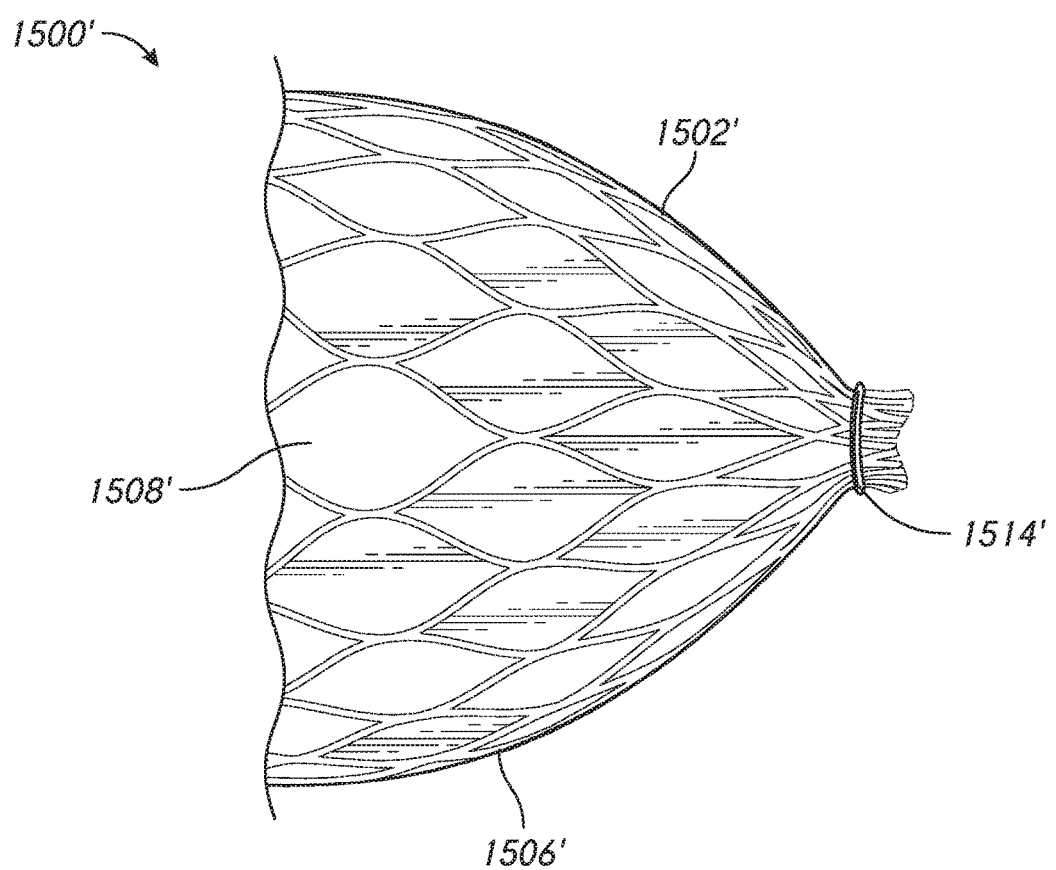
FIG. 15B illustrates the embodiment of the occlusion device shown in FIG. 15B having a marker coil.

In some embodiments, a radiopaque wire can be wrapped around one or more struts to form a large marker coil 1514' (see FIG. 15B). For example, individual struts at the end of an occlusion device 1500' can be joined by the marker coil 1514'. Since it can be difficult to insert struts at an end portion of the occlusion device into a tubular marker band, use of the marker coil 1514' can be especially useful with occlusion devices having narrowed ends (e.g., occlusion device 1500'). The marker coil 1514' can form a substantial marker and secure the struts or strands at a first end portion 1502'. Further, use of the radiopaque wire permits storage of a reduced number of spools of wire rather than a large number of discrete bands. In certain aspects, additional adhesive or heat shrink tubing can be applied to the marker coil to add integrity.

In some embodiments, a fine radiopaque powder can be added to the membrane material to make the entire coating visible. Integrating the radiopaque marker into the coating eliminates the manufacturing step of having to secure a marker to the occlusion device. Alternatively, the fine radiopaque powder can be painted onto the occlusion device or the occlusion device can be dipped into the radiopaque powder.

Methods of Coating the Expandable Frame

In any of the occlusion devices described above, a membrane can be deposited at least substantially uniformly using an electrospinning process. Further, using an electrospinning process, the porosity can be controlled of the membrane can be controlled to achieve different properties. For example, the membrane can be formed having sufficient tensile strength to resist yielding, stretching, or breaking under at least normal blood pressures, preferably at least about 140 mmHg or 160 mmHg. Further, the fibers forming the membrane can have a cross-sectional diameter between about 5 microns and about 25 microns, such that the membrane can be elongated at least about two to five times greater with 25%-75% less force than that of the native material having the same thickness. An average pore size can be less than or equal to about 100 microns or less than or equal to about 50 microns. Additionally, the coated occlusion device can weigh less than or equal to about 1 gram, preferably less than or equal to about 0.6 grams.

In general, the expandable frame can be coated by applying a dissolved polymer onto the expandable frame to encapsulate at least some of the struts or strands. The membrane material can be heated to form a viscous liquid solution that is placed in a syringe. The membrane material can be advanced by a piston or plunger through a nozzle having one or more outlets, where the material flows out onto a rotating mandrel as fine fibers. The fine fibers can form a fibrous mat or covering of biocompatible covering material on the rotating mandrel. As the membrane material cools, the fibers solidify, and adjacent, contacting fibers are sintered to one another. Controlling the number of layers of fiber that are applied to the rotating mandrel provides control over the porosity of membrane.

Figure 18:
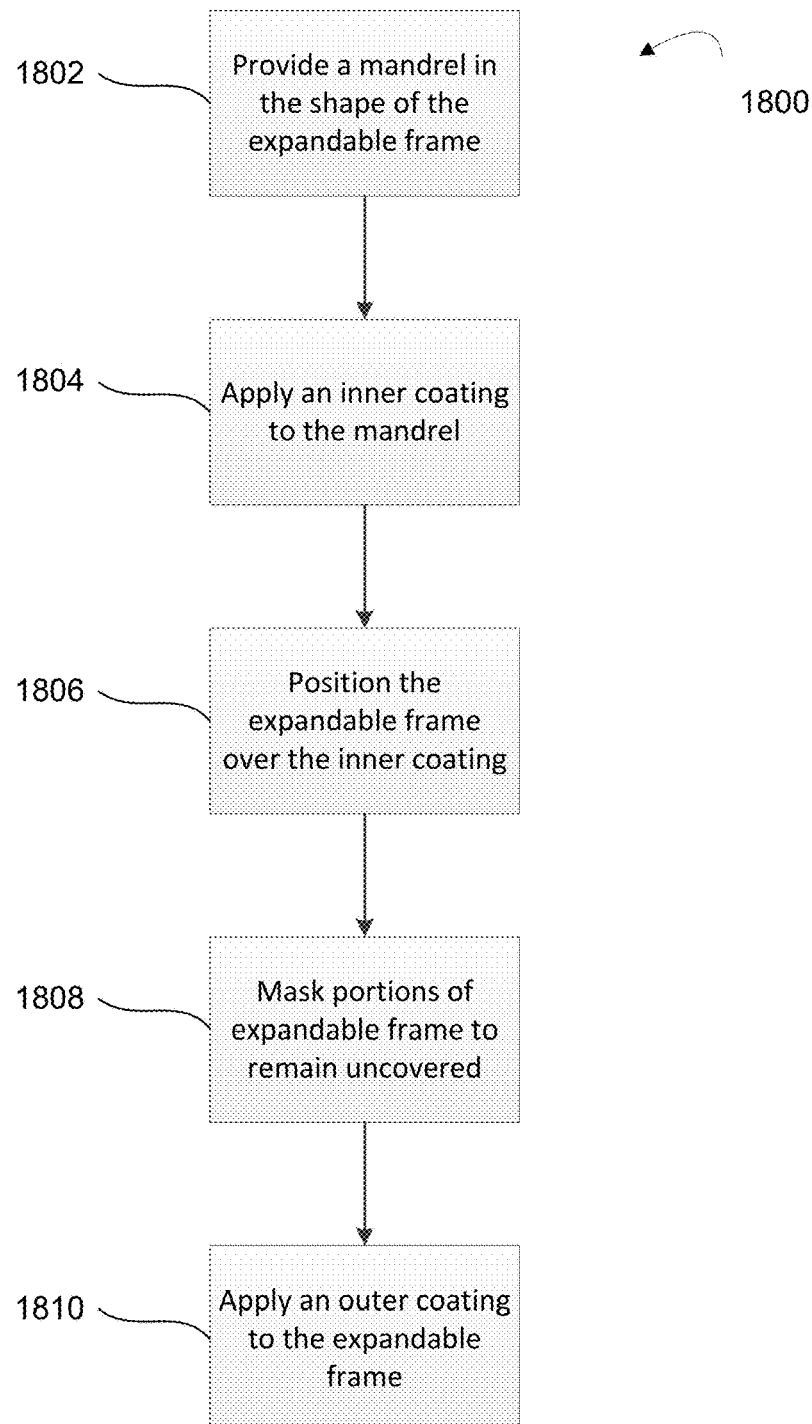
FIG. 18 is a block diagram of a method of coating an occlusion device described herein.

FIG. 18 is a flow chart illustrating one method 1800 of coating an expandable frame that can be applied to any of the occlusion devices described above. The method can include providing a mandrel in the shape of the expandable frame (block 1802). Optionally, portions of the mandrel can be masked to outline the form of an inner coating. Thereafter, an inner coating can be applied to the mandrel using an electrospinning process (block 1804). When the inner coating is complete, the expandable frame can be positioned over the inner coating, such that the expandable frame is in intimate contact with the inner coating (block 1806). If portions of the expandable frame are intended to remain uncovered, those uncovered portions can be masked before application of the outer coating (blocks 1808 and 1810). For example, the expandable frame can be masked by loading uncovered portions of the expandable frame into a tube. The outer coating can adhere to the inner coating to from a single coating that encapsulates at least some of struts or strand portions.

Depending on the membrane material, application of the inner coating to the membrane may be unnecessary. For example, if the membrane includes Kynar, a single outer coating can be applied to the expandable frame without the use of a mandrel. The single outer coating can flow around the struts or strands to encapsulate and adhere to the struts or strands. Application of the outer coating alone can also be useful for occlusion device designs that may be difficult to position on a mandrel.

The suitability of the membrane can be determined using a number of factors. For example, when visually inspecting the membrane, the membrane should not include any cuts, tears, or large gaps. Further, for at least a Kynar membrane, the membrane should be white or opaque, which suggests that the membrane has a porosity and that the membrane is sufficiently flexible. As another example, the coated occlusion device should allow less than or equal to about 200 cc/min at 20 mmHg, such as to between about 50 cc/min and about 150 cc/min, preferably less than about 130 cc/min, less than about 100 cc/min at 20 mmHg or less than about 65 cc/min at 20 mmHg within about five minutes. Further, the occlusion device 1200a can limit the flow rate through a vessel to no more than about 400 cc/min at 60 mmHg or no more than about 330 cc/min at 60 mmHg, such as to between about 150 cc/min and about 250 cc/min, preferably less than or equal to about 175 cc/min at 60 mmHg within about five minutes. The occlusion device 1200a can limit the flow rate through a vessel to about no more than 600 cc/min at about 100 mmHg or 430 cc/min at 100 mmHg, such as to between about 200 mmHg and about 250 mmHg, preferably less than about 225 cc/min at about 100 mmHg within about five minutes, according to the Occlusion Protocol described below. Additionally, the force to load the coated occlusion device should be less than or equal to about 0.5 lbs.

In some embodiments, the mandrel can have a thin, elongated section that extends through the center of the occlusion device. When the membrane 1208a is formed, the coating can be applied to the elongated section to produce a thin extended tubular section of coating 1250a through which the guide wire (e.g., a 0.018" guidewire) can be introduced (see FIG. 12F or 13A). Further, depending on the membrane material, the elongated inner mandrel can help eliminate irregular buildup of coating on the mandrel. The elongated mandrel can also aids in reducing stray charges from carrying the coating away from the mandrel.

Method of Delivering an Occlusion Device

In any of the embodiments disclosed herein configured for over the wire delivery, a small (e.g., approximately 0.020") aperture will remain in the membrane following removal of the guide wire. Occlusion will be primarily mechanical due to the membrane, but a small blood flow through the guidewire aperture will gradually stop via natural biological mechanisms. It may be desirable to achieve rapid, essentially completely mechanical occlusion, which can be done by mechanically patching the aperture. This can be accomplished in any of a variety of ways, by placing an occluder across the aperture. The occluder may take the form of a flap of material attached to the membrane of frame or a plug that is forced by blood flow into or across the opening following retraction of the guidewire.

The occlusion devices described herein can be advanced to the target vessel using any of the delivery systems described herein. In use, the access to the vasculature can be provided using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery in emergencies.

The guide wire 128 (e.g., 0.018" guidewire or smaller) can be delivered to the target vessel. Thereafter, the delivery system 100, 200 can be delivered over the guide wire 128 to the target vessel with sufficient trackability as defined herein. The outer catheter 110, 210 (e.g., 5 F or smaller) and the inner catheter 120, 220 can be delivered together with the occlusion device pre-loaded into the delivery system 100, 200. Alternatively, the outer catheter 110, 210 can be delivered first, followed by the inner catheter 120, 220 carrying the occlusion device. Once the delivery system 100, 200 has been delivered to the target vessel, the inner catheter 120, 220 can move axially until the occlusion device extends from the distal end 114, 224 of the outer catheter 110,220, as shown in FIG. 3A. In some embodiments, the outer catheter 110, 210 can include features shown in FIG. 1B-1 or 2N to delivery contrast dye and monitor performance of the occlusion device. In some instances, after the performance assessment, it may be necessary to resheath and reposition the occlusion device to position the occlusion device accurately.

The occlusion device can be released from the delivery system 100, 200 using any of the techniques described above or any other conventional technique (see e.g., FIGS. 2A to 2K and related discussion). Alternatively, as shown in FIGS. 3D-3F, the support tube 134 can move axially to push the occlusion device off the inner catheter 120. Alternatively, the delivery system 100 may utilize any of the interlock assemblies 150, 170, or 180 described herein.

As described above, in some embodiments, the occlusion device can include one opened end and one closed end (e.g., covered, structurally closed, or otherwise blocked). In some instances, the closed end can be downstream from the opened end. Preferably, the closed end would be on the upstream end of the device. This would have the tendency to minimize "wind-socking" of the device due to blood flow forces and would permit the open downstream end to act as an anchor. Blood pressure on the occluded upstream end would have the effect of foreshortening the device frame, which would secondarily cause an expansion of the distal end accentuating the anchoring force of the device. This effect is particularly evident in a braided frame in which the downstream end is open.

In other embodiments, the occlusion device can include an hourglass design (see, e.g., FIG. 12A or 13A). As described above, it can be preferable to deploy a bare, distal portion prior to deploying a covered, proximal portion. The bare end portion can at least partially anchor the occlusion device in the vessel before deploying the covered second end portion, which facilitates precise placement of the occlusion device. Further, when the covered end portion is upstream (i.e., proximal) from the bare end portion, the increase in arterial pressure at the proximal end increases the radially outward forces that can help the occlusion device resist migration.

Figure 2S:
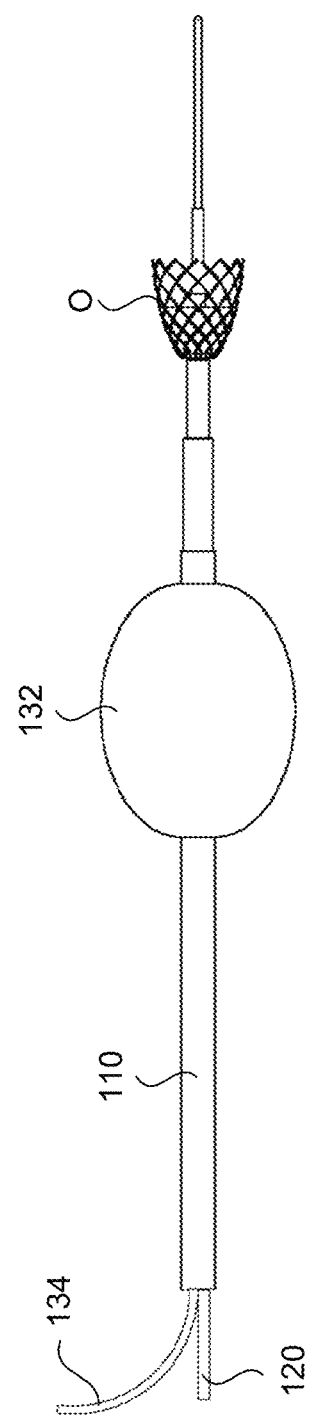
FIG. 2S illustrates an embodiment of a delivery system for delivering an occlusion device having a test balloon.

In some instances, as shown in FIG. 2S, the delivery system can include a test balloon 132. Prior to deploying the occlusion device O, the test balloon 132 can be inflated through inflation lumen 134 to occlude the vessel temporarily. After the occlusion device O is delivered, the test balloon 132 can be deflated, and the delivery system can be withdrawn.

In certain variants, the occlusion device can be reinforced using other reinforcing devices or techniques. For example, one or more coils can be deployed within the expandable structure. As another example, the expandable structure can be reinforced with an occlusion balloon. In yet another example, the method can include ligation to close off the target vessel.

In Vitro Test Protocols

The performance characteristics of the present disclosure are verified using a series of in vitro test protocols, including: (1) Delivery, Deployment, and Retraction Test Protocol; (2) Acute Migration Test Protocol; (3) Occlusion Effectiveness Test Protocol; and (4) Contrast injection Test Protocol.

Trackability Test & Delivery Deployment, and Retraction Test

The Delivery, Deployment, and Retraction Test Protocol ("Trackability Protocol") may be used to measure a series of delivery system performance characteristics for any of the delivery systems described herein, including: luer compatibility, pressure integrity, guidewire compatibility, introducer sheath compatibility, trackability, working length, deployment force, embolic re-sheathing, post-deployment retraction, delivery accuracy, and post-procedure integrity. "Trackability" refers to the relative ability to navigate an endovascular device or delivery system through a tortuous vascular environment. As described herein, the Trackability Protocol provides a consistent, repeatable, in vitro environment in which to evaluate this device characteristic, in addition to the other performance and compatibility characteristics noted above.

The Trackability Protocol is performed using a Trackability Protocol fixture (see FIG. 19A) comprising a water reservoir 1902, a water heater 1904 (e.g., PolyScience Heater model 7306AC1B or equivalent), a peristaltic pump 1906 (e.g., 913 MityFlex Peristaltic Pump S/N P321 or equivalent), anatomical model ("model") 1908 (e.g., using Modified PAVM 1010 with uterine vessel from DialAct Corp. (Asset #4008)), a back pressure column 1910, and the corresponding tubes and connectors. The Trackability Protocol fixture of FIG. 19 is constructed using the following steps. First, the water reservoir 1902 is filled with water. Second, the water is heated to approximately 97° F. (37° C.), thereby simulating internal human body temperature. Third, the reservoir 1902 is connected to the peristaltic pump 1906. Fourth, the pump 1906 is connected in series to the model 1908 using the requisite tubes and connectors. The model 1908 can include a sheath introducer valve 1916 through which the delivery system may be inserted. Fifth, the back pressure column 1910 is connected between an outlet of the model 1912 and an inlet of the water reservoir 1914, thereby regulating the fluid pressure within the model. Once the tubes and connectors are secure, the pump 1906 is initiated and water begins to flow through the model 1908 to simulate the physiological blood flow rate of the human body.

Figure 19A:
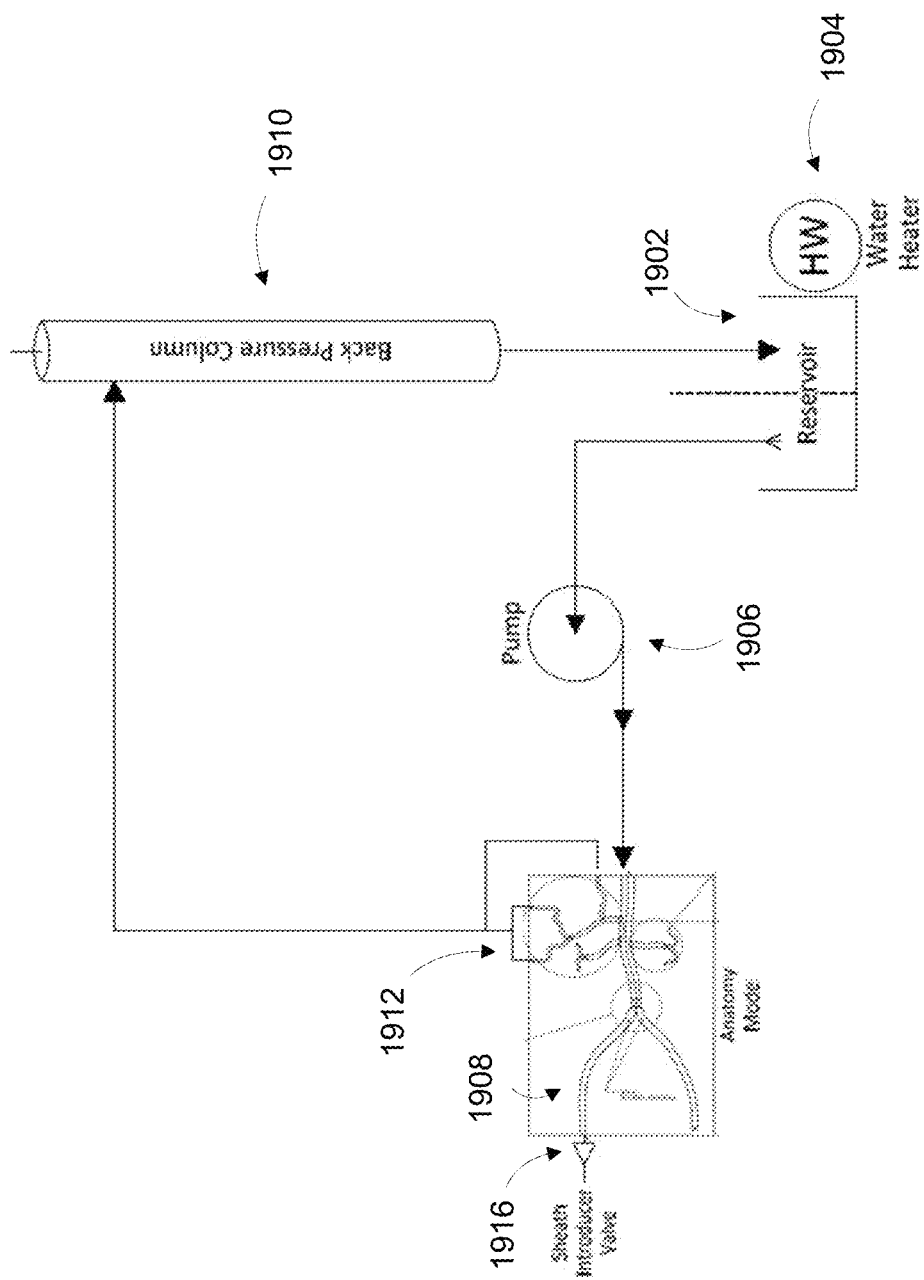
FIG. 19A illustrates a Trackability Protocol fixture.
Figure 19F:
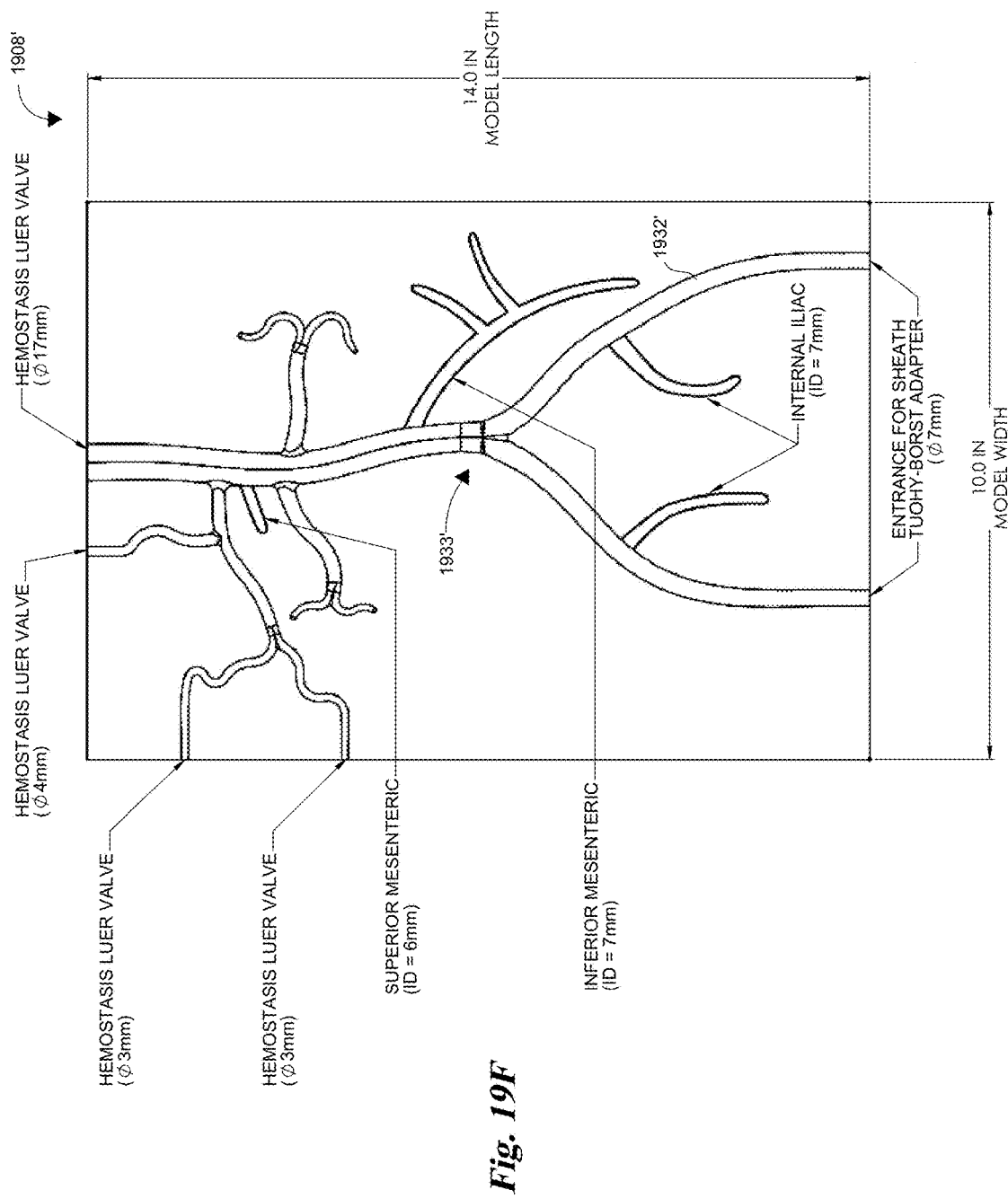
FIG. 19F illustrates another model for the Trackability Protocol fixture.

FIG. 19B illustrates an enlarged view of the Trackability Protocol fixture model 1908 drawn to scale, and FIGS. 19C to 19D illustrate enlarged views of different portions of the model 1908. The model 1908 generally consists of a series of vessels to simulate vascular pathways. Dimensions for the model 1908 are provided on the figures. FIG. 19F illustrates a model 1908' that includes additional vessels that can be used as the target vessel. Numerals used to identify vessels in model 1908 include an apostrophe (') to identify like vessels in model 1908'.

The Trackability Protocol may be initiated as soon as fluid begins to flow through the model 1908. The Trackability Protocol consists of the following steps. First, the embolic device is loaded into the delivery system. At this time, the characteristics of delivery system luer compatibility and delivery system pressure integrity may be evaluated. Luer compatibility may be evaluated by filling a standard 5 cc or 10 cc syringe with water and connecting the syringe to the proximal luer of the delivery system. The syringe may then be evacuated, which flushes water through the delivery system. If the syringe is capable of being connected and disconnected to the delivery system luer, and the delivery system is capable of being flushed without bursting or leaking, then the delivery system may receive a passing grade.

Second, the delivery system is advanced over a 0.018" guidewire. At this time, guidewire compatibility may be evaluated. This may be accomplished by tracking the guidewire through the delivery system until the proximal end of the guidewire extends beyond the proximal end of the delivery system. If the guidewire does not buckle or bind during tracking, then the delivery system may receive a passing grade.

Third, the delivery system assembly, which now includes the 0.018" guidewire and the embolic device, is inserted into the test fixture through a 5 F sheath introducer. At this time, delivery system compatibility with the sheath introducer may be evaluated. This may be accomplished by determining whether the delivery system is capable of being inserted into and through the 5 F sheath introducer.

Fourth, delivery system trackability is assessed. This may be accomplished by pushing, or "tracking," the delivery system through the model 1908. The delivery system is delivered through a sheath introducer valve 1916 and into a model femoral 1932, a model abdominal aorta 1933, a deployment target vessel 1936 (shown as the common hepatic or celiac in model 1908 but can be any other vessel shown in the model for other trackability tests) and toward a target vessel location 1934 (shown as the right hepatic but can be any other vessel shown in the model for other trackability tests). An enlarged view of the target vessel location 1934 is shown in FIG. 19D.

Figure 19G:
FIG. 19G illustrates a measurement of the linear distance between the distal tip of the delivery system to a predefined location in the model shown in FIG. 19A.
Figure 19H:
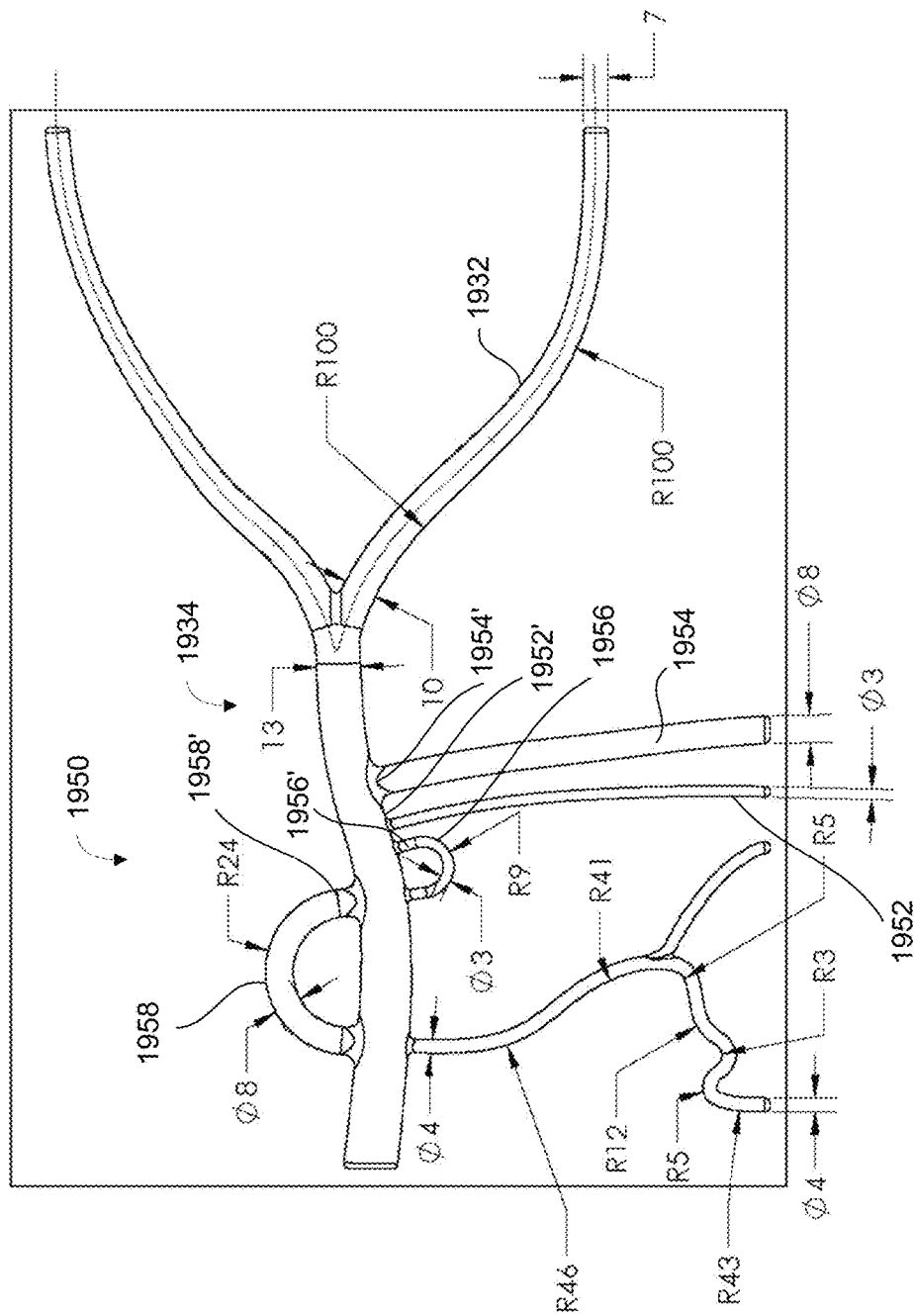
FIG. 19H illustrates another model of the anatomic model that can be used to assess delivery, deployment, and retraction.

The delivery system is tracked through the model 1908 and toward the target vessel 1934 until the delivery system cannot be advanced further into the model 1908. Trackability may then be quantified by measuring the linear distance between the distal tip of the delivery system to a predefined location in the model. By way of example, FIG. 19G is a photo of a portion of the test fixture 1908. As shown in FIG. 19G, the measurement is taken from the distal tip of the delivery system 1922 to the vessel bifurcation point 1944. To achieve a passing grade in the model embodied in FIG. 19G, the delivery system must be capable of tracking to a linear distance at least 4 cm from (i.e., beyond) the bifurcation 1944.

Fifth, referring back to FIG. 19B, the delivery system is pulled proximal to the target vessel 1934 and into a predefined deployment vessel 1936. Reference line 1938 represents the target location of the proximal end of the occlusion device.

For detachable and standard pushable devices, deployment force may be evaluated at this time. For detachable devices only, re-sheathing performance may be evaluated at this time.

Sixth, the occlusion device is fully deployed at the deployment location 1938 (or, if possible, tested for partial deployment and retraction as described below). At this time, post-deployment delivery system retraction may be assessed. This may be accomplished by repositioning the occlusion device while it is still attached to the delivery system. The maximum acceptable retraction force is 4.5N.

Seventh, the delivery system is detached from the occlusion device and the delivery system is removed from the model. At this time, occlusion device delivery accuracy and post-procedure delivery system integrity may be assessed. Delivery accuracy may be quantified by measuring the distance from the proximal end of the occlusion device to the reference line 1938 in the deployment vessel 1936. Delivery system integrity may be assessed by visually observing the physical condition of the delivery system after it has been removed from the Trackability Protocol fixture model 1908. If the delivery system has not suffered any obvious kinks, severe bends or curls, or physical breaks or separations, then the delivery system may receive a passing grade.

Following the trackability test, the model 1908 can be replaced with model 1950 to test the delivery, deployment, and retraction of the occlusion device in a T-shaped or B-shaped vessel. The model can be constructed from polycarbonate with the dimensions of the model labeled on the figure. After the delivery system is advanced over the guidewire and into a 5 F sheath introducer, the delivery system is tracked over the guidewire through the femoral 1932 and into one of the mock T-shaped (3 mm—1952; 8 mm—1954) or B-shaped vessels (3 mm—1956; 8 mm—1958). Once in position, the occlusion device can be partially deployed. Before full release, the occlusion device can be resheathed by pulling the occlusion device back into the delivery system. The delivery system should be able to resheath the occlusion device with minimal force, as defined above, and without visible damage to the occlusion device or to the delivery system. Thereafter, the full occlusion device is deployed. The target location for the proximal end of the occlusion device is the ostium into the T-shaped or B-shaped vessel. The distance between the proximal end of the occlusion device and the ostium of the T-shaped 1952', 1954' or B-shaped vessel 1956', 1958' is measured. To pass, the occlusion device must be positioned within 5 mm of the target site (i.e., the ostium).

Acute Migration Test

The Acute Migration Test Protocol ("Migration Protocol") may be used to measure the stability of an implanted occlusion device (e.g., any of the occlusion devices described herein). The term "stability" refers to the relative ability of the occlusion device to withstand fluid pressure and thus maintain its position at a target deployment location.

Figure 20A:
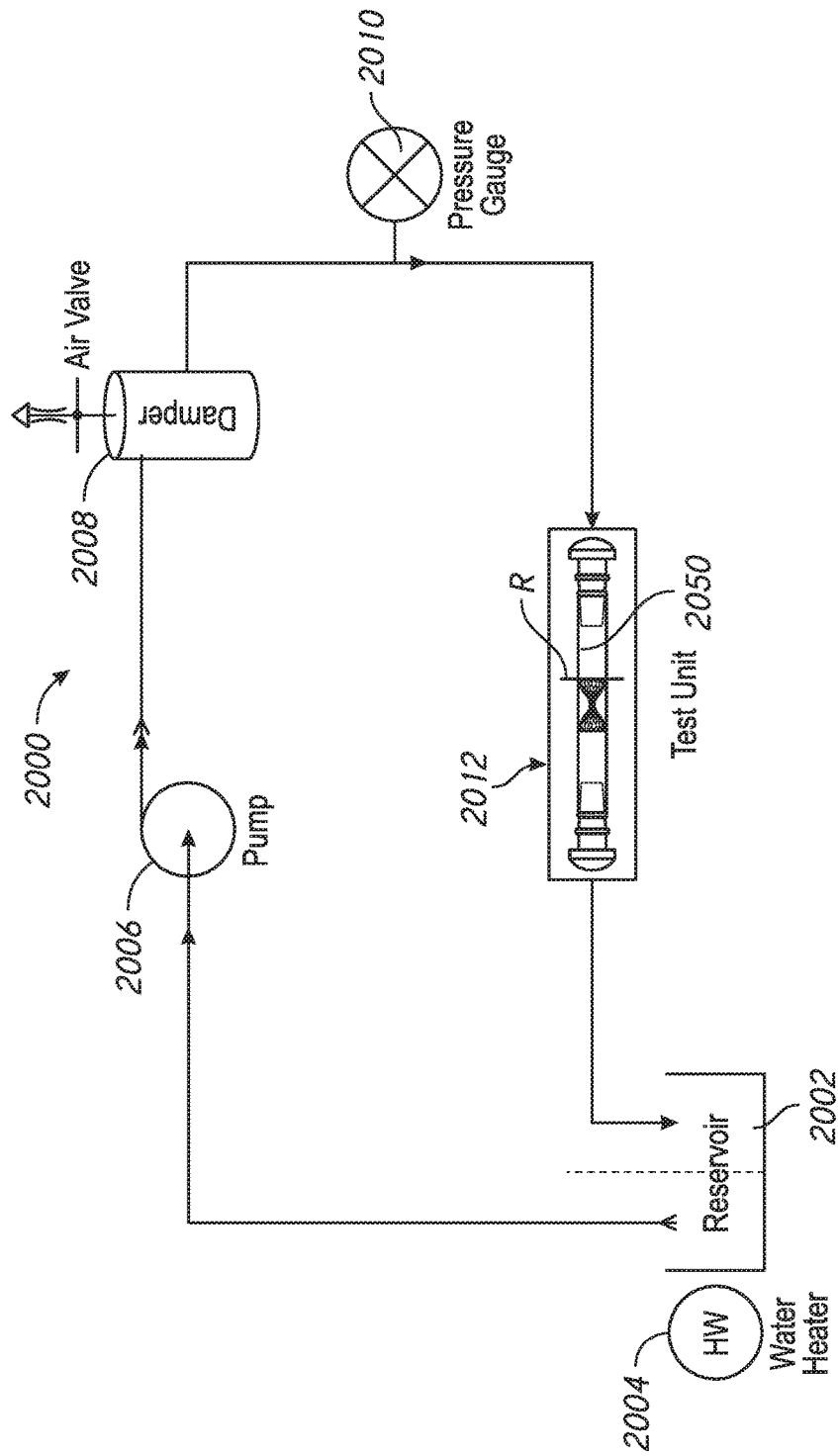
FIG. 20A illustrates a Migration Protocol test fixture.
Figure 20B:
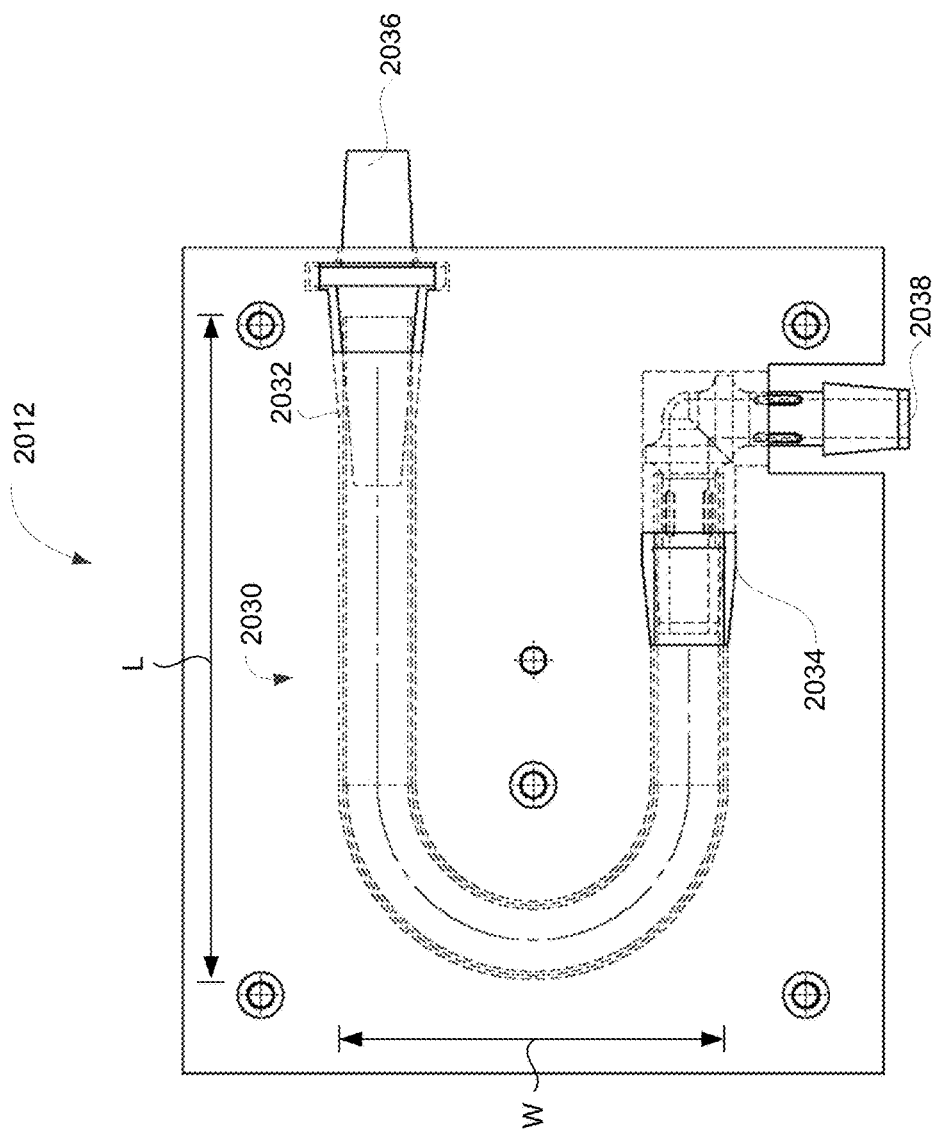
FIG. 20B illustrates a mock 8 mm curved vessel.
Figure 20C:
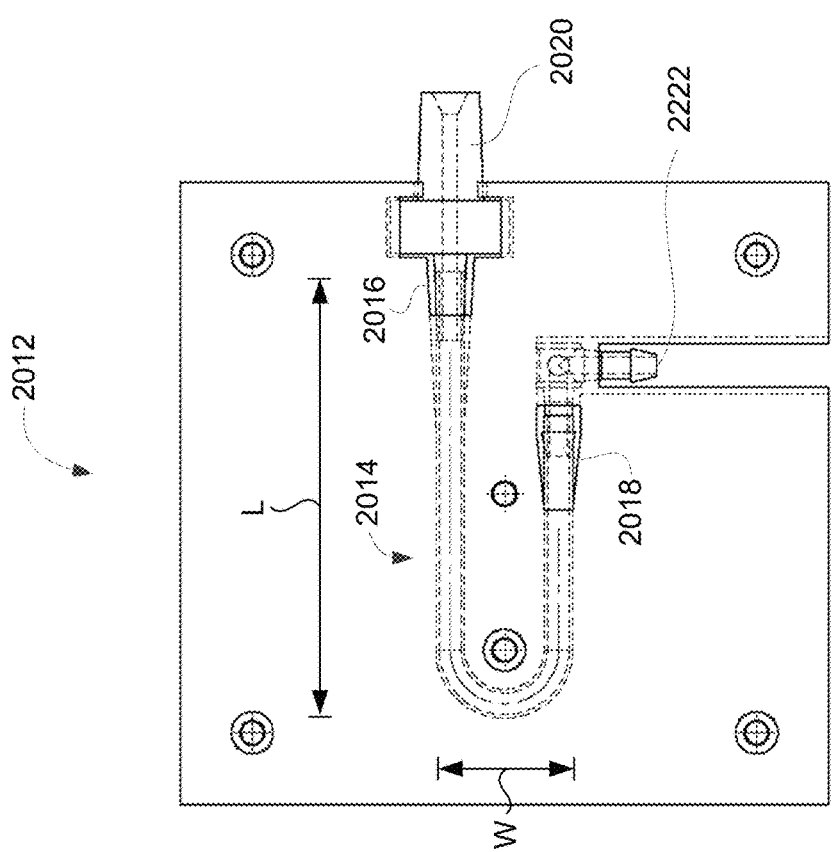
FIG. 20C illustrates a mock 3 mm curved vessel.

As shown in FIG. 20A, the Migration Protocol is performed using a test fixture 2000 comprising a water reservoir 2002, a water heater 2004 (e.g., PolyScience Heater model 7306AC1B or equivalent), a peristaltic pump (or equivalent) 2006 (e.g., 913 MityFlex Peristaltic Pump S/N P321 or equivalent), a damping reservoir 2008 (e.g., Air/Oil Reservoir, Grainger item 1U550), a pressure gauge 2010 (e.g., Allheart Pressure Gauge 20-300 mmHg), a simulated vessel fixture 2012, a simulated vessel 2050 (e.g., a 3 mm or 8 mm straight, mock vessel using 1014 Silicone or a curved vessel as shown in FIGS. 20B and 20C), and corresponding tubes and connectors. FIG. 20 shows a schematic of the Migration Protocol test fixture.

FIGS. 20B and 20C illustrate the simulated vessel fixtures 2012 positioned in an acrylic stand. The mock 8 mm curved vessel 2030 can be constructed from silicone and have a 8 mm internal diameter (see FIG. 20B). The mock curved vessel 2030 can have a length L of about 85 mm and a width W of about 49 mm. The mock curved vessel 2030 can have a 20 mm radius to centerline of vessel. A tapered, male fitting 2036 can be positioned at a first end 2032 of the mock vessel for connecting to the test fixture 2000, and a 5/16 inch, 90 degree elbow fitting 2038 can be positioned at a second end 2034 of the mock vessel 2030 for connecting to the text fixture 2000.

The mock 3 mm curved vessel 2014 can have a 3 mm internal diameter (see FIG. 20C). The mock 3 mm curved vessel 2014 can have a length L of about 62 mm and a width W of about 19 mm with a 7.5 mm radius to centerline of vessel. A tapered, male fitting 2020 can be positioned at a first end 2016 of the mock vessel for connecting to the test fixture 2000, and a 1/8 inch, 90 degree elbow fitting 2022 can be positioned at a second end 2018 of the mock vessel 2014 for connecting to the text fixture 2000.

The Migration Protocol test fixture of FIG. 20A is constructed according to the following steps. First, the water reservoir 2002 is filled with water. Second, the water is heated to approximately 97° F. (37° C.), thereby simulating internal human body temperature. Third, an outlet of the water reservoir 2002 is connected to the peristaltic pump 2006. Fourth, the pump 2006 is connected in series to the damping reservoir 2008 using the requisite tubes and connectors. Fifth, the pressure gauge 2010 is connected in distal to the damping reservoir 2008. Finally, the vessel fixture 2012 is connected in series with an inlet of the water reservoir 2002.

Figure 20D:
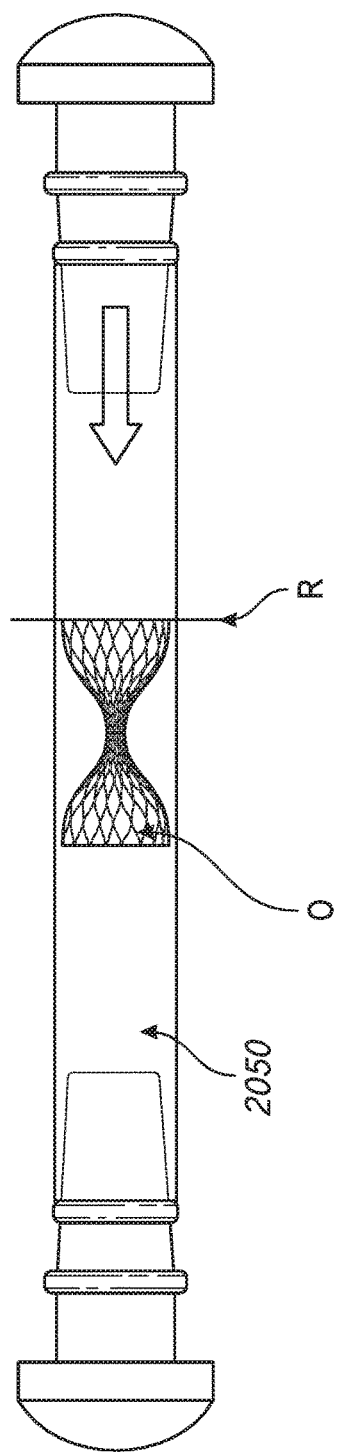
FIG. 20D illustrates a vessel that can be used in connection with the test fixture shown in FIG. 20A.

FIG. 20D illustrates an enlarged view of the straight vessel fixture 2012. The vessel fixture 2012 generally consists of a tube 2050 defined by a known length and internal diameter. For example, the diameter of the tube 2050 used in any given Migration Protocol may vary from 3 mm to 10 mm. The migration data recited herein was determined using a tube 2050 with a diameter of 3 mm or 8 mm and a length of 15 cm.

The Migration Protocol below is described in connection with the tube 2050; however, any one of the vessel fixtures shown in FIGS. 20B and 20C can be used. First, an appropriately-sized tube 2050 may be selected. The size of the tube 2050 should correspond to the size of the selected occlusion device O. Second, the occlusion device O is deployed within the tube 2050. Third, the tube 2050 is connected to the vessel fixture 2012. Fourth, a reference line R is drawn on the tube 2050 which marks the proximal end of the occlusion device O inside the tube 2050. Fifth, the pump 2006 is turned on to initiate fluid flow through the Migration Protocol test fixture 2000 and remove any latent air bubbles. Sixth, a valve 2016 associated with the damping reservoir 2008 is opened to allow approximately one inch of water to enter the damping reservoir 2008 and then the valve 2016 is closed. Seventh, the pump speed is slowly increased to increase the fluid pressure in the Migration Protocol test fixture 2000. The fluid pressure may be continuously observed using the pressure gauge 2010. The pump speed continues to be increased while the movement of the occlusion device O within the tube 2050 is observed. Finally, at the moment the occlusion device O moves, or "migrates," more than 5 mm within the tube 2050, the pressure is recorded. This pressure represents the minimum pressure necessary to cause occlusion device O migration within the tube 2050.

Occlusion Effectiveness Test

The Occlusion Effectiveness Test ("Occlusion Protocol") may be used to measure the efficacy of an implanted occlusion device (e.g., any of the occlusion devices described herein). The term "efficacy" refers to the relative ability of the occlusion device to occlude fluid flow at a target deployment location.

Figure 21:
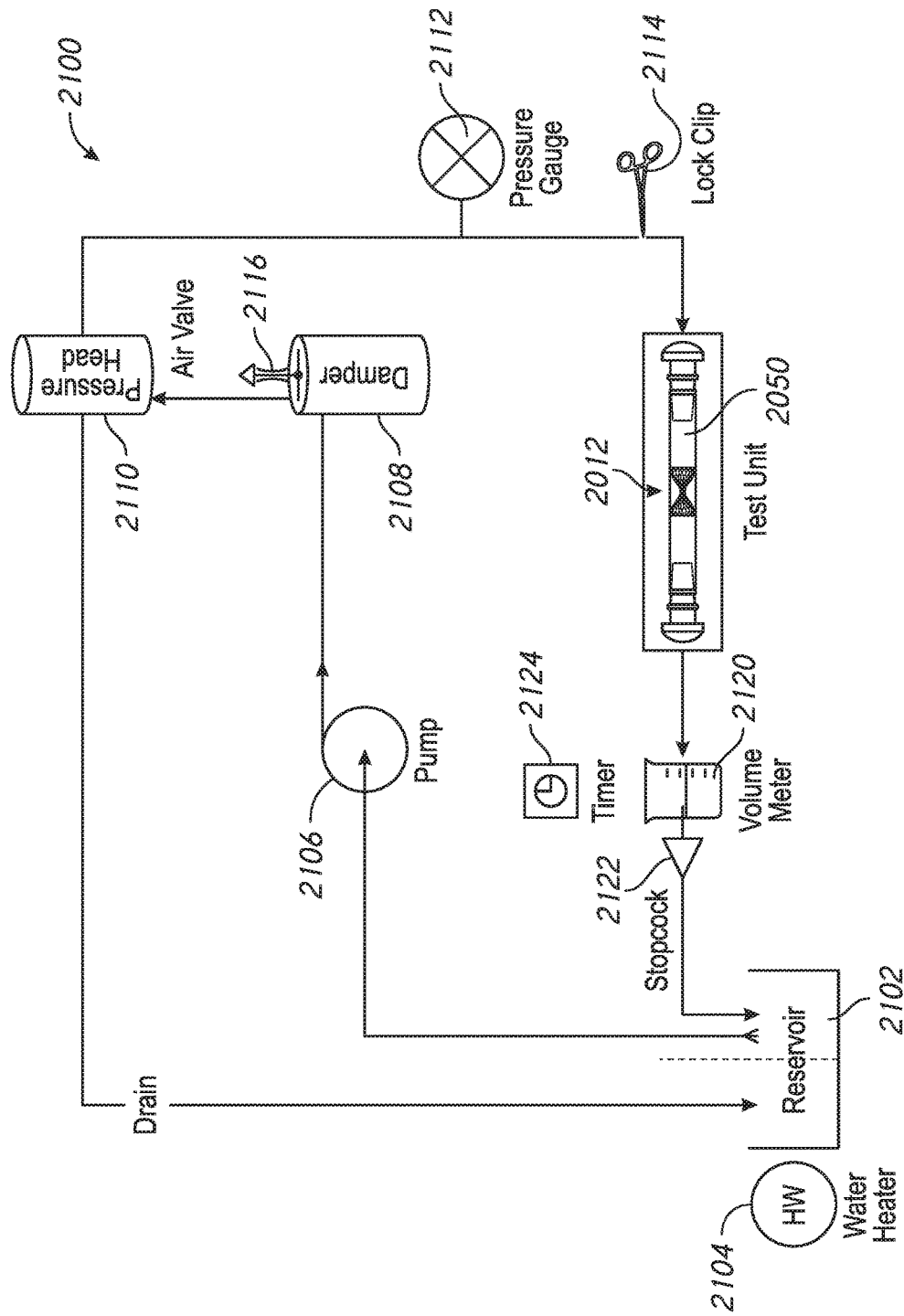
FIG. 21 illustrates a schematic of an Occlusion Protocol test fixture.

As shown in FIG. 21, the Occlusion Protocol is performed using a test fixture 2100 comprising a water reservoir 2102, a water heater 2104, a peristaltic pump (or equivalent) 2106 (e.g., PolyScience Heater model 7306AC1B or equivalent), a damping reservoir 2108 (e.g., Air/Oil Reservoir, Grainger item 1U550), a pressure head reservoir 2110, a pressure gauge 2112 (e.g., Allheart Pressure Gauge 20-300 mmHg), a lock clip (or valve) 2114, a simulated vessel fixture 2112, a simulated vessel 2050 (e.g., see FIG. 20D), a volume meter 2120 (e.g., 140 cc syringe), a two-way stopcock 2122, a timer (or stopwatch) 2124, and corresponding tubes and connectors. FIG. 21A shows a schematic of the Occlusion Protocol test fixture 2100. The simulated vessel 2150 can be any of the vessels shown in FIGS. 20B to 20C or described in connection with test fixture 2000.

The Occlusion Protocol test fixture of FIG. 21 is constructed according to the following steps. First, the water reservoir 2102 is filled with water. Second, the water is heated to approximately 97° F., thereby simulating internal human body temperature. Third, an outlet of the water reservoir 2102 is connected to the peristaltic pump 2106. Fourth, the pump 2106 is connected in series to the damping reservoir 2108 using the requisite tubes and connectors. Fifth, the damping reservoir 2108 is connected in series to the pressure head 2110, which is connected to both the water reservoir 2102 and vessel fixture 2112. Sixth, the vessel fixture 2112 is connected to the volume meter 2120, which is controlled with the stopcock 2122 and drains into the water reservoir 2102. Finally, the pressure gauge 2112 is connected proximal to the vessel fixture 2112 to monitor system pressure.

The vessel fixture 2112 generally consists of a tube 2150 defined by a known length and internal diameter. For example, the diameter of the tube 2150 used in any given Occlusion Protocol may vary from 3 mm to 10 mm. The occlusion data recited herein was determined using a tube 2150 with a diameter of 3 mm or 8 mm and a length of 15 cm.

The Occlusion Protocol consists of the following steps. An appropriately-sized vessel 2150 may be selected. The occlusion device O is then deployed within the vessel 2150. Although the protocol is described in accordance with the vessel 2150, any of the vessels shown in FIG. 21B or 21C can also be used.

Figure 22B:
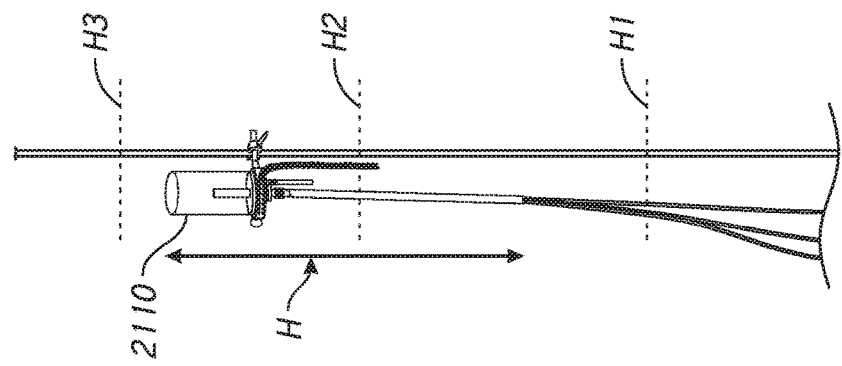
FIGS. 22A and 22B illustrates different steps of the Occlusion Protocol.
Figure 22A:
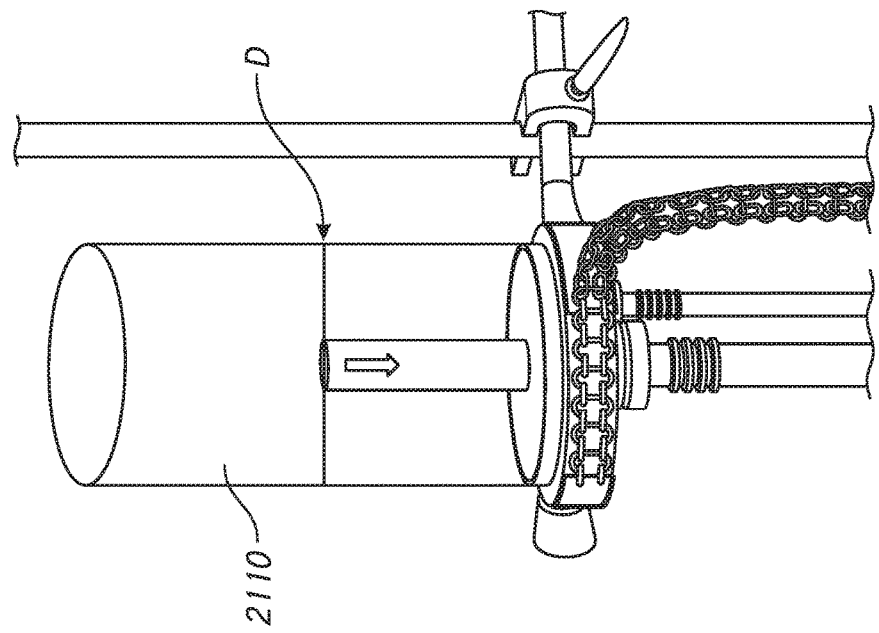

Next, the vessel 2150 is connected to the vessel fixture 2112. The pump 2106 is then turned on to initiate fluid flow through the Occlusion Protocol test fixture 2100 and remove any latent air bubbles. Next, a valve 2126 associated with the damping reservoir 2108 is opened to allow approximately one inch of water to enter the damping reservoir 2108 and then the valve 2126 is closed. Referring now to FIG. 22B, the pump 2106 continues to run until the pressure head reservoir 2110 is filled to the drain line D. Next, as shown in FIG. 22B, the height H of the pressure head 2110 is adjusted until the desired pressure H1, H2, H3 is achieved, as indicated on the pressure gauge 2112. Depending on the specific test being performed, the desired pressure may range from 20 mmHg H1 to 100 mmHg H3. The pump speed is then adjusted to achieve equilibrium between the system pressure, as shown on the pressure gauge 2112, and the fill volume of the pressure head reservoir 2110. The flow is then stopped by closing the lock clip 2114 distal to the pressure gauge 2112 and allowing the water to drain from the volume meter 2120. Next, the stopcock 2122 is closed, simultaneously opening the lock clip 2114 and starting the timer 2124. The timer 2124 should be stopped when the target volume in the volume meter 2120 is reached. Finally, the final target volume and time are recorded. Occlusion effectiveness is calculated by dividing the recorded volume by the recorded time and reporting the outcome as cc/min. For purposes of the Occlusion Protocol, the target volume is arbitrary, however, the target volume must be known in order to calculate occlusion effectiveness, as described.

Contrast Injection Test

The Contrast Injection Test ("Injection Protocol") may be used to measure the contrast injection performance of a delivery system (e.g., any of the contrast injection delivery systems described herein). Contrast injection performance quantifies the time required to inject a known volume of contrast agent through the delivery system. Contrast agent refers to the material, such as Isovue-300 Iopamidol Injection 61% or Optiray-320 Ioversol Injection 68% (or equivalent), that a physician may use to visualize the vasculature over the course of an endovascular procedure. Such visualization is accomplished using standard imaging techniques.

Figure 23:
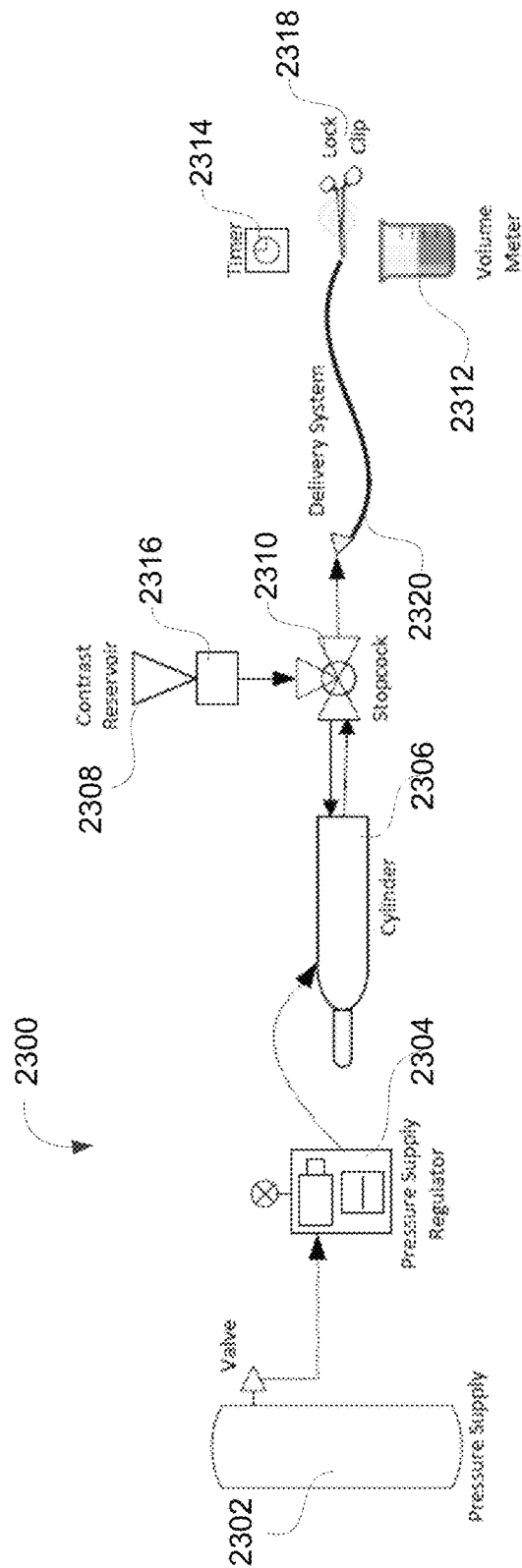
FIG. 23 illustrates a schematic of an Injection Protocol test fixture.

The Injection Protocol is performed using a test fixture 2300 comprising a pressure supply 2302 (e.g., a nitrogen tank), a pressure supply regulator 2304, a cylinder (or piston) 2306 (e.g., a Bimba Stainless SR-0910-D (factor 1.21 to 1)), a contrast reservoir 2308 (e.g., a 25 cc Hand Injector), a high pressure three-way stopcock 2310, a volume meter 2312 (e.g., a graduated cylinder), a timer (or stopwatch) 2314, contrast solution 2316, a syringe, a lock clip 2318, and corresponding tubes and connectors. FIG. 23 shows a schematic of the Injection Protocol test fixture 2300.

The Injection Protocol test fixture of FIG. 23 is constructed according to the following steps. The pressure supply 2302 is connected to the pressure regulator 2304, which is then connected to the cylinder 2306. In turn, the cylinder 2306 is connected to the stopcock 2310, which is connected to the contrast reservoir 2308, which contains contrast agent 2316. The stopcock 2310 is also connected to the delivery system 2320. The distal end of the delivery system is placed into the volume meter 2312.

The Injection Protocol consists of the following steps. First, 100 mL of contrast agent 2316 is prepared by mixing equal parts contrast fluid with water. Next, the contrast reservoir 2308 is filled with the contrast agent 2316. The contrast agent 2316 is then transferred to the cylinder 2306 by opening the stopcock 2310 between the cylinder 2306 and contrast reservoir 2308. Next, the delivery system 2320 is flushed with excess contrast agent using a standard syringe. Next, the regulator 2304 is set to the desired pressure (e.g., 100 psi). The distal tip of the delivery system 2320 is then sealed using the lock clip 2318 under the assumption that the occlusion device prevents contrast dye from exiting the distal end of the delivery system. A side port of the delivery system 2320 is then connected to the closed end of the three-way stopcock 2310. Next, the stopcock 2310 is turned to connect the delivery system 2320 with the cylinder 2306 and pressurize the cylinder 2306. The pressure regulator 2304 is then adjusted to the desired pressure, based on the relevant cylinder factor. Of course, the cylinder factor may vary depending on the type of cylinder used. Next, the pressure supply regulator 2304 is turned and the timer 2314 is simultaneously started. The timer 2314 should be stopped when the target volume in the volume meter 2312 is reached. Finally, the final target volume and time are recorded. Injection performance is calculated by dividing the recorded volume by the recorded time and reporting the outcome in cc/min. For purposes of the Injection Protocol, the target volume is arbitrary, however, the target volume must be known in order to calculate contrast injection rate, as described.

TERMINOLOGY

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, depending on the context, the terms "approximately", "about", and "substantially" may refer to an amount that is within less than 10% of, within less than 5% of, within less than 1% of, within less than 0.1% of, and within less than 0.01% of the stated amount.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

The ranges provided herein are set forth solely for illustrating typical device dimensions. The actual dimensions of a device constructed according to the principles of the present invention may obviously vary outside of the listed ranges without departing from those basic principles. For example, diameter outside of the preferred ranges may also be used, provided that the functional consequences of the diameter are acceptable for the intended purpose of the catheter. In particular, the lower limit of the diameter for any portion of catheter body 110 in a given application will be a function of the number of fluid or other functional lumen contained in the catheter, together with the acceptable minimum aspiration flow rate and collapse resistance.

Although certain embodiments and examples have been described herein, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Any methods disclosed herein need not be performed in the order recited. The methods disclosed herein include certain actions taken by a practitioner; however, they can also include any third-party instruction of those actions, either expressly or by implication. For example, actions such as "expanding an expandable structure" includes "instructing expansion of an expandable structure."

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

EXAMPLE EMBODIMENTS

The following example embodiments identify some possible permutations of combinations of features disclosed herein, although other permutations of combinations of features are also possible.

1. A vascular occlusion device, comprising:
a frame comprising a proximal embolic zone and a distal anchoring zone separated by a hub;
the proximal and distal zones self-expandable from a constrained diameter to an unconstrained diameter of at least about 500% of the constrained diameter;
a guidewire lumen through the hub, to permit placement over a guidewire; and
a valve in communication with the guidewire lumen.

2. The endovascular occlusion device as in Embodiment 1, having an expansion ratio of at least about 6:1.

3. The endovascular occlusion device as in Embodiment 1, having an expansion ratio of at least about 7:1.

4. The endovascular occlusion device as in any one of Embodiments 1 to 3, having an unconstrained expanded diameter of at least about 1.5 mm and which can be deployed from a 0.7 mm or smaller inside diameter lumen.

5. The endovascular occlusion device as in any one of Embodiments 1 to 3, having an unconstrained expanded diameter of at least about 6.0 mm and which can be deployed from a 0.7 mm or smaller inside diameter lumen.

6. The endovascular occlusion device as in any one of Embodiments 1 to 5, wherein the device is configured to occlude at least about 90 percent of flow through a vessel when the expandable tubular frame is in an expanded configuration.

7. An endovascular occlusion device, comprising an expandable occlusive element for expansion within and occlusion of a vessel, the occlusive element having an expansion ratio of at least about 5:1.

8. A delivery system for delivering an occlusion device, the delivery system comprising:
an outer catheter;
an inner catheter axially movable within the outer catheter, the inner catheter configured to deliver the occlusion device out of the outer catheter, wherein the occlusion device comprises:
an expandable structure configured to move between an unexpanded configuration and an expanded configuration, the expandable structure having a proximal portion, a middle portion, and a distal portion,
wherein the expandable structure has an expansion ratio of at least about 5:1,
and wherein the occlusion device is configured to prevent substantially all fluid from flowing past the occlusion device when the occlusion device is in the expanded configuration in the vessel.

9. The delivery system of Embodiment 8, further comprising a support tube axially disposed between the outer catheter and the inner catheter.

10. The delivery system of Embodiment 8 or 9, wherein the outer catheter includes an inner diameter of less than or equal to about 2 mm.

11. The delivery system of any one of Embodiments 8 to 10, wherein the inner catheter is configured to carry the expandable structure on a distal portion of the inner catheter.

12. The delivery system of any one of Embodiments 8 to 11, wherein the inner catheter releasably engages at least one of the proximal end or the distal end of the expandable structure.

13. A method of occluding a vessel, the method comprising:
advancing a delivery system over a guidewire in the vessel;
deploying a single occlusion device from the delivery system, the single occlusion device having at least one closed end and an occlusive membrane extending across at least the closed end, wherein the single occlusion device has an expansion ratio of at least about 5:1.

14. The method of Embodiment 13, wherein a diameter of the expandable structure in the unexpanded configuration is less than or equal to about 2 mm.

15. The method of Embodiment 13 or 14, wherein the delivery system comprises an outer catheter having an inner diameter of less than or equal to about 2 mm.

16. The method of any one of Embodiments 13 to 15, wherein positioning the delivery system comprises advancing the delivery system over a guide wire.

17. An endovascular occlusion device for occluding blood flow through a vessel, comprising:
an expandable frame; and
a membrane carried by the frame;
wherein the frame and the membrane are dimensioned for deployment from a tube having an inside diameter of no more than about 2 mm, and are expandable to a diameter of at least about 8 mm following deployment from the tube; and the membrane has a porosity which achieves a reduction in blood flow of at least about 80% within 5 minutes of deployment from the tube in a blood vessel.

18. An endovascular occlusion device as in Embodiment 17, configured to achieve a reduction in blood flow of at least about 80% within 2 minutes of deployment from the tube in a blood vessel.

19. An endovascular occlusion device as in Embodiment 18, configured to achieve a reduction in blood flow of at least about 80% within 1 minute of deployment from the tube in a blood vessel.

20. An endovascular occlusion device as in any one of Embodiments 17 to 19, configured to achieve total occlusion within 5 minutes of deployment from the tube in a blood vessel.

21. An endovascular occlusion device as in Embodiment 20, configured to achieve total occlusion within 1 minute of deployment from the tube in a blood vessel.

22. An endovascular occlusion device as in any one of Embodiments 17 to 21, having an expansion ratio of at least about 6:1.

23. An endovascular occlusion device as in any one of Embodiments 17 to 21, having an expansion ratio of at least about 7:1.

24. An endovascular occlusion device as in any one of Embodiments 17 to 23, deliverable over an 0.018 inch guidewire.

25. An endovascular occlusion device as in any one of Embodiments 17 to 24, wherein the device has an average COP across a diameter of 2.5 mm to 8.0 mm of between about 30 mmHg and about 140 mmHg.

26. An endovascular occlusion device for achieving mechanical occlusion of blood flow in a vessel, without requiring biological processes to achieve occlusion, comprising:

an expandable support structure, carrying a porous membrane, wherein the membrane is configured to obstruct blood flow through the vessel when the support structure is in an expanded configuration; the membrane having an average pore size of no more than about 100 microns.

27. An endovascular occlusion device as in Embodiment 26, wherein the membrane comprises an average pore size of no more than about 50 microns.

28. An endovascular occlusion device as in Embodiment 26, or 27 wherein the membrane comprises an average thickness of no more than about 30 microns.

29. An endovascular occlusion device as in any one of Embodiments 26 to 28, wherein the occlusion device is deliverable from a lumen having an inside diameter of no more than about 2 mm.

30. An endovascular occlusion device as in Embodiment 29, wherein the occlusion device is deliverable from a lumen having an outside diameter of less than or equal to about 1.67 mm.

31. An endovascular occlusion device as in any one of Embodiments 26 to 30, deliverable over an 0.018 inch guidewire.

32. An endovascular occlusion device as in any one of Embodiments 26 to 31, wherein the device has an average COP across a diameter of 2.5 mm to 8.0 mm of between about 30 mmHg and about 140 mmHg.

33. An endovascular occlusion device for occluding blood flow through a vessel, the occlusion device comprising a frame that is expandable through a range from a first, compressed diameter to a second, maximum expanded diameter, wherein the range of expansion is sufficient to occlude blood vessels having inside diameters anywhere within the range from about 2.5 mm to about 8 mm.

34. An endovascular occlusion device as in Embodiment 33, wherein the range of expansion is sufficient to occlude blood vessels having inside diameters anywhere within the range from about 2.5 mm to about 8 mm.

35. An endovascular occlusion device as in Embodiment 33 or 34, wherein the first, compressed diameter is small enough that the occlusion device is deployable from a lumen having an inside diameter of no more than about 2 mm.

36. An endovascular occlusion device as in Embodiment 35, wherein the first, compressed diameter is small enough that the occlusion device is deployable from a lumen having an outside diameter of less than or equal to about 1.67 mm.

37. An endovascular occlusion device as in Embodiment 36, having an expansion ratio of at least about 6:1.

38. An endovascular occlusion device as in Embodiment 37, having an expansion ratio of at least about 7:1.

39. An endovascular occlusion device as in any one of Embodiments 33 to 38, deliverable over an 0.018 inch guidewire.

40. An endovascular occlusion device as in any one of Embodiment 33 to 39, wherein the device has an average COP across a diameter of 2.5 mm to 8.0 mm of between about 30 mmHg and about 140 mmHg.

41. A low crossing profile, high dynamic range endovascular occlusion device having an opening for receiving a guidewire therethrough, the occlusion device expandable from a first diameter for transvascular navigation within a deployment catheter to a deployment site, to a second diameter for occluding a vessel following deployment from the catheter, wherein the catheter has a diameter of no greater than about 5 French and the expansion ratio is at least about 6×.

42. A low crossing profile, high dynamic range endovascular occlusion device as in Embodiment 41, wherein the expansion ratio is at least about 8×.

43. A low crossing profile, high dynamic range endovascular occlusion device as in Embodiment 41 or 42, comprising an expandable frame and an occlusion membrane.

44. An endovascular occlusion deployment system for navigating tortuous vasculature to deploy an occlusion device at a target site in a vessel, comprising:
an elongate, flexible tubular body, having a proximal end, a distal end, and a diameter of no more than about 5 French; and
an occlusion device releasably carried in the distal end of the tubular body, the occlusion device having an expansion ratio of at least about 5 to 1;
wherein the distal end is advanceable to the trackability target vessel as determined by the test protocol identified in Trackability Protocol described herein.

45. A low crossing profile, high dynamic range endovascular occlusion device with low elongation, the occlusion device expandable from a first diameter for transvascular navigation within a deployment catheter to a deployment site, to a second diameter for occluding a vessel following deployment from the catheter, wherein the catheter has a diameter of no greater than about 5 French, the occlusion device has an expansion ratio of at least about 5×, and the elongation of the device between the first diameter and the second diameter is no more than about 20%.

46. A migration resistant endovascular occlusion device for occluding blood flow through a vessel, comprising:
an expandable frame comprising an upstream lobe and a downstream lobe separated by a neck portion; and
a membrane carried by the frame;
wherein the frame and membrane are dimensioned for deployment from a tube having an inside diameter of no more than about 2 mm, and are expandable to a diameter of at least about 8 mm following deployment from the tube; and
wherein the occlusion device exhibits a migration of less than about 5 mm in 10 minutes as determined by the test protocol identified in Migration Protocol described herein.

47. An endovascular occlusion deployment system with contrast injection capability, for navigating tortuous vasculature to deploy an occlusion device at a target site in a vessel, comprising:
an elongate, flexible tubular body, having a proximal end, a distal end, and a diameter of no more than about 5 French; and
an occlusion device releasably carried in the distal end of the tubular body, the occlusion device having an expansion ratio of at least about 5 to 1; and
a contrast injection port on the body, proximal to the occlusion device;
wherein the contrast injection port permits injection of contrast while the occlusion device is in an expanded configuration and prior to release of the occlusion device from the tubular body.

48. An endovascular occlusion device for mechanical occlusion of blood flow in a vessel, comprising:
a support structure, expandable from a reduced cross section for transluminal navigation to an enlarged cross section for occluding a vessel;
an upstream lobe on the support structure, separated from a downstream lobe by a neck portion;
a guidewire lumen extending through the neck portion;

the upstream lobe comprising a concave configuration which is concave in a direction away from the downstream lobe;
a valve in the guidewire lumen; and
a porous membrane carried by the upstream lobe.

49. An endovascular occlusion device as in Embodiment 48, wherein the downstream lobe comprises a concave configuration, concave in a direction facing away from the upstream lobe.

50. An endovascular occlusion device as in Embodiment 49, wherein the upstream lobe comprises a plurality of side wall struts.

51. An endovascular occlusion device as in Embodiment 50, wherein the side wall struts carry the membrane.

52. An endovascular occlusion device as in any one of Embodiments 48 to 51, wherein the valve comprises a collapsible tube extending from the neck portion into the upstream lobe.

53. An endovascular occlusion device as in any one of Embodiments 48 to 52, wherein the downstream lobe comprises a plurality of side wall struts.

54. An endovascular occlusion device as in any one of Embodiments 48 to 53, wherein following deployment in an artery with the upstream lobe in an anatomically proximal orientation, blood pressure on the concave side of the upstream lobe generates a radially outward force from the upstream lobe against the artery wall.

55. An endovascular occlusion device as in Embodiment 54, wherein blood pressure on the concave side of the upstream lobe generates an axially distal force on the neck portion.

56. The endovascular occlusion device as in any one of Embodiments 48 to 55, having an expansion ratio of at least about 6:1.

57. The endovascular occlusion device as in any one of Embodiment 48 to 55, having an expansion ratio of at least about 7:1.

58. The endovascular occlusion device as in any one of Embodiment 48 to 57, having an unconstrained expanded diameter of at least about 6.0 mm and which can be deployed from a 1 mm or smaller inside diameter lumen.

59. The endovascular occlusion device as in any one of Embodiment 48 to 58, wherein the device is configured to occlude at least about 90 percent of flow through a vessel when the expandable tubular frame is in an expanded configuration.

60. An endovascular occlusion device as in any one of Embodiment 48 to 59, configured to achieve a reduction in blood flow of at least about 80% within 2 minutes of deployment from the tube in a blood vessel.

61. An endovascular occlusion device as in any one of Embodiment 48 to 60, configured to achieve a reduction in blood flow of at least about 80% within 1 minute of deployment from the tube in a blood vessel.

62. An endovascular occlusion device as in any one of Embodiment 48 to 61, configured to achieve total occlusion within 5 minutes of deployment from the tube in a blood vessel.

63. An endovascular occlusion device as in Embodiment 62, configured to achieve total occlusion within 1 minute of deployment from the tube in a blood vessel.

64. An endovascular occlusion device deployment system, comprising the endovascular occlusion device of any one of Embodiment 48 to 63, oriented on an elongate, flexible deployment catheter having a proximal end and a distal end such that the upstream lobe faces the proximal end of the catheter.

65. A method of occluding a vessel, comprising the steps of:
deploying an anchoring lobe of an occlusion device in a vessel, without occluding blood flow;
thereafter deploying an occlusion lobe of the device in the vessel to occlude blood flow;
wherein the anchoring lobe is downstream of the occlusion lobe.

66. A method of occluding a vessel as in Embodiment 65, additionally comprising evaluating the position of the occlusion device in the vessel prior to the deploying an occlusion lobe step.

67. An endovascular occlusion device for occlusion of blood flow in a vessel, comprising:
a support structure, self-expandable from a reduced cross section for transluminal navigation to an enlarged cross section for occluding a vessel;
the support structure defining a first axially outwardly facing concavity when in the enlarged configuration, the concavity having an upstream opening and a downstream end;
a guidewire opening in the downstream end; and
a collapsible tube extending from the guidewire opening in an upstream direction into the concavity.

68. An endovascular occlusion device as in Embodiment 67, further comprising a membrane carried by the support structure.

69. An endovascular occlusion device as in Embodiment 68, wherein the support structure additionally comprises a downstream lobe.

70. An endovascular occlusion device as in Embodiment 69, wherein the downstream lobe comprises a plurality of struts spaced apart when in the enlarged configuration, to provide a plurality of openings therethrough.

71. An endovascular occlusion device as in Embodiment 70, wherein the struts define a second concavity, facing in an opposite direction from the first, upstream facing concavity.

72. A vascular occlusion device, comprising:
a frame comprising a proximal lobe and a distal lobe separated by a hub;
the proximal and distal lobes self-expandable from a constrained diameter to an unconstrained diameter of at least about 500% of the constrained diameter;
a hinge on the hub, to permit relative lateral deflection of the proximal and distal lobes to allow the frame to conform to a curved vessel; and
an embolic membrane carried by the proximal lobe.

73. A vascular occlusion device as in Embodiment 72, wherein the hinge comprises at least one slot in a side wall of the hub.

74. A vascular occlusion device as in Embodiment 72, wherein the hinge comprises a spiral slot in a side wall of the hub.

75. A vascular occlusion device as in any one of Embodiments 72 to 74, further comprising a guidewire lumen extending through the hub.

76. A vascular occlusion device as in Embodiment 75, further comprising an occluder for occluding the guidewire lumen.

77. A vascular occlusion device as in Embodiment 76, wherein the occluder comprises a membrane configured to occlude the guidewire lumen following removal of a guidewire.

78. A vascular occlusion device as in Embodiment 77, wherein the occluder comprises a tubular membrane having a central lumen for removably receiving a guidewire.

79. A vascular occlusion device as in Embodiment 78, wherein the tubular membrane is connected to the embolic membrane.

80. A vascular occlusion device as in Embodiment 78, wherein the tubular membrane is integrally formed with the embolic membrane.

81. A vascular occlusion device as in Embodiment 78, wherein the tubular membrane has a first end which is anchored with respect to the hub, and a free end spaced apart from the anchored end.

82. A vascular occlusion device as in Embodiment 81, wherein the tubular membrane is invertible, such that the free end can be moved between the distal lobe and the proximal lobe.

83. A vascular occlusion device as in Embodiment 81, wherein the distal lobe has a distal landing zone and a proximal tapered zone which tapers radially inwardly in the proximal direction to permit retraction of the distal lobe into a tubular sheath.

84. A vascular occlusion device as in any one of Embodiments 72 to 83, wherein the embolic membrane is concave in the proximal direction.

85. A vascular occlusion device as in Embodiment 84, wherein the embolic membrane extends along an axis between a distal apex and a proximal opening, and the length of the membrane measured along the axis is no more than about 50% of the length of the device.

86. A vascular occlusion device as in Embodiment 85, wherein the length of the membrane measured along the axis is no more than about 40% of the length of the device.

87. A vascular occlusion device, comprising:
 a frame comprising a proximal embolic zone and a distal anchoring zone separated by a hub;
 the proximal and distal zones self-expandable from a constrained diameter to an unconstrained diameter of at least about 500% of the constrained diameter;
 a guidewire lumen through the hub, to permit placement over a guidewire; and
 a valve in communication with the guidewire lumen.

What is claimed is:

1. An endovascular occlusion device for occlusion of blood flow in a vessel, comprising:
 a support structure, self-expandable from a reduced cross section for transluminal navigation to an enlarged configuration for occluding a vessel;
 the support structure defining a first axially outwardly facing concavity when in the enlarged configuration, the first axially outwardly facing concavity having an upstream opening and a downstream end;
 a guidewire opening in the downstream end; and
 a collapsible tube extending from the guidewire opening in an upstream direction into the first axially outwardly facing concavity.

2. An endovascular occlusion device as in claim 1, further comprising a membrane carried by the support structure.

3. An endovascular occlusion device as in claim 2, wherein the support structure comprises an upstream lobe that defines the first axially outwardly facing concavity, and wherein the support structure additionally comprises a downstream lobe.

4. An endovascular occlusion device as in claim 3, wherein the downstream lobe comprises a plurality of downstream lobe struts spaced apart when in the enlarged configuration, to provide a plurality of openings therethrough.

5. An endovascular occlusion device as in claim 4, wherein the downstream lobe struts define a second concavity, facing in an opposite direction from the first axially outwardly facing concavity.

6. An endovascular occlusion device as in claim 4, wherein expansion of the downstream lobe permits flow between the downstream lobe struts.

7. An endovascular occlusion device as in claim 4, wherein the upstream lobe comprises a plurality of upstream lobe struts.

8. An endovascular occlusion device as in claim 7, wherein the membrane extends between the plurality of upstream lobe struts to occlude flow between the upstream lobe struts upon expansion of the upstream lobe.

9. An endovascular occlusion device as in claim 3, wherein the upstream lobe is expandable to include a plurality of upstream lobe struts having a first laterally outward facing concave structure, and wherein the downstream lobe is expandable to include a plurality of downstream lobe struts having a second outwardly concave structure.

10. An endovascular occlusion device as in claim 9, wherein a radius of a first best fit circle conforming to the first laterally facing concave structure is less than a radius of a second best fit circle conforming to the second outwardly concave structure, the second best fit circle being measured at a same circumferential position as the first best fit circle.

11. An endovascular occlusion device as in claim 3, wherein the upstream lobe and the downstream lobe are separated by a hub.

12. An endovascular occlusion device as in claim 11, wherein the hub is flexible to allow bending between the upstream and downstream lobes.

13. An endovascular occlusion device as in claim 11, wherein the hub is partially expandable.

14. An endovascular occlusion device as in claim 3, wherein the downstream lobe comprises an open distal end.

15. An endovascular occlusion device as in claim 3, wherein when in the enlarged configuration, the occlusion device has bilateral asymmetry across a plane extending between the upstream lobe and the downstream lobe.

16. An endovascular occlusion device as in claim 1, wherein when in the enlarged configuration, the occlusion device has bilateral asymmetry.

17. An endovascular occlusion device as in claim 1, having an expansion ratio of at least about 5:1.

18. An endovascular occlusion device as in claim 1, having an expansion ratio of at least about 6:1.

19. An endovascular occlusion device as in claim 1, having an expansion ratio of at least about 7:1.

20. An endovascular occlusion device as in claim 1, wherein the device is configured to occlude at least about 90 percent of flow through a vessel when the support structure is in an expanded configuration.

21. An endovascular occlusion device as in claim 1, wherein a maximum expanded diameter of the support structure is at the upstream opening.

* * * * *